United States Patent
Maehata et al.

(10) Patent No.: US 12,225,904 B2
(45) Date of Patent: Feb. 18, 2025

(54) PHENYLPYRAZOLE COMPOUND AND METHOD FOR CONTROLLING PLANT DISEASE

(71) Applicant: SUMITOMO CHEMICAL COMPANY, LIMITED, Chuo-ku (JP)

(72) Inventors: Nao Maehata, Takarazuka (JP); Hiroshi Sakaguchi, Takarazuka (JP); Shuhei Azuma, Osaka (JP); Yusuke Ota, Osaka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 0 days.

(21) Appl. No.: 17/285,687

(22) PCT Filed: Oct. 18, 2019

(86) PCT No.: PCT/JP2019/041139
§ 371 (c)(1),
(2) Date: Apr. 15, 2021

(87) PCT Pub. No.: WO2020/080534
PCT Pub. Date: Apr. 23, 2020

(65) Prior Publication Data
US 2021/0321614 A1    Oct. 21, 2021

(30) Foreign Application Priority Data
Oct. 18, 2019  (JP) ................. 2018-196428

(51) Int. Cl.
| | | |
|---|---|---|
| A01N 43/56 | (2006.01) | |
| A01N 43/76 | (2006.01) | |
| A01N 43/78 | (2006.01) | |
| A01N 43/82 | (2006.01) | |
| A01N 43/84 | (2006.01) | |

(52) U.S. Cl.
CPC ............. *A01N 43/56* (2013.01); *A01N 43/76* (2013.01); *A01N 43/78* (2013.01); *A01N 43/82* (2013.01); *A01N 43/84* (2013.01)

(58) Field of Classification Search
None
See application file for complete search history.

(56) References Cited

U.S. PATENT DOCUMENTS

| | | | |
|---|---|---|---|
| 3,560,485 A | 2/1971 | Schinzel et al. | |
| 5,523,280 A | 6/1996 | Chene et al. | |
| 5,663,119 A * | 9/1997 | Chene ................. | C07D 231/12 548/356.1 |
| 6,054,413 A * | 4/2000 | Zagar ................. | C07D 231/24 504/169 |
| 6,414,011 B1 | 7/2002 | Hogenkamp et al. | |
| 6,737,418 B2 | 5/2004 | Hogenkamp et al. | |
| 7,226,930 B2 | 6/2007 | Hopper et al. | |
| 7,495,017 B2 | 2/2009 | Hopper et al. | |
| 7,608,563 B2 | 10/2009 | Tsukamoto et al. | |
| 7,964,531 B2 | 6/2011 | Tsukamoto et al. | |
| 8,822,521 B2 | 9/2014 | Taggi et al. | |
| 9,198,433 B2 | 12/2015 | Taggi et al. | |
| 9,828,389 B2 | 11/2017 | Arimori et al. | |
| 2003/0069292 A1 | 4/2003 | Hogenkamp et al. | |
| 2004/0229918 A1 | 11/2004 | Hopper et al. | |
| 2005/0037925 A1 | 2/2005 | Tsukamoto et al. | |
| 2007/0203197 A1 | 8/2007 | Hopper et al. | |
| 2009/0221661 A1 | 9/2009 | Hopper et al. | |
| 2010/0041555 A1 | 2/2010 | Tsukamoto et al. | |

(Continued)

FOREIGN PATENT DOCUMENTS

| | | |
|---|---|---|
| AU | 2931295 A | 2/1996 |
| CN | 1071162 A | 4/1993 |

(Continued)

OTHER PUBLICATIONS

Koyanagi et al. (Bioisosterism in agrochemicals, Chapter 2, synthesis and chem. of agrochemicals IV, 1995, p. 15-24).*
Patani (Bioisosterism in Drug design, Chem Rev. 1996, 96(8), 3147-3176).*
UNL dessicants/chemical effects (https://web.archive.org/web/20150602011516/https://cropwatch.unl.edu/potato/dessication_chemical.*
UNL Plant disease definition (https://web.archive.org/web/20191018181244/https://cropwatch.unl.edu/soybean-management/plant-disease).*
European Office Action issued Dec. 5, 2023 in European Patent Application No. 19873239.8, 9 pages.

(Continued)

*Primary Examiner* — Erin E Hirt
(74) *Attorney, Agent, or Firm* — Oblon, McClelland, Maier & Neustadt, L.L.P.

(57) ABSTRACT

The present invention provides a method for controlling a plant disease which comprises applying a compound represented by formula (I) [wherein Z represents a C1-C6 chain hydrocarbon group and the like, $R^1$ and $R^2$ are identical to or different from each other and represent a hydrogen atom or a fluorine atom, and $R^3$, $R^4$, $R^5$, $R^6$ and $R^7$ are identical to or different from each other and represent a C1-C6 chain hydrocarbon group and the like] to a plant or a soil, which has excellent control efficacies against plant diseases.

(I)

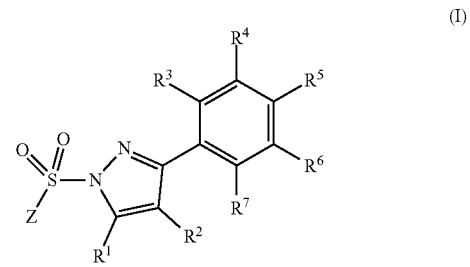

8 Claims, No Drawings

(56) References Cited

U.S. PATENT DOCUMENTS

| | | | |
|---|---|---|---|
| 2010/0120714 | A1 | 5/2010 | Finkelstein et al. |
| 2014/0323436 | A1 | 10/2014 | Finkelstein et al. |
| 2015/0203511 | A1 | 7/2015 | Arimori et al. |
| 2015/0335023 | A1 | 11/2015 | Finkelstein et al. |

FOREIGN PATENT DOCUMENTS

| | | | |
|---|---|---|---|
| CN | 1079735 | A | 12/1993 |
| CN | 106455572 | A | 2/2017 |
| EP | 0 538 156 | A1 | 4/1993 |
| EP | 0 931 072 | A1 | 7/1999 |
| EP | 1 426 365 | A1 | 6/2004 |
| ES | 8301217 | | 11/1982 |
| JP | 6-1769 | A | 1/1994 |
| JP | 10-502661 | A | 3/1998 |
| JP | 11-171877 | A | 6/1999 |
| JP | 2001-506581 | A | 5/2001 |
| JP | 2002-540155 | A | 11/2002 |
| JP | 2006-523719 | A | 10/2006 |
| JP | 2010-523570 | A | 7/2010 |
| JP | 2015-27978 | A | 2/2015 |
| WO | WO 96/02138 | A1 | 2/1996 |
| WO | WO 1996/031123 | | 10/1996 |
| WO | WO 98/12182 | A1 | 3/1998 |
| WO | WO 00/057877 | A1 | 10/2000 |
| WO | WO 03/016286 | A1 | 2/2003 |
| WO | WO 2004/094411 | A1 | 11/2004 |
| WO | WO 2014/051165 | A1 | 4/2014 |

OTHER PUBLICATIONS

Office Action issued Mar. 16. 2022 in corresponding Chinese Patent Application No. 201980067897.0 (with English Translation), 10 pages.

Indian Office Action issued Nov. 1, 2022 in Indian Patent Application No. 202147016973, 7 pages.

International Search Report issued Jan. 21, 2020 in PCT/JP2019/041139 (submitting English translation only), 6 pages.

International Preliminary Report on Patentability and Written Opinion of the International Searching Authority issued Apr. 14, 2021 in PCT/JP2019/041139 (submitting English translation only), 9 pages.

P. J. Dudfield, et al., "A Convenient Synthesis of 2-Cyanoimidazoles" Synlett, No. 5, 1990, pp. 277-278.

J. Panteleev, et al., "Alkylation of Nitrogen-Containing Heterocycles via In Situ Sulfonyl Transfer" Synlett, vol. 26, No. 7, 2015, pp. 953-959.

"CAS registration No. 1022100-48-6" Database Registry [Online] Retrieved from STN, Dec. 17, 2019, Entered STN: May 23, 2008, 1 page.

"CAS registration No. 959578-95-1, 959569-06-3" Database Registry [Online] Retrieved from STN, Dec. 17, 2019, Entered STN: Dec. 26, 2007, 1 page.

"CAS registration No. 321998-84-9" Database Registry [Online] Retrieved from STN, Dec. 17, 2019, Entered STN: Feb. 19, 2001, 1 page.

"CAS registration No. 321385-88-0" Database Registry [Online] Retrieved from STN, Dec. 17, 2019, Entered STN: Feb. 12, 2001, 1 page.

Rejection Decision issued Jan. 9, 2023 in Chinese Patent Application No. 201980067897.0 (with English language translation), 10 pages.

Extended European Search Report issued Jun. 15, 2022, in corresponding European Patent Application No. 19873239.8, 113 pages.

Notice of Reasons for Refusal issued Jun. 27, 2023 in Japanese Patent Application No. 2020-553347 (with English machine translation), 11 pages.

Jane Panteleev, et al., "Alkylation of Nitrogen-Containing Heterocycles via In Situ Sulfonyl Transfer," Synlett, vol. 26, 2015, 9 pages (reference previously filed, additional page added).

Combined Chinese Office Action and Search Report issued Oct. 15, 2021 in Chinese Patent Application No. 201980067897.0 (with English translation), 13 pages.

* cited by examiner

PHENYLPYRAZOLE COMPOUND AND METHOD FOR CONTROLLING PLANT DISEASE

CROSS-REFERENCE TO RELATED APPLICATIONS

The present application is a 35 U.S.C. § 371 national stage patent application of International Patent Application PCT/JP2019/041139, filed on Oct. 18, 2019, which is based on and claims the benefits of priority to Japanese Application No. 2018-196428, filed on Oct. 18, 2018. The entire contents of these applications are incorporated herein by reference.

TECHNICAL FIELD

This application claims priorities to and the benefits of Japanese Patent Application No. 2018-196428 filed on Oct. 18, 2019, the entire contents of which are incorporated herein by reference.

The present invention relates to phenylpyrazole compounds and a method for controlling plant diseases.

BACKGROUND ART

Patent documents 1 to 3 describe phenylpyrazole compounds.

CITATION LIST

Patent Document

Patent Document 1: WO 1998/12182
Patent Document 2: WO 1996/02138
Patent Document 3: EP patent publication No. 538156

SUMMARY OF THE INVENTION

Problems to be Solved by Invention

An object of the present invention is to provide method having an excellent efficacy for controlling plant diseases

Means to Solve Problems

The present inventors have studied so as to find a method having an excellent efficacy for controlling plant diseases, and have found out that the compound represented by the following formula (I) has an excellent efficacy on controlling plant diseases.

That is, the present invention is as follows.
[1] A method for controlling a plant disease which comprises applying a compound represented by formula (I) to a plant or a soil:

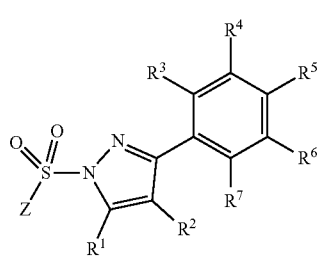

(I)

[wherein
Z represents a C1-C6 chain hydrocarbon group optionally having one or more substituents selected from Group I, a C3-C6 cycloalkyl group optionally having one or more halogen atoms, a three to seven membered non-aromatic heterocyclic group {the three to seven membered non-aromatic heterocyclic group may optionally have one or more substituents selected from the group consisting of a C1-C3 alkyl group optionally having one or more halogen atoms and a halogen atom}, or —NR$^8$R$^9$, R$^8$ and R$^9$ are identical to or different from each other and represent a C1-C6 chain hydrocarbon group optionally having one or more substituents selected from Group I, a C3-C6 cycloalkyl group optionally having one or more halogen atoms or a hydrogen atom, R$^1$ and R$^2$ are identical to or different from each other and represent a hydrogen atom or a fluorine atom, R$^3$, R$^4$, R$^5$, R$^6$ and R$^7$ are identical to or different from each other and represent a C1-C6 chain hydrocarbon group optionally having one or more substituents selected from Group I, a C3-C6 cycloalkyl group, a C6-C10 aryl group, a five to ten membered aromatic heterocyclic group {the C3-C6 cycloalkyl group, the C6-C10 aryl group and the five to ten membered aromatic heterocyclic group may optionally have one or more substituents selected from group K}, a hydrogen atom, a halogen atom, a nitro group, a cyano group, —OR$^{15}$, —CR$^{39}$R$^{40}$OR$^{41}$, —CR$^{43}$R$^{44}$SR$^{45}$, —S(O)$_n$R$^{16}$, —C(O)R$^{17}$, —CR$^{18}$=N—O—R$^{19}$, —O—N=CR$^{20}$R$^{46}$, —N=N—CR$^{21}$R$^{47}$, —C(O)NR$^{22}$R$^{23}$, —NR$^{24}$C(O)R$^{25}$, —C(O)N(OR$^{26}$)R$^{27}$, —N(OR$^{28}$)C(O)R$^{29}$, —NR$^{30}$C(O)NR$^{31}$R$^{32}$, —OC(O)NR$^{33}$R$^{34}$, —NR$^{35}$C(O)OR$^{36}$, —NR$^{45}$C(O)C(O)NR$^{49}$R$^{50}$, —CR$^{51}$R$^{52}$NR$^{53}$C(O)C(O)NR$^{54}$R$^{55}$, or —NR$^{56}$C(O)C(O)N(OR$^{57}$)R$^{58}$, R$^{15}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$, R$^{32}$, R$^{33}$, R$^{34}$, R$^{35}$, R$^{39}$, R$^{40}$, R$^{41}$, R$^{43}$, R$^{44}$, R$^{45}$, R$^{46}$, R$^{47}$, R$^{48}$, R$^{49}$, R$^{50}$, R$^{51}$, R$^{52}$, R$^{53}$, R$^{54}$, R$^{55}$, R$^{56}$, R$^{52}$, and R$^{53}$ are identical to or different from each other and represent a C1-C6 chain hydrocarbon group optionally having one or more substituents selected from Group L, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group K} or a hydrogen atom, R$^{36}$ represents a C1-C6 chain hydrocarbon group optionally having one or more substituents selected from Group L, a C3-C6 cycloalkyl group, a C6-C10 aryl group, or a five to ten membered aromatic heterocyclic group {each of the C3-C6 cycloalkyl group, the C6-C10 aryl group and the five to ten membered aromatic heterocyclic group may optionally have one or more substituents selected from Group K}, R$^{16}$ represents a C1-C6 chain hydrocarbon group optionally having one or more substituents selected from Group L, or a C3-C6 cycloalkyl group {the C3-C6 cycloalkyl group may optionally have one or more substituents selected from a halogen atom and a cyano group}, n is 0, 1 or 2, R$^3$ and R$^4$ may be taken together with a carbon atom to which they are attached to form a C4-C7 carbocycle group, or a five to seven membered heterocyclic group {each of the C4-C7 carbocycle group and the five to seven membered heterocyclic group may optionally have one or more substituents selected from Group J}, R$^4$ and R$^5$ may be taken together with a carbon atom to which they are attached to form a C4-C7 carbocycle group, or a five to seven membered heterocyclic group {each of the C4-C7 carbocycle group and the five to seven membered heterocyclic group may optionally have one or more substituents selected from Group J}.

Group I: a group consisting of a halogen atom, a cyano group, a C3-C6 cycloalkyl group, a C1-C3 alkoxy group and a C1-C3 alkylthio group {each of the C3-C6 cycloalkyl group, the C1-C3 alkoxy group and the C1-C3 alkylthio group may optionally have one or more halogen atoms}.

Group J: a group consisting of a C1-C3 chain hydrocarbon group optionally having one or more halogen atoms, a C3-C6 cycloalkyl group optionally having one or more halogen atoms, a C1-C3 alkoxy group optionally having one or more halogen atoms, a halogen atom, a nitro group and a cyano group.

Group K: a group consisting of a C1-C3 chain hydrocarbon group, a C3-C6 cycloalkyl group, a C1-C3 alkoxy group, a C1-C3 alkylthio group {each of the C1-C3 chain hydrocarbon group, the C3-C6 cycloalkyl group, the C1-C3 alkoxy group and the C1-C3 alkylthio group may optionally have one or more substituents selected from the group consisting of a halogen atom and a cyano group}, a halogen atom, and cyano group.

Group L: a group consisting of a C1-C3 alkoxy group, a C1-C3 alkylthio group {each of the C1-C3 alkoxy group and the C1-C3 alkylthio group may optionally have one or more halogen atoms}, a C3-C6 cycloalkyl group, a C6-C10 aryl group, a five to ten membered aromatic heterocyclic group {each of the C3-C6 cycloalkyl group, the C6-C0 aryl group and the five to ten membered aromatic heterocyclic group may optionally have one or more substituents selected from Group K}, a halogen atom, and cyano group.]

(hereinafter, referred to as "Present compound X").

[2] The method described in [1] wherein the compound represented by formula (I) is a compound by formula (I) wherein R$^5$ represents a C1-C6 chain hydrocarbon group optionally having one or more substituents selected from Group I, a C3-C6 cycloalkyl group optionally having one or more halogen atoms, a halogen atom, a nitro group, a cyano group, —OR$^{10}$, —S(O)$_m$R$^{11}$, —C(O)R$^{12}$, or —CR$^{13}$=N—O—R$^{14}$, R$^3$, R$^4$, R$^6$ and R$^7$ are identical to or different from each other and represent a C1-C6 chain hydrocarbon group optionally having one or more substituents selected from Group I, a C3-C6 cycloalkyl group optionally having one or more halogen atoms, a hydrogen atom, a halogen atom, a nitro group, a cyano group, —OR$^{15}$, —S(O)$_n$R$^{16}$, —C(O)R$^{17}$, or —CR$^{18}$=N—O—R$^{19}$, R$^{10}$, R$^{12}$, R$^{13}$, R$^{14}$, R$^{15}$, R$^{17}$, R$^{18}$, and R$^{19}$ are identical to or different from each other and represent a C1-C6 chain hydrocarbon group optionally having one or more halogen atoms or a hydrogen atom, R$^{11}$ and R$^{16}$ are identical to or different from each other and represent a C1-C6 chain hydrocarbon group optionally having one or more halogen atoms, m and n are independently of each other 0, 1, or 2, R$^3$ and R$^4$ may be taken together with a carbon atom to which they are attached to form a C4-C7 carbocycle group, or a five to seven membered heterocyclic group {the C4-C7 carbocycle group and the five to seven membered heterocyclic group may optionally have one or more substituents selected from Group J}, R$^4$ and R$^5$ may be taken together with a carbon atom to which they are attached to form a C4-C7 carbocycle group, or a five to seven membered heterocyclic group {the C4-C7 carbocycle group and the five to seven membered heterocyclic group may optionally have one or more substituents selected from Group J.}

(hereinafter, referred to as "Present compound").

[3] A compound represented by formula (II):

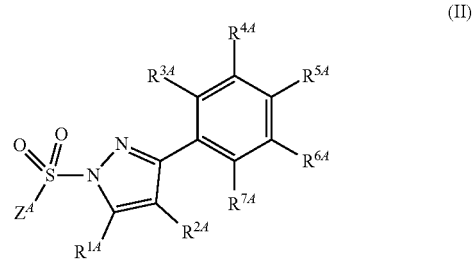

(II)

[wherein

Z$^A$ represents a C1-C6 chain hydrocarbon group optionally having one or more substituents selected from Group I$^A$, a C3-C6 cycloalkyl group optionally having one or more halogen atoms, a three to seven membered non-aromatic heterocyclic group {the three to seven membered non-aromatic heterocyclic group may optionally have one or more substituents selected from a group consisting of a C1-C3 alkyl group optionally having one or more halogen atoms and a halogen atom}, or —NR$^{8A}$R$^{9A}$, R$^{8A}$ and R$^{9A}$ are identical to or different from each other and represent a C1-C6 chain hydrocarbon group optionally having one or more substituents selected from Group I$^A$, a C3-C6 cycloalkyl group optionally having one or more halogen atoms or a hydrogen atom, R$^{1A}$, R$^{2A}$, R$^{3A}$ and R$^{7A}$ are identical to or different from each other and represent a hydrogen atom or a fluorine atom, a combination of R$^{4A}$, R$^{5A}$ and R$^{6A}$ represents any combination of a or b.

a: a combination wherein R$^{5A}$ represents a hydrogen atom, R$^{4A}$ represents a C1-C6 chain hydrocarbon group optionally having one or more substituents selected from Group I$^B$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group K$^B$}, a halogen atom, a cyano group, —OR$^{15B}$, —CR$^{39B}$R$^{40B}$OR$^{41B}$, —CR$^{43B}$R$^{44B}$SR$^{45B}$, —S(O)$_q$R$^{16B}$, —C(O)R$^{17B}$, —CR$^{18B}$=N—O—R$^{19B}$, —O—N=CR$^{20B}$R$^{46B}$, —N=N—CR$^{21B}$R$^{47B}$, —C(O)NR$^{22B}$R$^{23B}$, —NR$^{24B}$C(O)R$^{25B}$, —C(O)N(OR$^{26B}$)R$^{27B}$, —N(OR$^{28B}$)C(O)R$^{29B}$, —NR$^{30B}$C(O)NR$^{31B}$R$^{32B}$, —OC(O)NR$^{33B}$R$^{34B}$, —NR$^{35B}$C(O)OR$^{36B}$, —NR$^{48B}$C(O)C(O)NR$^{49B}$R$^{50B}$, —CR$^{51B}$R$^{52B}$NR$^{53B}$C(O)C(O)NR$^{54B}$R$^{55B}$, or —NR$^{56B}$C(O)C(O)N(OR$^{57B}$)R$^{58B}$, and R$^{6A}$ represents a C1-C6 chain hydrocarbon group optionally having one or more substituents selected from Group I$^B$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^B$}, a hydrogen atom, a halogen atom, a cyano group, $-OR^{15B}$, $-CR^{39B}R^{40B}OR^{41B}$, $-CR^{43B}R^{44B}SR^{45B}$, $-S(O)_qR^{16B}$, $-C(O)R^{17B}$, $-CR^{18B}=N-O-R^{19B}$, $-O-N=CR^{20B}R^{46B}$, $-N=N-CR^{21B}R^{47B}$, $-C(O)NR^{22B}R^{23B}$, $-NR^{24B}C(O)R^{25B}$, $-C(O)N(OR^{26B})R^{27B}$, $-N(OR^{28B})C(O)R^{29B}$, $-NR^{30B}C(O)NR^{31B}R^{32B}$, $-OC(O)NR^{33B}R^{34B}$, $-NR^{35B}C(O)OR^{36B}$, $-NR^{48B}C(O)C(O)NR^{49B}R^{50B}$, $-CR^{51B}R^{52B}NR^{53B}C(O)C(O)NR^{54B}R^{55B}$, or $-NR^{56B}C(O)C(O)N(OR^{57B})R^{58B}$;

b: a combination wherein $R^{5A}$ represents a C1-C6 chain hydrocarbon group optionally having one or more substituents selected from Group $I^A$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$}, a halogen atom, a nitro group, a cyano group, $-OR^{10A}$, $-CR^{39A}R^{40A}OR^{41A}$, $-CR^{43A}R^{44A}SR^{45A}$, $-S(O)_pR^{16A}$, $-C(O)R^{17A}$, $-CR^{18A}=N-O-R^{19A}$, $-O-N=CR^{20A}R^{46A}$, $-N=N-CR^{21A}R^{47A}$, $-C(O)NR^{22A}R^{23A}$, $-NR^{24A}C(O)R^{25A}$, $-C(O)N(OR^{26A})R^{27A}$, $-N(OR^{28A})C(O)R^{29A}$, $-NR^{30A}C(O)NR^{31A}R^{32A}$, $-OC(O)NR^{33A}R^{34A}$, $-NR^{35A}C(O)OR^{36A}$, $-NR^{48A}C(O)C(O)NR^{49A}R^{50A}$, $-CR^{51A}R^{52A}NR^{53A}C(O)C(O)NR^{54A}R^{55A}$, or $-NR^{56A}C(O)C(O)N(OR^{57A})R^{58A}$, and $R^{4A}$ and $R^{6A}$ are identical to or different from each other and represent a C1-C6 chain hydrocarbon group optionally having one or more substituents selected from Group $I^A$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$}, a hydrogen atom, a halogen atom, a nitro group, a cyano group, $-OR^{15A}$, $-CR^{39A}R^{40A}OR^{41A}$, $-CR^{43A}R^{44A}SR^{45A}$, $-S(O)_pR^{16A}$, $-C(O)R^{17A}$, $-CR^{18A}=N-O-R^{19A}$, $-O-N=CR^{20A}R^{46A}$, $-N=N-CR^{21A}R^{47A}$, $-C(O)NR^{22A}R^{23A}$, $-NR^{24A}C(O)R^{25A}$, $-C(O)N(OR^{26A})R^{27A}$, $-N(OR^{28A})C(O)R^{29A}$, $-NR^{30A}C(O)NR^{31A}R^{32A}$, $-OC(O)NR^{33A}R^{34A}$, $-NR^{35A}C(O)OR^{36A}$, $-NR^{48A}C(O)C(O)NR^{49A}R^{50A}$, $-CR^{51A}R^{52A}NR^{53A}C(O)C(O)NR^{54A}R^{55A}$, or $-NR^{56A}C(O)C(O)N(OR^{57A})R^{58A}$;

$R^{3A}$ and $R^{4A}$ may be taken together with a carbon to which they are attached to form a C4-C7 carbocycle group, or a five to seven membered heterocyclic group {each of the C4-C7 carbocycle group and the five to seven membered heterocyclic group may optionally have one or more substituents selected from Group $J^A$}, $R^{4A}$ and $R^{5A}$ may be taken together with a carbon to which they are attached to form a C4-C7 carbocycle group, or a five to seven membered heterocyclic group {each of the C4-C7 carbocycle group and the five to seven membered heterocyclic group may optionally have one or more substituents selected from Group $J^A$}, $R^{15A}$ represents a C1-C6 chain hydrocarbon group optionally having one or more substituents selected from Group $L^A$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$} or a hydrogen atom, $R^{15B}$ represents a C1-C6 chain hydrocarbon group optionally having one or more substituents selected from Group $L^B$, a C3-C6 cycloalkyl group, a C6-C10 aryl group, a five to ten membered aromatic heterocyclic group (with the proviso that a pyridyl group is excluded) {each of the C3-C6 cycloalkyl group, the C6-C10 aryl group and the five to ten membered aromatic heterocyclic group (with the proviso that a pyridyl group is excluded) may optionally have one or more substituents selected from Group $K^{5B}$} or a hydrogen atom, $R^{10A}$ represents a C1-C6 chain hydrocarbon group optionally having one or more substituents selected from Group $L^A$, or a hydrogen atom, $R^{17A}$, $R^{18A}$, $R^{19A}$, $R^{20A}$, $R^{21A}$, $R^{22A}$, $R^{23A}$, $R^{24A}$, $R^{25A}$, $R^{26A}$, $R^{27A}$, $R^{28A}$, $R^{29A}$, $R^{30A}$, $R^{31A}$, $R^{32A}$, $R^{33A}$, $R^{34A}$, $R^{35A}$, $R^{39A}$, $R^{40A}$, $R^{41A}$, $R^{43A}$, $R^{44A}$, $R^{45A}$, $R^{46A}$, $R^{47A}$, $R^{48A}$, $R^{49A}$, $R^{50A}$, $R^{51A}$, $R^{52A}$, $R^{53A}$, $R^{54A}$, $R^{55A}$, $R^{56A}$, $R^{57A}$, $R^{58A}$, $R^{17B}$, $R^{18B}$, $R^{19B}$, $R^{20B}$, $R^{21B}$, $R^{22B}$, $R^{23B}$, $R^{24B}$, $R^{25B}$, $R^{26B}$, $R^{27B}$, $R^{28B}$, $R^{29B}$, $R^{30B}$, $R^{31B}$, $R^{32B}$, $R^{33B}$, $R^{34B}$, $R^{35B}$, $R^{39B}$, $R^{40B}$, $R^{41B}$, $R^{43B}$, $R^{44B}$, $R^{45B}$, $R^{46B}$, $R^{47B}$, $R^{48B}$, $R^{49B}$, $R^{50B}$, $R^{51B}$, $R^{52B}$, $R^{53B}$, $R^{54B}$, $R^{55B}$, $R^{56B}$, $R^{57B}$, and $R^{58B}$ are identical to or different from each other and represent a C1-C6 chain hydrocarbon group optionally having one or more substituents selected from Group $L^A$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$} or a hydrogen atom, $R^{36A}$ and $R^{36B}$ are identical to or different from each other and represent a C1-C6 chain hydrocarbon group optionally having one or more substituents selected from Group $L^A$, a C3-C6 cycloalkyl group, a C6-C10 aryl group, or a five to ten membered aromatic heterocyclic group {each of the C3-C6 cycloalkyl group, the C6-C10 aryl group and the five to ten membered aromatic heterocyclic group may optionally have one or more substituents selected from Group $K^A$}, $R^{16A}$ and $R^{16B}$ are identical to or different from each other and represent a C1-C6 chain hydrocarbon group optionally having one or more substituents selected from Group $L^A$, or a C3-C6 cycloalkyl group {the C3-C6 cycloalkyl group may optionally have one or more substituents selected from a group consisting a halogen atom and a cyano group}, p and q are identical to or different from each other and represent 0, 1 or 2, Group $I^A$: a group consisting of a halogen atom, a cyano group, a C3-C6 cycloalkyl group, a C1-C3 alkoxy group and a C1-C3 alkylthio group {each of the C3-C6 cycloalkyl group, the C1-C3 alkoxy group and the C1-C3 alkylthio group may optionally have one or more halogen atoms}, Group $J^A$: a group consisting of a C1-C3 chain hydrocarbon group optionally having one or more halogen atoms, a C3-C6 cycloalkyl group optionally having one or more halogen atoms, a C1-C3 alkoxy group optionally having one or more halogen atoms, a halogen atom, a nitro group and a cyano group, Group $K^A$: a group consisting of a C1-C3 chain hydrocarbon group, a C3-C6 cycloalkyl group, a C1-C3 alkoxy group, a C1-C3 alkylthio group {each of the C1-C3 chain hydrocarbon group, the C3-C6 cycloalkyl group, the C1-C3 alkoxy group and the C1-C3 alkylthio group may optionally have one or more substituents selected from a group consisting a halogen atom and a cyano group}, a halogen atom, and cyano group.

Group $L^A$: a group consisting of a C1-C3 alkoxy group, a C1-C3 alkylthio group {each of the C1-C3 alkoxy group and the C1-C3 alkylthio group may optionally have one or more halogen atoms}, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$}, a halogen atom, and cyano group.

Group $I^B$: a group consisting of a halogen atom, a cyano group, a C3-C6 cycloalkyl group, a C1-C3 alkoxy group and a C1-C3 alkylthio group {each of the C3-C6 cycloalkyl group, the C1-C3 alkoxy group and the C1-C3 alkylthio group may optionally have one or more halogen atoms}, Group $K^B$: a group consisting of a C1-C3 chain hydrocarbon group, a C3-C6 cycloalkyl group, a C1-C3 alkoxy group, a C1-C3 alkylthio group {each of the C1-C3 chain hydrocarbon group, the C3-C6 cycloalkyl group, the C1-C3 alkoxy group and the C1-C3 alkylthio group may optionally have one or more substituents selected from a group consisting a halogen atom and a cyano group}, a halogen atom, and a cyano group, Group $L^B$: a group consisting of a C1-C3 alkoxy group, a C1-C3 alkylthio group {each of the C1-C3 alkoxy group and the C1-C3 alkylthio group may optionally have one or more halogen atoms}, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$}, a halogen atom, and a cyano group]

(hereinafter, referred to as "Compound X of the present invention").

[4] The compound described in [3] wherein $R^{5A}$ represents a hydrogen atom, $R^{4A}$ represents a C1-C6 chain hydrocarbon group optionally having one or more substituents selected from Group $I^A$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$}, a halogen atom, a cyano group, —$OR^{15B}$, —$CR^{39B}R^{40B}OR^{41B}$, —$CR^{43B}R^{44B}SR^{45B}$, —$S(O)_qR^{16B}$, —$C(O)R^{17B}$, —$CR^{18B}$=N—O—$R^{19B}$, —O—N=$CR^{20B}R^{46B}$, —N=N—$CR^{21B}R^{47B}$, —$C(O)NR^{22B}R^{23B}$, —$NR^{24B}C(O)R^{25B}$, —$C(O)N(OR^{26B})R^{27B}$, —$N(OR^{28B})C(O)R^{29B}$, —$NR^{30B}C(O)NR^{31B}R^{32B}$, —$OC(O)NR^{33B}R^{34B}$, —$NR^{35B}C(O)OR^{36B}$, —$NR^{48B}C(O)C(O)NR^{49B}R^{50B}$, —$CR^{51B}R^{52B}NR^{53B}C(O)C(O)NR^{54B}R^{55B}$, or —$NR^{56B}C(O)C(O)N(OR^{57B})R^{58B}$, $R^{6A}$ represents a C1-C6 chain hydrocarbon group optionally having one or more substituents selected from Group $I^A$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$}, a hydrogen atom, a halogen atom, a cyano group, —$OR^{15B}$, —$CR^{39B}R^{40B}OR^{41B}$, —$CR^{43B}R^{44B}SR^{45B}$, —$S(O)_qR^{16B}$, —$C(O)R^{17B}$, —$CR^{18B}$=N—O—$R^{19B}$, —O—N=$CR^{20B}R^{46B}$, —N=N—$CR^{21B}R^{47B}$, —$C(O)NR^{22B}R^{23B}$, —$NR^{24B}C(O)R^{25B}$, —$C(O)N(OR^{26B})R^{27B}$, —$N(OR^{28B})C(O)R^{29B}$, —$NR^{30B}C(O)NR^{31B}R^{32B}$, —$OC(O)NR^{33B}R^{34B}$, —$NR^{35B}C(O)OR^{36B}$, —$NR^{48B}C(O)C(O)NR^{49B}R^{50B}$, —$CR^{51B}R^{52B}NR^{53B}C(O)C(O)NR^{54B}R^{55B}$, or —$NR^{56B}C(O)C(O)N(OR^{57B})R^{58B}$.

[5] The compound described in [3] wherein $R^{5A}$ represents a C1-C6 chain hydrocarbon group optionally having one or more substituents selected from Group $I^A$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$}, a halogen atom, a nitro group, a cyano group, —$OR^{10A}$, —$CR^{39A}R^{40A}OR^{41A}$, —$CR^{43A}R^{44A}SR^{45A}$, —$S(O)_pR^{16A}$, —$C(O)R^{17A}$, —$CR^{18A}$=N—O—$R^{19A}$, —N=$CR^{20A}R^{46A}$, —N=N—$CR^{21A}R^{47A}$, —$C(O)NR^{22A}R^{23A}$, —$NR^{24A}C(O)R^{25A}$, —$C(O)N(OR^{26A})R^{27A}$, —$N(OR^{28A})C(O)R^{29A}$, —$NR^{30A}C(O)NR^{31A}R^{32A}$, —$OC(O)NR^{33A}R^{34A}$, —$NR^{35A}C(O)OR^{36A}$, —$NR^{48A}C(O)C(O)NR^{49A}R^{50A}$, —$CR^{51A}R^{52A}NR^{53A}C(O)C(O)NR^{54A}R^{55A}$, or —$NR^{56A}C(O)C(O)N(OR^{57A})R^{58A}$, $R^{4A}$ and $R^{6A}$ are identical to or different from each other and represent a C1-C6 chain hydrocarbon group optionally having one or more substituents selected from Group $I^A$, a C3-C6 cycloalkyl group, a C6-C10 aryl group, a five to ten membered aromatic heterocyclic group {each of the C3-C6 cycloalkyl group, the C6-C10 aryl group and the five to ten membered aromatic heterocyclic group may optionally have one or more substituents selected from Group $K^A$}, a hydrogen atom, a halogen atom, a nitro group, a cyano group, —$OR^{15A}$, —$CR^{39A}R^{40A}OR^{41A}$, —$CR^{43A}R^{44A}SR^{45A}$, —$S(O)_pR^{16A}$, —$C(O)R^{17A}$, —$CR^{18A}$=N—O—$R^{19A}$, —O—N=$CR^{20A}R^{46A}$, —N=N—$CR^{21A}R^{47A}$, —$C(O)NR^{22A}R^{23A}$, —$NR^{24A}C(O)R^{25A}$, —$C(O)N(OR^{26A})R^{27A}$, —$N(OR^{28A})C(O)R^{29A}$, —$NR^{30A}C(O)NR^{31A}R^{32A}$, —$OC(O)NR^{33A}R^{34A}$, —$NR^{35A}C(O)OR^{36A}$, —$NR^{48A}C(O)C(O)NR^{49A}R^{50A}$, —$CR^{51A}R^{52A}NR^{53A}C(O)C(O)NR^{54A}R^{55A}$, or —$NR^{56A}C(O)C(O)N(OR^{57A})R^{58A}$, $R^{3A}$ and $R^{4A}$ may be taken together with a carbon atom to which they are attached to form a C4-C7 carbocycle group, or a five to seven membered heterocyclic group {each of the C4-C7 carbocycle group and the five to seven membered heterocyclic group may optionally have one or more substituents selected from Group $J^A$}, $R^{4A}$ and $R^{5A}$ may be taken together with a carbon atom to which they are attached to form a C4-C7 carbocycle group, or a five to seven membered heterocyclic group {each of the C4-C7 carbocycle group and the five to seven membered heterocyclic group may optionally have one or more substituents selected from Group $J^A$}.

[6] The compound described in [5] wherein $R^{5A}$ represents a C1-C6 chain hydrocarbon group optionally having one or more substituents selected from Group $I^A$, a C3-C6 cycloalkyl group optionally having one or more halogen atoms, a halogen atom, a nitro group, a cyano group, —$OR^{10A}$, —$S(O)_mR^{11A}$, —$C(O)R^{12A}$, or —$CR^{13A}$=N—O—$R^{14A}$, $R^{4A}$ and $R^{6A}$ are identical to or different from each other and represent a C1-C6 chain hydrocarbon group optionally having one or more substituents selected from Group $I^A$, a C3-C6 cycloalkyl group optionally having one or more halogen atoms, a hydrogen atom, a halogen atom, a nitro group, a cyano group, —OR$^{15A}$, —S(O)$_n$R$^{16A}$, —C(O)R$^{17A}$, or —CR$^{18A}$=N—O—R$^{19A}$, R$^{10A}$, R$^{12A}$, R$^{13A}$, R$^{14A}$, R$^{15A}$, R$^{17A}$, R$^{18A}$, and R$^{19A}$ are identical to or different from each other and represent a C1-C6 chain hydrocarbon group optionally having one or more halogen atoms or a hydrogen atom, R$^{11A}$ and R$^{16A}$ are identical to or different from each other and represent a C1-C6 chain hydrocarbon group optionally having one or more halogen atoms, m and n are identical to or different from each other and represent 0, 1 or 2, R$^{3A}$ and R$^{4A}$ may be taken together with a carbon atom to which they are attached to form a C4-C7 carbocycle group, or a five to seven membered heterocyclic group {each of the C4-C7 carbocycle group and the five to seven membered heterocyclic group may optionally have one or more substituents selected from Group J$^A$}, R$^{4A}$ and R$^{5A}$ may be taken together with a carbon atom to which they are attached to form a C4-C7 carbocycle group, or a five to seven membered heterocyclic group {each of the C4-C7 carbocycle group and the five to seven membered heterocyclic group may optionally have one or more substituents selected from Group J$^A$}, (hereinafter, referred to as "Compound of the present invention").

[7] The compound described in [6] wherein Z$^A$ represents a C1-C6 chain hydrocarbon group, a C3-C6 cycloalkyl group, a three to five membered nitrogen atom-containing non-aromatic heterocyclic group in which the ring-constituting nitrogen atom is attached to S(O)$_2$, or —NR$^{8A}$R$^{9A}$, R$^{8A}$ and R$^{9A}$ are identical to or different from each other and represent a C1-C6 chain hydrocarbon group, R$^{1A}$, R$^{2A}$, R$^{3A}$ and R$^{7A}$ represent a hydrogen atom, R$^{5A}$ represents a C1-C6 chain hydrocarbon group, a C3-C6 cycloalkyl group {each of the C1-C6 chain hydrocarbon group and the C3-C6 cycloalkyl group may optionally have one or more halogen atoms}, a halogen atom, a nitro group, or —S(O)$_2$R$^{11A}$, R$^{11A}$ represents a C1-C4 chain hydrocarbon group optionally having one or more halogen atoms, R$^{4A}$ and R$^{6A}$ are identical to or different from each other and represent a C1-C6 chain hydrocarbon group optionally having one or more halogen atoms, a halogen atom, a nitro group, or a hydrogen atom, R$^{4A}$ and R$^{5A}$ may be taken together with a carbon atom to which they are attached to form a C4-C7 carbocycle group, or a five to seven membered heterocyclic group {each of the C4-C7 carbocycle group and the five to seven membered heterocyclic group may optionally have one or more substituents selected from a halogen atom and a C1-C3 chain hydrocarbon group}.

[8] A composition for controlling a plant disease comprising the compound described in any one of [3] to [7].

[9] A method for controlling a plant disease which comprises applying an effective amount of the compound described in any one of [3] to [7] to a plant or a soil.

[10] Use of the compound described in any one of [3] to [7] for controlling a plant disease.

[11] A composition comprising one or more ingredients selected from the group consisting of the following Group (a), Group (b), Group (c), and Group (d), and the compound represented by formula (I) described in [1], Group (a): a group consisting of insecticidal ingredients, miticidal ingredients, and nematicidal ingredients;
Group (b): fungicidal ingredients;
Group (c): plant growth modulating ingredients;
Group (d): repellent ingredients.

[12] A seed or vegetative reproductive organ carrying an effective amount of any one of the compound represented by formula (I) described in [1] or [2], the compounds described in any one of [3] to [7], or the composition described in [11].

The present invention can control plant diseases.

MODE FOR CARRYING OUT THE INVENTION

The substituents as used herein are explained as follows.
The term "halogen atom" represents a fluorine atom, a chlorine atom, a bromine atom, or an iodine atom.

When a substituent has two or more halogen atoms, the halogen atoms may be identical to or different from each other.

The expression "CY-CW" as used herein represents that the number of carbon atoms is from Y to W. For example, the expression "C1-C6" represents that the number of carbon atoms is from 1 to 6.

The term "chain hydrocarbon group" represents an alkyl group, an alkenyl group, or an alkynyl group.

Examples of the alkyl group include methyl group, ethyl group, propyl group, isopropyl group, 1,1-dimethylpropyl group, 1,2-dimethylpropyl group, butyl group, sec-butyl group, tert-butyl group, pentyl group, and hexyl group.

Examples of the alkenyl group include vinyl group, 1-propenyl group, 2-propenyl group, 1-methyl-1-propenyl group, 1-methyl-2-propenyl group, 1,2-dimethyl-1-propenyl group, 3-butenyl group, 4-pentenyl group, and 5-hexenyl group.

Examples of the alkynyl group include ethynyl group, 1-propynyl group, 2-propynyl group, 1-methyl-2-propynyl group, 1,1-dimethyl-2-propynyl group, 2-butynyl group, 4-pentynyl group, and 5-hexynyl group.

Examples of the cycloalkyl group include cyclopropyl group, cyclobutyl group, cyclopentyl group, and cyclohexyl group.

The term of "alkoxy group" as used herein represents a group in which the above-mentioned alkyl group is attached to an oxygen atom, and for example, includes methoxy group, ethoxy group, propoxy group, and isopropoxy group.

The term of "alkylthio group" as used herein represents a group in which the above-mentioned alkyl group is attached to a sulfur atom, and for example, includes methylthio group, ethylthio group, and isopropylthio group.

Examples of "aryl group" include phenyl group and naphthyl group.

Examples of "three (3) to seven (7) membered non-aromatic heterocyclic group" includes aziridinyl group, oxiranyl group, thilanyl group, azetidinyl group, oxetanyl group, thietanyl group, pyrrolidinyl group, tetrahydrofuranyl group, tetrahydrothieny group, piperidyl group, pyranyl group, tetrahydropyranyl group, tetrahydrothiopyranyl group, azepanyl group, oxepanyl group, thiepanyl group, pyrazolynyl group, pyrazolydinyl group, imidazolinyl group, imidazolidinyl group, oxazolinyl group, thiazolinyl group, oxazolidinyl group, thiazolidinyl group, isoxazolinyl group, isoxazolidinyl group, isothiazolinyl group, isothiazolidinyl group, morpholinyl group, thiomorpholinyl group, and piperazinyl group.

Examples of "three (3) to five (5) membered nitrogen-containing non-aromatic heterocyclic group" includes aziridinyl group, azetidinyl group, pyrrolidinyl group, pyrazolynyl group, pyrazolydinyl group, imidazolinyl group, and imidazolidinyl group.

Examples of "five (5) to ten (10) membered aromatic heterocyclic group" includes furyl group, thienyl group, pyrrolyl group, pyrazolyl group, imidazolyl group, oxazolyl group, isoxazolyl group, thiazolyl group, isothiazolyl group, triazolyl group, oxadiazolyl group, thiadiazolyl group, pyridyl group, pyridazinyl group, pyrimidinyl group, pyrazinyl group, quinolinyl group, isoquinolinyl group, quinazolinyl group, phthalazinyl group, pteridinyl group, indolyl group, benzimidazolyl group, and benzofuranyl group.

Examples of "five (5) to ten (10) membered aromatic heterocyclic group (with the proviso that a pyridyl group is excluded)" includes furyl group, thienyl group, pyrrolyl group, pyrazolyl group, imidazolyl group, oxazolyl group, isoxazolyl group, thiazolyl group, isothiazolyl group, triazolyl group, oxadiazolyl group, thiadiazolyl group, pyridazinyl group, pyrimidinyl group, pyrazinyl group, quinolinyl group, isoquinolinyl group, quinazolinyl group, phthalazinyl group, pteridinyl group, indolyl group, benzimidazolyl group, and benzofuranyl group.

Examples of "C4-C7 carbocycle group" includes cyclobutene ring, cyclopentene ring, cyclopentadiene ring, cyclohexene ring, cyclohexadiene ring, benzene ring, and cycloheptene ring.

Examples of "five (5) to seven (7) membered heterocyclic group include furan ring, dihydrofuran ring, thiophene ring, dihydrothiophene ring, pyrrole ring, dihydropyrrole ring, pyrazole ring, imidazole ring, oxazole ring, isoxazole ring, thiazole ring, isothiazole ring, 1,3-dioxole ring, triazole ring, oxadiazole ring, thiadiazole ring, pyridine ring, pyridazine ring, pyrimidine ring, pyrazine ring, pyran ring, and dihydropyran ring.

The present compound, the present compound X, the compound of the present invention, and the compound X of the present invention may encompass one or more stereoisomer(s) thereof. Examples of the stereoisomer include enantiomer, diastereomer, atropisomer and geometric isomer. The present invention encompasses each of the stereoisomers and a mixture of the stereoisomers in an arbitrary ratio.

The present compound, the present compound X, the compound of the present invention, and the compound X of the present invention may be mixed with acids such as hydrochloric acid, sulfuric acid, nitric acid, phosphoric acid, acetic acid, benzoic acid and the like to form acid addition salts such as hydrochloride, sulfate, nitrate, phosphate, acetate, benzoate and the like.

Embodiments of the compound of the present invention include the following compounds.

Embodiment 1

A compound of the present invention wherein
$R^{3A}$ and $R^{7A}$ represent a hydrogen atom,
a combination of $R^{4A}$ and $R^{5A}$ is a combination wherein $R^{4A}$ represents a C1-C6 chain hydrocarbon group optionally having one or more halogen atoms, a halogen atom, a nitro group or a hydrogen atom, and $R^{5A}$ represents a C1-C6 chain hydrocarbon group, a C3-C6 cycloalkyl group {each of the C1-C6 chain hydrocarbon group and the C3-C6 cycloalkyl group may optionally have one or more halogen atoms}, a halogen atom, a nitro group, or —S(O)$_2$R$^{16A}$; or
$R^{4A}$ and $R^{5A}$ may be taken together with a carbon atom to which they are attached to form a C4-C7 carbocycle group, or a five to seven membered heterocyclic group {each of the C4-C7 carbocycle group and the five to seven membered heterocyclic group may optionally have one or more substituents selected from a halogen atom and a C1-C3 chain hydrocarbon group}, $R^{16A}$ represents a C1-C4 chain hydrocarbon group optionally having one or more halogen atoms,
$R^{6A}$ represents a C1-C6 chain hydrocarbon group optionally having one or more halogen atoms, a C1-C6 chain hydrocarbon group, a halogen atom, a nitro group, or a hydrogen atom.

Embodiment 2

A compound of the present invention wherein
$R^{3A}$ and $R^{7A}$ represent a hydrogen atom,
$R^{5A}$ represents a C1-C6 chain hydrocarbon group, a C3-C6 cycloalkyl group {each of the C1-C6 chain hydrocarbon group and the C3-C6 cycloalkyl group may optionally have one or more halogen atoms}, a halogen atom, a nitro group, or —S(O)$_2$R$^{16A}$,
$R^{16A}$ represents a C1-C4 chain hydrocarbon group optionally having one or more halogen atoms,
$R^{4A}$ and $R^{6A}$ are identical to or different from each other and represent a C1-C6 chain hydrocarbon group optionally having one or more halogen atoms, a halogen atom, a nitro group, or a hydrogen atom.

Embodiment 3

A compound of the present invention wherein
$R^{3A}$ and $R^{7A}$ represent a hydrogen atom,
$R^{4A}$ and $R^{6A}$ are identical to or different from each other and represent a C1-C6 chain hydrocarbon group optionally having one or more halogen atoms, a halogen atom or a hydrogen atom,
$R^{5A}$ represents a C1-C6 chain hydrocarbon group optionally having one or more halogen atoms or a halogen atom.

Embodiment 4

A compound of the present invention wherein $R^{1A}$ and $R^{2A}$ represent a hydrogen atom.

Embodiment 5

The compound described in Embodiment 1 wherein $R^{1A}$ and $R^{2A}$ represent a hydrogen atom.

Embodiment 6

The compound described in Embodiment 2 wherein $R^{1A}$ and $R^{2A}$ represent a hydrogen atom.

Embodiment 7

The compound described in Embodiment 3 wherein $R^{1A}$ and $R^{2A}$ represent a hydrogen atom.

Embodiment 8

The compound described in any one of Embodiment 1 to Embodiment 7 or the compound of the present invention wherein $Z^A$ represents a C1-C6 chain hydrocarbon group optionally having one or more substituents selected from Group I$^A$, or a C3-C6 cycloalkyl group optionally having one or more halogen atoms.

Embodiment 9

The compound described in any one of Embodiment 1 to Embodiment 7 or the compound of the present invention wherein Z$^A$ represents a C1-C6 chain hydrocarbon group or a C3-C6 cycloalkyl group.

Embodiment 10

The compound described in any one of Embodiment 1 to Embodiment 7 or the compound of the present invention wherein Z$^A$ represents a C1-C6 chain hydrocarbon group optionally having one or more substituents selected from Group I$^A$.

Embodiment 11

The compound described in any one of Embodiment 1 to Embodiment 7 or the compound of the present invention wherein Z$^A$ represents a C1-C6 chain hydrocarbon group.

Embodiment 12

The compound described in any one of Embodiment 1 to Embodiment 7 or the compound of the present invention, wherein Z$^A$ represents a C3-C6 cycloalkyl group.

Embodiment 13

The compound described in any one of Embodiment 1 to Embodiment 7 or the compound of the present invention wherein Z$^A$ represents a three to seven membered non-aromatic heterocyclic group or —NR$^{8A}$R$^{9A}$.

Embodiment 14

The compound described in any one of Embodiment 1 to Embodiment 7 or the compound of the present invention, wherein Z$^A$ represents a three to seven membered non-aromatic heterocyclic group.

Embodiment 15

The compound described in any one of Embodiment 1 to Embodiment 7 or the compound of the present invention, wherein Z$^A$ represents a three to five membered nitrogen atom-containing non-aromatic heterocyclic group in which the ring-constituting nitrogen atom is attached to S(O)$_2$.

Embodiment 16

The compound described in any one of Embodiment 1 to Embodiment 7 or the compound of the present invention, wherein Z$^A$ represents —NR$^{8A}$R$^{9A}$.

Embodiment 17

The compound described in any one of Embodiment 1 to Embodiment 7 or the compound of the present invention, wherein Z$^A$ represents —NR$^{8A}$R$^{9A}$, and R$^{8A}$ and R$^{9A}$ are identical to or different from each other and represent a C3-C6 cycloalkyl group optionally having one or more halogen atoms or a hydrogen atom.

Embodiment 18

The compound described in any one of Embodiment 1 to Embodiment 7 or the compound of the present invention, wherein Z$^A$ represents —NR$^{8A}$R$^{9A}$, and R$^{8A}$ and R$^{9A}$ are identical to or different from each other and represent a C1-C6 chain hydrocarbon group optionally having one or more substituents selected from Group I$^A$, or a hydrogen atom.

Embodiment 19

A compound of the present invention wherein Z$^A$ represents a C1-C6 chain hydrocarbon group optionally having one or more halogen atoms, a C3-C6 cycloalkyl group, a three to seven membered non-aromatic heterocyclic group or —NR$^{8A}$R$^{9A}$, R$^{8A}$ and R$^{9A}$ are identical to or different from each other and represent a C1-C6 chain hydrocarbon group, or a hydrogen atom, R$^{1A}$, R$^{2A}$, R$^{6A}$ and R$^{7A}$ represent a hydrogen atom, a combination of R$^{3A}$, R$^{4A}$ and R$^{5A}$ represents a combination wherein R$^{3A}$ represents a hydrogen atom or a fluorine atom, R$^{4A}$ represents a C1-C6 chain hydrocarbon group optionally having one or more halogen atoms, a C3-C6 cycloalkyl group, a hydrogen atom, a halogen atom, a nitro group, or —OR$^{10A}$, and R$^{5A}$ represents a C1-C6 chain hydrocarbon group optionally having one or more halogen atoms, a C3-C6 cycloalkyl group, a halogen atom, a nitro group, a cyano group, —OR$^{15A}$, or —S(O)$_2$R$^{16A}$; or a combination wherein R$^{3A}$ represents a hydrogen atom, and R$^{4A}$ and R$^{5A}$ may be taken together with a carbon atom to which they are attached to form a C4-C7 carbocycle group optionally having one or more halogen atoms or a five to seven membered heterocyclic group, and R$^{10A}$, R$^{15A}$, and R$^{16A}$ are identical to or different from each other and represent a C1-C6 chain hydrocarbon group.

Examples of the embodiment of the compound X of the present invention include the following compounds.

Embodiment 1-1

A compound X of the present invention wherein R$^{5A}$ represents a hydrogen atom, Z$^A$ represents a C1-C6 chain hydrocarbon group optionally having one or more halogen atoms, R$^{4A}$ represents —C(O)NR$^{22B}$R$^{23B}$, and R$^{22B}$ and R$^{23B}$ are identical to or different from each other and represent a C1-C6 chain hydrocarbon group optionally having one or more substituents selected from Group L$^A$, a C3-C6 cycloalkyl group, a C6-C10 aryl group {each of the C3-C6 cycloalkyl group and the C6-C0 aryl group may optionally have one or more substituents selected from Group K$^A$} or a hydrogen atom.

Embodiment 1-2

The compound described in Embodiment 1-1 wherein R$^{1A}$, R$^{2A}$, R$^{3A}$ and R$^{7A}$ represent a hydrogen atom.

Embodiment 1-3

The compound described in Embodiment 1-1 wherein R$^{1A}$, R$^{2A}$, R$^{3A}$, R$^{6A}$ and R$^{7A}$ represent a hydrogen atom.

Embodiment 1-4

The compound described in Embodiment 1-1 wherein $R^{1A}$, $R^{2A}$, $R^{3A}$, and $R^{7A}$ represent a hydrogen atom, and $R^{6A}$ represents a halogen atom.

Embodiment 1-5

A compound X of the present invention wherein $R^{5A}$ represents a hydrogen atom, $Z^A$ represents a C1-C6 chain hydrocarbon group optionally having one or more halogen atoms, $R^{4A}$ represents a —C(O)NR$^{22B}$R$^{23B}$, and $R^{22B}$ and $R^{23B}$ are identical to or different from each other and represent a C1-C6 chain hydrocarbon group optionally having one or more substituents selected from Group $L^A$, a C3-C6 cycloalkyl group {the C3-C6 cycloalkyl group may optionally have one or more substituents selected from Group $K^A$} or a hydrogen atom.

Embodiment 1-6

The compound described in Embodiment 1-5 wherein $R^{1A}$, $R^{2A}$, $R^{3A}$ and $R^{7A}$ represent a hydrogen atom.

Embodiment 1-7

The compound described in Embodiment 1-5 wherein $R^{1A}$, $R^{2A}$, $R^{3A}$, $R^{6A}$ and $R^{7A}$ represent a hydrogen atom.

Embodiment 1-8

The compound described in Embodiment 1-5 wherein $R^{1A}$, $R^{2A}$, $R^{3A}$, and $R^{7A}$ represent a hydrogen atom, and $R^{6A}$ represents a halogen atom.

Embodiment 1-9

A compound X of the present invention wherein $R^{5A}$ represents a hydrogen atom, $Z^A$ represents a C1-C6 chain hydrocarbon group optionally having one or more halogen atoms, $R^{4A}$ represents —C(O)NR$^{22B}$R$^{23B}$, and $R^{22B}$ and $R^{23B}$ are identical to or different from each other and represent a C1-C6 chain hydrocarbon group, a C3-C6 cycloalkyl group, or a hydrogen atom.

Embodiment 1-10

The compound described in the Embodiment 1-9 wherein $R^{1A}$, $R^{2A}$, $R^{3A}$ and $R^{7A}$ represent a hydrogen atom.

Embodiment 1-11

The compound described in the Embodiment 1-9 wherein $R^{1A}$, $R^{2A}$, $R^{3A}$, $R^{6A}$ and $R^{7A}$ represent a hydrogen atom.

Embodiment 1-12

The compound described in the Embodiment 1-9 wherein $R^{1A}$, $R^{2A}$, $R^{3A}$, and $R^{7A}$ represent a hydrogen atom, and $R^{6A}$ represents a halogen atom.

Embodiment 1-13

A compound X of the present invention wherein $R^{5A}$ represents a hydrogen atom, $Z^A$ represents a C1-C6 chain hydrocarbon group optionally having one or more halogen atoms, and $R^{4A}$ represents a halogen atom.

Embodiment 1-14

The compound described in the Embodiment 1-13 wherein $R^{1A}$, $R^{2A}$, $R^{3A}$, and $R^{1A}$ represent a hydrogen atom.

Embodiment 1-15

The compound described in the Embodiment 1-13 wherein $R^{1A}$, $R^{2A}$, $R^{3A}$, $R^{6A}$ and $R^{7A}$ represent a hydrogen atom.

Embodiment 1-16

The compound described in the Embodiment 1-13 wherein $R^{1A}$, $R^{2A}$, $R^{3A}$, and $R^{7A}$ represent a hydrogen atom, and $R^{6A}$ represents a halogen atom.

Embodiment 1-17

A compound X of the present invention wherein $R^{5A}$ represents a hydrogen atom, $Z^A$ represents a C3-C6 cycloalkyl group optionally having one or more halogen atoms, $R^{4A}$ represents —OR$^{15B}$, and $R^{15B}$ represents a C1-C6 chain hydrocarbon group optionally having one or more substituents selected from Group $L^B$.

Embodiment 1-18

The compound described in the Embodiment 1-17 wherein $R^{1A}$, $R^{2A}$, $R^{3A}$, and $R^{7A}$ represent a hydrogen atom.

Embodiment 1-19

The compound described in the Embodiment 1-17 wherein $R^{1A}$, $R^{2A}$, $R^{3A}$, $R^{6A}$ and $R^{7A}$ represent a hydrogen atom.

Embodiment 1-20

The compound described in the Embodiment 1-17 wherein $R^{1A}$, $R^{2A}$, $R^{3A}$, and $R^{7A}$ represent a hydrogen atom, and $R^{8A}$ represents a halogen atom.

Embodiment 1-21

A compound X of the present invention wherein $R^{5A}$ represents a hydrogen atom, $Z^A$ represents a three to seven membered non-aromatic heterocyclic group {the three to seven membered non-aromatic heterocyclic group may optionally have a C1-C3 alkyl group optionally having one or more halogen atoms, and a halogen atom}, $R^{4A}$ represents a —OR$^{15B}$, and $R^{15B}$ represents a C1-C6 chain hydrocarbon group optionally having one or more substituents selected from Group $L^B$.

Embodiment 1-22

The compound described in the Embodiment 1-21 wherein $R^{1A}$, $R^{2A}$, $R^{3A}$, and $R^{7A}$ represent a hydrogen atom.

Embodiment 1-23

The compound described in the Embodiment 1-21 wherein $R^{1A}$, $R^{2A}$, $R^{3A}$, $R^{6A}$ and $R^{7A}$ represent a hydrogen atom.

Embodiment 1-24

The compound described in the Embodiment 1-21 wherein $R^{1A}$, $R^{2A}$, $R^{3A}$, and $R^{7A}$ represent a hydrogen atom, and $R^{6A}$ represents a halogen atom.

Embodiment 1-25

A compound X of the present invention wherein $R^{5A}$ represents a hydrogen atom, $Z^A$ represents a C1-C6 chain hydrocarbon group optionally having one or more substituents selected from Group $I^B$, $R^{4A}$ represents a —$OR^{15B}$, and $R^{15B}$ represents a C1-C6 chain hydrocarbon group optionally having one or more substituents selected from Group $L^B$.

Embodiment 1-26

The compound described in the Embodiment 1-25 wherein $R^{1A}$, $R^{2A}$, $R^{3A}$, and $R^{7A}$ represent a hydrogen atom.

Embodiment 1-27

The compound described in the Embodiment 1-25 wherein $R^{1A}$, $R^{2A}$, $R^{3A}$, $R^{6A}$ and $R^{7A}$ represent a hydrogen atom.

Embodiment 1-28

The compound described in the Embodiment 1-25 wherein $R^{1A}$, $R^{2A}$, $R^{3A}$, and $R^{7A}$ represent a hydrogen atom, and $R^{6A}$ represents a halogen atom.

Embodiment 1-29

A compound X of the present invention wherein $R^{5A}$ represents a hydrogen atom, $Z^A$ represents —$NR^{3A}R^{9A}$, $R^{8A}$ and $R^{9A}$ are identical to or different from each other and represent a C1-C6 chain hydrocarbon group optionally having one or more substituents selected from Group $I^B$, a C3-C6 cycloalkyl group optionally having one or more halogen atoms or a hydrogen atom, $R^{6A}$ represents —$OR^{15B}$, and $R^{15B}$ represents a C1-C6 chain hydrocarbon group optionally having one or more substituents selected from Group $L^B$.

Embodiment 1-30

The compound described in the Embodiment 1-29 wherein $R^{1A}$, $R^{2A}$, $R^{3A}$, and $R^{7A}$ represent a hydrogen atom.

Embodiment 1-31

The compound described in the Embodiment 1-29 wherein $R^{1A}$, $R^{2A}$, $R^{3A}$, $R^{4A}$, $R^{6A}$ and $R^{7A}$ represent a hydrogen atom.

Embodiment 1-32

The compound described in the Embodiment 1-29 wherein $R^{1A}$, $R^{2A}$, $R^{3A}$, $R^{4A}$ and $R^{7A}$ represent a hydrogen atom, and $R^{6A}$ represents a halogen atom.

Embodiment 1-33

A compound X of the present invention wherein $Z^A$ represents a C1-C6 chain hydrocarbon group optionally having one or more substituents selected from Group $I^A$, $R^{4A}$ represents —$OR^{15A}$, and $R^{15A}$ represents a C1-C6 chain hydrocarbon group optionally having one or more substituents selected from Group $L^A$.

Embodiment 1-34

The compound described in the Embodiment 1-33 wherein $R^{1A}$, $R^{2A}$, $R^{3A}$, and $R^{7A}$ represent a hydrogen atom.

Embodiment 1-35

The compound described in the Embodiment 1-33 wherein $R^{1A}$, $R^{2A}$, $R^{3A}$, $R^{5A}$, $R^{6A}$ and $R^{7A}$ represent a hydrogen atom.

Embodiment 1-36

The compound described in the Embodiment 1-33 wherein $R^{1A}$, $R^{2A}$, $R^{3A}$, $R^{6A}$ and $R^{7A}$ represent a hydrogen atom, and $R^{5A}$ represents a halogen atom.

Embodiment 1-37

The compound described in the Embodiment 1-33 wherein $R^{1A}$, $R^{2A}$, $R^{3A}$, and $R^{7A}$ represent a hydrogen atom, and $R^{5A}$ and $R^{6A}$ represent a halogen atom.

Embodiment 1-38

The compound described in the Embodiment 1-33 wherein $R^{1A}$, $R^{2A}$, $R^{3A}$, and $R^{7A}$ represent a hydrogen atom, $R^{3A}$ and $R^{4A}$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group $J^A$}, and $R^{4A}$ and $R^{5A}$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group $J^A$}.

Embodiment 1-39

The compound described in Embodiment 1-33 wherein $R^{1A}$, $R^{2A}$, $R^{3A}$, and $R^{7A}$ represent a hydrogen atom, and $R^{4A}$ and $R^{5A}$ may be taken together with a carbon to which they are attached to form a C4-C7 carbocycle group, or five to seven membered heterocyclic group {each of the C4-C7 carbocycle group and the five to seven membered heterocyclic group may optionally have one or more substituents selected from Group $J^A$}.

Embodiment 1-40

The compound described in Embodiment 1-33 wherein $R^{1A}$, $R^{2A}$, $R^{3A}$, and $R^{7A}$ represent a hydrogen atom, and $R^{3A}$ and $R^{4A}$ may be taken together with a carbon to which they are attached to form a C4-C7 carbocycle group or a five to seven membered heterocyclic group {each of the C4-C7 carbocycle group and the five to seven membered heterocyclic group may optionally have one or more substituents selected from Group $J^A$}.

Embodiment 1-41

A compound X of the present invention wherein $Z^A$ represents a C1-C6 chain hydrocarbon group optionally having one or more halogen atoms, $R^{4A}$ represents —$OR^{15B}$, and $R^{15B}$ represents a C1-C6 chain hydrocarbon group {the C1-C6 chain hydrocarbon group may optionally have a phenyl group optionally having one or more substituents selected from Group $K^B$ and a C3-C6 cycloalkyl group optionally having one or more halogen atoms}.

Embodiment 1-42

The compound described in Embodiment 1-41 wherein $R^{1A}$, $R^{2A}$, $R^{3A}$, and $R^{7A}$ represent a hydrogen atom.

Embodiment 1-43

The compound described in Embodiment 1-41 wherein $R^{1A}$, $R^{2A}$, $R^{3A}$, and $R^{7A}$ represent a hydrogen atom, and $R^{5A}$ represents a halogen atom.

Embodiment 1-44

A compound X of the present invention wherein $Z^A$ represents —$NR^{8A}R^{9A}$, $R^{8A}$ and $R^{9A}$ are identical to or different from each other and represent a C1-C6 chain hydrocarbon group optionally having one or more substituents selected from Group $I^A$, a C3-C6 cycloalkyl group optionally having one or more halogen atoms or a hydrogen atom, $R^{4A}$ represents —$OR^{15B}$, and $R^{15B}$ represents a C1-C6 chain hydrocarbon group optionally having one or more substituents selected from Group $L^A$.

Embodiment 1-45

The compound described in Embodiment 1-44 wherein $R^{1A}$, $R^{2A}$, $R^{3A}$, and $R^{7A}$ represent a hydrogen atom.

Embodiment 1-46

The compound described in Embodiment 1-44 wherein $R^{1A}$, $R^{2A}$, $R^{3A}$, $R^{5A}$, $R^{6A}$ and $R^{7A}$ represent a hydrogen atom.

Embodiment 1-47

The compound described in Embodiment 1-44 wherein $R^{1A}$, $R^{2A}$, $R^{3A}$, $R^{6A}$ and $R^{7A}$ represent a hydrogen atom, and $R^{5A}$ represents a halogen atom.

Embodiment 1-48

The compound described in Embodiment 1-44 wherein $R^{1A}$, $R^{2A}$, $R^{3A}$, and $R^{7A}$ represent a hydrogen atom, and $R^{5A}$ and $R^{6A}$ are identical to or different from each other and represent a halogen atom.

Embodiment 1-49

The compound described in Embodiment 1-44 wherein $R^{1A}$, $R^{2A}$, $R^{3A}$ and $R^{7A}$ represent a hydrogen atom, $R^{3A}$ and $R^{4A}$ may be taken together with a carbon to which they are attached to form a C4-C7 carbocycle group, or five to seven membered heterocyclic group {each of the C4-C7 carbocycle group and the five to seven membered heterocyclic group may optionally have one or more substituents selected from Group $J^A$}, and $R^{4A}$ and $R^{5A}$ may be taken together with a carbon atom to which they are attached to form a C4-C7 carbocycle group or a five to seven membered heterocyclic group {the C4-C7 carbocycle group and the five to seven membered heterocyclic group may optionally have one or more substituents selected from Group $J^A$}.

Embodiment 1-50

A compound X of the present invention wherein $Z^A$ represents a C1-C6 chain hydrocarbon group optionally having one or more halogen atoms, a cyclopropyl group, a pyrrolidyl group, or —$NR^{8A}R^{9A}$, $R^{8A}$ and $R^{9A}$ represent a methyl group, $R^{1A}$ and $R^{2A}$ represent a hydrogen atom, and a combination of $R^{4A}$, $R^{5A}$ and $R^{6A}$ represent the following combination a1 or b1, a1: a combination wherein $R^{5A}$ represents a hydrogen atom, $R^{4A}$ represents a C1-C6 chain hydrocarbon group optionally having one or more halogen atoms, a phenyl group, a halogen atom, —$OR^{15B}$, —$C(O)NR^{22B}R^{23B}$, —$NR^{24B}C(O)R^{25B}$, or —$N(OR^{28B})C(O)R^{29B}$, and $R^{6A}$ represents a hydrogen atom;

b1: a combination wherein $R^{5A}$ represents a C1-C6 chain hydrocarbon group optionally having one or more substituents selected from Group $I^A$, a halogen atom, a nitro group, a cyano group, —$OR^{10A}$, or —$S(O)_2R^{16A}$, $R^{4A}$ represents a C1-C6 chain hydrocarbon group, a hydrogen atom, a halogen atom, a nitro group, a cyano group, or —$OR^{15A}$, $R^{6A}$ represents a hydrogen atom or a halogen atom, $R^{4A}$ and $R^{5A}$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group $J^{41}$}, $R^{15A}$ represents a C1-C6 chain hydrocarbon group or a hydrogen atom, $R^{15B}$ represents a C1-C6 hydrocarbon group optionally having one or more substituents selected from Group $L^{B1}$, a C6-C10 aryl group, or a hydrogen atom, $R^{10A}$ represents a C1-C6 chain hydrocarbon group optionally having one or more substituents selected from Group $L^{41}$, or a hydrogen atom, $R^{22B}$, $R^{23B}$, $R^{24B}$, $R^{25B}$, $R^{28B}$, and $R^{29B}$ are identical to or different from each other and represent a C1-C6 chain hydrocarbon group optionally having one or more substituents selected from Group $L^{41}$, a C3-C6 cycloalkyl group, a C6-C10 aryl group {each of the C3-C6 cycloalkyl group, the C6-C10 aryl group and the five to ten membered aromatic heterocyclic group may optionally have one or more substituents selected from Group $K^A$} or a hydrogen atom, and $R^{16A}$ represents a C1-C6 chain hydrocarbon group.

Group $J^{41}$: a group consisting of a C1-C3 chain hydrocarbon group and a halogen atom.

Group $L^{41}$: a group consisting of a C6-C10 aryl group and a halogen atom.

Group $L^{B1}$: a group consisting of a C3-C6 cycloalkyl group, a C6-C10 aryl group {the C6-C10 aryl group may optionally have one or more substituents selected from the group consisting of a halogen atom, a cyano group and a C1-C3 chain hydrocarbon group}, a halogen atom, and a cyano group.

Embodiment 1-51

A compound X of the present invention wherein $Z^A$ represents a C1-C6 chain hydrocarbon group optionally having one or more halogen atoms, a C3-C6 cycloalkyl group optionally having one or more halogen atoms, a five to seven membered non-aromatic heterocyclic group, or —$NR^{6A}R^{9A}$, $R^{8A}$ and $R^{9A}$ are identical to or different from each other and represent a C1-C6 chain hydrocarbon group, and a combination of $R^{4A}$, $R^{5A}$ and $R^{6A}$ represents the following combination of a2 or b2, a2: a combination wherein $R^{5A}$ represents a hydrogen atom, $R^{4A}$ represents a C1-C6 chain hydrocarbon group optionally having one or more substituents selected from Group $I^B$, a halogen atom, —$OR^{15B}$, —C(O)$NR^{22B}R^{23B}$, —$NR^{24B}C(O)R^{25B}$, or —$N(OR^{28B})C(O)R^{29B}$, and $R^{6A}$ represents a hydrogen atom or a halogen atom;

b2: a combination wherein $R^{5A}$ represents a C1-C6 chain hydrocarbon group optionally having one or more substituents selected from Group $I^A$, a C3-C6 cycloalkyl group, {the C3-C6 cycloalkyl group may optionally have one or more substituents selected from Group $K^A$}, a halogen atom, a nitro group, a cyano group, —$OR^{10A}$, or —$S(O)_pR^{16A}$, $R^{4A}$ and $R^{6A}$ are identical to or different from each other and represent a C1-C6 chain hydrocarbon group optionally having one or more substituents selected from Group $I^A$, a hydrogen atom, a halogen atom, a nitro group, or —$OR^{15A}$, $R^{4A}$ and $R^{5A}$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group $J^A$}, $R^{15A}$ represents a C1-C6 chain hydrocarbon group optionally having one or more substituents selected from Group $L^A$, a C6-C10 aryl group, {the C6-C10 aryl group may optionally have one or more substituents selected from Group $K^A$} or a hydrogen atom, $R^{15B}$ represents a C1-C6 chain hydrocarbon group optionally having one or more substituents selected from Group $L^B$, a C6-10 aryl group, {the C6-C10 aryl group may optionally have one or more substituents selected from Group $K^B$} or a hydrogen atom, $R^{10A}$ represents a C1-C6 chain hydrocarbon group optionally having one or more halogen atoms or a hydrogen atom, $R^{22B}$, $R^{23B}$, $R^{24B}$, $R^{25B}$, $R^{28B}$, $R^{29B}$, $R^{30B}$, $R^{31B}$, and $R^{32B}$ are identical to or different from each other and represent a C1-C6 chain hydrocarbon group optionally having one or more substituents selected from Group $L^B$, a C3-C6 cycloalkyl group, {the C3-C6 cycloalkyl group may optionally have one or more substituents selected from Group $K^A$} or a hydrogen atom, and $R^{16A}$ represents a C1-C6 chain hydrocarbon group optionally having one or more substituents selected from Group $L^A$.

Embodiment 1-52

A compound X of the present invention wherein $Z^A$ represents a C1-C6 chain hydrocarbon group optionally having one or more halogen atoms, a C3-C6 cycloalkyl group optionally having one or more halogen atoms, a five to seven membered non-aromatic heterocyclic group or —$NR^{8A}R^{9A}$, $R^{8A}$ and $R^{9A}$ are identical to or different from each other and represent a C1-C6 chain hydrocarbon group, $R^{5A}$ represents a hydrogen atom, $R^{4A}$ represents a C1-C6 chain hydrocarbon group optionally having one or more substituents selected from Group $I^B$, a halogen atom, —$OR^{15B}$, —$C(O)NR^{22B}R^{23B}$, —$NR^{24B}C(O)R^{25B}$, or —$N(OR^{28B})C(O)R^{29B}$, $R^{6A}$ represents a hydrogen atom or a halogen atom, $R^{15B}$ represents a C1-C6 chain hydrocarbon group optionally having one or more substituents selected from Group $L^B$, a C6-C10 aryl group, (the C6-10 aryl group may optionally have one or more substituents selected from Group $K^B$) or a hydrogen atom, $R^{22B}$, $R^{23B}$, $R^{24B}$, $R^{25B}$, $R^{28B}$, $R^{29B}$, $R^{30B}$, $R^{31B}$, and $R^{32B}$ are identical to or different from each other and represent a C1-C6 chain hydrocarbon group optionally having one or more substituents selected from Group $L^A$, a C3-C6 cycloalkyl group, {the C3-C6 cycloalkyl group may optionally have one or more substituents selected from Group $K^A$} or a hydrogen atom.

Embodiment 1-53

A compound X of the present invention wherein $Z^A$ represents a C1-C6 chain hydrocarbon group optionally having one or more halogen atoms, a C3-C6 cycloalkyl group optionally having one or more halogen atoms, a five to seven membered non-aromatic heterocyclic group, or —$NR^{8A}R^{9A}$, $R^{8A}$ and $R^{9A}$ are identical to or different from each other and represent a C1-C6 chain hydrocarbon group, $R^{5A}$ represents a C1-C6 chain hydrocarbon group optionally having one or more substituents selected from Group $I^A$, a C3-C6 cycloalkyl group, {the C3-C6 cycloalkyl group may optionally have one or more substituents selected from Group $K^A$}, a halogen atom, a nitro group, a cyano group, —$OR^{10A}$, or —$S(O)_pR^{16A}$, $R^{4A}$ and $R^{6A}$ are identical to or different from each other and represents a C1-C6 chain hydrocarbon group optionally having one or more substituents selected from Group $I^A$, a hydrogen atom, a halogen atom, a nitro group, or —$OR^{15A}$, $R^{4A}$ and $R^{5A}$ may be taken together with a carbon atom to which they are attached to form a C4-C7 carbocycle group, or a five to seven membered heterocyclic group {each of the C4-C7 carbocycle group and the five to seven membered heterocyclic group optionally having one or more substituents selected from Group $J^A$}, $R^{15A}$ represents a C1-C6 chain hydrocarbon group optionally having one or more substituents selected from Group $L^A$, a C6-C10 aryl group, {the C6-C10 aryl group may optionally have one or more substituents selected from Group $K^A$} or a hydrogen atom, $R^{10A}$ represents a C1-C6 chain hydrocarbon group optionally having one or more halogen atoms or a hydrogen atom, $R^{22B}$, $R^{23B}$, $R^{24B}$, $R^{25B}$, $R^{26B}$, $R^{27B}$, $R^{28B}$, $R^{29B}$, $R^{30B}$, $R^{31B}$, and $R^{32B}$ are identical to or different from each other and represent a C1-C6 chain hydrocarbon group optionally having one or more substituents selected from Group $L^A$, a C3-C6 cycloalkyl group, {the C3-C6 cycloalkyl group may optionally have one or more substituents selected from Group $K^A$} or a hydrogen atom, and $R^{16A}$ represents a C1-C6 chain hydrocarbon group optionally having one or more substituents selected from Group $L^A$.

Embodiment 1-54

A method for controlling soybean rust with an amino acid replacement at the F129L position in a mitochondrial cytochrome b protein, which comprises applying an effective amount of the compound X of the present invention to soybean or soils where soybean grows.

Embodiment 1-55

A method for controlling soybean rust, which comprises applying an effective amount of the compound X of the present invention to soybean or soils where soybean grows.

Embodiment 1-56

A method for controlling *Septoria* leaf blotch, which comprises applying an effective amount of the compound X of the present invention to wheat or soils where wheat grows.

Embodiment 1-57

A method for controlling tomato leaf mold, which comprises applying an effective amount of the compound X of the present invention to tomato or soils where tomato grows.

Embodiment 1-58

A method for controlling rice blast, which comprises applying an effective amount of the compound X of the present invention to rice or soils where rice grows.

Embodiment 1-59

A method for controlling wheat rust diseases, which comprises applying an effective amount of the compound X of the present invention to wheat or soils where wheat grows.

Embodiment 1-60

A method for controlling soybean powdery mildew, which comprises applying an effective amount of the compound X of the present invention to soybean or soils where soybean grows.

Embodiment 1-61

A method for controlling barley net blotch, which comprises applying an effective amount of the compound X of the present invention to barley or soils where barley grows.

Embodiment 1-62

A method for controlling barley scald, which comprises applying an effective amount of the compound X of the present invention to barley or soils where barley grows.

Embodiment 1-63

A method for controlling kidney bean *Sclerotinia* rot, which comprises applying an effective amount of the compound X of the present invention to kidney bean or soils where kidney bean grows.

Embodiment 1-64

A method for controlling cucumber powdery mildew, which comprises applying an effective amount of the compound X of the present invention to cucumber or soils where cucumber grows.

Embodiment 1-65

A method for controlling cucumber brown spot, which comprises applying an effective amount of the compound X of the present invention to cucumber or soils where cucumber grows.

Embodiment 1-66

A method for controlling cucumber anthracnose, which comprises applying an effective amount of the compound X of the present invention to cucumber or soils where cucumber grows.

Embodiment 1-67

A method for controlling soybean rust with an amino acid replacement at the F129L position in a mitochondrial cytochrome b protein, which comprises applying an effective amount of the compound described in Embodiment 1-52 to soybean or soils where soybean grows.

Embodiment 1-68

A method for controlling soybean rust, which comprises applying an effective amount of the compound described in Embodiment 1-52 to soybean or soils where soybean grows.

Embodiment 1-69

A method for controlling *Septoria* leaf blotch, which comprises applying an effective amount of the compound described in Embodiment 1-52 to wheat or soils where wheat grows.

Embodiment 1-70

A method for controlling soybean rust with an amino acid replacement at the F129L position in a mitochondrial cytochrome b protein, which comprises applying an effective amount of the compound described in Embodiment 1-51 to soybean or soils where soybean grows.

Embodiment 1-71

A method for controlling soybean rust, which comprises applying an effective amount of the compound described in Embodiment 1-51 to soybean or soils where soybean grows.

Embodiment 1-72

A method for controlling *Septoria* leaf blotch, which comprises applying an effective amount of the compound described in Embodiment 1-51 to wheat or soils where wheat grows.

Embodiment 1-73

A method for controlling soybean rust with an amino acid replacement at the F129L position in a mitochondrial cytochrome b protein, which comprises applying an effective amount of the compound described in Embodiment 1-50 to soybean or soils where soybean grows.

Embodiment 1-74

A method for controlling soybean rust, which comprises applying an effective amount of the compound described in Embodiment 1-50 to soybean or soils where soybean grows.

Embodiment 1-75

A method for controlling *Septoria* leaf blotch, which comprises applying an effective amount of the compound described in Embodiment 1-50 to wheat or soils where wheat grows.

Embodiment 1-76

A method for controlling soybean rust with an amino acid replacement at the F129L position in a mitochondrial cytochrome b protein, which comprises applying an effective amount of the compound described in Embodiment 1-43 to soybean or soils where soybean grows.

Embodiment 1-77

A method for controlling soybean rust, which comprises applying an effective amount of the compound described in Embodiment 1-43 to soybean or soils where soybean grows.

Embodiment 1-78

A method for controlling *Septoria* leaf blotch, which comprises applying an effective amount of the compound described in Embodiment 1-43 to wheat or soils where wheat grows.

Embodiment 1-79

A method for controlling soybean rust with an amino acid replacement at the F129L position in a mitochondrial cytochrome b protein, which comprises applying an effective amount of the compound described in Embodiment 1-49 to soybean or soils where soybean grows.

Embodiment 1-80

A method for controlling soybean rust, which comprises applying an effective amount of the compound described in Embodiment 1-49 to soybean or soils where soybean grows.

Embodiment 1-81

A method for controlling *Septoria* leaf blotch, which comprises applying an effective amount of the compound described in Embodiment 1-49 to wheat or soils where wheat grows.

Embodiment 1-82

A method for controlling soybean rust with an amino acid replacement at the F129L position in a mitochondrial cytochrome b protein, which comprises applying an effective amount of the compound described in Embodiment 1-38 to soybean or soils where soybean grows.

Embodiment 1-83

A method for controlling soybean rust, which comprises applying an effective amount of the compound described in Embodiment 1-38 to soybean or soils where soybean grows.

Embodiment 1-84

A method for controlling wheat *Septoria* leaf blotch, which comprises applying an effective amount of the compound described in Embodiment 1-38 to wheat or soils where wheat grows.

Embodiment 1-85

A method for controlling soybean rust with an amino acid replacement at the F129L position in a mitochondrial cytochrome b protein, which comprises applying an effective amount of the compound described in Embodiment 1-29 to soybean or soils where soybean grows.

Embodiment 1-86

A method for controlling soybean rust, which comprises applying an effective amount of the compound described in Embodiment 1-29 to soybean or soils where soybean grows.

Embodiment 1-87

A method for controlling *Septoria* leaf blotch, which comprises applying an effective amount of the compound described in Embodiment 1-29 to wheat or soils where wheat grows.

Embodiment 1-88

A method for controlling soybean rust with an amino acid replacement at the F129L position in a mitochondrial cytochrome b protein, which comprises applying an effective amount of the compound described in Embodiment 1-53 to soybean or soils where soybean grows.

Embodiment 1-89

A method for controlling soybean rust, which comprises applying an effective amount of the compound described in Embodiment 1-53 to soybean or soils where soybean grows.

Embodiment 1-90

A method for controlling wheat *Septoria* leaf blotch, which comprises applying an effective amount of the compound described in Embodiment 1-53 to wheat or soils where wheat grows.

Examples of the embodiment of the present compound include the following compounds.

Embodiment 2-1

The present compound wherein $R^5$ represents a C1-C6 chain hydrocarbon group optionally having one or more substituents selected from Group I, a halogen atom, a nitro group, a cyano group, $-OR^{10}$, or $-S(O)_mR^{11}$, $R^3$, $R^4$, $R^6$ and $R^7$ are identical to or different from each other and represent a C1-C6 chain hydrocarbon group optionally having one or more substituents selected from Group I, a halogen atom, a nitro group, a cyano group, or $-OR^{15}$, $R^{10}$ represents a C1-C6 chain hydrocarbon group optionally having one or more halogen atoms or a hydrogen atom, $R^1$ and $R^2$ represent a hydrogen atom, m is 2, $R^4$ and $R^5$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group J}.

Embodiment 2-2

A method for controlling soybean rust, which comprises applying an effective amount of the compound described in Embodiment 2-1 to soybean or soils where soybean grows.

Embodiment 2-3

A method for controlling *Septoria* leaf blotch, which comprises applying an effective amount of the compound described in Embodiment 2-1 to wheat or soils where wheat grows.

Embodiment 2-4

A method for controlling tomato leaf mold, which comprises applying an effective amount of the compound described in Embodiment 2-1 to tomato or soils where tomato grows.

Embodiment 2-5

A method for controlling rice blast, which comprises applying an effective amount of the compound described in Embodiment 2-1 to rice or soils where rice grows.

Embodiment 2-6

A method for controlling wheat rust diseases, which comprises applying an effective amount of the compound described in Embodiment 2-1 to wheat or soils where wheat grows.

Embodiment 2-7

A method for controlling soybean powdery mildew, which comprises applying an effective amount of the compound described in Embodiment 2-1 to soybean or soils where soybean grows.

Embodiment 2-8

A method for controlling barley net blotch, which comprises applying an effective amount of the compound described in Embodiment 2-1 to barley or soils where barley grows.

Embodiment 2-9

A method for controlling barley scald, which comprises applying an effective amount of the compound described in Embodiment 2-1 to barley or soils where barley grows.

Embodiment 2-10

A method for controlling kidney bean *Sclerotinia* rot, which comprises applying an effective amount of the compound described in Embodiment 2-1 to kidney bean or soils where kidney bean grows.

Embodiment 2-11

A method for controlling cucumber powdery mildew, which comprises applying an effective amount of the compound described in Embodiment 2-1 to cucumber or soils where cucumber grows.

Embodiment 2-12

A method for controlling cucumber brown spot, which comprises applying an effective amount of the compound described in Embodiment 2-1 to cucumber or soils where cucumber grows.

Embodiment 2-13

A method for controlling cucumber anthracnose, which comprises applying an effective amount of the compound described in Embodiment 2-1 to cucumber or soils where cucumber grows.

Embodiment 2-14

A method for controlling soybean rust with an amino acid replacement at the F129L position in a mitochondrial cytochrome b protein, which comprises applying an effective amount of the compound described in Embodiment 2-1 to soybean or soils where soybean grows.

Examples of the embodiment of the present compound X include the following compounds.

Embodiment 3-1

A present compound X wherein $R^5$ represents a hydrogen atom, Z represents a C1-C6 chain hydrocarbon group optionally having one or more halogen atoms, $R^4$ represents —C(O)$NR^{22}R^{23}$, $R^{22}$ and $R^{23}$ are identical to or different from each other and represent a C1-C6 chain hydrocarbon group optionally having one or more substituents selected from Group L, a C3-C6 cycloalkyl group, a C6-C10 aryl group {each of the C3-C6 cycloalkyl group and the C6-C10 aryl group may optionally have one or more substituents selected from group K} or a hydrogen atom.

Embodiment 3-2

The compound described in Embodiment 3-1 wherein $R^1$, $R^2$, $R^3$ and $R^7$ represent a hydrogen atom.

Embodiment 3-3

The compound described in Embodiment 3-1 wherein $R^1$, $R^2$, $R^3$, $R^6$ and $R^7$ represent a hydrogen atom.

Embodiment 3-4

The compound described in Embodiment 3-1 wherein $R^1$, $R^2$, $R^3$ and $R^7$ represent a hydrogen atom, and $R^6$ represents a halogen atom.

Embodiment 3-5

A present compound X wherein $R^5$ represents a hydrogen atom, Z represents a C1-C6 chain hydrocarbon group optionally having one or more halogen atoms, $R^4$ represents —C(O)$NR^{22}R^{23}$, $R^{22}$ and $R^{23}$ are identical to or different from each other and represent a C1-C6 chain hydrocarbon group optionally having one or more substituents selected from Group L, a C3-C6 cycloalkyl group {the C3-C6 cycloalkyl group may optionally have one or more substituents selected from group K} or a hydrogen atom.

Embodiment 3-6

The compound described in Embodiment 3-5 wherein $R^1$, $R^2$, $R^3$ and $R^7$ represent a hydrogen atom.

Embodiment 3-7

The compound described in Embodiment 3-5 wherein $R^1$, $R^2$, $R^3$, $R^6$ and $R^7$ represent a hydrogen atom.

Embodiment 3-8

The compound described in Embodiment 3-5 wherein $R^1$, $R^2$, $R^3$ and $R^7$ represent a hydrogen atom, and $R^6$ represents a halogen atom.

Embodiment 3-9

A present compound X wherein $R^5$ represents a hydrogen atom, Z represents a C1-C6 chain hydrocarbon group optionally having one or more halogen atoms, $R^4$ represents —C(O)NR$^{22}$R$^{23}$, $R^{22}$ and $R^{23}$ are identical to or different from each other and represent a C1-C6 chain hydrocarbon group, a C3-C6 cycloalkyl group or a hydrogen atom.

Embodiment 3-10

The compound described in Embodiment 3-9 wherein $R^1$, $R^2$, $R^3$ and $R^7$ represent a hydrogen atom.

Embodiment 3-11

The compound described in Embodiment 3-9 wherein $R^1$, $R^2$, $R^3$, $R^6$ and $R^7$ represent a hydrogen atom.

Embodiment 3-12

The compound described in Embodiment 3-9 wherein $R^1$, $R^2$, $R^3$ and $R^7$ represent a hydrogen atom, and $R^6$ represents a halogen atom.

Embodiment 3-13

A present compound X wherein $R^5$ represents a hydrogen atom, Z represents a C1-C6 chain hydrocarbon group optionally having one or more halogen atoms, and $R^4$ represents a halogen atom.

Embodiment 3-14

The compound described in Embodiment 3-13 wherein $R^1$, $R^2$, $R^3$ and $R^7$ represent a hydrogen atom.

Embodiment 3-15

The compound described in Embodiment 3-13 wherein $R^1$, $R^2$, $R^3$, $R^6$ and $R^7$ represent a hydrogen atom.

Embodiment 3-16

The compound described in Embodiment 3-13 wherein $R^1$, $R^2$, $R^3$ and $R^7$ represent a hydrogen atom, and $R^6$ represents a halogen atom.

Embodiment 3-17

A present compound X wherein $R^5$ represents a hydrogen atom, Z represents a C3-C6 cycloalkyl group optionally having one or more halogen atoms, $R^4$ represents —OR$^{15}$, and $R^{15}$ represents a C1-C6 chain hydrocarbon group optionally having one or more substituents selected from Group L.

Embodiment 3-18

The compound described in Embodiment 3-17 wherein $R^1$, $R^2$, $R^3$ and $R^7$ represent a hydrogen atom.

Embodiment 3-19

The compound described in Embodiment 3-17 wherein $R^1$, $R^2$, $R^3$, $R^6$ and $R^7$ represent a hydrogen atom.

Embodiment 3-20

The compound described in Embodiment 3-17 wherein $R^1$, $R^2$, $R^3$ and $R^7$ represent a hydrogen atom, and $R^6$ represents a halogen atom.

Embodiment 3-21

A present compound X wherein $R^5$ represents a hydrogen atom, Z represents a three to seven membered non-aromatic heterocyclic group {the three to seven membered non-aromatic heterocyclic group may optionally have one or more substituents selected from a C1-C3 alkyl group optionally having one or more halogen atoms and a halogen atom}, $R^4$ represents —OR$^{15}$, and $R^{15}$ represents a C1-C6 chain hydrocarbon group optionally having one or more substituents selected from Group L.

Embodiment 3-22

The compound described in Embodiment 3-21 wherein $R^1$, $R^2$, $R^3$ and $R^7$ represent a hydrogen atom.

Embodiment 3-23

The compound described in Embodiment 3-21 wherein $R^1$, $R^2$, $R^3$, $R^5$ and $R^7$ represent a hydrogen atom.

Embodiment 3-24

The compound described in Embodiment 3-21 wherein $R^1$, $R^2$, $R^3$ and $R^7$ represent a hydrogen atom, and $R^6$ represents a halogen atom.

Embodiment 3-25

A present compound X wherein $R^5$ represents a hydrogen atom, Z represents a C1-C6 chain hydrocarbon group optionally having one or more substituents selected from Group I, $R^4$ represents —OR$^{15}$, and $R^{15}$ represents a C1-C6 chain hydrocarbon group optionally having one or more substituents selected from Group L.

Embodiment 3-26

The compound described in Embodiment 3-25 wherein $R^1$, $R^2$, $R^3$ and $R^7$ represent a hydrogen atom.

Embodiment 3-27

The compound described in Embodiment 3-25 wherein $R^1$, $R^2$, $R^3$, $R^6$ and $R^7$ represent a hydrogen atom.

Embodiment 3-28

The compound described in Embodiment 3-25 wherein $R^1$, $R^2$, $R^3$ and $R^7$ represent a hydrogen atom, and $R^6$ represents a halogen atom.

Embodiment 3-29

A present compound X wherein $R^5$ represents a hydrogen atom, Z represents —$NR^8R^9$, Re and $R^9$ are identical to or different from each other and represents a C1-C6 chain hydrocarbon group optionally having one or more substituents selected from Group I, a C3-C6 cycloalkyl group optionally having one or more halogen atoms or a hydrogen atom, $R^6$ represents —$OR^{15}$, and $R^{15}$ represents a C1-C6 chain hydrocarbon group optionally having one or more substituents selected from Group L.

Embodiment 3-30

The compound described in Embodiment 3-29 wherein $R^1$, $R^2$, $R^3$ and $R^7$ represent a hydrogen atom.

Embodiment 3-31

The compound described in Embodiment 3-29 wherein $R^1$, $R^2$, $R^3$, $R^4$, $R^6$ and $R^7$ represent a hydrogen atom.

Embodiment 3-32

The compound described in Embodiment 3-29 wherein $R^1$, $R^2$, $R^3$, $R^4$, and $R^7$ represent a hydrogen atom, and $R^6$ represents a halogen atom.

Embodiment 3-33

A present compound X wherein Z represents a C1-C6 chain hydrocarbon group optionally having one or more substituents selected from Group I, $R^4$ represents —$OR^{15}$, and $R^{15}$ represents a C1-C6 chain hydrocarbon group optionally having one or more substituents selected from Group L.

Embodiment 3-34

The compound described in Embodiment 3-33 wherein $R^1$, $R^2$, $R^3$ and $R^7$ represent a hydrogen atom.

Embodiment 3-35

The compound described in Embodiment 3-33 wherein $R^1$, $R^2$, $R^3$, $R^6$, $R^6$ and $R^7$ represent a hydrogen atom.

Embodiment 3-36

The compound described in Embodiment 3-33 wherein $R^1$, $R^2$, $R^3$, $R^6$, and $R^7$ represent a hydrogen atom, and $R^5$ represents a halogen atom.

Embodiment 3-37

The compound described in Embodiment 3-33 wherein $R^1$, $R^2$, $R^3$ and $R^7$ represent a hydrogen atom, and $R^5$ and $R^6$ represent a halogen atom.

Embodiment 3-38

The compound described in Embodiment 3-33 wherein $R^1$, $R^2$, $R^3$ and $R^7$ represent a hydrogen atom, $R^3$ and $R^4$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group J}, $R^4$ and $R^5$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group J}.

Embodiment 3-39

The compound described in Embodiment 3-33 wherein $R^1$, $R^2$, $R^3$ and $R^7$ represent a hydrogen atom, $R^4$ and $R^5$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group J}.

Embodiment 3-40

The compound described in Embodiment 3-33 wherein $R^1$, $R^2$, $R^3$ and $R^7$ represent a hydrogen atom, $R^3$ and R may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group J}.

Embodiment 3-41

A present compound X wherein Z represents a C1-C6 chain hydrocarbon group optionally having one or more halogen atoms, $R^4$ represents —$OR^{15}$, $R^{15}$ represents a C1-C6 chain hydrocarbon group {the C1-C6 chain hydrocarbon group may optionally have one or more substituents selected from a phenyl group optionally having one or more substituents selected from Group K and a C3-C6 cycloalkyl group optionally having one or more halogen atoms}.

Embodiment 3-42

The compound described in Embodiment 3-41 wherein $R^1$, $R^2$, $R^3$ and $R^7$ represent a hydrogen atom.

Embodiment 3-43

The compound described in Embodiment 3-41 wherein $R^1$, $R^2$, $R^3$, and $R^7$ represent a hydrogen atom, and $R^5$ represents a halogen atom.

Embodiment 3-44

A present compound X wherein Z represents —$NR^8R^9$, $R^8$ and $R^9$ are identical to or different from each other and represent a C1-C6 chain hydrocarbon group optionally having one or more substituents selected from Group I, a C3-C6 cycloalkyl group optionally having one or more halogen atoms or a hydrogen atom, $R^4$ represents —$OR^{15}$, and $R^{15}$ represents a C1-C6 chain hydrocarbon group optionally having one or more substituents selected from Group L.

Embodiment 3-45

The compound described in Embodiment 3-44 wherein $R^1$, $R^2$, $R^3$ and $R^7$ represent a hydrogen atom.

Embodiment 3-46

The compound described in Embodiment 3-44 wherein $R^1$, $R^2$, $R^3$, $R^5$, $R^6$ and $R^7$ represent a hydrogen atom, and $R^5$ represents a halogen atom.

Embodiment 3-47

The compound described in Embodiment 3-44 wherein $R^1$, $R^2$, Ha, $R^6$ and $R^7$ represent a hydrogen atom, and $R^5$ represents a halogen atom.

Embodiment 3-48

The compound described in Embodiment 3-44 wherein $R^1$, $R^2$, $R^3$, and $R^7$ represent a hydrogen atom, and $R^5$ and $R^6$ are identical to or different from each other and represent a halogen atom.

Embodiment 3-49

The compound described in Embodiment 3-44 wherein $R^1$, $R^2$, $R^3$, and $R^7$ represent a hydrogen atom, $R^3$ and $R^4$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group J}, $R^4$ and $R^5$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group J}.

Embodiment 3-50

A present compound X wherein z represents a C1-C6 chain hydrocarbon group optionally having one or more halogen atoms, a cyclopropyl group, a pyrrolidyl group, or —$NR^8R^9$, $R^8$ and $R^9$ represent a methyl group, $R^1$ and $R^2$ represent a hydrogen atom, and a combination of $R^4$, $R^5$ and $R^6$ represents the following combination a1 or b1,
- a1: a combination wherein $R^5$ represents a hydrogen atom, $R^4$ represents a C1-C6 chain hydrocarbon group optionally having one or more halogen atoms, a phenyl group, a halogen atom, —$OR^{15}$, —$C(O)NR^{22}R^{23}$, —$NR^{24}C(O)R^{25}$, or —$N(OR^{28})C(O)R^{29}$, and $R^6$ represents a hydrogen atom; or
- b1: a combination wherein $R^5$ represents a C1-C6 chain hydrocarbon group optionally having one or more substituents selected from Group I, a halogen atom, a nitro group, a cyano group, —$OR^{10}$, or —$S(O)_2R^{16}$, $R^4$ represents a C1-C6 chain hydrocarbon group, a hydrogen atom, a halogen atom, a nitro group, a cyano group, or —$OR^{15}$, $R^6$ represents a hydrogen atom or a halogen atom, $R^4$ and $R^5$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group $J^1$};

$R^{15}$ represents a C1-C6 chain hydrocarbon group optionally having one or more substituents selected from Group $L^1$, a C6-C10 aryl group, or a hydrogen atom, RID represents a C1-C6 chain hydrocarbon group optionally having one or more substituents selected from Group $L^1$, or a hydrogen atom, $R^{22}$, $R^{23}$, $R^{24}$, $R^{25}$, $R^{28}$, and $R^{29}$ are identical to or different from each other and represent a C1-C6 chain hydrocarbon group optionally having one or more substituents selected from Group $L^1$, a C3-C6 cycloalkyl group, a C6-C10 aryl group {each of the C3-C6 cycloalkyl group, the C6-C10 aryl group and the five to ten membered aromatic heterocyclic group may optionally have one or more substituents selected from Group $K^1$} or a hydrogen atom, and $R^{16}$ represents a C1-C6 chain hydrocarbon group.

Group $J^1$: a group consisting of a C1-C3 chain hydrocarbon group and a halogen atom.

Group $K^1$: a group consisting of a C6-C10 aryl group and a halogen atom.

Group $L^1$: a group consisting of a C3-C6 cycloalkyl group, a C6-C10 aryl group, {the C6-C10 aryl group may optionally have one or more substituents selected from a halogen atom, a cyano group and a C1-C3 chain hydrocarbon group}, a halogen atom, and a cyano group.

Embodiment 3-51

The present compound X wherein Z represents a C1-C6 chain hydrocarbon group optionally having one or more halogen atoms, a C3-C6 cycloalkyl group optionally having one or more halogen atoms or a five to seven membered non-aromatic heterocyclic group, or $NR^8R^9$, $R^8$ and $R^9$ are identical to or different from each other and represent a C1-C6 chain hydrocarbon group, and a combination of $R^4$, $R^5$ and $R^6$ represents the following combination of a2 or b2,
- a2: a combination wherein $R^5$ represents a hydrogen atom, $R^4$ represents a C1-C6 chain hydrocarbon group optionally having one or more substituents selected from Group I, a halogen atom, —$OR^{15}$, —$C(O)NR^{22}R^{23}$, —$NR^{24}C(O)R^{25}$, or —$N(OR^{28})C(O)R^{29}$, and $R^6$ represents a hydrogen atom or a halogen atom;
- b2: a combination wherein $R^5$ represents a C1-C6 chain hydrocarbon group optionally having one or more substituents selected from Group I, a C3-C6 cycloalkyl group, {the C3-C6 cycloalkyl group may optionally have one or more substituents selected from group K}, a halogen atom, a nitro group, a cyano group, —$OR^{10}$, or —$S(O)_pR^{16}$, $R^4$ and $R^6$ are identical to or different form each other and represent a C1-C6 chain hydrocarbon group optionally having one or more substituents selected from Group I, a hydrogen atom, a halogen atom, a nitro group, or —$OR^{15}$, and $R^4$ and $R^5$ may be taken together with a carbon atom to which they are attached to form a C4-C7 carbocycle group or a five to seven membered heterocyclic group {each of the C4-C7 carbocycle group and the five to seven membered heterocyclic group may optionally have one or more substituents selected from Group J};

$R^{15}$ represents a C1-C6 chain hydrocarbon group optionally having one or more substituents selected from Group L, a C6-C10 aryl group {the C6-C10 aryl group may optionally have one or more substituents selected from group K} or a hydrogen atom, $R^{10}$ represents a C1-C6 chain hydrocarbon group optionally having one or more halogen atoms or a hydrogen atom, $R^{22}$, $R^{23}$, $R^{24}$, $R^{25}$, $R^{28}$, $R^{23}$, $R^{30}$, $R^{31}$, and $R^{32}$ are identical to or different from each other and represent a C1-C6 chain hydrocarbon group optionally having one or more substituents selected from Group L, a C3-C6 cycloalkyl group {the C3-C6 cycloalkyl group may optionally have one or more substituents selected from group K} or a hydrogen atom, and $R^{16}$ represents a C1-C6 chain hydrocarbon group optionally having one or more substituents selected from Group L.

Embodiment 3-52

The present compound X wherein Z represents a C1-C6 chain hydrocarbon group optionally having one or more halogen atoms, a C3-C6 cycloalkyl group optionally having one or more halogen atoms, a five to seven membered non-aromatic heterocyclic group, or —$NR^8R^9$, $R^8$ and $R^9$ are identical to or different from each other and represent a C1-C6 chain hydrocarbon group, $R^5$ represents a hydrogen atom, $R^4$ represents a C1-C6 chain hydrocarbon group optionally having one or more substituents selected from Group I, a halogen atom, —$OR^{15}$, —$C(O)NR^{22}R^{23}$, —$NR^{24}C(O)R^{25}$, or —$N(OR^{28})C(O)R^{29}$, $R^6$ represents a hydrogen atom, or a halogen atom, $R^{15}$ represents a C1-C6 chain hydrocarbon group optionally having one or more substituents selected from Group L, a C6-C10 aryl group {the C6-C10 aryl group may optionally have one or more substituents selected from group K} or a hydrogen atom, $R^{22}$, $R^{23}$, $R^{24}$, $R^{25}$, $R^{28}$, $R^{29}$, $R^{30}$, $R^{31}$, and $R^{32}$ are identical to or different from each other and represent a C1-C6 chain hydrocarbon group optionally having one or more substituents selected from Group L, a C3-C6 cycloalkyl group {the C3-C6 cycloalkyl group may optionally have one or more substituents selected from group K} or a hydrogen atom.

Embodiment 3-53

The present compound X wherein Z represents a C1-C6 chain hydrocarbon group optionally having one or more halogen atoms, a C3-C6 cycloalkyl group optionally having one or more halogen atoms, a five to seven membered non-aromatic heterocyclic group, or —$NR^8R^9$, $R^8$ and $R^9$ are identical to or different from each other and represent C1-C6 chain hydrocarbon group, $R^5$ represents a C1-C6 chain hydrocarbon group optionally having one or more substituents selected from Group I, a C3-C6 cycloalkyl group {the C3-C6 cycloalkyl group may optionally have one or more substituents selected from group K}, a halogen atom, a nitro group, a cyano group, —$OR^{10}$, or —$S(O)_pR^{16}$, $R^4$ and $R^6$ are identical to or different from each other and represent a C1-C6 chain hydrocarbon group optionally having one or more substituents selected from Group I, a hydrogen atom, a halogen atom, a nitro group, or $OR^{15}$, $R^4$ and $R^5$ may be taken together with a carbon atom to which they are attached to form a C4-C7 carbocycle group, or five to seven membered heterocyclic group {the C4-C7 carbocycle group and the five to seven membered heterocyclic group may optionally have one or more substituents selected from Group J}, $R^{15}$ represents a C1-C6 chain hydrocarbon group optionally having one or more substituents selected from Group L, a C6-C10 aryl group {the C6-C10 aryl group may optionally have one or more substituents selected from group K} or a hydrogen atom, $R^{10}$ represents a C1-C6 chain hydrocarbon group optionally having one or more halogen atoms or a hydrogen atom, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ are identical to or different from each other and represent a C1-C6 chain hydrocarbon group optionally having one or more substituents selected from Group L, a C3-C6 cycloalkyl group {the C3-C6 cycloalkyl group may optionally have one or more substituents selected from group K} or a hydrogen atom, and $R^{16}$ represents a C1-C6 chain hydrocarbon group optionally having one or more substituents selected from Group L.

Embodiment 3-54

A method for controlling soybean rust with an amino acid replacement at the F129L position in a mitochondrial cytochrome b protein, which comprises applying an effective amount of the present compound X to soybean or soils where soybean grows.

Embodiment 3-55

A method for controlling soybean rust, which comprises applying an effective amount of the present compound X to soybean or soils where soybean grows.

Embodiment 3-56

A method for controlling *Septoria* leaf blotch, which comprises applying an effective amount of the present compound X to wheat or soils where wheat grows.

Embodiment 3-57

A method for controlling tomato leaf mold, which comprises applying an effective amount of the present compound X to tomato or soils where tomato grows.

Embodiment 3-58

A method for controlling rice blast, which comprises applying an effective amount of the present compound X to rice or soils where rice grows.

Embodiment 3-59

A method for controlling wheat rust diseases, which comprises applying an effective amount of the present compound X to wheat or soils where wheat grows.

Embodiment 3-60

A method for controlling soybean powdery mildew, which comprises applying an effective amount of the present compound X to soybean or soils where soybean grows.

Embodiment 3-61

A method for controlling barley net blotch, which comprises applying an effective amount of the present compound X to barley or soils where barley grows.

Embodiment 3-62

A method for controlling barley scald, which comprises applying an effective amount of the present compound X to barley or soils where barley grows.

Embodiment 3-63

A method for controlling kidney bean *Sclerotinia* rot, which comprises applying an effective amount of the present compound X to kidney bean or soils where kidney bean grows.

Embodiment 3-64

A method for controlling cucumber powdery mildew, which comprises applying an effective amount of the present compound X to cucumber or soils where cucumber grows.

Embodiment 3-65

A method for controlling cucumber brown spot, which comprises applying an effective amount of the present compound X to cucumber or soils where cucumber grows.

Embodiment 3-66

A method for controlling cucumber anthracnose, which comprises applying an effective amount of the present compound X to cucumber or soils where cucumber grows.

Embodiment 3-67

A method for controlling soybean rust with an amino acid replacement at the F129L position in a mitochondrial cytochrome b protein, which comprises applying an effective amount of the compound described in the Embodiment 3-52 to soybean or soils where soybean grows.

Embodiment 3-68

A method for controlling soybean rust, which comprises applying an effective amount of the compound described in the Embodiment 3-52 to soybean or soils where soybean grows.

Embodiment 3-69

A method for controlling *Septoria* leaf blotch, which comprises applying an effective amount of the compound described in the Embodiment 3-52 to wheat or soils where wheat grows.

Embodiment 3-70

A method for controlling soybean rust with an amino acid replacement at the F129L position in a mitochondrial cytochrome b protein, which comprises applying an effective amount of the compound described in the Embodiment 3-51 to soybean or soils where soybean grows.

Embodiment 3-71

A method for controlling soybean rust, which comprises applying an effective amount of the compound described in the Embodiment 3-51 to soybean or soils where soybean grows.

Embodiment 3-72

A method for controlling *Septoria* leaf blotch, which comprises applying an effective amount of the compound described in the Embodiment 3-51 to wheat or soils where wheat grows.

Embodiment 3-73

A method for controlling soybean rust with an amino acid replacement at the F129L position in a mitochondrial cytochrome b protein, which comprises applying an effective amount of the compound described in the Embodiment 3-50 to soybean or soils where soybean grows.

Embodiment 3-74

A method for controlling soybean rust, which comprises applying an effective amount of the compound described in the Embodiment 3-50 to soybean or soils where soybean grows.

Embodiment 3-75

A method for controlling *Septoria* leaf blotch, which comprises applying an effective amount of the compound described in the Embodiment 3-50 to wheat or soils where wheat grows.

Embodiment 3-76

A method for controlling soybean rust with an amino acid replacement at the F129L position in a mitochondrial cytochrome b protein, which comprises applying an effective amount of the compound described in the Embodiment 3-43 to soybean or soils where soybean grows.

Embodiment 3-77

A method for controlling soybean rust, which comprises applying an effective amount of the compound described in the Embodiment 3-43 to soybean or soils where soybean grows.

Embodiment 3-78

A method for controlling *Septoria* leaf blotch, which comprises applying an effective amount of the compound described in the Embodiment 3-43 to wheat or soils where wheat grows.

Embodiment 3-79

A method for controlling soybean rust with an amino acid replacement at the F129L position in a mitochondrial cytochrome b protein, which comprises applying an effective amount of the compound described in the Embodiment 3-49 to soybean or soils where soybean grows.

Embodiment 3-80

A method for controlling soybean rust, which comprises applying an effective amount of the compound described in the Embodiment 3-49 to soybean or soils where soybean grows.

Embodiment 3-81

A method for controlling *Septoria* leaf blotch, which comprises applying an effective amount of the compound described in the Embodiment 3-49 to wheat or soils where wheat grows.

Embodiment 3-82

A method for controlling soybean rust with an amino acid replacement at the F129L position in a mitochondrial cytochrome b protein, which comprises applying an effective amount of the compound described in the Embodiment 3-38 to soybean or soils where soybean grows.

Embodiment 3-83

A method for controlling soybean rust, which comprises applying an effective amount of the compound described in the Embodiment 3-38 to soybean or soils where soybean grows.

Embodiment 3-84

A method for controlling *Septoria* leaf blotch, which comprises applying an effective amount of the compound described in the Embodiment 3-38 to wheat or soils where wheat grows.

Embodiment 3-85

A method for controlling soybean rust with an amino acid replacement at the F129L position in a mitochondrial cytochrome b protein, which comprises applying an effective amount of the compound described in the Embodiment 3-29 to soybean or soils where soybean grows.

Embodiment 3-86

A method for controlling soybean rust, which comprises applying an effective amount of the compound described in the Embodiment 3-29 to soybean or soils where soybean grows.

Embodiment 3-87

A method for controlling *Septoria* leaf blotch, which comprises applying an effective amount of the compound described in the Embodiment 3-29 to wheat or soils where wheat grows.

Embodiment 3-88

A method for controlling soybean rust with an amino acid replacement at the F129L position in a mitochondrial cytochrome b protein, which comprises applying an effective amount of the compound described in the Embodiment 3-53 to soybean or soils where soybean grows.

Embodiment 3-89

A method for controlling soybean rust, which comprises applying an effective amount of the compound described in the Embodiment 3-53 to soybean or soils where soybean grows.

Embodiment 3-90

A method for controlling *Septoria* leaf blotch, which comprises applying an effective amount of the compound described in the Embodiment 3-53 to wheat or soils where wheat grows.

Next, a process for preparing the present compound X is explained.

Process A

A compound represented by formula (I-A) (hereinafter, referred to as Compound (I-A)) can be prepared by reacting a compound represented by formula (A1) (hereinafter, referred to Compound (A1)) with a compound represented by formula (A2) (hereinafter, referred to Compound (A2)) in the presence of a base.

(A1) (A2) (I-A)

[wherein $X^1$ represents a chlorine atom or $OS(O)_2Z$, and the other symbols are the same as defined above.]

The reaction is usually carried out in a solvent. Examples of the solvent to be used in the reaction include hydrocarbons such as hexane, toluene and xylene (hereinafter, collectively referred to "hydrocarbons"); ethers such as methyl tert-butyl ether (hereinafter, referred to as MTBE), tetrahydrofuran (hereinafter, referred to as THF), and dimethoxyethane (hereinafter, collectively referred to as "ethers"); halogenated hydrocarbons such as chloroform and chlorobenzene (hereinafter, collectively referred to as "halogenated hydrocarbons"); amides such as dimethylformamide (hereinafter, referred to as DMF) and N-methyl pyrrolidone (hereinafter, collectively referred to as "amides"); esters such as methyl acetate and ethyl acetate (hereinafter, collectively referred to as "esters"); nitriles such as acetonitrile and propionitrile (hereinafter, collectively referred to as "nitriles"), water; and mixed solvents comprising two or more thereof.

Example of the base to be used in the reaction include organic bases such as triethylamine and pyridine (hereinafter, collectively referred to as "organic bases"), alkali metal carbonates such as sodium carbonate and potassium carbonate (hereinafter, collectively referred to as "alkali metal carbonates"); alkali metal hydrocarbonates such as sodium hydrocarbonate and potassium hydrocarbonate (hereinafter, collectively referred to as "alkali metal hydrocarbonates"); alkali metal hydroxides such as lithium hydroxide, sodium hydroxide, potassium hydroxide, and cesium hydroxide (hereinafter, collectively referred to as "alkali-metal hydroxides"); alkali metal hydrides such as lithium hydride and sodium hydride (hereinafter, collectively referred to as "alkali metal hydrides"); and alkali metal alkoxides such as sodium tert-butoxide and potassium tert-butoxide (hereinafter, collectively referred to as "alkali metal alkoxides") and the like.

In the reaction, Compound (A2) is used usually within a range of 1 to 10 molar ratio(s), and the base is usually used within a range of 1 to 10 molar ratio(s), as opposed to 1 mole of Compound (A1).

The reaction temperature is usually within a range of −20 to 150° C. The reaction period of the reaction is usually within a range of 0.1 to 120 hours.

When the reaction is completed, the reaction mixtures are mixed with water, the reaction mixtures are extracted with organic solvent(s), and the resulting organic layers are worked up (for example, drying and concentration) to isolate Compound (I-A).

The Compound (A2) is a commercially available compound, or may be prepared according to the publicly known method.

Process B

The present compound X can be prepared by reacting a compound represented by formula (B1) (hereinafter, referred to Compound (B1)) with a compound represented by formula (B2) (hereinafter, referred to as Compound (B2)) in the presence of a palladium catalyst and a base.

Examples of the palladium catalyst to be used in the reaction include palladium acetate(II), dichlorobis((triphenylphosphine)palladium(II), tetrakis(triphenylphosphine)palladium(0), [1,1'-bis(diphenylphosphino)ferrocene]palladium(II) dichloride, and tris(dibenzylideneacetone)dipalladium(0).

Example of the base to be used in the reaction include organic bases; alkali metal carbonates; alkali metal hydrocarbonates; alkali metal hydroxides; alkali metal fluorides such as sodium fluoride, potassium fluoride and cesium fluoride (hereinafter, collectively referred to as "alkali metal fluorides"); alkali metal hydride; and alkali metal alkoxides; and tripotassium phosphate.

In the reaction, Compound (B2) is used usually within a range of 1 to 10 molar ratio(s), the base is usually used within a range of 1 to 10 molar ratio(s), and the catalyst is usually used within a range of 0.0001 to 1 molar ratio(s), as opposed to 1 mole of Compound (B1).

The reaction temperature is usually within a range of 0 to 150° C. The reaction period of the reaction is usually within a range of 0.1 to 24 hours.

When the reaction is completed, the reaction mixtures are mixed with water, the reaction mixtures are extracted with organic solvent(s), and the resulting organic layers are worked up (for example, drying and concentration) to isolate the present Compound.

The compound (B2) is a commercially available compound, or may be prepared according to the method described in Chem. Rev., 1995, 95, 2457.

Process C

The present compound X can be prepared by reacting a compound represented by formula (C1) (hereinafter, referred to as Compound (C1)) with a compound represented by formula (C2) (hereinafter, referred to as Compound (C2)) in the presence of a palladium catalyst and a base.

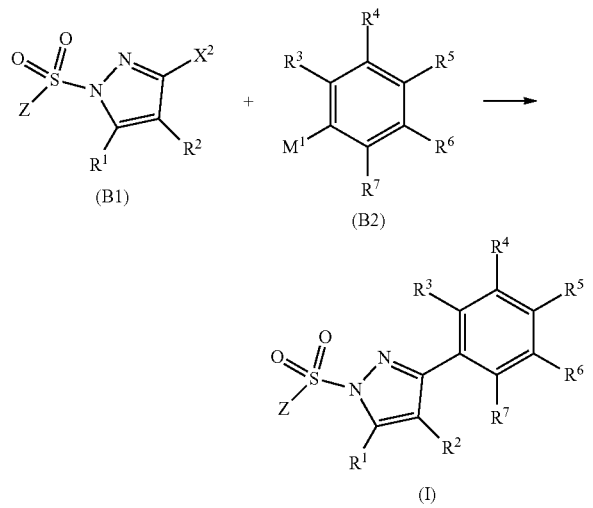

[wherein $X^2$ represents a chlorine atom, a bromine atom, an iodine atom, or a trifluoromethanesulfonyloxy group, $M^1$ represents $B(OH)_2$, or 4,4,5,5-tetramethyl-1,3,2-dioxaboran-2-yl group, and the other symbols are the same as defined above.]

The reaction is usually carried out in a solvent.

Examples of the solvent to be used in the reaction include hydrocarbons; ethers; halogenated hydrocarbons; amides; esters; sulfoxides such as dimethyl sulfoxide (hereinafter, referred to as "DMSO"); ketones such as acetone and methyl isobutyl ketone (hereinafter, collectively referred to as "ketones"; nitriles; alcohols such as methanol and ethanol (hereinafter, collectively referred to as "alcohols"); water; and mixed solvents comprising two or more thereof.

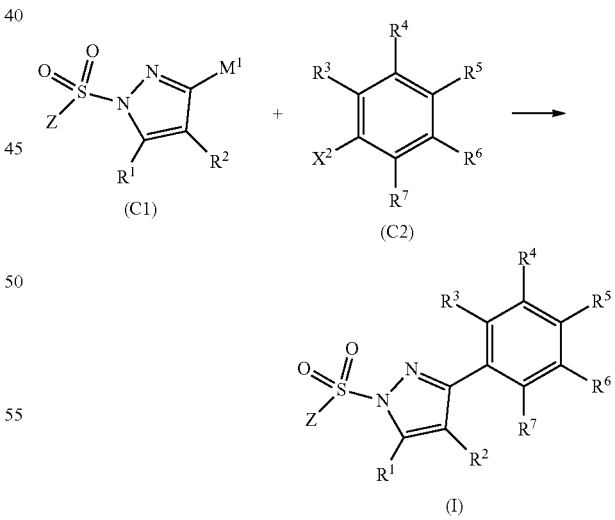

[wherein the symbols are the same as defined above.]

The reaction can be conducted by using the Compound (C2) in place of the Compound (B1) and the compound (C1) in place of the Compound (B2) according to the process B.

The Compound (C1) is a commercially available compound, or may be prepared according to the method described in Chem. Rev., 1995, 95, 2457. The compound (C2) is a commercially available compound, or may be prepared according to the method described in Tetrahedron Letters, 2003, 44, 8781.

Process D

A compound represented by formula (D1) (hereinafter, referred to as Compound (D1)) can be prepared by reacting a compound represented by formula (MQ1) (hereinafter, referred to as Compound (MQ1)) with a compound represented by formula (MD1) (hereinafter, referred to as Compound (MD1)),

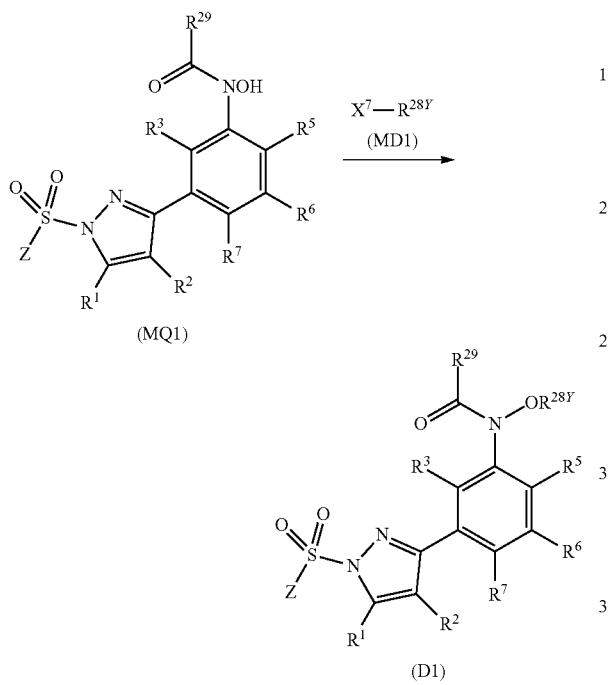

[wherein $R^{28Y}$ represents a C1-C6 chain hydrocarbon group or a C3-C6 cycloalkyl group, $X^7$ represents a halogen atom, $OS(O)_2(OR^{28Y})$, $OS(O)_2CF_3$, $OS(O)_2CH_3$ or $OS(O)_2(4\text{-MePh})$, and the other symbols are the same as defined above.]

The reaction is usually carried out in a solvent.

Examples of the solvent to be used in the reaction include hydrocarbons; ethers; halogenated hydrocarbons; amides; esters; sulfoxides; ketones; nitriles; alcohols; water; and mixed solvents comprising two or more thereof.

A base may be used in the reaction. Example of the base to be used in the reaction include organic bases; alkali metal carbonates; alkali metal hydrocarbonates; alkali metal hydroxides; alkali metal fluorides; alkali metal hydrides; and alkali metal alkoxides; and tripotassium phosphate.

In the reaction, Compound (MD1) is used usually within a range of 1 to 10 molar ratio(s) as opposed to 1 mole of Compound (MQ1). When the base is used in the reaction, the base is usually used within a range of 1 to 10 molar ratio(s) as opposed to 1 mole of Compound (MQ1).

The reaction temperature is usually within a range of −78 to 150° C. The reaction period of the reaction is usually within a range of 0.1 to 24 hours.

When the reaction is completed, the reaction mixtures are mixed with water, the reaction mixtures are extracted with organic solvent(s), and the resulting organic layers are worked up (for example, drying and concentration) to isolate the Compound (D1).

The reaction can be conducted according to a method described in, for example, Org. Lett. 2017, 19, 3059, Org. Synth. 1989, 67, 187, or Angew. Chem. Int. Ed. 2014, 53, 14559.

The Compound (MD1) is a publicly known, or may be prepared according to a publicly known method.

Process E

A compound represented by formula (E1) (hereinafter, referred to as Compound (E1)) can be prepared by reacting a compound represented by formula (MH2) (hereinafter, referred to as Compound (MH2)) with a compound represented by formula (MJ1) (hereinafter, referred to as Compound (MJ1)) in the presence of a base.

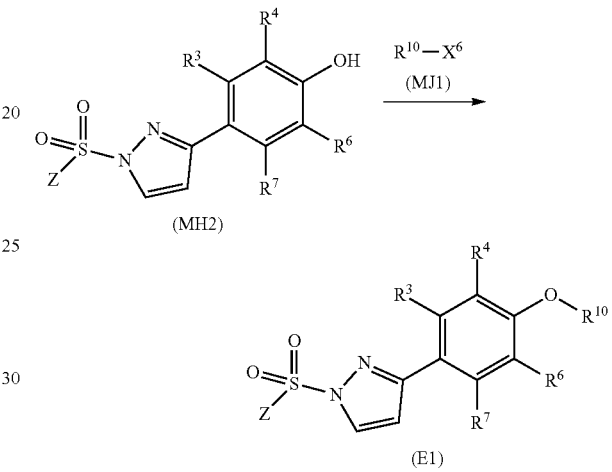

[wherein $X^6$ represents a chlorine atom, a bromine atom, or an iodine atom, and the other symbols are the same as defined above.]

The reaction is usually carried out in a solvent.

Examples of the solvent to be used in the reaction include hydrocarbons; ethers; amides; esters; sulfoxides; ketones; nitriles; and mixed solvents comprising two or more thereof.

Example of the base to be used in the reaction include organic bases; alkali metal carbonates; alkali metal hydrocarbonates; alkali metal hydrides; and alkali metal alkoxides.

In the reaction, Compound (MJ1) is used usually within a range of 1 to 10 molar ratio(s), and the base is usually used within a range of 1 to 10 molar ratio(s), as opposed to 1 mole of Compound (MH2).

The reaction temperature is usually within a range of −78 to 150° C. The reaction period of the reaction is usually within a range of 0.1 to 24 hours.

As needed, sodium iodide, potassium iodide, or tetrabutylammonium iodide and the like may be added to the reaction, and these compounds may be used usually within a range of 0.001 to 1.2 molar ratio(s), as opposed to 1 mole of Compound (MH2).

When the reaction is completed, the reaction mixtures are extracted with organic solvent(s), and the resulting organic layers are worked up (for example, drying and concentration) to isolate the Compound (E1).

The Compound (MJ1) is a publicly known, or may be prepared according to a publicly known method.

Process F

A compound represented by formula (F1) (hereinafter, referred to as Compound (F1)) can be prepared by reacting a compound represented by formula (MI2) (hereinafter, referred to as Compound (MI2)) with the compound (MJ1).

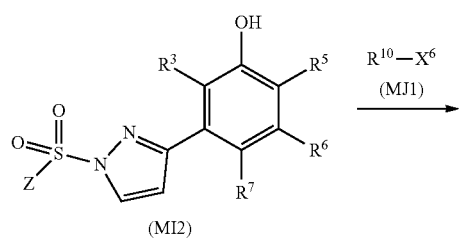

(MI2)

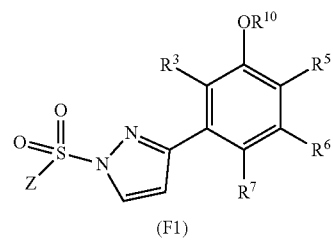

(F1)

[wherein the symbols are the same as defined above.]

The reaction can be conducted by using the Compound (MI2) in place of the Compound (MH2) according to the process E.

Process G

A compound represented by formula (G1) (hereinafter, referred to as Compound (G1)) can be prepared by reacting a compound represented by formula (MG2) (hereinafter, referred to as Compound (MG2)) with a compound represented by formula (MJ2) (hereinafter, referred to as Compound (MJ2)).

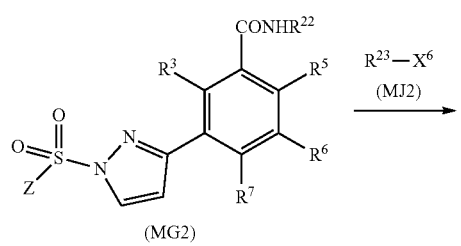

(MG2)

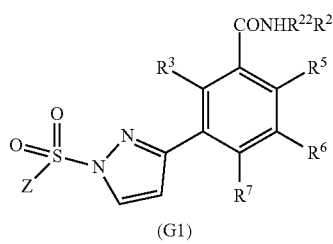

(G1)

[wherein the symbols are the same as defined above.]

The reaction is usually carried out in a solvent.

Examples of the solvent to be used in the reaction include hydrocarbons; ethers; amides; esters; sulfoxides; ketones; nitriles; and mixed solvents comprising two or more thereof.

Example of the base to be used in the reaction include organic bases; alkali metal carbonates; alkali metal hydrocarbonates; alkali metal hydrides; and alkali metal alkoxides.

In the reaction, Compound (MJ2) is used usually within a range of 1 to 10 molar ratio(s), and the base is usually used within a range of 1 to 10 molar ratio(s), as opposed to 1 mole of Compound (MG2).

The reaction temperature is usually within a range of 0 to 150° C. The reaction period of the reaction is usually within a range of 0.1 to 24 hours.

As needed, sodium iodide, potassium iodide, or tetrabutylammonium iodide and the like may be added to the reaction, and these compounds may be used usually within a range of 0.001 to 1.2 molar ratio(s), as opposed to 1 mole of Compound (MG2).

When the reaction is completed, the reaction mixtures are extracted with organic solvent(s), and the resulting organic layers are worked up (for example, drying and concentration) to isolate the Compound (G1).

The Compound (MJ2) is a publicly known, or may be prepared according to a publicly known method.

The Compound (MG42) can be prepared by any method of the above-described Process A, B or C.

Next, a process for preparing an intermediate compound for the present compound X is explained.

Reference Process A

A Compound (A1) can be prepared by reacting a compound represented by formula (MA1) (hereinafter, referred to as Compound (MA1)) with hydrazine.

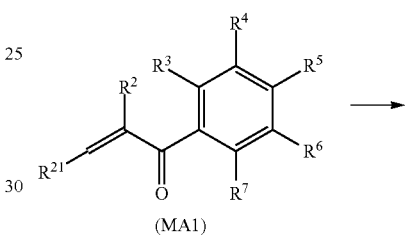

(MA1)

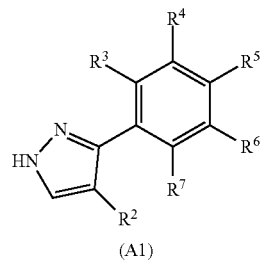

(A1)

[wherein, $R^{21}$ represents a hydroxy group, a dimethylamino group, or a diethylamino group, and the other symbols are the same as defined above.]

The reaction can be conducted according to the method described in, for example, Bioorganic and Medicinal Chemistry, 2014, 22, 4189. or J. Med. Chem., 2003, 46, 5416.

Reference Process B

A compound represented by formula (MA2) (hereinafter, referred to as Compound (MA2)) can be prepared by reacting a compound represented by formula (MB1) (hereinafter, referred to as Compound (MB1)) with a compound represented by formula (MB2) (hereinafter, referred to as Compound (MB2)).

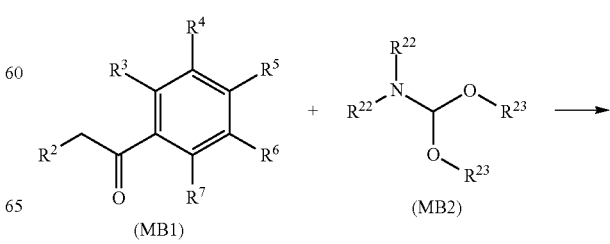

(MB1)  (MB2)

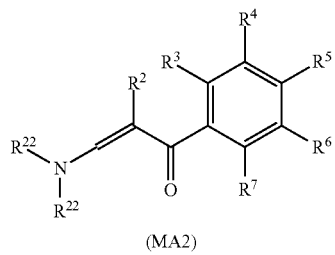

[wherein R$^{22}$ represents a methyl group or an ethyl group, R$^{23}$ represents a C1-C4 alkyl group or a benzyl group, and the other symbols are the same as defined above.]

The reaction can be conducted according to the method described in, for example, European Journal of Medicinal Chemistry, 2011, 46, 5817.

The Compound (MB2) is a commercially available compound, or can be prepared by a known method.

Reference Process C

A compound represented by formula (MA3) (hereinafter, referred to as Compound (MA3)) can be prepared by reacting the compound (MB1) with a compound represented by formula (MC1) (hereinafter, referred to as Compound (MC1)) in the presence of a base.

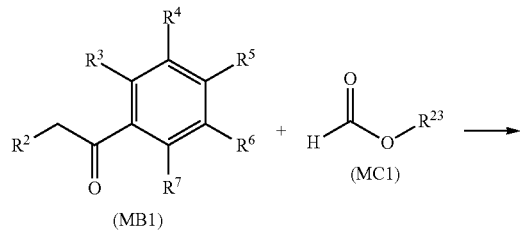

[wherein the symbols are the same as defined above.]

The reaction can be conducted according to the method described in, for example, J. Am. Chem. Soc., 2017, 139, 2421.

The Compound (MC1) is a commercially available compound, or can be prepared by a known method.

Reference Process D

The Compound (MB1) can be prepared by reacting a compound represented by formula (MD1) (hereinafter, referred to as Compound (MD1)) with a compound represented by formula (MD2) (hereinafter, referred to as Compound (MD2)).

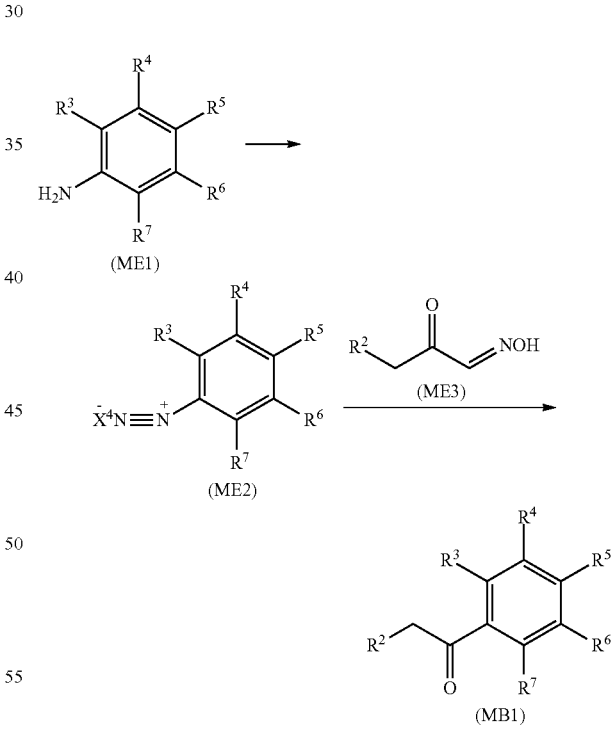

[wherein R$^{24}$ represents a cyano group, a chlorocarbonyl group, a di(C1-C4 alkyl)carbamoyl group, a N-methoxy-N-methylcarbamoyl group, a morpholinocarbonyl group, a pyrrol-1-ylcarbonyl group, a pyrazol-1-ylcarbonyl group, an imidazol-1-ylcarbonyl group, or a benzotriazol-1-ylcarbonyl group, X$^3$ represents a chlorine atom, a bromine atom, or an iodine atom, and the other symbols are the same as defined above.]

The reaction can be conducted according to the method described in, for example, Synthesis, 2008, 28, 3707.

The compound (MD1) is a commercially available compound, or can be prepared according to the method described in Synthesis, 2008, 28, 3707. The Compound (MD2) is a commercially available compound, or can be prepared according to the known method.

Reference Process E

The Compound (MB1) can be prepared according to the following scheme.

[wherein X$^4$ represents HSO$_4$ or Cl, and the other symbols are the same as defined above.]

A compound represented by formula (ME2) (hereinafter, referred to as Compound (ME2)) can be prepared by reacting a compound represented by formula (ME1) (hereinafter, referred to as Compound (ME1)) with sodium nitrite in the presence of a strong acid. The reaction can be conducted according to the method described in US patent publication No. 2017/137385.

The Compound (MB1) can be prepared by reacting the Compound (ME2) with a compound represented by formula (ME3) (hereinafter, referred to as Compound (ME3)) in the presence of copper halide (I). The reaction can be conducted according to the method described in US Patent Publication No. 2017/137385.

The Compound (ME1) and the Compound (ME3) are commercially available compounds, or can be prepared by using a known method.

Reference Process F

A compound represented by formula (MB3) (hereinafter, referred to as Compound (MB3)) can be prepared by the following scheme.

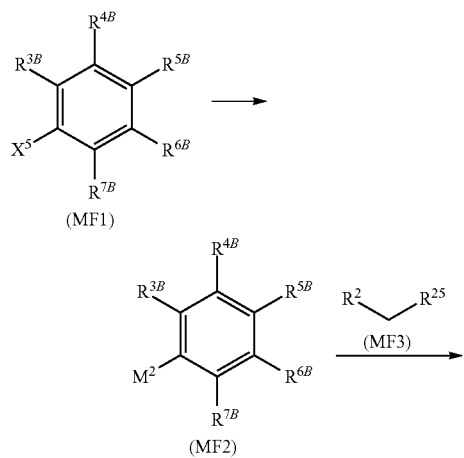

[wherein $X^5$ represents a bromine atom or an iodine atom, $M^2$ represents a lithium atom, MgBr or MgCl, $R^{3B}$, $R^{4B}$, $R^{5B}$, $R^{6B}$ and $R^{7B}$ are identical to or different from each other and represent a C1-C6 alkyl group optionally having one or more fluorine atoms, a fluorine atom, a chlorine atom, or a hydrogen atom, $R^{25}$ represents a cyano group, a chlorocarbonyl group, a di(C1-C4 alkyl)carbamoyl group, a N-methoxy-N-methylcarbamoyl group, a morpholinocarbonyl group, a (pyrol-1-yl)carbonyl group, a (pyrazol-1-yl)carbonyl group, an (imidazol-1-yl)carbonyl group, a (benzotriazol-1-yl)carbonyl group, —C(O)OC(C)CH$_2$R$_2$, a C2-C4 alkoxycarbonyl group, and the other symbols are the same as defined above.]

A compound represented by formula (MF2) (hereinafter, referred to as Compound (MF2)) can be prepared by reacting a compound represented by formula (MF1) (hereinafter, referred to as Compound (MF1)) with butyl lithium, isopropyl magnesium bromide or isopropyl magnesium chloride.

The Compound (MB3) can be prepared by reacting the Compound (MF2) with a compound represented by formula (MF3) (hereinafter, referred to as Compound (MF3)).

These reactions can be conducted according to the method described in, for example, Chinese patent publication No. 105461538.

The Compound (MF1) is a commercially available compound, or can be prepared according to a method described in J. Am. Chem. Soc., 2012, 134, 20597.

The Compound (MF3) is a commercially available compound, or can be prepared by using a known method.

Reference Process G

The Compound (B1) can be prepared by reacting a compound represented by formula (MG1) (hereinafter, referred to as Compound (MG1)) with the Compound (A2) in the presence of a base.

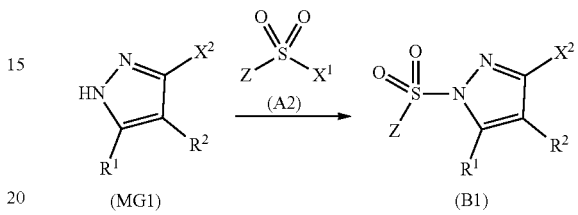

[wherein the symbols are the same as defined above.]

The reaction can be conducted according to Process A.

The Compound (MG1) is a commercially available compound, or can be prepared by the method described in Medicinal Chemistry Letters, 2007, 17, 6274.

Reference Process H

The Compound (MH2) can be prepared from a compound represented by formula (MH1) (hereinafter, referred to as Compound (MH1)).

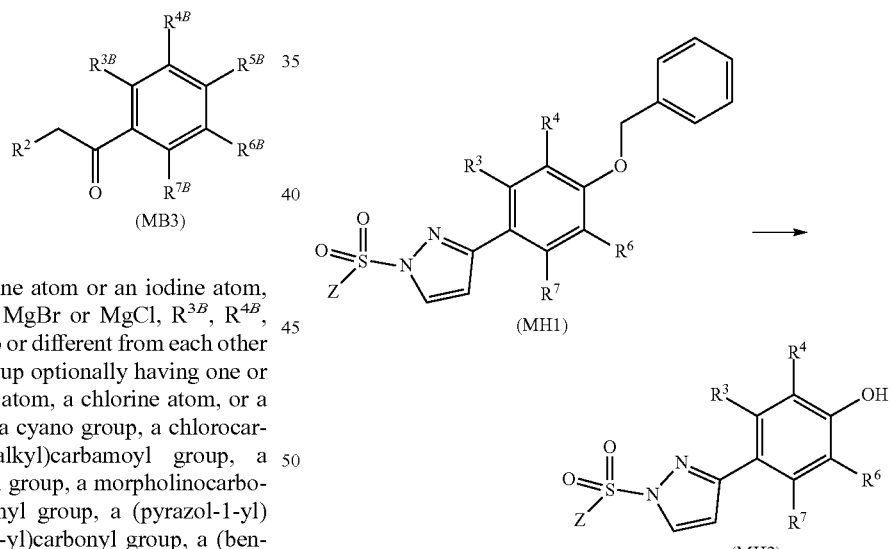

[wherein the symbols are the same as defined above.]

The reaction can be conducted according to the method described in, for example, Tetrahedron Lett., 1998, 39, 7127, Synlett, 2001, 1590, Tetrahedron Lett., 1997, 38, 399, or J. Org. Chem., 1978, 43, 4194.

The Compound (MH1) is a commercially available compound, or can be prepared by using a known method.

Reference Process I

The Compound (MI2) can be prepared from a compound represented by formula (MI1) according to the Reference Process H.

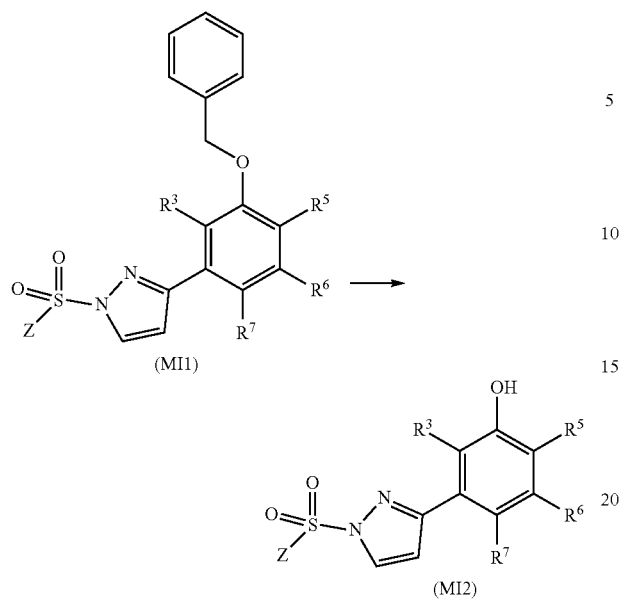

(MI1)

(MI2)

[wherein the symbols are the same as defined above.]

Reference Process K

A compound represented by formula (MK2) (hereinafter, referred to Compound (MK2)) can be prepared from a compound represented by formula (MK1) (hereinafter, referred to as Compound (MK1)).

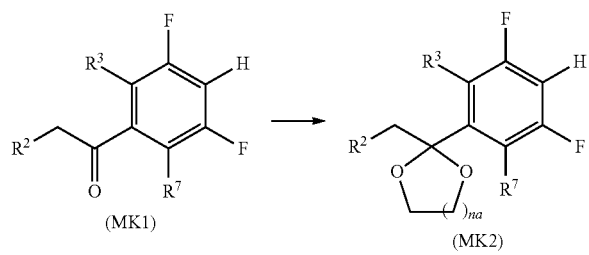

[wherein, na is an integer of 1 to 3, and the other symbols are the same as defined above.]

The Compound (MK2) can be prepared by reacting the Compound (MK1) with ethylene glycol, propanediol or butanediol in the presence of a strong acid.

The reaction can be conducted according to the method described in, for example, Organic Letters, 2013, 15, 6190.

Reference Process L

A compound represented by formula (ML2) (hereinafter, referred to as Compound (ML2)) can be prepared according to the below-mentioned scheme.

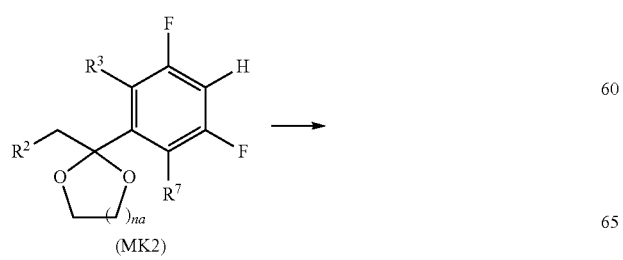

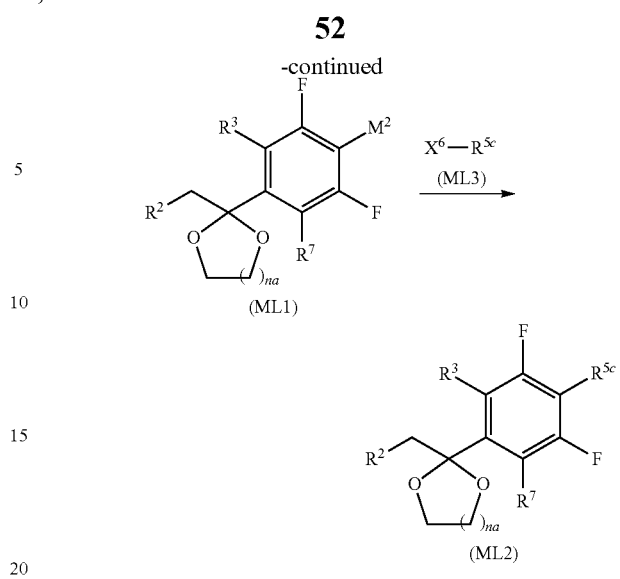

[wherein $R^{5c}$ represents a C1-C6 alkyl group optionally having one or more fluorine atoms, and the other symbols are the same as defined above.]

A compound represented by formula (ML1) (hereinafter, referred to as Compound (ML1)) can be prepared by the Compound (MK2) with butyl lithium, isopropyl magnesium bromide or isopropyl magnesium chloride.

The reaction can be conducted according to the method described in, for example, WO 2008/021851 A.

The Compound (ML2) can be prepared by reacting the Compound (ML1) with a compound represented by formula (ML3) (hereinafter, referred to as Compound (ML3)). The Compound (ML1) and the Compound (ML3) are commercially available compounds, or can be prepared by using a known method.

Reference Process M

A compound represented by formula (MM2) (hereinafter, referred to as Compound (MM2)) can be prepared by reacting the compound (ML1) with a halogenating agent.

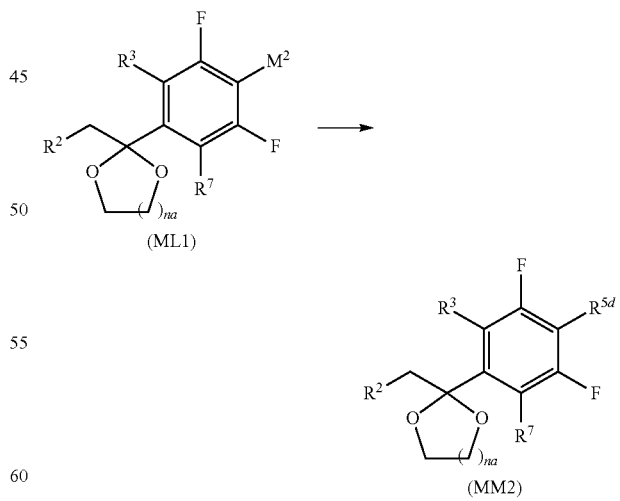

[wherein $R^{5d}$ represents a fluorine atom, a chlorine atom, a bromine atom, an iodine atom, and the other symbols are the same as defined above.]

The halogenating agents are commercially available compounds, or can be prepared by a known method. Examples of the halogenating agents include iodine, bromine, N-bromosuccinimide, and N-chlorosuccinimide, which are not limited thereto.

The reaction may be conducted according to a method described in, for example, WO 2008/021851 A.

Reference Process N

A compound represented by formula (MN1) (hereinafter, referred to as Compound (MN1)) can be prepared according to the below-mentioned scheme.

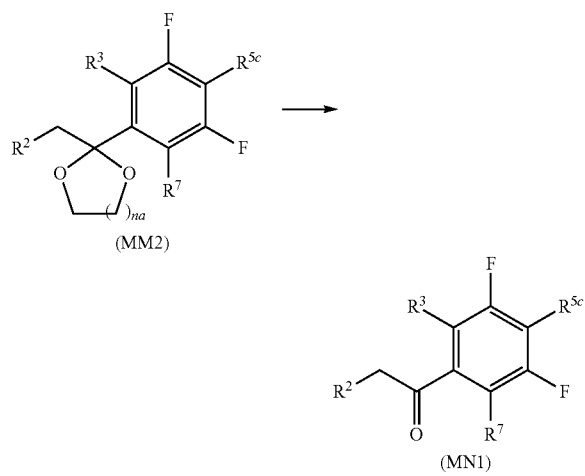

[wherein the symbols are the same as defined above.]

The Compound (MN1) can be prepared by reacting the Compound (MM2) with water in the presence of an acid.

The reaction can be conducted according to the method described in, for example, Angew. Chem. Int. Ed. 2014, 53, 8668.

Reference Process O

A compound represented by formula (MP1) (hereinafter, referred to as Compound (MP1)) can be prepared according to the below-mentioned scheme.

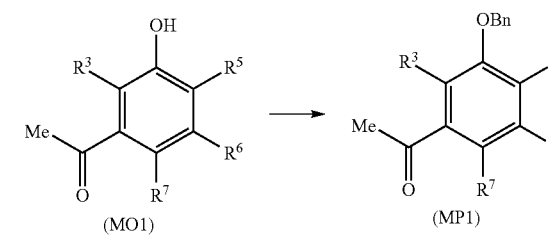

[wherein Bn represents a benzyl group, and the other symbols are the same as defined above.]

The Compound (MP1) can be prepared by reacting the Compound (MO1) with benzyl halide in the presence of a base.

The reaction can be conducted according to the method described in J. Med. Chem. 1988, 31, 2132, Synth. Commun. 1996, 26, 593, Org. Lett. 2002, 4, 3087, J. Org. Chem. 1983, 48, 1469, J. Am. Chem. Soc. 2004, 126, 12897, or J. Am. Chem. Soc. 2004, 126, 7359.

Reference Process P

A compound represented by formula (MP2) (hereinafter, referred to as Compound (MP2)) can be prepared according to the below-mentioned scheme.

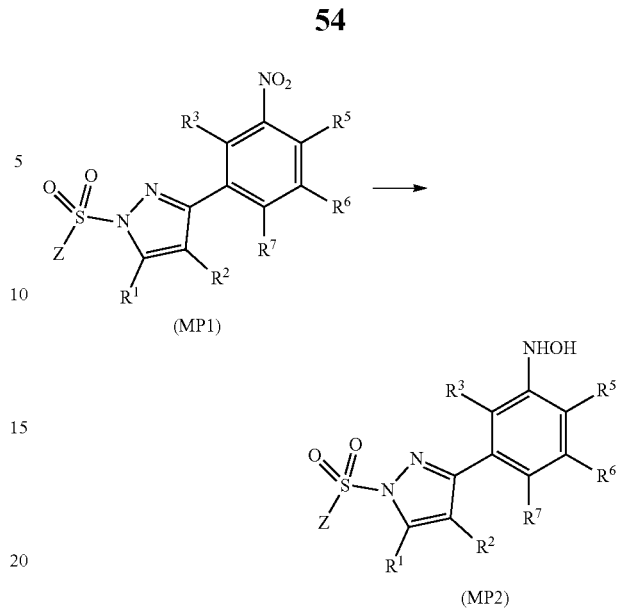

[wherein the symbols are the same as defined above.]

The Compound (MP2) can be prepared by reacting the Compound (MP1) with a reducing agent.

The reaction can be conducted according to the method described in, for example, Angew. Chem. Int. Ed. 2018, 57, 8714, Eur. J. Org. Chem. 2013, 2013, 1158, Synth. Commun. 2017, 47, 1085, or Org. Lett. 2017, 19, 3059.

Reference Process Q

A compound represented by formula (MQ1) (hereinafter, referred to as Compound (MQ1)) can be prepared according to the below-mentioned scheme.

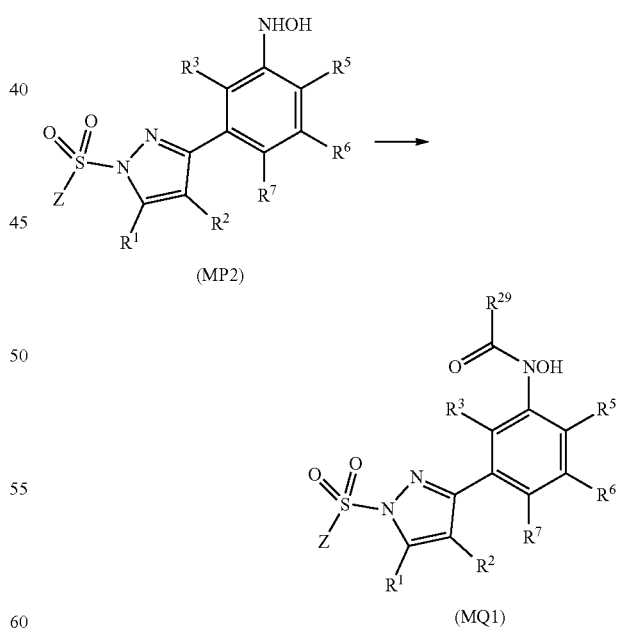

[wherein the symbols are the same as defined above.]

The Compound (MQ1) can be prepared reacting the Compound (MP2) with an acid halide or an acid anhydride.

The reaction can be conducted according to the method described in, for example, Eur. J. Org. Chem. 2013, 2013, 1158, Tetrahedron Lett. 2015, 56, 5282, Synth. Comun. 2017, 47, 1085, Org. Lett. 2017, 19, 3059, or Org. Synth. 1989, 67, 187.

Reference Process R

A compound represented by formula (MR1) (hereinafter, referred to as Compound (MR1)) can be prepared according to the below-mentioned scheme.

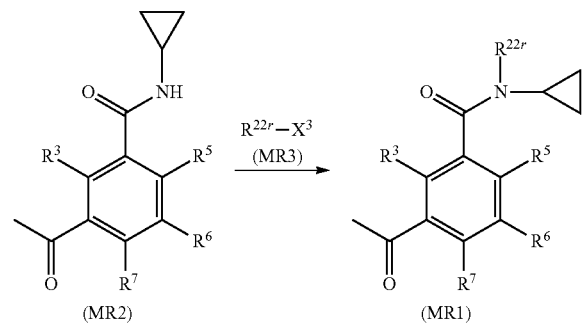

[wherein $R^{22r}$ represents a C6-C10 aryl group optionally having one or more substituents selected from group K or a five to ten membered aromatic heterocyclic group optionally having one or more substituents selected from group K, and the other symbols are the same as defined above.]

The Compound (MR1) can be prepared by reacting a compound represented by formula (MR2) (hereinafter, referred to as Compound (MR2)) with a compound represented by formula (MR3)) (hereinafter, referred to as Compound (MR3)).

The reaction can be conducted according to the method described in, for example, Eur. Org. Lett. 2011, 13, 2818.

The Compound (MR2) and the Compound (MR3) are commercially available compounds, or can be prepared by using a known method.

The present compound or the present compound X can be mixed or combined with one or more ingredients selected from the group consisting of the following Group (a), Group (b), Group (c), and Group (d) (hereinafter, referred to as "present ingredient").

The above-described defined mixing or combining represents that the present compound or the present compound X and the present ingredient are used concurrently, separately, or at an interval.

When the present compound or the present compound X and the present ingredient are concurrently used, the present compound or the present compound X and the present ingredient may be incorporated as a separate formulation or one formulation.

One aspect of the present invention relates to a composition comprising one or more ingredients selected from the group consisting of the Group (a), the Group (b), the Group (c) and the Group (d), and the present compound.

One aspect of the present invention relates to a composition comprising one or more ingredients selected from the group consisting of the Group (a), the Group (b), the Group (c) and the Group (d), and the present compound X (hereinafter, referred to as "composition A").

The Group (a) represents a group consisting of acetylcholinesterase inhibitors (for example, carbamate insecticides and organophosphate insecticides), GABA-gated chloride ion channel antagonists (for example, phenylpyrazole insecticides), sodium channel modulators (for example, pyrethroid insecticides), nicotinic acetylcholine receptor antagonist modulators (for example, neonicotinoid insecticides), nicotinic acetylcholine receptor allosteric modulators, glutamate-gated chloride ion channel allosteric modulators (for example, macrolide insecticides), juvenile hormone mimics, multisite inhibitors, chordotonal organ TRPV channel modulators, mites growth regulators, mitochondrial ATP synthase inhibitors, uncouplers of oxidative phosphorylation, nicotinic acetylcholine receptor channel blockers (for example, nereistoxin insecticides), inhibitors of chitin biosynthesis, moulting disruptors, ecdysone receptor agonists, octopamine receptor agonists, Inhibitors of mitochondrial electron transport chain complex I, II, III, and IV, voltage-dependent sodium channel blockers, Inhibitors of acetyl CoA carboxylase, ryanodine receptor modulators (for example, diamide insecticides), chordotonal organ modulators, each active ingredient of microbial fungicides, and other insecticidal ingredients, miticidal ingredients and nematicidal ingredients. These agents are described in the classification based on the IRAC mode of action.

The Group (b) represents a group consisting of nucleic acid synthesis inhibitors (for example, phenylamide fungicides and acylamino acid fungicides), cytostatic and cytoskeletal inhibitors (for example, MBC fungicides), respiration inhibitors (for example, QoI fungicides and QiI fungicides), amino-acid synthesis and protein synthesis inhibitors (for example, anilinopyridine fungicides), signal-transduction inhibitors, lipid synthesis and membrane synthesis inhibitors, sterol biosynthesis inhibitors (for example, DMI fungicides such as triazoles), cell wall synthesis inhibitors, melanin synthesis inhibitors, plant defense inducer, multisite fungicides, microbial fungicides, and other fungicidal ingredients. These agents are described in the classification based on the FRAC mode of action.

The Group (c) represents a group of plant growth modulating ingredients (including mycorrhizal fungus and rhizobia).

The Group (d) represents a group of repellent ingredients consisting of bird repellent ingredients and insect repellent ingredients.

Examples of combinations of the present ingredient and the present compound X are recited as follows. For example, the "alanycarb+SX" indicates a combination of alanycarb and SX.

The abbreviation "SX" means to any one of the present compounds selected from the present compound T described in Examples. Further, any of the present ingredients as described below are a known ingredient, and can be obtained as a commercially available drug or prepared by using a known method. When the present ingredient represents a microorganism, the present ingredient can be obtained from a microorganism depositary authority. The number in parentheses represents CAS RN (registered trademark).

A combination of the present ingredient in the above-mentioned Group (a) and the present compound X:

abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dinotefuran+SX, disodium octaborate+SX, disulfoton+SX, DNOC(2-methyl-4,6-dinitrophenol)+SX, doramectin+SX, dried leaves of Dryopteris filix-mas+SX, emamectin-benzoate+SX, empenthrin+SX, endosulfan+SX, EPN(O-ethyl Q-(4-nitrophenyl)phenylphosphonothicate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of *Clitoria ternatea*+SX, extract of *Symphytum officinale*+SX, extracts or simulated blend of *Chenopodium ambrosioides*+SX, extract of *Tanacetum vulgare*+SX, extract of *Urtica dicica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, enpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalotbrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imidaclothiz+SX, imiprothrin+SX, indoxacarb+SX, isocycloseram+SX, isofenphos+SX, isoprocarb+SX, isopropyl-O-(methoxyaminothiophosphoryl) salicylate+SX, isoxathion+SX, ivermectin+SX, kadethrin+SX, kappa-tefluthrin+SX, kappa-bifenthrin+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methcmyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *Chenopodium ambrosioides* near ambrosioides+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium)+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, N-[3-chloro-1-(pyridin-3-yl)-1H-pyrazol-4-yl]-N-ethyl-3-(3,3,3-trifluoropropanesulfinyl)propanamide (1477923-37-7)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluoropropan-2-yl)phenyl]-3-{ethyl[(pyridin-4-yl)carbonyl)amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-(2-bromo-6-(difluoromethoxy)-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfanyl]phenyl}-3-(trifluoromethyl)-1H-1,2,4-triazol-5-amine (885026-50-6)+SX, N-ethyl-5-methyl-1-(3-methylbutan-2-yl)-N-(pyridazin-4-yl)-1H-pyrazole-4-carboxamide (1403615-77-9)+SX, (1Z)-2-(4-tert-butylphenyl)-2-cyano-1-(1-ethyl-3-methyl-1H-pyrazol-5-yl)ethenyl 2,2-dimethylpropanoate (1253429-01-4)+SX, N-[(1S,2S)-2-(2,4-dichlorophenyl)cyclobutyl]-2-(trifluoromethyl)pyridine-3-carboxamide (1644251-74-C)+SX, 2-chloro-4-fluoro- 5-{[5-(trifluoromethylthio)pentyl]oxy}phenyl 2,2,2-trifluoroethyl sulfoxide (1472050-04-6)+SX, 4-chloro-5-[2,2-difluoro-2-(3,4,5-trifluorophenyl)ethoxy]-2-methylphenyl 2,2,2-trifluoroethyl sulfoxide (1632218-00-8)+SX, 4-fluoro-5-[2,2-difluoro-2-(3,4,5-trifluorophenyl)ethoxy]-2-methylphenyl 2,2,2-trifluoroethyl sulfoxide (1632217-98-1)+SX, (3R)-3-(2-chlorothiazol-5-yl)-8-methyl-7-oxo-6-phenyl-2,3-dihydrothiazolo[3,2-a]pyrimidin-4-ium-5-olate (2249718-27-0)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, *Adoxophyes orana* granulosis virus strain BV-0001+SX, *Anticarsia gemmatalis* mNPV+SX, *Autographa californica* mNPV+SX, *Cydia pomonella* GV strain V15+SX, *Cydia pomonella* GV strain V22+SX, *Cryptophlebia leucotreta* GV+SX, *Dendrolimus punctatus* cypovirus+SX, *Helicoverpa armigera* NPV strain BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* strain GB-126+SX, *Bacillus firmnus* strain I-1582+SX, *Bacillus megaterium*+SX, *Bacillus* sp. strain AQ175+SX, *Bacillus* sp. strain AQ177+SX, *Bacillus* sp. strain AQ178+SX, *Bacillus sphaericus* strain 2362+SX, *Bacillus sphaericus* strain ABTS1743+SX, *Bacillus sphaericus* Serotype strain H5a5b+SX, *Bacillus thuringiensis* strain AQ52+SX, *Bacillus thuringiensis* strain BD #32+SX, *Bacillus thuringiensis* strain CR-371+SX, *Bacillus thuringiensis* subsp. *aizawai* strain ABTS-1857+SX, *Bacillus thuringiensis* subsp. *aizawai* strain AM65-52+SX, *Bacillus thuringiensis* subsp. *aizawai* strain GC-91+SX, *Bacillus thuringiensis* subsp. *aizawai* Serotype strain H-7+SX, *Bacillus thuringiensis* subsp. *kurstaki* strain ABTS351+SX, *Bacillus thuringiensis* subsp. *kurstaki* strain BMP123+SX, *Bacillus thuringiensis* subsp. *kurstaki* strain EG234+SX, *Bacillus thuringiensis* subsp. *kurstaki* strain EG7841+SX, *Bacillus thuringiensis* subsp. *kurstaki* strain EVB113-19+SX, *Bacillus thuringiensis* subsp. *kurstaki* strain F810+SX, *Bacillus thuringiensis* subsp. *kurstaki* strain HD-1+SX, *Bacillus thuringiensis* subsp. *kurstaki* strain PB54+SX, *Bacillus thuringiensis* subsp. *kurstaki* strain SA-11+SX, *Bacillus thuringiensis* subsp. *kurstaki* strain SA-12+SX, *Bacillus thuringiensis* subsp. *tenebriosis* strain NB176+SX, *Bacillus thuringiensis* subsp. *Thuringiensis* strain MPPL002+SX, *Bacillus thuringiensis* subsp. *morrisoni*+SX, *Bacillus thuringiensis* var. colmeri+SX, *Bacillus thuringiensis* var. darmstadiensis strain 24-91+SX, *Bacillus thuringiensis* var. dendrolimus+SX, *Bacillus thuringiensis* var. galleriae+SX, *Bacillus thuringiensis* var. israelensis strain BM2144+SX, *Bacillus thuringiensis* var. israelensis serotype strain H-14+SX, *Bacillus thuringiensis* var. japonensis strain Buibui+SX, *Bacillus thuringiensis* var. san diego strain M-7+SX, *Bacillus thuringiensis* var. 7216+SX, *Bacillus thuringiensis* var. aegypti+SX, *Bacillus thuringiensis* var. T36+SX, *Beauveria bassiana* strain ANT-03+SX, *Beauveria bassiana* strain ATCC74040+SX, *Beauveria bassiana* strain GHA+SX, *Beauveria brongniartii*+SX, *Burkholderia rinojensis* strain A396+SX, *Chromobacterium subtsugae* strain PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX, *Lagenidium giganteum*+SX, *Lecanicillium lecanii* strain KV01+SX, *Lecanicillium lecanii* conidia of strain DAOM198499+SX, *Lecanicillium lecanii* conidia of strain DAOM216596+SX, *Lecanicillium muscarium* strain Ve6+SX, *Metarhizium anisopliae* strain F52+SX, *Metarhizium anisopliae* var. acridum+SX, *Metarhizium anisopliae* var. anisopliae BIPESCO 5/F52+SX, *Metarhizium flavoviride*+SX, *Monacrosporium phymatopagum*+SX, *Paecilomyces fumosoroseus* Apopka strain 97+SX, *Paecilomyces lilacinus* strain 251+SX, *Paecilomyces tenuipes* strain T1+SX, *Paenibacillus popilliae*+SX, *Pasteuria nishizawae* strain Pn1+SX, *Pasteuria penetrans*+SX, *Pasteuria usgae*+SX, *Pasteuria thoynei*+SX, *Serratia entomophila*+SX, *Verticillium chlamydosporium*+SX, *Verticillium lecani* strain NCIM1312+SX.

A combination of the present ingredient in the above-mentioned Group (b) and the present compound X:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthiavalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cypredinil+SX, dichlobentiazox+SX, dichlofluanid+SX, diclacymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from Reynoutria sachalinensis+SX, extract from the cotyledons of lupine plantlets ("BLAD")+SX, extract of *Allium sativum*+SX, extract of *Eauisetum arvense*+SX, extract of *Tropaeolum majus*+SX, famoxadone+SX, fenamidone+SX, fenaminstrobin+SX, fenarimol+SX, fenbuconazole+SX, fenfuram+SX, enhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of Quercus+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraciostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, Quillaja extract+SX, quinconazole+SX, quinofumelin+SX, quinoxyfen+SX, quintozene+SX, Saponins of Chenopodium quinoa+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-((3-((4-chlorophenyl)methyl]-1,2,4-thiadiazol-5-yl)oxy]-2,5-dimethylphenyl)-N-ethyl-N-methylmethanimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate (1360819-11-9)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]pyrimidin-4-amine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1-ylmethyl)cyclopentan-1-ol (1394057-11-4)+SX, (1R,2S,5S)-5-(4-chlorobenzyl)-2-(chloromethyl)-2-methyl-1-(1H-1,2,4-triazol-1-ylmethyl)cyclopentan-1-ol (1801930-06-2)+SX, (1S,2R, 5R)-5-(4-chlorobenzyl)-2-(chloromethyl)-2-methyl-1-(1H-1,2,4-triazol-1-ylmethyl)cyclopentan-1-ol (1801930-07-3)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R,2S,5S)-2-(chloromethyl)-5-(4-fluorobenzyl)-2-methyl-1-(1H-1,2,4-triazol-1-ylmethyl)cyclopentan-1-ol (1801930-08-4)+SX, (1S,2R,5R)-2-(chloromethyl)-5-(4-fluorobenzyl)-2-methyl-1-(1H-1,2,4-triazol-1-ylmethyl)cyclopentan-1-ol (1801930-09-5)+SX, methyl 3-[(4-chlorophenyl)methyl]-2-hydroxy-1-methyl-2-(1H-1,2,4-triazol-1-ylmethyl)cyclopentan-1-carboxylate (1791398-02-1)+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, N'-[5-choro-4-(2-fluorophenoxy)-2-methylphenyl)-N-ethyl-N-methylmethanimidamide (2055589-28-9)+SX, N'-[2-choro-4-(2-fluorophenoxy)-5-methylphenyl)-N-ethyl-N-methylmethanimidamide (2055756-21-1)+SX, N'-[4-(1-hydroxy-1-phenyl-2,2,2-trifluoroethyl)-2-methyl-5-methoxyphenyl)-N-isopropyl-N-methylmethanimidamide (2101814-55-3)+SX, N'-[5-bromo-6-(1-methyl-2-propoxyethoxy)-2-methylpyridin-3-yl)-N-ethyl-N-methylmethanimidamide (1817828-69-5)+SX, 1-(2,4-difluorophenyl)-2-(1H-1,2,4-triazol-1-yl)-1-[1-(4-bromo-2,6-difluorophenoxy)cyclopropyl]ethanol (2019215-86-0)+SX, 1-(2,4-difluorophenyl)-2-(1H-1,2,4-triazol-1-yl)-1-[1-(4-chloro-2,6-difluorophenoxy)cyclopropyl]ethanol (2019215-84-8)+SX, 1-[2-(1-chlorocyclopropyl)-3-(2-fluorophenyl)-2-hydroxypropyl]-1H-imidazole-5-carbonitrile (2018316-13-5)+SX, 1-[2-(1-chlorocyclopropyl)-3-(2,3-difluorophenyl)-2-hydroxypropyl]-1H-imidazole-5-carbonitrile (2018317-25-2)+SX, 4-({6-[2-(2,4-difluorophenyl)-1,1-difluoro-2-hydroxy-3-(1H-1,2,4-triazol-1-yl)propyl]pyridin-3-yl}oxy)benzonitrile (2046300-61-0)+SX, 2-[6-(4-bromophenoxy)-2-(trifluoromethyl)pyridin-3-yl]-1-(1H-1,2,4-triazol-1-yl)propan-2-ol (2082661-43-4)+SX, 2-[6-(4-chlorophenoxy)-2-(trifluoromethyl)pyridin-3-yl]-1-(1H-1,2,4-triazol-1-yl)

propan-2-ol (2082660-27-1)+SX, (2E,3Z)-5-{[1-(2,4-dichlorophenyl)-1H-pyrazol-3-yl]oxy)-2-(methoxyimino)-N,3-dimethylpent-3-enamide (1445331-54-3)+SX, 5-chloro-4-({2-[6-(4-chlorophenoxy)pyridin-3-yl]ethyl}amino)-6-methylpyrimidine (1605340-92-8)+SX, N-(1-benzyl-1,3-dimethylbutyl)-8-fluoroquinoline-3-carboxamide (2132414-04-9)+SX, N-(1-benzyl-3,3,3-trifluoro-1-methylpropyl)-8-fluoroquinoline-3-carboxamide (2132414-00-5)+SX, 4,4-dimethyl-2-({4-[5-(trifluoromethyl)-1,2,4-oxadiazol-3-yl]phenyl}methyl)isoxazolidin-3-one (2098918-25-1)+SX, 5,5-dimethyl-2-((4-[5-(trifluoromethyl)-1,2,4-oxadiazol-3-yl]phenyl}methyl)isoxazolidin-3-one (2098918-26-2)+SX, Agrobacterium radiobactor strain K1026+SX, Agrobacterium radiobactor strain K84+SX, Bacillus amyloliquefaciens (Aveo(trademark) EZ Nematicide)+SX, Bacillus amyloliquefaciens strain AT332+SX, Bacillus amyloliquefaciens strain B3+SX, Bacillus amyloliquefaciens strain D747+SX, Bacillus amyloliquefaciens strain DB101+SX, Bacillus amyloliquefaciens strain DB102+SX, Bacillus amyloliquefaciens strain GB03+SX, Bacillus amyloliquefaciens strain FZB24+SX, Bacillus amyloliquefaciens strain FZB42+SX, Bacillus amyloliquefaciens strain IN937a+SX, Bacillus amyloliquefaciens strain 1 MBI600+SX, Bacillus amyloliquefaciens strain QST713+SX, Bacillus amyloliquefaciens isolate strain B246+SX, Bacillus amyloliquefaciens strain F727+SX, Bacillus amyloliquefaciens subsp. plantarum strain D747+SX, Bacillus licheniformis strain HB-2+SX, Bacillus licheniformis strain SB3086+SX, Bacillus pumilus strain AQ717+SX, Bacillus pumilus strain BUF-33+SX, Bacillus pumilus strain GB34+SX, Bacillus pumilus strain QST2808+SX, Bacillus simplex strain CGF2B56+SX, Bacillus subtilis strain AQ153+SX, Bacillus subtilis strain AQ743+SX, Bacillus subtilis strain BUIS14+SX, Bacillus subtilis strain D747+SX, Bacillus subtilis strain DB101+SX, Bacillus subtilis strain FZB24+SX, Bacillus subtilis strain GB03+SX, Bacillus subtilis strain HAI0404+SX, Bacillus subtilis strain IAB/BS03+SX, Bacillus subtilis strain MBI600+SX, Bacillus subtilis strain QST30002/AQ30002+SX, Bacillus subtilis strain QST30004/AQ30004+SX, Bacillus subtilis strain QST713+SX, Bacillus subtilis strain QST714+SX, Bacillus subtilis var. Amyloliquefaciens strain FZB24+SX, Bacillus subtilis strain Y1336+SX, Burkholderia cepacia+SX, Burkholderia cepacia type Wisconsin strain J82+SX, Burkholderia cepacia type Wisconsin strain M54+SX, Candida oleophila strain O+SX, Candida saitoana+SX, Chaetomium cupreum+SX, Clonostachys rosea+SX, Coniothyrium minitans strain CGMCC8325+SX, Coniothyrium minitans strain CON/M/91-8+SX, Cryptococcus albidus+SX, Erwinia carotovora subsp. carotovora strain CGE234M403+SX, Fusarium oxysporum strain Fo47+SX, Gliocladium catenulatum strain J1446+SX, Paenibacillus polymyxa strain AC-1+SX, Paenibacillus polymyxa strain BS-0105+SX, Pantoea agglomerans strain E325+SX, Phlebiopsis gigantea strain VRA1992+SX, Pseudomonas aureofaciens strain TX-1+SX, Pseudomonas chlororaphis strain 63-28+SX, Pseudomonas chlororaphis strain AFS009+SX, Pseudomonas chlororaphis strain MA342+SX, Pseudomonas fluorescens strain 1629RS+SX, Pseudomonas fluorescens strain A506+SX, Pseudomonas fluorescens strain CL145A+SX, Pseudomonas fluorescens strain G7090+SX, Pseudomonas sp. strain CAB-02+SX, Pseudomonas syringae strain 742RS+SX, Pseudomonas syringae strain MA-4+SX, Pseudozyma flocculosa strain PF-A22UL+SX, Pseudomonas rhodesiae strain HAI-0804+SX, Pythium oligandrum strain DV74+SX, Pythium oligandrum strain M1+SX, Streptomyces griseoviridis strain K61+SX, Streptomyces lydicus strain WYCD10BUS+SX, Streptomyces lydicus strain WYEC108+SX, Talaromyces flavus strain SAY-Y-94-01+SX, Talaromyces flavus strain V117b+SX, Trichoderma asperellum strain ICC012+SX, Trichoderma asperellum SKT-1+SX, Trichoderma asperellum strain T25+SX, Trichoderma asperellum strain T34+SX, Trichoderma asperellum strain TV1+SX, Trichoderma atroviride strain CNCM 1-1237+SX, Trichoderma atroviride strain LC52+SX, Trichoderma atroviride strain IMI 206040+SX, Trichoderma atroviride strain SC1+SX, Trichoderma atroviride strain SKT-1+SX, Trichoderma atroviride strain T11+SX, Trichoderma gamsii strain ICC080+SX, Trichoderma harzianum strain 21+SX, Trichoderma harzianum strain DB104+SX, Trichoderma harzianum strain DSM 14944+SX, Trichoderma harzianum strain ESALQ-1303+SX, Trichoderma harzianum strain ESALQ-1306+SX, Trichoderma harzianum strain IIHR-Th-2+SX, Trichoderma harzianum strain ITEM908+SX, Trichoderma harzianum strain kd+SX, Trichoderma harzianum strain MO1+SX, Trichoderma harzianum strain SF+SX, Trichoderma harzianum strain T22+SX, Trichoderma harzianum strain T39+SX, Trichoderma harzianum strain T78+SX, Trichoderma harzianum strain TH35+SX, Trichoderma polysporum strain IMI206039+SX, Trichoderma stromaticum+SX, Trichoderma virens strain G-41+SX, Trichoderma virens strain GL-21+SX, Trichoderma viride+SX, Variovorax paradoxus strain CGF4526+SX, Harpin protein+SX.

A combination of the present ingredient in the above-mentioned Group (c) and the present compound X:

1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX,

[4-oxo-4-(2-phenylmethyl)amino]butyric acid+SX, methyl 5-(trifluoromethyl)benzo[b]thiophen-2-carboxylate+SX, 3-[(6-chloro-4-phenylquinazolin-2-yl)amino]-1-propanol+SX, *Claroideoglomus etunicatum*+SX, *Claroideoglomus claroideum*+SX, *Funneliformis mosseae*+SX, *Gigaspora margarita*+SX, *Gigaspora rosea*+SX, *Glomus aggregatum*+SX, *Glomus deserticola*+SX, *Glomus monosporum*+SX, *Paraglomus brasillianum*+SX, *Rhizophagus clarus*+SX, *Rhizophagus intraradices* RTI-801+SX, *Rhizophagus irregularis* DAOM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Bradyrhizobium lupini*+SX, *Delftia acidovorans* RAY209+SX, *Mesorhizobium ciceri*+SX, *Mesorhizobium huakii*+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *viciae*+SX, *Rhizobium trifolii*+SX, *Rhizobium tropici*+SX, *Sinorhizobium fredii*+SX, *Sinorhizobium meliloti*+SX, Zucchini Yellow Mosaik Virus weak strain+SX.

A combination of the present ingredient in the above-mentioned Group (d) and the present compound X: anthraguinone+SX, deet)+SX, icaridin+SX.

Examples of a ratio of the present compound X to the present ingredient include, but are not particularly limited to 1000:1 to 1:1000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, and 1:50, and the others in the weight ratio (the present compound X:the present ingredient).

The present compound X can be mixed or combined with chemical fertilizers (for example, ammonium sulfate, ammonium phosphate, ammonium nitrate, urea, or ammonium chloride).

The present compound, the present compound X, the compound of the present invention, the compound X of the present invention, or the composition A can be controlled plant diseases caused by phytopathogenic microorganism. Examples of the plant disease include the followings. Here the descriptions in a parenthesis indicates an academic name of phytopathogenic microorganism that causes the disease.

Rice Diseases:

blast (*Pyricularia oryzae*), brown spot (*Cochiiobolus miyabeanus*), sheath blight (*Rhizocronia solani*), bakanae disease (*Gibberella fujikuroi*), downy mildew (*Sclerophthora macrospora*), false blast and head blight (*Epicoccum nigrum*), and seedling blight (*Trichoderma viride, Rhizopus oryzae*);

Wheat Diseases:

powdery mildew (*Blumeria graminis*), fusarium blight (*Fusarium gaminearum, Fusarium avenaceum, Fusarium culmorum, Microdochium nivale*), stripe rust (*Puccinia striiformis*), stem rust (*Puccinia graminis*), leaf rust (*Puccinia recondita*), snow mould (*Micronectriella nivale, Microdochium majus*), *Typhula* snow blight (*Typhula incarnata, Typhula ishikariensis*), loose smut (*Ustilago tritici*), stinking smut (*Tilletia caries, Tilletia controversa*), eyespot (*Pseudocercosporella herpotrichoides*), *Septoria* leaf blotch (*Septoria tritici*), glume blotch (*Stagonospora nodorum*), tan spot (*Pyrenophora tritici-repentis*), *Rhizoctonia* seeding blight (*Rhizoctonia solani*), take-all disease (*Gaeumannomyces graminis*), and blast (*Pyricularia graminis-tritici*);

Barley Diseases:

powdery mildew (*Blumeria graminis*), fusarium head blight (*Fusarium gaminearum, Fusarium avenaceum, Fusarium culmorum, Microdochium nivale*), stripe rust (*Puccinia striiformis*), stem rust (*Puccinia graminis*), dwarf leaf rust (*Puccinia hordei*), loose smut (*Ustilago nuda*), scald (*Rhynchosporium secalis*), net blotch (*Pyrenophora teres*), spot blotch (*Cochliobolus sativus*), stripe (*Pyrenophora graminea*), *Ramularia* disease (*Ramularia collo-cygni*), and *Rhizoctonia* seeding blight (*Rhizoctonia solani*);

Corn Diseases:

rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), *Phaeosphaeria* leaf spot (*Phaeosphaeria maydis*), diplodia rot (*Stenocarpella maydis, Stenocarpella macrospora*), stalk rot (*Fusarium graminearum, Fusarium verticillioides, Colletotrichum graminicola*), smut (*Ustilago maydis*), and *Physoderma* brown spot and *Physoderma* stalk rot (*Physoderma maydis*);

Cotton Diseases:

anthracnose (*Colletotrichum gossypii*), grey mildew (*Ramularia areola*), *Alternaria* leaf spot (*Alternaria macrospora, Alternaria gossypii*), and black root rot (*Thielaviopsis basicola*);

Coffee Diseases:

rust (*Hemileia vastatrix*), and leaf spot (*Cercospora coffeicola*);

Rape Seed Diseases:

*Sclerotinia* rot (*Sclerotinia sclerotiorum*), gray leaf spot (*Alternaria brassicae*), root rot (*Phoma lingam*), and light leaf spot (*Pyrenopeziza brassicae*);

Sugar Cane Diseases:

rust (*Puccinia melanocephela, Puccinia kuehnii*), and smut (*Ustilago scitaminea*);

Sunflower Diseases:

rust (*Puccinia helianthi*), and downy mildew (*Plasmopara halstedii*);

Citrus Diseases:

melanose (*Diaporthe citri*), scab (*Elsinoe fawcetti*), green mold (*Penicillium digitatum*), blue mold (*Penicillium italicum*), *Phytophthora* rot (*Phytophthora parasitica, Phytophthora citrophthora*), and aspergillus rot (*Aspergillus niger*);

Apple Diseases:

blossom blight (*Monilinia mali*), *Valsa* canker (*Valsa ceratosperma*), powdery mildew (*Podosphaera leucotricha*), *Alternaria* leaf spot (*Alternaria alternata* apple pathotype), scab (*Venturia inaequalis*), bitter rot (*Glomerella cingulata, Colletotrichum acutatum*), blotch (*Diplocarpon mali*), ring rot (*Botryosphaeria berengeriana*), crown rot (*Phytophtora cactorum*), and rust (*Gymnosporangium juniperi-virginianae, Gymnosporangium yamadae*);

Pear Diseases:
  scab (*Venturia nashicola, Venturia pirina*), black spot (*Alternaria alternata* Japanese pear pathotype), and rust (*Gymnosporangium haraeanum*);
Peach Diseases:
  brown rot (*Monilinia fructicola*), scab (*Cladosporium carpophilum*), Phomopsis rot (*Phomopsis* sp., and leaf curl (*Taphrina deformans*);
Grapes Diseases:
  anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*);
Japanese Persimmon Diseases:
  anthracnose (*Gloeosporium kaki, Colletotrichum acutatum*), and leaf spot (*Cercospora kaki, Mycosphaerella nawae*);
Diseases of Gourd Family:
  anthracnose (*Colletotrichum lagenarium*), powdery mildew (*Sphaerotheca fuliginea*), gummy stem blight (*Didymella bryoniae*), *Corynespora* leaf spot (*Corynespora cassiicola*), fusarium wilt (*Fusarium oxysporum*), downy mildew (*Pseudoperonospora cubensis*), *Phytophthora* rot (*Phytophthora capsici*), and damping-off (*Pythium* sp.);
Tomato Diseases:
  early blight (*Alternaria solani*), leaf mold (*Cladosporium fulvum*), *Cercospora* leaf mold (*Pseudocercospora fuligena*), late blight (*Phytophthora infestans*), and powdery mildew (*Leveillula taurica*);
Eggplant Diseases:
  brown spot (*Phomopsis vexans*), and powdery mildew (*Erysiphe cichoracearum*);
Cruciferous Vegetables Diseases:
  *Alternaria* leaf spot (*Alternaria japonica*), white spot (*Cercosporella brassicae*), clubroot (*Plasmodiophora brassicae*), downy mildew (*Peronospora parasitica*), and white rust (*Albugo candida*);
Welsh Onion Disease:
  rust (*Puccinia allii*);
Soybean Diseases:
  purple stain (*Cercospora kikuchii*), sphaceloma scab (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, Colletotrichum truncatum*), *Rhizoctonia* rot (*Rhizoctonia solani*), *Septoria* brown spot (*Septoria glycines*), Cercospora leaf spot (*Cercospora sojina*), stem rot (*Sclerotinia sclerotiorum*), powdery mildew (*Microsphaera diffusa*), *Phytophthora* stem and root rot (*Phytophthora sojae*), downy mildew (*Peronospora manshurica*), sudden death syndrome (*Fusarium virguliforme*), red crown rot (*Calonectria ilicicola*), and *Diaporthe/Phomopsis* complex (*Diaporthe longicolla*);
Kidney Bean Diseases:
  stem rot (*Sclerotinia sclerotiorum*), rust (*Uromyces appendiculatus*), angular leaf spot (*Phaeoisariopsis griseola*), and anthracnose (*Colletotrichum lindemuthianum*), and *Fusarium* root-rot (*Fusarium solani*);
Peanut Diseases:
  leaf spot (*Cercospora personata*), brown leaf spot (*Cercospora arachidicola*), southern blight (*Sclerotium rolfsii*), and Cylindrocladium black rot (*Calonectria ilicicola*);
Garden Pea Disease:
  powdery mildew (*Erysiphe pisi*), and root rot (*Fusarium solani*);
Potato Diseases:
  early blight (*Alternaria solani*), late blight (*Phytophthora infestans*), Pink rot (*Phytophthora erythroseptica*), powdery scab (*Spongospora subterranea* f. sp. *subterranea*), *Verticillium* wilt (*Verticillium albo-atrum, Verticillium dahliae, Verticillium nigrescens*), dry rot (*Fusarium solani*), and potato wart (*Synchytrium endobioticum*);
Strawberry Disease:
  powdery mildew (*Sphaerotheca humuli*);
Tea Diseases:
  net blister blight (*Exobasidium reticulatum*), white scab (*Elsinoe leucospila*), gray blight (*Pestalotiopsis* sp.), and anthracnose (*Colletotrichum theae-sinensis*);
Tobacco Diseases:
  brown spot (*Alternaria longipes*), anthracnose (*Colletotrichum tabacum*), blue mold (*Peronospora tabacina*), and black shank (*Phytophthora nicotianae*);
Sugar Beet Diseases:
  *Cercospora* leaf spot (*Cercospora beticola*), leaf blight (*Thanatephorus cucumeris*), root rot (*Thanatephorus cucumeris*), and *Aphanomyces* root rot (*Aphanomyces cochlioides*), and rust (*Uromyces betae*);
Rose Diseases:
  black spot (*Diplocarpon rosae*), and powdery mildew (*Sphaerotheca pannosa*);
Chrysanthemum Diseases:
  leaf blight (*Septoria chrysanthemi-indici*), and white rust (*Puccinia horiana*);
Onion Diseases:
  *Botrytis* leaf blight (*Botrytis cinerea, Botrytis byssoidea, Botrytis squamosa*), gray-mold neck rot (*Botrytis allii*), and small sclerotial neck rot (*Botrytis squamosa*);
Various Crops Diseases:
  *Botrytis* rot (*Botrytis cinerea*), *Sclerotinia* rot (*Sclerotinia sclerotiorum*), seedling blight (*Pythium aphanidermatum, Pythium irregulare, Pythium ultimum*);
Japanese Radish Disease:
  *Alternaria* leaf spot (*Alternaria brassicicola*);
Turfgrass Diseases:
  dollar spot (*Sclerotinia homoeocarpa*), brown patch and large patch (*Rhizoctonia solani*), and *Pythium* blight (*Pythium aphanidermatum*);
Banana Disease:
  Sigatoka disease (*Mycosphaerella fijiensis, Mycosphaerella musicola*);
Lentils Disease:
  *Ascochyta* blight (*Ascochyta lentis*);
Chickpea Disease:
  *Ascochyta* blight (*Ascochyta rabiei*);
Green Pepper Disease:
  anthracnose (*Colletotrichum scovillei*);
Mango Disease:
  anthracnose (*Colletotrichum acutatum*);
Fruit Trees Diseases:
  white root rot (*Rosellinia necatrix*), and violet root rot (*Helicobasidium mompa*);
Postharvest Disease of Fruits (for Example, Apple and Pear):
  *Mucor* rot diseases (*Mucor piriformis*);
  Seed diseases or diseases in the early stages of the growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp. or *Diplodia* spp.; and the like;

Viral Diseases:

Lettuce big-vein disease transmitted by *Olpidium brassicae*, and viral diseases of several crops transmitted by *Polymixa* spp. (e.g. *Polymyxa betae* and *Polymyxa graminis*);

Diseases Caused by Bacteria:

bacterial seedling blight of rice (*Burkholderia plantarii*), bacterial spot of cucumber (*Pseudomonas syringae* pv. *Lachrymans*), bacterial wilt of eggplant (*Ralstonia solanacearum*), canker of citrus (*Xanthomonas citri*), bacterial soft rot of Chinese cabbage (*Erwinia carotovora*), scab of potato (*Streptomyces scabiei*), Goss's wilt of corn (*Clavibacter michiganensis*), Pierce's disease of grapes, olive and peach (*Xylella fastidiosa*), and crown gall of Rosacead plants such as apple, peach, cherries (*Agrobacterium tumefaciens*).

A method for controlling plant diseases of the present invention is conducted by applying each effective amount of the present compound, the present compound X, the compound of the present invention, the compound X of the present invention, or the composition A to a plant or soils. Examples of the application method include an application to stems and leaves, an application to soils, and an application to seeds.

The present compound, the present compound X, the compound of the present invention, the compound X of the present invention, or the composition A is mixed with a solid carrier, a liquid carrier and the like, and if necessary, adding surfactants and other auxiliary agents for formulation to formulate into emulsifiable concentrates, oil solutions, powders, granules, wettable powders, water dispersible powders, flowables, dry flowables, microcapsules and the others. These formulations comprise usually 0.1 to 99% by weight of the present compound, the present compound X, the compound of the present invention, the compound X of the present invention or the composition A.

Examples of the solid carrier include fine powders or granules such as clays (for example, kaolin clay, diatomaceous earth, bentonite, or acid white clay), dry process silica, wet process silica, talcs, ceramics, other inorganic minerals (for example, sericite, quartz, sulfur, active carbon, or calcium carbonate) as well as synthetic resins (for example, polyester resins such as polypropylene, polyacrylonitrile, polymethyl methacrylate and polyethylene terephthalate; nylon resins such as nylon-6, nylon-11 and nylon-66; polyamide resins; polyamide resins, polyvinyl chloride, polyvinylidene chloride, vinyl chloride-propylene copolymers, and the others).

Examples of the liquid carrier include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl ether, 1,4-dioxane, 1,2-dimethoxyethane, diethylene glycol dimethyl ether, diethylene glycol monomethyl ether, propylene glycol monomethyl ether, dipropylene glycol monomethyl ether, or 3-methoxy-3-methyl-1-butanol); amides (for example, DMF, or N,N-dimethylacetamide); sulfoxides (for example, DMSO); propylene carbonate; and vegetable oils (for example, soybean oil, or cottonseed oil).

Examples of the surfactant include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates. Specific examples thereof include Nimbus (Registered Trademark), Assist (Registered Trademark), Aureo (Registered Trademark), Iharol (Registered Trademark), Silwet L-77 (Registered Trademark), BreakThru (Registered Trademark), SundanceII (Registered Trademark), Induce (Registered Trademark), Penetrator (Registered Trademark), AgriDex (Registered Trademark), Lutensol A8 (Registered Trademark), NP-7 (Registered Trademark), Triton (Registered Trademark), Nufilm (Registered Trademark), Emulgator NP7 (Registered Trademark), Emulad (Registered Trademark), TRITON X 45 (Registered Trademark), AGRAL 90 (Registered Trademark), AGROTIN (Registered Trademark), ARPON (Registered Trademark), EnSpray N (Registered Trademark), and BANOLE (Registered Trademark) and the others.

Examples of other auxiliary agent for formulation include a binder, a dispersant, a colorant, and a stabilizer, and specific examples include casein, gelatin, polysaccharides (for example, starch, gum arabic, cellulose derivatives, and alginic acid), lignin derivatives, bentonite, water-soluble synthetic polymers (for example, polyvinyl alcohol, polyvinyl pyrrolidone, and polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

As used herein, examples of the plant include whole plant, and special parts of the plant, and includes, for example, stem and leaf, flower, ear, fruit, tree stem, branch, crown, seed, vegetative reproductive organ, and seedling.

The vegetative reproductive organ represents a part of plant such as root, stem and leaf, which has a growth capacity if the part is cut off from its plant and then placed in the soil. Examples of the vegetative reproductive organ include tuberous root, creeping root, bulb, corm or solid bulb, tuber, rhizome, stolon, rhizophore, cane cuttings, propagule, and vine cutting. The "stolon" is often referred to as "runner", and the "propagule" is often referred to as "brood bud", which is divided into broad bud and bulbil. The vine cutting represents a shoot (which is a generic name of leaf and stem) of sweet potato (*Ipomoea batatas*) and Japanese yam (*Dioscorea japonica*), etc. The bulb, corm or solid bulb, tuber, rhizome, cane cuttings, rhizophore, and tuberous root are also collectively referred to as "bulb". For example, when the cultivation of potato starts with planting tubers in the soil, the used tuber is generally referred to as "seed potato".

Examples of the application to seeds (or seed treatments) include an application of the present compound, the present compound X, the compound of the present invention, the compound X of the present invention, or the composition A to seeds or vegetative reproductive organs, and specific examples thereof include spraying treatment in which a suspension of the present compound, the present compound X, the compound of the present invention, the compound X of the present invention, or the composition A is sprayed onto seed surface or the vegetative reproductive organ surface in the form of mist; smearing treatment in which the present compound, the present compound X, the compound of the present invention, the compound X of the present invention, or the composition A is coated a surface of seeds or the vegetative reproductive organ; a soaking treatment in which the seeds are soaked into the solution of the present compound, the present compound X, the compound of the present invention, the compound X of the present invention, or the composition A for a certain time; and a method for coating the seeds or the vegetative reproductive organ with a carrier containing the present compound, the present compound X, the compound of the present invention, the compound X of the present invention, or the composition A (film coating treatment, pellet coating treatment). Examples of the above-described vegetative reproductive organ include particularly seed potato.

When the composition A is applied to seeds or vegetative reproductive organs, the composition A may be also applied to seeds or vegetative reproductive organs as a single formulation, or the composition A may be applied to seeds or vegetative reproductive organs as a divided plural of formulations by a plurality of times. Examples of the method in which the composition A is applied as a divided plural of formulations by a plurality of times include, for example, a method in which the formulations comprising as an active component the present compound X only are applied, and seeds or vegetative reproductive organs are air dried, followed by applying the formulations comprising the present ingredient: and a method in which the formulations comprising as an active component the present compound X and the present ingredients are applied, and seeds or vegetative reproductive organs are air dried, followed by applying the formulations comprising the present ingredients other than the already-applied present ingredients, are included.

As used herein, seeds or vegetative reproductive organs carrying the present compound, the present compound X, the compound of the present invention, the compound X of the present invention, or the composition A means seeds or vegetative reproductive organs in the state where the present compound, the present compound X, the compound of the present invention, the compound X of the present invention, or the composition A is adhered to a surface of the seeds or the vegetative reproductive organ. The above-described seeds or vegetative reproductive organs carrying the present compound, the present compound X, the compound of the present invention, the compound X of the present invention, or the composition A may be adhered by any other materials that are different from the present compound, the present compound X, the compound of the present invention, the compound X of the present invention or the composition A before or after being adhered the present compound, the present compound X, the compound of the present invention, the compound X of the present invention, or the composition A to the seeds or vegetative reproductive organs.

Also, when the composition A is adhered in a form of layer(s) to a surface of seeds or vegetative reproductive organ, the layer(s) is/are composed of one layer or a plural of layers. Also, when a plural layers are formed, each of the layer may be composed of a layer comprising one or more active ingredients, or a combination of a layer comprising one or more active ingredients and a layer not comprising an active ingredient.

Seeds or vegetative reproductive organs carrying the present compound, the present compound X, the compound of the present invention, the compound X of the present invention, or the composition A can be obtained, for example, by applying the formulations comprising the present compound, the present compound X, the compound of the present invention, the compound X of the present invention, or the composition A by the above-described application method to seeds to seeds or vegetative reproductive organs.

The application dose of the present compound, the present compound X, the compound of the present invention, the compound X of the present invention, or the composition A may be varied depending on a climate condition, a formulation form, an application period, an application method, an application site, plant diseases to be controlled, plant to be applied, and the others, and in the cases where they are applied to stems and leaves or soils, the application dose thereof is usually within a range of usually 1 to 500 g per 1,000 m$^2$. In the case of being applied to seeds, the dose of application dose of the present compound, the present compound X, the compound of the present invention, the compound X of the present invention, or the composition A is usually within a range of 0.001 to 100 g per 1 Kg of seeds. When the present compound, the present compound X, the compound of the present invention, the compound X of the present invention, or the composition A is formulated into an emulsifiable concentrate, a wettable powder or a flowable etc., they are usually applied by diluting them with water so as to make an effective concentration of the active ingredients 0.01 to 10000 ppm, and the dust formulation or the granular formulation, etc., is usually applied as itself without diluting them.

The present compound, the present compound X, the compound of the present invention, the compound X of the present invention, or the composition A can be used as an agent for controlling plant diseases in the agricultural land such as field, paddy, lawn and orchard. Examples of the plants include the followings.

Crops:
    corn, rice, wheat, barley, rye, oat, sorghum, cotton, soybean, peanut, buckwheat, beet, rapeseed, sunflower, sugarcane, tobacco, and the others;

Vegetables:
    solanaceous vegetables (for example, eggplant, tomato, green pepper, hot pepper, and potato),
    cucurbitaceous vegetables (for example, cucumber, pumpkin, zucchini, water melon, and melon),
    cruciferous vegetables (for example, Japanese radish, white turnip, horseradish, kohlrabi, Chinese cabbage, cabbage, leaf mustard, broccoli, and cauliflower),
    asteraceous vegetables (for example, burdock, crown daisy, artichoke, and lettuce),
    liliaceous vegetables (for example, green onion, onion, garlic, and asparagus),
    ammiaceous vegetables (for example, carrot, parsley, celery, and parsnip),
    chenopodiaceous vegetables (for example, spinach and Swiss chard),
    lamiaceous vegetables (for example, *Perilla frutescens*, mint, and basil),
    strawberry, sweet potato, *Dioscorea japonica*, colocasia, flowering plants, Fruits:
    pomaceous fruits (for example, apple, pear, Japanese pear, Chinese quince, and quince),
    stone fleshy fruits (for example, peach, plum, nectarine, Prunus mume, cherry fruit, apricot, and prune),
    citrus fruits (for example, citrus unshiu, orange, lemon, lime, and grapefruit),
    nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, tea, mulberry, floage plants, forest plants, turfs, and pastures.

The above-described plants encompass genetically modified crops.

EXAMPLES

Hereinafter, the present invention is explained in more detail by using Preparation examples, Reference preparation examples, Formulation examples, and Test examples, however, the present invention should not be limited to these examples.

As used herein, "Me" represents a methyl group, "Et" represents an ethyl group, "Pr" represents a propyl group, "i-Pr" represents an isopropyl group, "c-Pr" represents a cyclopropyl group, "Bu" represents a butyl group, "Ph" represents a phenyl group, "Bn" represents a benzyl group, and "•" represents a biding site. When Ph has a substituent, the substituent is written with its substituted position before the symbol. For example, "2-CN-Ph" represents a 2-cyanophenyl group, and "3,4-F2-Ph" represents a 3,4-difluorophenyl group.

Preparation examples of the present compound X (including the present compound, the compound X of the present invention, and the compound of the present invention) is described.

Reference Preparation Example 1

A mixture of 1-(4-butylphenyl)ethane-1-one 4.0 g, N,N-dimethyl formamide dimethyl acetal 5.0 mL, and DMF 5 mL was stirred under reflux for 4 hours. The resulting mixtures were concentrated under reduced pressure. To the resulting solids were added ethanol 5 ml and hydrazine monohydrate 1.87 g successively, and the mixtures were stirred at 60° C. for 4 hours. The resulting mixtures were concentrated under reduced pressure. The resulting residues were subjected to silica gel column chromatography to give an intermediate compound 1-6 represented by the following formula 4.2 g.

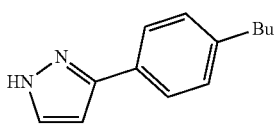

Intermediate compound 1-6: $^1$H-NMR (CDCl$_3$) δ: 2.65 (2H, d), 7.61 (1H, d), 7.23 (2H, d), 6.58 (1H, d), 2.64 (2H, t), 1.66-1.58 (2H, n), 1.42-1.33 (2H, m), 0.94 (3H, t).

Reference Preparation Example 1-1

The compounds that were prepared according to the Reference preparation example 1 and their physical properties are indicated below.

A compound represented by formula (rE1):

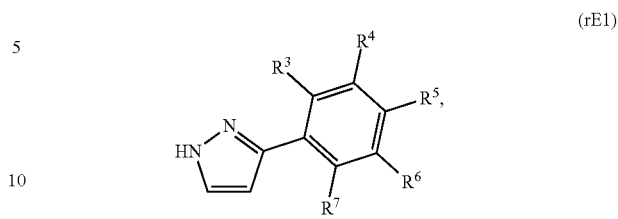

wherein R$^3$, R$^4$, R$^5$, R$^6$ and R$^7$ represents any combination that are indicated in [Table rE1] or [Table rE2].

TABLE rE1

[Table 1]

| intermediate compound | R$^3$ | R$^4$ | R$^5$ | R$^6$ | R$^7$ |
|---|---|---|---|---|---|
| 1-1 | H | H | c-Pr | H | H |
| 1-2 | Cl | Cl | Cl | H | H |
| 1-3 | H | Me | Cl | H | H |
| 1-4 | H | Me | Me | H | H |
| 1-5 | H | H | i-Pr | H | H |
| 1-7 | H | H | I | H | H |
| 1-8 | H | CF$_3$ | Cl | H | H |
| 1-9 | H | Cl | Me | H | H |
| 1-10 | H | NO$_2$ | Cl | H | H |
| 1-11 | H | CF$_3$ | F | H | H |
| 1-12 | H | F | F | F | H |
| 1-13 | H | Cl | F | H | H |
| 1-14 | H | F | CF$_3$ | H | H |
| 1-15 | H | F | Cl | H | H |

Intermediate compound 1-1: $^1$H-NMR (CDCl$_3$) δ: 7.63-7.61 (3H, m), 7.14-7.10 (2H, m), 6.57 (1H, d), 1.96-1.89 (1H, m), 1.02-0.97 (2H, m), 0.75-0.71 (2H, m).

Intermediate compound 1-2: $^1$H-NMR (CDCl$_3$) δ: 7.66 (1H, d), 7.58 (1H, d), 7.43 (1H, d), 6.78 (1H, d).

Intermediate compound 1-3: $^1$H-NMR (CDCl$_3$) δ: 7.63 (1H, s), 7.61 (1H, d), 7.51 (1H, d), 7.35 (1H, d), 6.59 (1H, d), 2.40 (3H, s).

Intermediate compound 1-4: $^1$H-NMR (CDCl$_3$) δ: 7.60 (1H, d), 7.52 (1H, s), 7.46 (1H, d), 7.16 (1H, d), 6.57 (1H, d), 2.29 (6H, s).

Intermediate compound 1-5: $^1$H-NMR (CDCl$_3$) δ: 7.66 (2H, d), 7.61 (1H, d), 7.29 (2H, d), 6.58 (1H, d), 2.94 (1H, m), 1.28 (6H, d).

Intermediate compound 1-7: $^1$H-NMR (CDCl$_3$) b: 7.76-7.73 (2H, m), 7.62 (1H, d), 7.53 (2H, d), 6.62 (1H, d).

Intermediate compound 1-9: $^1$H-NMR (CDCl$_3$) δ: 7.76 (1H, d), 7.62 (1H, d), 7.55 (1H, dd), 7.27-7.25 (1H, m), 6.59 (1H, d), 2.40 (3H, s).

Intermediate compound 1-10: $^1$H-NMR (CDCl$_3$) δ: 10.77 (1H, br s), 8.31 (1H, d), 7.95 (1H, dd), 7.67 (1H, d), 7.57 (1H, d), 6.68 (1H, d).

Intermediate compound 1-11: $^1$H-NMR (CDCl$_3$) δ: 8.05 (1H, d), 7.99-7.96 (1H, m), 7.65 (1H, d), 7.27-7.22 (1H, m), 6.64 (1H, d).

Intermediate compound 1-12: $^1$H-NMR (CDCl$_3$) δ: 10.3 (1H, br s), 7.63 (1H, d), 7.47-7.39 (2H, m), 6.58 (1H, d).

Intermediate compound 1-13: $^1$H-NMR (CDCl$_3$) δ: 7.83 (1H, dd), 7.66-7.61 (2H, m), 7.17 (1H, t), 6.58 (1H, d).

Intermediate compound 1-14: $^1$H-NMR (CDCl$_3$) δ: 10.56 (1H, br s), 7.68-7.61 (4H, m), 6.69 (1H, d).

Intermediate compound 1-15: $^1$H-NMR (CDCl$_3$) δ: 11.20 (1H, br s), 7.62 (1H, d), 7.57 (1H, dd), 7.50 (1H, dd), 7.41 (1H, t), 6.61 (1H, d).

TABLE rE2

[Table 2]

| intermediate compound | R³ | R⁴ | R⁵ | R⁶ | R⁷ |
|---|---|---|---|---|---|
| 1-16 | H | F | Me | H | H |
| 1-17 | H | Me | F | H | H |
| 1-18 | F | F | F | H | H |
| 1-19 | H | Me | Br | H | H |
| 1-20 | H | NO₂ | Br | H | H |
| 1-21 | H | NO₂ | Me | H | H |
| 1-22 | H | Cl | Br | H | H |
| 1-23 | H | F | Br | H | H |
| 1-24 | H | Br | F | H | H |
| 1-25 | H | F | Br | F | H |
| 1-26 | H | F | CF₃ | F | H |
| 1-27 | H | F | Cl | F | H |
| 1-28 | H | F | Me | F | H |
| 1-29 | H | F | I | F | H |
| 1-30 | H | Br | Br | H | H |
| 1-31 | H | CF₃ | Br | H | H |
| 1-32 | H | I | Br | H | H |
| 1-33 | H | CO₂Me | Br | H | H |
| 1-34 | H | OMe | Br | H | H |
| 1-35 | H | CN | Br | H | H |
| 1-36 | H | CONHc-Pr | H | H | H |
| 1-37 | H | NHCOPh | H | H | H |
| 1-38 | H | CONHPh | H | H | H |
| 1-39 | H | OCH₂Ph | H | H | H |
| 1-40 | H | H | SPh | H | H |
| 1-41 | H | H | NO₂ | H | H |
| 1-42 | H | NO₂ | H | H | H |
| 1-43 | H | OMe | H | H | H |
| 1-44 | H | CF₃ | H | H | H |
| 1-45 | H | Br | H | H | H |
| 1-46 | H | Et | H | H | H |
| 1-47 | H | F | H | H | H |
| 1-48 | H | OC₆H₅ | H | H | H |
| 1-51 | H | OCH₂Ph | Br | H | H |

Intermediate compound 1-16: ¹H-NMR (CDCl₃) δ: 10.86 (1H, br s), 7.61 (1H, d), 7.44-7.40 (2H, m), 7.21 (1H, t), 6.58 (1H, d), 2.30 (3H, d).

Intermediate compound 1-17: ¹H-NMR (CDCl₃) δ: 11.89 (1H, br s), 7.57 (2H, dd), 7.53-7.49 (1H, m), 7.00 (1H, t), 6.54 (1H, d), 2.28 (3H, d).

Intermediate compound 1-18: ¹H-NMR (CDCl₃) δ: 7.66-7.60 (2H, m), 7.06-6.99 (1H, m), 6.74 (1H, t).

Intermediate compound 1-19: ¹H-NMR (CDCl₃) δ: 7.63 (1H, d), 7.43 (1H, m), 7.38-7.33 (2H, m), 6.45 (1H, d), 2.42 (3H, s).

Intermediate compound 1-20: ¹H-NMR (CDCl₃) δ: 8.28 (1H, d), 7.88 (1H, dd), 7.76 (1H, d), 7.67 (1H, d), 6.69 (1H, d).

Intermediate compound 1-21: ¹H-NMR (CDCl₃) δ: 8.39 (1H, d), 7.95 (1H, dd), 7.66 (1H, d), 7.39 (1H, d), 6.69 (1H, d), 2.63 (3H, s).

Intermediate compound 1-22: ¹H-NMR (CDCl₃) δ: 7.91 (1H, d), 7.66-7.63 (2H, m), 7.56 (1H, dd), 6.63 (1H, d).

Intermediate compound 1-23: ¹H-NMR (CDCl₃) δ: 7.63 (1H, d), 7.60-7.56 (2H, m), 7.47 (1H, dd), 6.62 (1H, d).

Intermediate compound 1-24: ¹H-NMR (CDCl₃) δ: 8.00 (1H, dd), 7.73-7.69 (1H, m), 7.63 (1H, d), 7.16 (1H, t), 6.59 (1H, d).

Intermediate compound 1-25: ¹H-NMR (CDCl₃) δ: 7.64 (1H, d), 7.44-7.40 (2H, m), 6.63 (1H, d).

Intermediate compound 1-26: ¹H-NMR (CDCl₃) δ: 10.32 (1H, br s), 7.67 (1H, d), 7.46 (2H, d), 6.68 (1H, d).

Intermediate compound 1-27: ¹H-NMR (CDCl₃) δ: 10.19 (1H, br s), 7.64 (1H, d), 7.46-7.41 (2H, m), 6.62 (1H, d).

Intermediate compound 1-28: ¹H-NMR (CDCl₃) δ: 10.36 (1H, br s), 7.62 (1H, dd), 7.28 (2H, d), 6.59 (1H, d), 2.21 (3H, s).

Intermediate compound 1-29: ¹H-NMR (CDCl₃) δ: 10.66 (1H, br s), 7.65 (1H, d), 7.38-7.31 (2H, m), 6.64 (1H, d).

Intermediate compound 1-30: ¹H-NMR (CDCl₃) δ: 8.08 (1H, d), 7.66-7.59 (3H, m), 6.63 (1H, d).

Intermediate compound 1-31: ¹H-NMR (CDCl₃) δ: 8.14 (1H, d), 7.82 (1H, dd), 7.75 (1H, d), 7.66 (1H, d), 6.68 (1H, d).

Intermediate compound 1-32: ¹H-NMR (CDCl₃) δ: 8.31 (1H, s), 7.64 (3H, dd), 6.62 (1H, d).

Intermediate compound 1-33: ¹H-NMR (CDCl₃) δ: 8.23 (1H, d), 7.79-7.64 (4H, m), 6.67 (1H, d), 3.97 (3H, d).

Intermediate compound 1-34: ¹H-NMR (CDCl₃) δ: 7.97 (1H, d), 7.69 (1H, dd), 7.61 (1H, d), 6.95 (1H, d), 6.56 (1H, d), 3.94 (3H, s).

Intermediate compound 1-35: ¹H-NMR (CDCl₃) δ: 8.11 (1H, d), 7.90 (1H, dd), 7.72 (1H, d), 7.66 (1H, d), 6.66 (1H, d).

Intermediate compound 1-36: ¹H-NMR (DMSO-D₆) δ: 8.60 (1H, d), 8.23 (1H, s), 8.21 (1H, br s), 7.94 (1H, s), 7.76-7.71 (2H, m), 7.50 (1H, t), 6.78 (1H, d), 2.89-2.84 (1H, m), 0.76-0.72 (2H, m), 0.62-0.58 (2H, m).

Intermediate compound 1-37: ¹H-NMR (DMSO-D₆) δ: 8.21 (1H, s), 8.03-7.97 (3H, m), 7.74-7.68 (2H, m), 7.64-7.52 (4H, m), 7.41 (1H, dd), 6.67 (1H, d), 6.36 (1H, s).

Intermediate compound 1-38: ¹H-NMR (DMSO-D₆) δ: 10.34 (1H, s), 8.37 (1H, s), 8.32 (1H, s), 8.02 (1H, s), 7.87-7.84 (2H, m), 7.81-7.79 (2H, m), 7.56 (1H, t), 7.38-7.36 (214, m), 7.11 (1H, t), 6.83 (1H, s).

Intermediate compound 1-39: ¹H-NMR (CDCl₃) δ: 8.02 (1H, s), 7.62 (1H, br s), 7.47-7.31 (7H, m), 6.97-6.94 (1H, m), 6.62 (1H, br s), 5.12 (2H, s).

Intermediate compound 1-40: ¹H-NMR (CDCl₃) δ: 7.71 (2H, d), 7.62 (1H, d), 7.40-7.36 (4H, m), 7.34-7.24 (3H, m), 6.61 (1H, d).

Intermediate compound 1-41: ¹H-NMR (CDCl₃) δ: 10.31 (1H, br s), 8.31-8.27 (2H, m), 7.99 (2H, d), 7.69 (1H, d), 6.76 (1H, d).

Intermediate compound 1-42: ¹H-NMR (CDCl₃) δ: 8.66 (1H, s), 8.19-8.16 (2H, m), 7.69 (1H, d), 7.59 (1H, t), 6.75 (1H, d).

Intermediate compound 1-43: ¹H-NMR (CDCl₃) δ: 7.62 (1H, d), 7.34-7.32 (3H, m), 6.91-6.88 (1H, m), 6.62 (1H, d), 3.87 (3H, s).

Intermediate compound 1-44: ¹H-NMR (CDCl₃) δ: 8.07 (1H, s), 7.98 (1H, d), 7.66 (1H, s), 7.59-7.52 (2H, m), 6.70 (1H, s).

Intermediate compound 1-45: ¹H-NMR (CDCl₃) δ: 7.95 (1H, s), 7.72 (1H, d), 7.63 (1H, d), 7.46 (1H, d), 7.30 (1H, d), 6.63 (1H, d).

Intermediate compound 1-46: ¹H-NMR (CDCl₃) δ: 7.62-7.54 (3H, m), 7.34 (1H, t), 7.18 (1H, d), 6.62 (1H, s), 2.70 (2H, q), 1.28 (3H, t).

Intermediate compound 1-47: ¹H-NMR (CDCl₃) δ: 7.63 (1H, d), 7.56 (1H, d), 7.50 (1H, d), 7.41-7.35 (1H, m), 7.05-7.00 (1H, m), 6.63 (1H, d).

Intermediate compound 1-48: ¹H-NMR (CDCl₃) δ: 7.60 (1H, d), 7.51 (1H, d), 7.43 (1H, s), 7.40-7.33 (3H, m), 7.11 (1H, t), 7.05 (2H, d), 6.98 (1H, dd), 6.59 (1H, d).

Intermediate compound 1-51: ¹H-NMR (CDCl₃) δ: 7.99 (1H, s), 7.64 (1H, d), 7.60 (1H, d), 7.49 (2H, d), 7.40 (2H, t), 7.34-7.29 (1H, m), 6.98 (1H, d), 6.55 (1H, d), 5.20 (2H, s).

Reference Preparation Example 2

The compounds that were prepared according to the Reference preparation example 1 and their physical properties are indicated below.

A compound represented by formula (rE2):

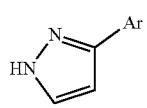

(rE2)

Wherein Ar represents any group indicated in [Table rE3].

TABLE 30

Table rE3

| intermediate compound | Ar |
|---|---|
| 2-1 | indane group |
| 2-2 | 2,2-difluoro-1,3-benzodioxole group |
| 2-3 | 2,3-dihydrobenzofuran group |
| 2-4 | benzo[c][1,2,5]oxadiazole group |
| 2-5 | benzothiazole group |

Intermediate compound 2-1: $^1$H-NMR (CDCl$_3$) δ: 7.59 (2H, d), 7.51 (1H, d), 7.24 (1H, d), 6.56 (1H, d), 2.94-2.89 (4H, m), 2.13-2.05 (2H, m).

Intermediate compound 2-2: $^1$H-NMR (CDCl$_3$) δ: 10.81 (1H, br s), 7.61 (1H, d), 7.51-7.48 (2H, m), 7.08 (1H, d), 6.57 (1H, d).

Intermediate compound 2-3: $^1$H-NMR (CDCl$_3$) δ: 7.59-7.58 (2H, m), 7.49-7.47 (1H, m), 6.82 (1H, d), 6.50 (1H, d), 4.60 (2H, t), 3.23 (2H, t).

Intermediate compound 2-4: $^1$H-NMR (DMSO-D6) δ: 8.37 (1H, d), 8.24 (1H, d), 8.10 (1H, d), 7.90 (1H, s), 7.08 (1H, d).

Intermediate compound 2-5: $^1$H-NMR (CDCl$_3$) δ: 8.99 (1H, s), 8.37 (1H, d), 8.15 (1H, dd), 7.95 (1H, dd), 7.66 (1H, d), 6.70 (1H, d).

Reference Preparation Example 3

A mixture of benzothiazol-6-carboxylic acid 5.0 g, thionyl chloride 50 mL, a catalyst amount of DMF was stirred under reflux for 3 hours. The resulting mixture was concentrated under reduced pressure. To the resulting residue were added THF 55 mL and triethylamine 6.5 g successively, and the mixtures were stirred. To the resulting mixtures was added N,O-dimethylhydroxylamine hydrochloride 3.1 g at 0° C., and the mixtures were stirred at room temperature for 18 hours. To the resulting mixtures was added 2M hydrochloric acid, and the mixtures were extracted with ethyl acetate. The resulting organic layers were washed with saturated sodium bicarbonate aqueous solution and brine, and dried over magnesium sulfate, and concentrated under reduced pressure to obtain an intermediate compound 3-1 represented by below-mentioned formula 3.47 g.

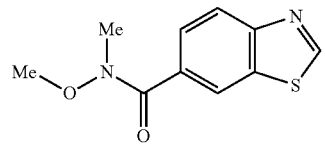 [SMILES: CON(C)C(=O)c1ccc2ncsc2c1]

Intermediate compound 3-1: $^1$H-NMR (CDCl$_3$) δ: 9.10 (1H, s), 8.36 (1H, d), 8.16 (1H, d), 7.87 (1H, dd), 3.56 (3H, s), 3.42 (3H, s).

Reference Preparation Example 3-1

The compounds that were prepared according to the Reference preparation example 3 and their physical properties are indicated below.

A compound represented by formula (rE3):

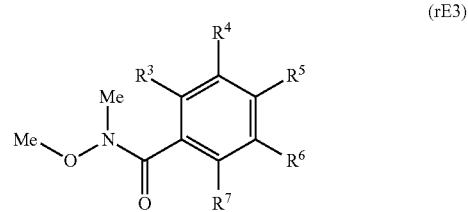

(rE3)

wherein $R^3$, $R^4$, $R^5$, $R^6$ and $R^7$ represents any combination indicated in [Table rE4].

TABLE rE4

[Table 4]

| intermediate compound | $R^3$ | $R^4$ | $R^5$ | $R^6$ | $R^7$ |
|---|---|---|---|---|---|
| 3-2 | H | F | CF$_3$ | F | H |
| 3-3 | H | F | Cl | F | H |
| 3-4 | H | F | Me | F | H |

Intermediate compound 3-2: $^1$H-NMR (CDCl$_3$) δ: 7.36 (2H, d), 3.58 (3H, s), 3.38 (3H, s).

Intermediate compound 3-3: $^1$H-NMR (CDCl$_3$) δ: 7.42-7.38 (2H, m), 3.57 (3H, s), 3.37 (3H, s).

Intermediate compound 3-4: $^1$H-NMR (CDCl$_3$) δ: 7.28-7.22 (2H, m), 3.57 (3H, s), 3.36 (3H, s), 2.23 (3H, t).

Reference Preparation Example 4

To a mixture of the intermediate compound 3-1 3.47 g and THF 21 mL was added dropwise methyl magnesium bromide 18 ml, (1M, THF solution) at 0° C., and the mixtures were stirred at room temperature for 2 hours. To the resulting mixtures was added aqueous ammonium chloride solution, and the mixtures were extracted with ethyl acetate. The resulting organic layers were washed with brine, dried over magnesium sulfate, and concentrated under reduced pressure. The resulting residues were subjected to silica gel column chromatography to obtain an intermediate compound 4-1 represented by below-mentioned formula 1.69 g.

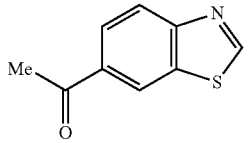 [SMILES: CC(=O)c1ccc2ncsc2c1]

Intermediate compound 4-1: $^1$H-NMR (CDCl$_3$) δ: 9.17 (1H, s), 8.62 (1H, d), 8.20 (1H, d), 8.12 (1H, dd), 2.71 (3H, s).

Reference Preparation Example 4-2

The compounds that were prepared according to the Reference preparation example 4 and their physical properties are indicated below.

A compound represented by formula (rE4)

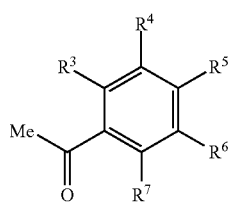

wherein R$^3$, R$^4$, R$^5$, R$^6$ and R$^7$ represents any combination indicated in [Table rE5].

TABLE rE5

| [Table 5] | | | | | |
|---|---|---|---|---|---|
| intermediate compound | R$^3$ | R$^4$ | R$^5$ | R$^6$ | R$^7$ |
| 4-2 | H | F | CF$_3$ | F | H |
| 4-3 | H | F | Cl | F | H |
| 4-4 | H | F | Me | F | H |

Intermediate compound 4-2: $^1$H-NMR (CDCl$_3$) δ: 7.56 (2H, d), 2.62 (3H, s).
Intermediate compound 4-3: $^1$H-NMR (CDCl$_3$) δ: 7.59-7.54 (2H, m), 2.59 (3H, s).
Intermediate compound 4-4: $^1$H-NMR (CDCl$_3$) δ: 7.46-7.40 (2H, m), 2.57 (3H, s), 2.26 (3H, t).

Reference Preparation Example 5

A mixture of 5-bromo-1,1-dimethyl-1,3-dihydro-2-benzofuran 1.60 g, bis(pinacolato)dibolon 1.65 g, [1,1'-bis(diphenylphosphino)ferrocene]palladium (II) dichloride 0.73 g, potassium acetate 1.47 g, and DMSO 20 mL was stirred at 90° C. for 5 hours. To the resulting mixtures was added water, and the mixtures were extracted with ethyl acetate. The resulting organic layers were washed with brine, dried over magnesium sulfate, and concentrated under reduced pressure. The resulting residues were subjected to silica gel column chromatography to obtain an intermediate compound 5-1 represented by the below-mentioned formula 0.85 g.

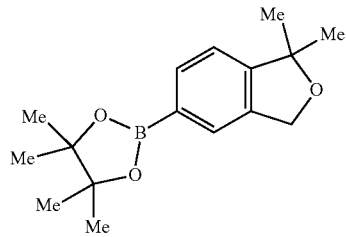 [SMILES: CC1(C)OCc2cc(B3OC(C)(C)C(C)(C)O3)ccc21]

Intermediate compound 5-1: $^1$H-NMR (CDCl$_3$) δ: 7.74 (1H, d), 7.66 (1H, s), 7.14 (1H, d), 5.06 (2H, s), 1.49 (6H, s), 1.34 (12H, s).

Reference Preparation Example 6

The compounds that were prepared according to the Preparation example 1 and their physical properties are indicated below.

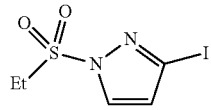 [SMILES: CCS(=O)(=O)n1ccc(I)n1]

Intermediate compound 6-1: $^1$H-NMR (CDCl$_3$) δ: 7.85 (1H, d), 6.61 (1H, d), 3.54 (2H, q), 1.28 (3H, t).

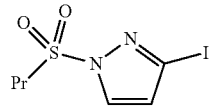

Intermediate compound 6-2: $^1$H-NMR (CDCl$_3$) δ: 7.85 (1H, d), 6.60 (1H, d), 3.49-3.45 (2H, m), 1.79-1.69 (2H, m), 1.03 (3H, t).

Reference Preparation Example 7

To a mixture of 3-(4,4,5,5-tetramethyl-1,3,2-dioxaborolan-2-yl)-1H-pyrazole 1.2 g, triethylamine 0.84 mL, and THF 10 mL was added dropwise ethanesulfonyl chloride 1.64 mL at 0° C., and the mixtures were stirred at room temperature for 3 hours. To the resulting mixtures was added water, and the mixtures were extracted with ethyl acetate, and the resulting organic layers were dried over sodium sulfate, and concentrated under reduced pressure. The resulting residues were subjected to silica gel column chromatography to obtain an intermediate compound 7-1 represented by the below-mentioned formula 1.1 g.

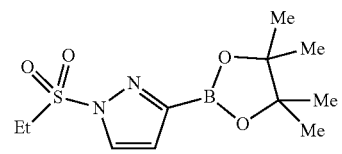 [SMILES: CCS(=O)(=O)n1ccc(B2OC(C)(C)C(C)(C)O2)n1]

Intermediate compound 7-1: $^1$H-NMR (CDCl$_3$) δ: 8.08 (1H, d), 6.77 (1H, d), 3.59 (2H, q), 1.37 (12H, s), 1.23 (3H, t).

Reference Preparation Example 7-1

The compounds that were prepared according to the Reference Preparation example 7 and their physical properties are indicated below.

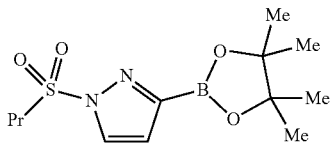

Intermediate compound 7-2: ¹H-NMR (CDCl₃) b: 8.07 (1H, d), 6.76 (1H, d), 3.54-3.50 (2H, m), 1.75-1.65 (2H, m), 1.37 (12H, s), 1.00 (3H, t).

Reference Preparation Example 8

To a mixture of 3-[3-(benzyloxy)phenyl]-1H-pyrazole 1 g, triethylamine 1.12 mL, and tetrahydrofuran 10 mL was added dropwise 0.45 mL at 0° C., and the mixtures were stirred at room temperature for 3 hours. To the resulting mixtures was added water, and the mixtures were extracted with ethyl acetate, and the resulting organic layers were concentrated under reduced pressure. The resulting residues were subjected to silica gel column chromatography to obtain 3-(3-(benzyloxy)phenyl)-1-[ethylsulfonyl]-1H-pyrazole 1.3 g. Then, a mixture of 3-{3-(benzyloxy)phenyl}-1-{ethylsulfonyl}-1H-pyrazole 1.3 g, palladium-carbon 0.16 g, and ethanol 10 mL was heated to 40° C. under hydrogen atmosphere, and the mixtures were stirred for 10 hours. The resulting mixtures were filtered through Celite (Registered Trademark) and concentrated to obtain an intermediate compound 1-49 represented by the below-mentioned formula 1.1 g.

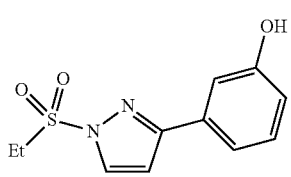

Intermediate compound 1-49: ¹H-NMR (CDCl₃) δ: 8.07 (1H, d), 7.42-7.40 (2H, m), 7.31 (1H, t), 6.90-6.87 (1H, m), 6.74 (1H, d), 3.55 (2H, q), 1.29 (3H, t).

Reference Preparation Example 9

The compounds that were prepared according to the Reference Preparation example 8 and their physical properties are indicated below.

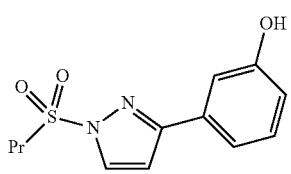

Intermediate compound 1-50: ¹H-NMR (CDCl₃) δ: 8.05 (1H, d), 7.41-7.39 (2H, m), 7.31 (1H, t), 6.91-6.88 (1H, m), 6.73 (1H, d), 5.36 (1H, br s), 3.51-3.47 (2H, m), 1.78-1.73 (2H, m), 1.02 (3H, t).

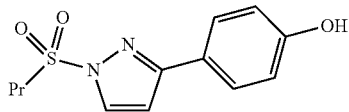

Intermediate compound 1-52: ¹H-NMR (CDCl₃) δ: 8.03 (1H, d), 7.78 (1H, t), 7.76 (1H, t), 6.91 (1H, t), 6.88 (1H, t), 6.68 (1H, d), 4.93 (1H, br s), 3.50-3.46 (2H, m), 1.80-1.70 (2H, m), 1.02 (3H, t).

Reference Preparation Example 10

To a mixture of 1-(3,5-difluorophenyl)ethan-1-one 1.6 g, ethylene glycol 2.3 mL and toluene 20 mL was added p-toluene sulfonic acid monohydrate 0.2 g, and the mixture was stirred at 110° C. for 8 hours. To the resulting mixtures was added saturated sodium bicarbonate aqueous solution, and the mixtures were extracted with ethyl acetate. The resulting organic layers were dried over magnesium sulfate, and concentrated under reduced pressure. The resulting residues were subjected to silica gel column chromatography to obtain an intermediate compound 9 represented by the below-mentioned formula 1.8 g.

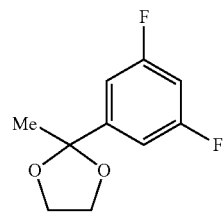 [SMILES: CC1(c2cc(F)cc(F)c2)OCCO1]

Intermediate compound 9: ¹H-NMR (CDCl₃) δ: 7.04-6.96 (2H, m), 6.77-6.69 (1H, m), 4.08-4.00 (2H, m), 3.82-3.73 (2H, m), 1.62 (3H, s).

Reference Preparation Example 10-1

To a mixture of the intermediate compound 9 1.8 g and THF 20 mL was added dropwise butyl lithium (1.6 M, hexane solution) 6.5 mL at −78° C., and the mixtures were stirred at −78° C. for 30 minutes, and thereto was added iodine 2.8 g, and the mixtures were stirred at room temperature for 4 hours. To the resulting mixtures was added saturated ammonium chloride aqueous solution, and the mixtures were extracted with ethyl acetate. The resulting organic layers were washed with brine, dried over magnesium sulfate, and concentrated under reduced pressure. The resulting residues were subjected to silica gel column chromatography to obtain an intermediate compound 9-1 represented by the below-mentioned formula 2.2 g.

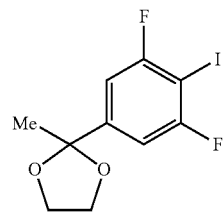 [SMILES: CC1(c2cc(F)c(I)c(F)c2)OCCO1]

Intermediate compound 9-1: $^1$H-NMR (CDCl$_3$) δ: 7.05-7.00 (2H, m), 4.08-4.00 (2H, m), 3.82-3.72 (2H, m), 1.61 (3H, s).

Reference Preparation Example 10-2

A mixture of the intermediate compound 9-1 2.2 g, acetic acid 3.0 mL, hydrochloric acid 3.0 mL, and THF 20 mL was stirred at 60° C. for 6 hours. To the resulting mixtures was added saturated sodium bicarbonate aqueous solution, and the mixtures were extracted with ethyl acetate. The resulting organic layers were dried over magnesium sulfate, and concentrated under reduced pressure. The resulting residues were subjected to silica gel column chromatography to obtain an intermediate compound 9-2 by the below-mentioned formula 1.7 g.

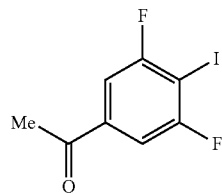

Intermediate compound 9-2: $^1$H-NMR (CDCl$_3$) δ: 7.47-7.42 (2H, m), 2.59 (3H, s).

Reference Preparation Example 11

A mixture of 1-(4-bromo-3-hydroxyphenyl)ethanone 1 g, benzyl bromide 0.6 mL, potassium carbonate 1.1 g, and acetone 20 mL was stirred at 70° C. for 6 hours, and the resulting mixtures were concentrated under reduced pressure. The resulting residues were subjected to silica gel column chromatography to obtain an intermediate compound 11-1 by the below-mentioned formula 1.4 g.

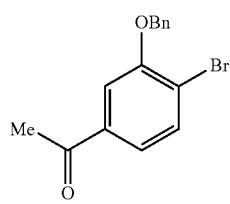 [SMILES: CC(=O)c1ccc(Br)c(OCc2ccccc2)c1]

Intermediate compound 11-1: $^1$H-NMR (CDCl$_3$) δ: 8.19 (1H, d), 7.87 (1H, dd), 7.48-7.46 (2H, m), 7.43-7.32 (3H, m), 6.97 (1H, d), 5.24 (2H, s), 2.55 (3H, s).

Reference Preparation Example 12-1

A mixture of the present compound 138 0.9 g, zinc 0.45 g, ammonium chloride 0.20 g, tetrahydrofuran 14 mL, and water 14 mL was stirred at 0° C. for 1 hour, and to the mixtures were added zinc 0.45 g and ammonium chloride 0.20 g, and the resulting mixtures were stirred at 0° C. for 2 hours. The resulting mixtures were filtered through Celite (registered Trademark), and to the resulting filtrates was added brine, and the mixtures were extracted with ethyl acetate. The resulting organic layers were dried over sodium sulfate and concentrated under reduced pressure. The resulting residues were subjected to silica gel column chromatography to obtain an intermediate compound 12-1 represented by the below-mentioned formula 0.9 g.

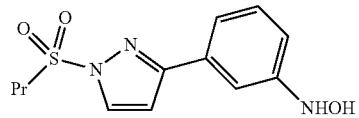

Intermediate compound 12-1: $^1$H-NMR (CDCl$_3$) S: 8.06-8.05 (1H, m), 7.56 (1H, s), 7.45 (1H, d), 7.35 (1H, t), 7.04 (1H, d), 6.75 (1H, m), 5.24 (1H, br s), 3.51-3.47 (2H, m), 1.80-1.71 (2H, m), 1.02 (3H, t).

Reference Preparation Example 12-2

To a mixture of the intermediate compound 12-1 0.9 g, pyridine 0.31 mL and chloroform 5 ml was added dropwise benzoyl chloride 0.37 mL at 0° C., and the mixtures were stirred at 0° C. for 2 hours. To the resulting mixtures were added water, and the mixtures were extracted with ethyl acetate. The resulting organic layers were washed with brine, dried over sodium sulfate, and concentrated under reduced pressure. The resulting residues were subjected to silica gel column chromatography to obtain an intermediate compound 12-2 represented by the below-mentioned formula 0.3 g.

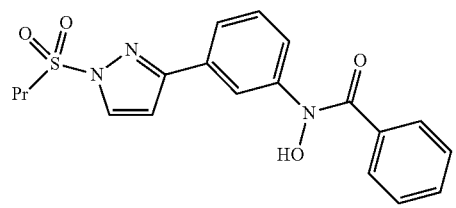

Intermediate compound 12-2: $^1$H-NMR (CDCl$_3$) δ: 8.05 (1H, d), 7.79-7.77 (2H, m), 7.48-7.47 (2H, m), 7.40 (1H, t), 7.35-7.27 (3H, m), 7.13 (1H, d), 6.62 (1H, d), 3.51-3.47 (2H, m), 1.77-1.74 (2H, m), 1.03 (3H, t).

Reference Preparation Example 13-1

To a mixture of 3-acetylbenzoic acid 4 g, dimethylformamide 0.02 mL, and tetrahydrofuran 25 mL was added dropwise oxalyl chloride 2.1 mL at room temperature. The resulting mixtures were stirred at room temperature for 3 hours, and concentrated under reduced pressure. To the resulting residues were added triethylamine 10 mL, cyclopropylamine 1.7 mL and tetrahydrofuran 25 mL, and the mixtures were stirred at room temperature for 12 hours. To the resulting mixtures was added water and the mixtures were extracted with ethyl acetate. The resulting organic layers were washed with brine, dried over sodium sulfate, and concentrated under reduced pressure. The resulting solids were washed with ethyl acetate, and concentrated under reduced pressure to obtain an intermediate compound 13-1 by represented by the below-mentioned formula 1 g.

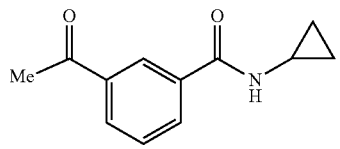 [SMILES: CC(=O)c1cccc(C(=O)NC2CC2)c1]

Intermediate compound 13-1: $^1$H-NMR (CDCl$_3$) δ: 8.28 (1H, s), 8.08 (1H, d), 8.00 (1H, d), 7.55 (1H, t), 6.34 (1H, s), 2.93 (1H, dq), 2.65 (3H, s), 0.90 (2H, dd), 0.66 (214, m).

Reference Preparation Example 13-2

A mixture of the intermediate compound 13-1 1 g, iodobenzene 0.73 g, copper(I) iodide 0.17 g, dipivaloyl methane 0.33 g, tripotassium phosphate 1.53 g, and toluene 4 mL was stirred at 130° C. for 10 hours. To the resulting mixtures was added water, and the mixtures were extracted with ethyl acetate. The resulting organic layers were washed with saturated brine, and dried over sodium sulfate, and concentrated under reduced pressure. The resulting residues were subjected to silica gel column chromatography to obtain an intermediate compound 13-2 represented by the below-mentioned formula 0.4 g.

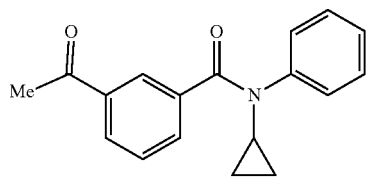 [SMILES: CC(=O)c1cccc(C(=O)N(c2ccccc2)C2CC2)c1]

Intermediate compound 13-2: $^1$H-NMR (CDCl$_3$) δ: 7.88 (1H, s), 7.84 (1H, d), 7.53 (1H, d), 7.32-7.23 (3H, m), 7.18 (1H, t), 7.05-7.03 (2H, m), 3.35-3.29 (1H, m), 2.47 (3H, s), 0.89 (2H, dd), 0.61-0.57 (2H, m).

Reference Preparation Example 13-3

The intermediate compound 13-3 0.4 g was prepared by using the intermediate compound 13-2 0.4 g according to the Reference preparation example 1.

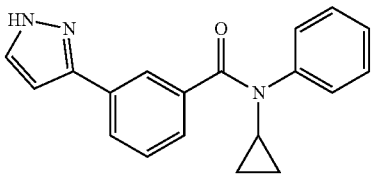 [SMILES: O=C(c1cccc(-c2cc[nH]n2)c1)N(c1ccccc1)C1CC1]

Intermediate compound 13-3: $^1$H-NMR (CDCl$_3$) δ: 7.76 (1H, s), 7.69-7.66 (1H, m), 7.59 (1H, d), 7.26-7.22 (5H, m), 7.19-7.15 (1H, m), 7.09-7.06 (2H, m), 6.50 (1H, s), 3.35-3.29 (1H, m), 0.90-0.85 (2H, m), 0.61-0.57 (2H, m).

Reference Preparation Example 14-1

A mixture of N-cyclopropyl benzamide 0.5 g, iodobenzene 0.64 g, copper(I) iodide 0.12 g, dipivaloyl methane 0.24 g, tripotassium phosphate 1.1 g, and toluene 3 mL was stirred at 130° C. for 8 hours. To the resulting mixtures was added brine, and the mixtures were extracted with ethyl acetate. The resulting organic layers were washed with brine, and dried over sodium sulfate, and concentrated under reduced pressure. The resulting residues were subjected to silica gel column chromatography to obtain an intermediate compound 14-1 represented by the below-mentioned formula 0.6 g.

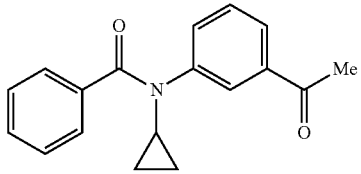 [SMILES: CC(=O)c1cccc(N(C(=O)c2ccccc2)C2CC2)c1]

Intermediate compound 14-1: $^1$H-NMR (CDCl$_3$) δ: 7.76-7.74 (1H, m), 7.69 (1H, t), 7.37-7.34 (3H, m), 7.31-7.22 (4H, m), 3.29-3.23 (1H, m), 2.53 (3H, s), 0.91-0.85 (2H, m), 0.58-0.54 (2H, m).

Reference Preparation Example 14-2

The intermediate compound 14-2 0.3 g was prepared by using the intermediate compound 14-1 0.6 g according to the Reference preparation example 1.

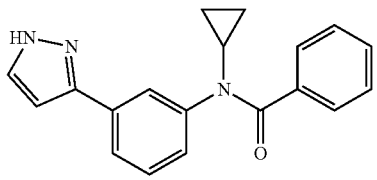 [SMILES: O=C(c1ccccc1)N(c1cccc(-c2cc[nH]n2)c1)C1CC1]

Intermediate compound 14-2: $^1$H-NMR (CDCl$_3$) δ: 7.61-7.60 (1H, m), 7.57 (1H, d), 7.52 (1H, s), 7.39-7.37 (2H, m), 7.29-7.19 (5H, m), 6.97 (1H, d), 6.54 (1H, d), 3.33-3.28 (1H, m), 0.91-0.86 (2H, m), 0.64-0.59 (2H, m).

Preparation Example 1

To a mixture of 3-(p-tolyl)-1H-pyrazol 0.4 g, triethylamine 0.33 g, and THF 5 mL was added dropwise ethanesulfonyl chloride 0.39 g, and the mixtures were stirred at room temperature for 3 hours. To the resulting mixtures was added ethyl acetate, and the mixtures were filtered, and the resulting filtrates were concentrated under reduced pressure. The resulting residues were washed with saturated sodium bicarbonate aqueous solution and hexane successively, and concentrated under reduced pressure to obtain the present compound 17 represented by the below-mentioned formula 0.46 g.

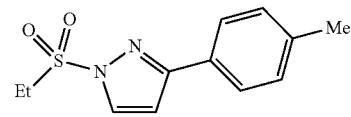 [SMILES: CCS(=O)(=O)n1ccc(-c2ccc(C)cc2)n1]

Present compound 17: $^1$H-NMR (CDCl$_3$) δ: 8.06 (1H, d), 7.79-7.76 (2H, m), 7.26-7.23 (2H, m), 6.73 (1H, d), 3.55 (2H, q), 2.40 (3H, s), 1.28 (3H, t).

Preparation Example 1-1

The compounds that were prepared according to the Preparation example 1 and their physical properties are indicated below.

A compound represented by formula (pE1-1)

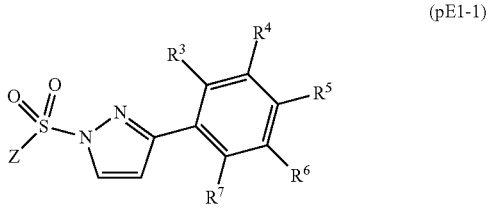

Wherein Z, $R^3$, $R^4$, $R^5$, $R^6$ and $R^7$ represents any combination indicated in [Table pE1], (Table pE2), [Table pE3], [Table pE4], [Table pE5], [Table pE6] and (Table pE10].

TABLE pE1

[Table 6]

| Present compound | Z | $R^3$ | $R^4$ | $R^5$ | $R^6$ | $R^7$ |
|---|---|---|---|---|---|---|
| 1 | Et | H | H | CN | H | H |
| 2 | Me | H | H | Cl | H | H |
| 3 | i-Pr | H | H | Cl | H | H |
| 4 | Pr | H | H | Cl | H | H |
| 5 | Bu | H | H | Cl | H | H |
| 6 | Et | H | H | Cl | H | H |
| 7 | $CH_2CH_2CH_2Cl$ | H | H | Cl | H | H |
| 8 | $CF_2CF_2CF_2CF_3$ | H | H | Cl | H | H |
| 9 | Et | H | H | F | H | H |
| 10 | Et | H | H | Br | H | H |
| 11 | Et | H | Cl | Cl | H | H |
| 12 | Et | F | H | F | H | F |
| 13 | Et | H | F | F | F | H |
| 14 | Me | H | Cl | Cl | H | H |
| 15 | c-Pr | H | H | Cl | H | H |

Present compound 1: $^1$H-NMR (CDCl$_3$) δ: 8.13 (1H, d), 8.01-7.98 (2H, m), 7.76-7.73 (2H, m), 6.82 (1H, d), 3.59 (2H, q), 1.32 (3H, t).

Present compound 2: $^1$H-NMR (CDCl$_3$) δ: 8.08 (1H, d), 7.83-7.80 (2H, m), 7.43-7.40 (2H, m), 6.74 (1H, d), 3.39 (3H, s).

Present compound 3: $^1$H-NMR (CDCl$_3$) δ: 8.07 (1H, d), 7.83-7.80 (2H, m), 7.43-7.39 (2H, m), 6.74 (1H, d), 3.85-3.78 (1H, m), 1.38 (6H, d).

Present compound 4: $^1$H-NMR (CDCl$_3$) δ: 8.07 (1H, d), 7.83-7.80 (2H, m), 7.43-7.40 (2H, m), 6.73 (1H, d), 3.51-3.47 (2H, m), 1.81-1.72 (2H, m), 1.03 (3H, t).

Present compound 5: $^1$H-NMR (CDCl$_3$) δ: 8.07 (1H, d), 7.83-7.80 (2H, m), 7.43-7.40 (2H, m), 6.73 (1H, d), 3.53-3.49 (2H, m), 1.73-1.66 (2H, m), 1.47-1.37 (2H, m), 0.91 (3H, t).

Present compound 6: $^1$H-NMR (CDCl$_3$) δ: 8.08 (1H, d), 7.83-7.79 (2H, m), 7.42-7.39 (2H, m), 6.73 (1H, d), 3.56 (2H, q), 1.30 (3H, t).

Present compound 7: $^1$H-NMR (CDCl$_3$) δ: 8.08 (1H, d), 7.83-7.79 (2H, m), 7.44-7.40 (2H, m), 6.75 (1H, d), 3.73-3.69 (2H, m), 3.62 (2H, t), 2.27-2.20 (2H, m).

Present compound 8: $^1$H-NMR (CDCl$_3$) δ: 8.12 (1H, d), 7.86-7.83 (2H, m), 7.47-7.43 (2H, m), 6.94 (1H, d).

Present compound 9: $^1$H-NMR (CDCl$_3$) δ: 8.07 (1H, d), 7.89-7.84 (2H, m), 7.16-7.10 (2H, m), 6.72 (1H, d), 3.56 (2H, q), 1.30 (3H, t).

Present compound 10: $^1$H-NMR (CDCl$_3$) δ: 8.08 (1H, d), 7.77-7.74 (2H, m), 7.59-7.55 (2H, m), 6.74 (1H, d), 3.56 (2H, q), 1.30 (3H, t).

Present compound 11: $^1$H-NMR (CDCl$_3$) δ: 8.10 (1H, d), 7.99 (1H, d), 7.70 (1H, dd), 7.51 (1H, d), 6.74 (1H, d), 3.58 (2H, q), 1.31 (3H, t).

Present compound 12: $^1$H-NMR (CDCl$_3$) δ: 8.13 (1H, d), 6.82-6.75 (2H, m), 6.73-6.71 (1H, m), 3.57 (2H, q), 1.32 (3H, t).

Present compound 13: $^1$H-NMR (CDCl$_3$) δ: 8.10 (1H, d), 7.55-7.48 (2H, m), 6.69 (1H, d), 3.57 (2H, q), 1.31 (3H, t).

Present compound 14: $^1$H-NMR (CDCl$_3$) δ: 8.10 (1H, d), 7.99 (1H, d), 7.70 (1H, dd), 7.52 (1H, d), 6.74 (1H, d), 3.41 (3H, s).

Present compound 15: $^1$H-NMR (CDCl$_3$) δ: 8.03 (1H, d), 7.84-7.81 (2H, m), 7.43-7.40 (2H, m), 6.73 (1H, d), 2.86-2.80 (1H, m), 1.54-1.49 (2H, m), 1.22-1.17 (2H, m).

TABLE pE2

[Table 7]

| Present compound | Z | $R^3$ | $R^4$ | $R^5$ | $R^6$ | $R^7$ |
|---|---|---|---|---|---|---|
| 16 | Et | H | H | $CF_3$ | H | H |
| 18 | Et | H | H | OMe | H | H |
| 19 | Et | Cl | Cl | Cl | H | H |
| 20 | Et | H | Me | Cl | H | H |
| 21 | Et | H | F | F | H | H |
| 22 | Et | H | Me | Me | H | H |
| 23 | Et | H | H | i-Pr | H | H |
| 24 | Et | H | H | Et | H | H |
| 25 | Et | H | H | Bu | H | H |
| 26 | Et | H | H | I | H | H |
| 27 | Et | H | Cl | Cl | Cl | H |
| 28 | Pr | H | Cl | Cl | H | H |
| 29 | Et | H | H | c-Pr | H | H |
| 30 | $NMe_2$ | H | H | Cl | H | H |

Present compound 16: $^1$H-NMR (CDCl$_3$) δ: 8.12 (1H, d), 8.00 (2H, d), 7.70 (2H, d), 6.81 (1H, d), 3.58 (2H, q), 1.31 (3H, t).

Present compound 18: $^1$H-NMR (CDCl$_3$) δ: 8.05 (1H, d), 7.83-7.80 (2H, m), 6.98-6.94 (2H, m), 6.70 (1H, d), 3.86 (3H, s), 3.55 (2H, q), 1.28 (3H, t).

Present compound 19: $^1$H-NMR (CDCl$_3$) δ: 8.11 (1H, d), 7.68 (1H, d), 7.47 (1H, d), 6.94 (1H, d), 3.57 (2H, q), 1.32 (3H, t).

Present compound 20: $^3$H-NMR (CDCl$_3$) δ: 8.07 (1H, d), 7.78 (1H, d), 7.61 (1H, dd), 7.40 (1H, d), 6.73 (1H, d), 3.56 (2H, q), 2.43 (3H, s), 1.29 (3H, t).

Present compound 21: $^1$H-NMR (CDCl$_3$) δ: 8.09 (1H, d), 7.73 (1H, ddd), 7.61-7.57 (1H, m), 7.24-7.20 (1H, m), 6.71 (1H, d), 3.57 (2H, q), 1.31 (3H, t).

Present compound 22: $^1$H-NMR (CDCl$_3$) δ: 8.05 (1H, d), 7.69 (1H, s), 7.58 (1H, dd), 7.20 (1H, d), 6.73 (1H, d), 3.55 (2H, q), 2.32 (3H, s), 2.30 (3H, s), 1.28 (31H, t).

Present compound 23: $^1$H-NMR (CDCl$_3$) δ: 8.06 (1H, d), 7.82-7.79 (2H, m), 7.32-7.29 (2H, m), 6.74 (1H, d), 3.55 (2H, q), 2.95 (1H, m), 1.30-1.24 (9H, m).

Present compound 24: $^1$H-NMR (CDCl$_3$) δ: 8.06 (1H, d), 7.81-7.78 (2H, m), 7.29-7.26 (2H, m), 6.74 (1H, d), 3.55 (2H, q), 2.69 (2H, q), 1.29-1.24 (6H, m).

Present compound 25: $^1$H-NMR (CDCl$_3$) δ: 8.06 (1H, d), 7.79 (2H, d), 7.25 (2H, d), 6.74 (1H, d), 3.55 (2H, q), 2.65 (2H, t), 1.64-1.58 (2H, m), 1.41-1.32 (2H, m), 1.27 (3H, t), 0.93 (3H, t).

Present compound 26: $^1$H-NMR (CDCl$_3$) δ: 8.08 (1H, d), 7.80-7.76 (2H, m), 7.63-7.60 (2H, m), 6.74 (1H, d), 3.56 (2H, q), 1.30 (3H, t).

Present compound 27: $^1$H-NMR (CDCl$_3$) δ: 8.11 (1H, d), 7.90 (2H, s), 6.74 (1H, d), 3.58 (2H, q), 1.31 (3H, t).

Present compound 28: $^1$H-NMR (CDCl$_3$) δ: 8.09 (1H, d), 7.99 (1H, d), 7.70 (1H, dd), 7.51 (1H, d), 6.73 (1H, d), 3.53-3.49 (2H, m), 1.82-1.72 (2H, m), 1.04 (3H, t).

Present compound 29: $^1$H-NMR (CDCl$_3$) δ: 8.05 (1H, d), 7.76 (2H, dt), 7.13 (2H, dt), 6.72 (1H, d), 3.54 (2H, q), 1.96-1.90 (1H, m), 1.28 (3H, t), 1.04-0.99 (2H, m), 0.76-0.72 (2H, m).

Present compound 30: $^1$H-NMR (CDCl$_3$) δ: 8.01 (1H, d), 7.81-7.78 (2H, m), 7.42-7.38 (2H, m), 6.68 (1H, d), 3.00 (6H, s)

TABLE pE3

[Table 8]

| Present compound | Z | R$^3$ | R$^4$ | R$^5$ | R$^6$ | R$^7$ |
|---|---|---|---|---|---|---|
| 31 | CF$_3$ | H | H | Cl | H | H |
| 32 | Et | H | H | NO$_2$ | H | H |
| 33 | Et | H | CF$_3$ | Cl | H | H |
| 34 | Et | H | Cl | Me | H | H |
| 35 | Et | H | OMe | OMe | H | H |
| 36 | Et | H | NO$_2$ | Cl | H | H |
| 37 | Et | Cl | H | Cl | H | H |
| 38 | Et | H | H | OCF$_3$ | H | H |
| 39 | Et | H | CF$_3$ | F | H | H |
| 40 | Pr | H | H | Br | H | H |
| 41 | Pr | H | H | CF$_3$ | H | H |
| 42 | Pr | H | F | F | H | H |
| 43 | Pr | H | Me | Cl | H | H |
| 44 | Pr | H | F | F | F | H |
| 45 | Et | H | Cl | F | H | H |

Present compound 31: $^1$H-NMR (CDCl$_3$) δ: 8.12 (1H, d), 7.86-7.82 (2H, m), 7.47-7.43 (2H, m), 6.93 (1H, d).

Present compound 32: $^1$H-NMR (CDCl$_3$) δ: 8.33-8.29 (2H, m), 8.15 (1H, d), 8.08-8.04 (2H, m), 6.86 (1H, d), 3.60 (2H, q), 1.33 (3H, t).

Present compound 33: $^1$H-NMR (CDCl$_3$) δ: 8.18 (1H, s), 8.13-8.12 (1H, m), 7.98 (1H, d), 7.58 (1H, d), 6.79-6.78 (1H, m), 3.59 (2H, q), 1.31 (3H, t).

Present compound 34: $^1$H-NMR (CDCl$_3$) δ: 8.07 (1H, d), 7.87 (1H, d), 7.64 (1H, dd), 7.29 (1H, d), 6.72 (1H, d), 3.56 (2H, q), 2.41 (3H, s), 1.29 (3H, t).

Present compound 35: $^1$H-NMR (CDCl$_3$) δ: 8.05 (1H, d), 7.47 (1H, d), 7.37 (1H, dd), 6.92 (1H, d), 6.71 (1H, d), 3.97 (3H, s), 3.93 (3H, s), 3.55 (2H, q), 1.29 (3H, t).

Present compound 36: $^1$H-NMR (CDCl$_3$) δ: 8.36 (1H, d), 8.14 (1H, d), 8.02 (1H, dd), 7.63 (1H, d), 6.80 (1H, d), 3.59 (2H, q), 1.32 (3H, t).

Present compound 37: $^1$H-NMR (CDCl$_3$) δ: 8.10 (1H, d), 7.79 (1H, d), 7.50 (1H, d), 7.33 (1H, dd), 6.96 (1H, d), 3.56 (2H, q), 1.31 (3H, t).

Present compound 38: $^1$H-NMR (CDCl$_3$) δ: 8.09 (1H, d), 7.93-7.89 (2H, m), 7.30-7.27 (2H, m), 6.75 (1H, d), 3.57 (2H, q), 1.30 (3H, t).

Present compound 39: $^1$H-NMR (CDCl$_3$) δ: 8.13-8.10 (2H, m), 8.07-8.03 (1H, m), 7.30 (1H, d), 6.76 (1H, d), 3.58 (2H, a), 1.31 (3H, t).

Present compound 40: $^1$H-NMR (CDCl$_3$) δ: 8.07 (1H, d), 7.77-7.73 (2H, m), 7.59-7.55 (2H, m), 6.73 (1H, d), 3.51-3.47 (2H, m), 1.81-1.72 (2H, m), 1.03 (3H, t).

Present compound 41: $^1$H-NMR (CDCl$_3$) δ: 8.11 (1H, d), 8.01-7.99 (2H, m), 7.71-7.69 (2H, m), 6.81 (1H, d), 3.54-3.50 (2H, m), 1.83-1.73 (2H, m), 1.04 (3H, t).

Present compound 42: $^1$H-NMR (CDCl$_3$) δ: 8.07 (1H, d), 7.75-7.70 (1H, m), 7.61-7.57 (1H, m), 7.24-7.20 (1H, m), 6.70 (1H, d), 3.52-3.48 (2H, m), 1.82-1.72 (2H, m), 1.04 (3H, t).

Present compound 43: $^1$H-NMR (CDCl$_3$) δ: 8.06 (1H, d), 7.78 (1H, d), 7.61 (1H, dd), 7.40 (1H, d), 6.72 (1H, d), 3.52-3.47 (2H, m), 2.43 (3H, s), 1.81-1.71 (2H, m), 1.03 (3H, t).

Present compound 44: $^1$H-NMR (CDCl$_3$) δ: 8.09 (1H, d), 7.55-7.47 (2H, m), 6.68 (1H, d), 3.52-3.48 (2H, m), 1.82-1.73 (2H, m), 1.04 (3H, t).

Present compound 45: $^1$H-NMR (CDCl$_3$) δ: 8.08 (1H, d), 7.95 (1H, dd), 7.75-7.71 (1H, m), 7.21 (1H, t), 6.71 (1H, d), 3.57 (2H, q), 1.31 (3H, t).

TABLE pE4

[Table 9]

| Present compound | Z | R$^3$ | R$^4$ | R$^5$ | R$^6$ | R$^7$ |
|---|---|---|---|---|---|---|
| 46 | Et | H | F | CF$_3$ | H | H |
| 47 | Et | H | F | Cl | H | H |
| 48 | Et | H | F | Me | H | H |
| 49 | Et | H | Me | F | H | H |
| 50 | Et | F | F | F | H | H |
| 51 | Et | H | F | Br | H | H |
| 52 | Et | H | Me | Br | H | H |
| 53 | Et | H | NO$_2$ | Br | H | H |
| 54 | Et | H | NO$_2$ | Me | H | H |
| 55 | Et | H | Cl | Br | H | H |
| 56 | Pr | H | H | I | H | H |
| 58 | NMe$_2$ | H | F | Br | H | H |
| 59 | Pr | H | F | Br | H | H |
| 60 | Et | H | Br | F | H | H |

Present compound 46: $^1$H-NMR (CDCl$_3$) δ: 8.13 (1H, d), 7.75-7.72 (2H, m), 7.69-7.65 (1H, m), 6.79 (1H, d), 3.59 (2H, q), 1.32 (3H, t).

Present compound 47: $^1$H-NMR (CDCl$_3$) δ: 8.09 (1H, d), 7.68 (1H, dd), 7.60-7.58 (1H, m), 7.46 (1H, t), 6.73 (1H, d), 3.57 (2H, q), 1.31 (3H, t).

Present compound 48: $^1$H-NMR (CDCl$_3$) δ: 8.07 (1H, d), 7.55-7.52 (2H, m), 7.26-7.22 (1H, m), 6.71 (1H, d), 3.56 (2H, q), 2.31 (3H, d), 1.30 (3H, t).

Present compound 49: $^1$H-NMR (CDCl$_3$) δ: 8.06 (1H, d), 7.74 (1H, dd), 7.65-7.61 (1H, m), 7.06 (1H, t), 6.70 (1H, d), 3.55 (2H, q), 2.33 (3H, d), 1.29 (3H, t).

Present compound 50: $^1$H-NMR (CDCl$_3$) δ: 8.12 (1H, d), 7.85-7.79 (1H, m), 7.09-7.02 (1H, m), 6.87 (1H, dd), 3.56 (2H, q), 1.31 (3H, t).

Present compound 51: $^1$H-NMR (CDCl$_3$) δ: 8.10 (1H, d), 7.68-7.60 (2H, m), 7.53 (1H, ddd), 6.73 (1H, d), 3.57 (2H, q), 1.31 (3H, t).

Present compound 52: $^1$H-NMR (CDCl$_3$) δ: 8.10 (1H, d), 7.45-7.38 (3H, m), 6.61 (1H, d), 3.56 (2H, q), 2.47 (3H, s), 1.31 (3H, t).

Present compound 53: $^1$H-NMR (CDCl$_3$) δ: 8.33 (1H, d), 8.14 (1H, d), 7.93 (1H, dd), 7.81 (1H, d), 6.80 (1H, d), 3.59 (2H, q), 1.32 (3H, t).

Present compound 54: $^1$H-NMR (CDCl$_3$) δ: 8.45 (1H, d), 8.12 (1H, d), 8.03 (1H, dd), 7.43 (1H, d), 6.80 (1H, d), 3.59 (2H, q), 2.65 (3H, s), 1.32 (3H, t).

Present compound 55: $^1$H-NMR (CDCl$_3$) δ: 8.09 (1H, d), 7.99 (1H, d), 7.68 (1H, d), 7.61 (1H, dd), 6.74 (1H, d), 3.57 (2H, q), 1.31 (3H, t).

Present compound 56: $^1$H-NMR (CDCl$_3$) δ: 8.07 (1H, d), 7.79-7.76 (2H, m), 7.63-7.60 (2H, m), 6.73 (1H, d), 3.51-3.47 (2H, m), 1.81-1.72 (2H, m), 1.03 (3H, t).

Present compound 58: $^1$H-NMR (CDCl$_3$) δ: 8.02 (1H, d), 7.65-7.58 (2H, m), 7.50 (1H, ddd), 6.68 (1H, d), 3.01 (6H, s).

Present compound 59: $^1$H-NMR (CDCl$_3$) δ: 8.08 (1H, d), 7.68-7.60 (2H, m), 7.53 (1H, dd), 6.73 (1H, d), 3.52-3.48 (2H, m), 1.82-1.71 (2H, m), 1.04 (3H, t).

Present compound 60: $^1$H-NMR (CDCl$_3$) δ: 8.11 (1H, dd), 8.09 (1H, d), 7.79-7.76 (1H, m), 7.19 (1H, t), 6.71 (1H, d), 3.57 (2H, q), 1.30 (3H, t).

TABLE 10

Table pE5

| Present compound | Z | R³ | R⁴ | R⁵ | R⁶ | R⁷ |
|---|---|---|---|---|---|---|
| 61 | Pr | H | Br | F | H | H |
| 62 | Pr | H | F | Cl | H | H |
| 63 | Pr | H | F | Me | H | H |
| 64 | NMe₂ | H | Br | F | H | H |
| 65 | NMe₂ | H | F | F | F | H |
| 66 | NMe₂ | H | F | Me | H | H |
| 67 | NMe₂ | H | H | I | H | H |
| 68 | NMe₂ | H | F | Cl | H | H |
| 69 | Et | H | F | Br | F | H |
| 70 | Pr | H | F | Br | F | H |
| 71 | NMe₂ | H | F | Br | F | H |
| 72 | NMe₂ | H | Me | Cl | H | H |
| 73 | pyrrolidinyl | H | F | Br | H | H |
| 74 | CH₂CH=CH₂ | H | F | Br | H | H |
| 75 | CH=CHCH₃ | H | F | Br | H | H |

TABLE 11

Table pE6

| Present compound | Z | R³ | R⁴ | R⁵ | R⁶ | R⁷ |
|---|---|---|---|---|---|---|
| 76 | Et | H | H | S(O)₂Me | H | H |
| 77 | Me | H | F | Br | F | H |
| 78 | Me | H | F | Br | H | H |
| 79 | pyrrolidinyl | H | F | Br | F | H |
| 80 | Bu | H | F | Br | H | H |
| 81 | c-Pr | H | F | Br | H | H |
| 82 | morpholinyl | H | F | Br | H | H |
| 83 | NEt₂ | H | F | Br | H | H |
| 84 | Et | H | F | CF₃ | H | H |
| 85 | Pr | H | F | CF₃ | F | H |
| 86 | Et | H | F | Cl | F | H |
| 87 | Pr | H | F | Cl | F | H |
| 88 | Pr | H | F | CF₃ | H | H |
| 89 | Et | H | F | Me | F | H |
| 90 | Pr | H | F | Me | F | H |
| 91 | CH₂CF₃ | H | F | Br | H | H |
| 92 | CH₂CF₃ | H | F | Br | H | H |
| 93 | CH₂CH(CH₃)₂ | H | F | Br | H | H |
| 94 | Et | H | F | I | F | H |
| 95 | Pr | H | F | I | F | H |

Present compound 61: ¹H-NMR (CDCl₃) δ: 8.11 (1H, dd), 8.08 (1H, d), 7.80-7.76 (1H, m), 7.19 (1H, t), 6.71 (1H, d), 3.52-3.48 (2H, m), 1.82-1.72 (2H, m), 1.04 (3H, t).

Present compound 62: ¹H-NMR (CDCl₃) δ: 8.08 (1H, d), 7.69 (1H, dd), 7.60-7.58 (1H, m), 7.48-7.44 (1H, m), 6.72 (1H, d), 3.52-3.48 (2H, m), 1.82-1.73 (2H, m), 1.04 (3H, t).

Present compound 63: ¹H-NMR (CDCl₃) δ: 8.06 (1H, d), 7.56-7.52 (2H, m), 7.23 (1H, d), 6.71 (1H, d), 3.51-3.47 (2H, m), 2.32 (3H, d), 1.81-1.71 (2H, m), 1.03 (3H, t).

Present compound 64: ¹H-NMR (CDCl₃) δ: 8.07 (1H, dd), 8.01 (1H, d), 7.78-7.74 (1H, m), 7.18 (1H, t), 6.65 (1H, d), 3.00 (6H, s).

Present compound 65: ¹H-NMR (CDCl₃) δ: 8.03 (1H, d), 7.50-7.45 (2H, m), 6.64 (1H, d), 3.01 (6H, s).

Present compound 66: ¹H-NMR (CDCl₃) δ: 8.00 (1H, d), 7.53-7.50 (2H, m), 7.25-7.21 (1H, m), 6.66 (1H, d), 3.00 (6H, s), 2.31 (3H, d).

Present compound 67: ¹H-NMR (CDCl₃) δ: 8.01 (1H, d), 7.78-7.75 (2H, m), 7.61-7.58 (2H, m), 6.68 (1H, d), 2.99 (6H, s).

Present compound 68: ¹H-NMR (CDCl₃) δ: 8.02 (1H, d), 7.66 (1H, dd), 7.58-7.55 (1H, m), 7.47-7.43 (1H, m), 6.67 (1H, d), 3.01 (6H, s).

Present compound 69: ¹H-NMR (CDCl₃) δ: 8.11 (1H, d), 7.50-7.46 (2H, m), 6.73 (1H, d), 3.58 (2H, q), 1.32 (3H, t).

Present compound 70: ¹H-NMR (CDCl₃) δ: 8.10 (1H, d), 7.50-7.46 (2H, m), 6.72 (1H, d), 3.53-3.49 (2H, m), 1.83-1.73 (2H, m), 1.04 (3H, t).

Present compound 71: ¹H-NMR (CDCl₃) δ: 8.03 (1H, d), 7.47-7.43 (2H, m), 6.67 (1H, d), 3.01 (6H, s).

Present compound 72: ¹H-NMR (CDCl₃) δ: 8.00 (1H, d), 7.74 (1H, d), 7.62-7.59 (1H, m), 7.39 (1H, d), 6.67 (1H, d), 2.99 (6H, s), 2.43 (3H, s).

Present compound 73: ¹H-NMR (CDCl₃) δ: 8.04 (1H, d), 7.64-7.58 (2H, m), 7.49 (1H, dd), 6.66 (1H, d), 3.55-3.51 (4H, m), 1.91-1.87 (4H, m).

Present compound 74: ¹H-NMR (CDCl₃) δ: 8.04 (1H, d), 7.68-7.52 (3H, m), 6.70 (1H, d), 5.77-5.66 (1H, dd), 5.38 (1H, dd), 5.24 (1H, dd), 4.23 (2H, d).

Present compound 75: ¹H-NMR (CDCl₃) δ: 8.06 (1H, d), 7.66-7.58 (2H, m), 7.51 (1H, dd), 7.26-7.18 (1H, m), 6.71 (1H, d), 6.49 (1H, dq), 2.01 (3H, dd).

Present compound 76: ¹H-NMR (CDCl₃) δ: 8.14 (1H, d), 8.10-8.07 (2H, m), 8.03-8.00 (2H, m), 6.84 (1H, d), 3.59 (2H, q), 3.09 (3H, s), 1.33 (3H, t).

Present compound 77: ¹H-NMR (CDCl₃) δ: 8.11 (1H, dd), 7.50-7.46 (2H, m), 6.73 (1H, d), 3.41 (3H, s).

Present compound 78: ¹H-NMR (CDCl₃) δ: 8.10 (1H, d), 7.68-7.60 (2H, m), 7.53 (1H, dd), 6.74 (1H, d), 3.40 (3H, s).

Present compound 79: ¹H-NMR (CDCl₃) δ: 8.05 (1H, d), 7.45-7.41 (2H, m), 6.65 (1H, d), 3.55-3.52 (4H, m), 1.92-1.88 (4H, m).

Present compound 80: ¹H-NMR (CDCl₃) δ: 8.08 (1H, d), 7.68-7.60 (2H, m), 7.53 (1H, dd), 6.73 (1H, d), 3.54-3.50 (2H, m), 1.74-1.66 (2H, m), 1.43 (2H, td), 0.91 (3H, t).

Present compound 81: ¹H-NMR (CDCl₃) δ: 8.05 (1H, d), 7.68-7.60 (2H, m), 7.54 (1H, dd), 6.73 (1H, d), 2.86-2.80 (1H, m), 1.55-1.50 (2H, m), 1.24-1.18 (2H, m).

Present compound 82: ¹H-NMR (CDCl₃) δ: 8.01 (1H, d), 7.65-7.59 (2H, m), 7.50 (1H, dd), 6.70 (1H, d), 3.78-3.75 (4H, m), 3.41-3.38 (4H, m).

Present compound 83: ¹H-NMR (CDCl₃) δ: 8.00 (1H, d), 7.63-7.57 (2H, m), 7.49 (1H, dd), 6.64 (1H, d), 3.47 (4H, q), 1.17 (6H, t).

Present compound 84: ¹H-NMR (CDCl₃) δ: 8.14 (1H, d), 7.52 (2H, d), 6.77 (1H, d), 3.59 (2H, q), 1.32 (3H, t).

Present compound 85: ¹H-NMR (CDCl₃) δ: 8.13 (1H, d), 7.55-7.50 (2H, m), 6.77 (1H, d), 3.54-3.50 (2H, m), 1.83-1.74 (2H, m), 1.05 (3H, t).

Present compound 86: ¹H-NMR (CDCl₃) δ: 8.11 (1H, d), 7.53-7.48 (2H, m), 6.72 (1H, d), 3.58 (2H, q), 1.32 (3H, t).

Present compound 87: ¹H-NMR (CDCl₃) δ: 8.10 (1H, d), 7.53-7.49 (2H, m), 6.71 (1H, d), 3.53-3.49 (2H, m), 1.82-1.73 (2H, m), 1.04 (3H, t).

Present compound 88: ¹H-NMR (CDCl₃) δ: 8.12 (1H, d), 7.75-7.73 (2H, m), 7.67 (1H, t), 6.79 (1H, d), 3.54-3.50 (2H, m), 1.83-1.74 (2H, m), 1.04 (3H, t).

Present compound 89: ¹H-NMR (CDCl₃) δ: 8.08 (1H, d), 7.40-7.34 (2H, m), 6.70 (1H, d), 3.57 (2H, q), 2.23 (3H, s), 1.30 (3H, t).

Present compound 90: ¹H-NMR (CDCl₃) δ: 8.07 (1H, d), 7.39-7.33 (2H, m), 6.69 (1H, d), 3.52-3.48 (2H, m), 2.23 (3H, s), 1.82-1.72 (2H, m), 1.03 (3H, t).

Present compound 91: ¹H-NMR (CDCl₃) δ: 8.14 (1H, s), 7.48 (2H, d), 6.78 (1H, s), 4.35 (2H, q).

Present compound 92: ¹H-NMR (CDCl₃) δ: 8.11 (1H, d), 7.68-7.62 (2H, m), 7.53 (1H, d), 6.79 (1H, d), 4.34 (2H, q).

Present compound 93: ¹H-NMR (CDCl₃) δ: 8.09 (1H, d), 7.68-7.60 (2H, m), 7.54-7.51 (1H, m), 6.72 (1H, d), 3.42 (2H, d), 2.32-2.22 (1H, m), 1.09 (6H, d).

Present compound 94: ¹H-NMR (CDCl₃) δ: 8.11 (1H, d), 7.39-7.44 (2H, m), 6.74 (1H, d), 3.58 (2H, q), 1.31 (3H, t).

Present compound 95: ¹H-NMR (CDCl₃) δ: 8.10 (1H, d), 7.39-7.44 (2H, m), 6.73 (1H, d), 3.48-3.54 (2H, m), 1.72-1.83 (2H, m), 1.04 (3H, t).

TABLE pE10

[Table 12]

| Present compound | Z | R³ | R⁴ | R⁵ | R⁶ | R⁷ |
|---|---|---|---|---|---|---|
| 117 | i-Pr | H | F | Br | F | H |
| 119 | Et | H | I | Br | H | H |
| 120 | Pr | H | I | Br | H | H |
| 121 | Et | H | CO₂Me | Br | H | H |
| 122 | Pr | H | CO₂Me | Br | H | H |
| 123 | Pr | H | OMe | Br | H | H |
| 124 | Et | H | CF₃ | Br | H | H |
| 125 | Pr | H | Br | Br | H | H |
| 126 | Et | H | Br | Br | H | H |
| 127 | Et | H | OMe | Br | H | H |
| 128 | Et | H | CN | Br | H | H |
| 129 | Pr | H | CF₃ | Br | H | H |
| 130 | Pr | H | CN | Br | H | H |
| 133 | Et | H | H | SPh | H | H |
| 134 | Pr | H | H | SPh | H | H |
| 135 | Et | H | H | NO₂ | H | H |
| 136 | Pr | H | H | NO₂ | H | H |
| 137 | Et | H | NO₂ | H | H | H |
| 139 | Pr | H | NO₂ | H | H | H |
| 139 | Et | H | OMe | H | H | H |
| 140 | Pr | H | OMe | H | H | H |
| 141 | Et | H | CF₃ | H | H | H |
| 142 | Pr | H | CF₃ | H | H | H |
| 143 | Et | H | OCH₂Ph | H | H | H |
| 144 | Pr | H | OCH₂Ph | H | H | H |
| 145 | Et | H | Br | H | H | H |
| 146 | Pr | H | Br | H | H | H |
| 147 | Et | H | Et | H | H | H |
| 148 | Pr | H | Et | H | H | H |
| 149 | Et | H | F | H | H | H |
| 150 | Pr | H | F | H | H | H |
| 151 | Et | H | OPh | H | H | H |
| 152 | Pr | H | OPh | H | H | H |
| 159 | Et | H | NHCOc-Pr | H | H | H |
| 160 | Me | H | CONHc-Pr | H | H | H |
| 161 | Pr | H | CONHc-Pr | H | H | H |
| 162 | CH=CH₂ | H | CONHc-Pr | H | H | H |
| 163 | Et | H | NHCOPh | H | H | H |
| 164 | CH₂Cl | H | CONHc-Pr | H | H | H |
| 165 | Pr | H | CONHPh | H | H | H |
| 166 | CH=CH₂ | H | CONHPh | H | H | H |
| 183 | Et | H | H | OCH₂Ph | H | H |
| 184 | Et | H | OCH₂Ph | Br | H | H |
| 196 | Et | H | CONHPh | H | H | H |

Present compound 117: ¹H-NMR (CDCl₃) δ: 8.10 (1H, d), 7.51-7.45 (2H, m), 6.73 (1H, d), 3.88-3.77 (1H, m), 1.38 (6H, d).

Present compound 119: ¹H-NMR (CDCl₃) δ: 8.38 (1H, d), 8.09 (1H, d), 7.69-7.68 (2H, m), 6.73 (1H, d), 3.58 (2H, q), 1.30 (3H, t).

Present compound 120: ¹H-NMR (CDCl₃) δ: 8.38 (1H, s), 8.08 (1H, dd), 7.70-7.67 (2H, m), 6.73 (1H, dd), 3.55-3.47 (2H, m), 1.81-1.71 (2H, m), 1.04 (3H, t).

Present compound 121: ¹H-NMR (CDCl₃) δ: 8.28 (1H, d), 8.11 (1H, d), 7.84 (1H, dd), 7.74 (1H, d), 6.79 (1H, d), 3.98 (3H, s), 3.58 (2H, q), 1.31 (3H, t).

Present compound 122: ¹H-NMR (CDCl₃) δ: 8.28 (1H, d), 8.10 (1H, d), 7.84 (1H, dd), 7.74 (1H, d), 6.78 (1H, d), 3.98 (3H, s), 3.53-3.49 (2H, m), 1.81-1.72 (2H, m), 1.04 (3H, t).

Present compound 123: ¹H-NMR (CDCl₃) δ: 8.09 (1H, d), 8.05 (1H, d), 7.78 (1H, dd), 6.95 (1H, d), 6.68 (1H, d), 3.95 (3H, s), 3.51-3.47 (2H, m), 1.82-1.71 (2H, m), 1.03 (3H, t).

Present compound 124: ¹H-NMR (CDCl₃) δ: 8.18 (1H, d), 8.12 (1H, d), 7.89 (1H, dd), 7.79 (1H, d), 6.79 (1H, d), 3.59 (2H, q), 1.31 (3H, t).

Present compound 125: ¹H-NMR (CDCl₃) δ: 8.15 (1H, d), 8.08 (1H, d), 7.70-7.63 (2H, m), 6.73 (1H, d), 3.52-3.48 (2H, m), 1.82-1.72 (2H, m), 1.04 (3H, t).

Present compound 126: ¹H-NMR (CDCl₃) δ: 8.16 (1H, d), 8.09 (1H, d), 7.70-7.63 (2H, m), 6.74 (1H, d), 3.57 (2H, q), 1.31 (3H, t).

Present compound 127: ¹H-NMR (CDCl₃) δ: 8.09 (1H, dd), 8.06 (1H, dd), 7.78 (1H, dd), 6.95 (1H, d), 6.69 (1H, dd), 3.95 (3H, s), 3.56 (2H, q), 1.29 (3H, t).

Present compound 128: ¹H-NMR (CDCl₃) δ: 8.16 (1H, d), 8.13 (1H, d), 7.95 (1H, dd), 7.76 (1H, d), 6.77 (1H, d), 3.58 (2H, q), 1.32 (3H, t).

Present compound 129: ¹H-NMR (CDCl₃) δ: 8.18 (1H, d), 8.11 (1H, d), 7.89 (1H, dd), 7.79 (1H, d), 6.78 (1H, d), 3.54-3.50 (2H, m), 1.82-1.73 (2H, m), 1.04 (3H, t).

Present compound 130: ¹H-NMR (CDCl₃) δ: 8.16 (1H, d), 8.12 (1H, d), 7.95 (1H, dd), 7.76 (1H, d), 6.76 (1H, d), 3.54-3.50 (2H, m), 1.83-1.74 (2H, m), 1.05 (3H, t).

Present compound 133: ¹H-NMR (CDCl₃) δ: 8.07 (1H, d), 7.81-7.77 (2H, m), 7.42-7.39 (2H, m), 7.37-7.28 (5H, m), 6.73 (1H, d), 3.55 (2H, q), 1.29 (3H, t).

Present compound 134: ¹H-NMR (CDCl₃) δ: 8.06 (1H, m), 7.79 (2H, m), 7.43-7.29 (7H, m), 6.72 (1H, m), 3.51-3.47 (2H, m), 1.80-1.71 (2H, m), 1.02 (3H, t).

Present compound 135: ¹H-NMR (CDCl₃) δ: 8.31 (2H, d), 8.15 (1H, d), 8.05 (2H, d), 6.85 (1H, d), 3.60 (2H, q), 1.33 (3H, t).

Present compound 136: ¹H-NMR (CDCl₃) δ: 8.31 (2H, d), 8.14 (1H, d), 8.06 (2H, d), 6.85 (1H, d), 3.55-3.51 (2H, m), 1.84-1.75 (2H, m), 1.05 (3H, t).

Present compound 137: ¹H-NMR (CDCl₃) δ: 8.71 (1H, s), 8.27-8.23 (2H, m), 8.15 (1H, d), 7.64 (1H, t), 6.86 (1H, d), 3.61 (2H, q), 1.33 (3H, t).

Present compound 138: ¹H-NMR (CDCl₃) δ: 8.71 (1H, s), 8.28-8.22 (2H, m), 8.14 (1H, d), 7.64 (1H, t), 6.85 (1H, d), 3.56-3.52 (2H, m), 1.84-1.75 (2H, m), 1.05 (3H, t).

Present compound 139: ¹H-NMR (CDCl₃) δ: 8.07 (1H, d), 7.45-7.42 (2H, m), 7.35 (1H, t), 6.97-6.94 (1H, m), 6.75 (1H, d), 3.88 (3H, s), 3.56 (2H, q), 1.29 (3H, t).

Present compound 140: ¹H-NMR (CDCl₃) δ: 8.06 (1H, d), 7.46-7.43 (2H, m), 7.35 (1H, t), 6.99-6.92 (1H, m), 6.74 (1H, d), 3.89 (3H, s), 3.53-3.48 (2H, m), 1.81-1.71 (2H, m), 1.03 (3H, t).

Present compound 141: ¹H-NMR (CDCl₃) δ: 8.14 (1H, s), 8.12 (1H, d), 8.06 (1H, d), 7.66 (1H, d), 7.57 (1H, t), 6.81 (1H, d), 3.59 (2H, q), 1.31 (3H, t).

Present compound 142: ¹H-NMR (CDCl₃) δ: 8.14 (1H, s), 8.11 (1H, dd), 8.06 (1H, d), 7.66 (1H, d), 7.57 (1H, t), 6.80 (1H, dd), 3.54-3.50 (2H, m), 1.83-1.73 (2H, m), 1.04 (3H, t).

Present compound 143: ¹H-NMR (CDCl₃) δ: 8.07 (1H, d), 7.54 (1H, dd), 7.48-7.32 (7H, m), 7.02 (1H, ddd), 6.74 (1H, d), 5.14 (2H, s), 3.56 (2H, q), 1.29 (3H, t).

Present compound 144: ¹H-NMR (CDCl₃) δ: 8.06 (1H, d), 7.55 (1H, d), 7.47-7.32 (7H, m), 7.02 (1H, d), 6.73 (1H, d), 5.14 (2H, s), 3.52-3.47 (2H, m), 1.80-1.70 (2H, m), 1.02 (3H, t).

Present compound 145: ¹H-NMR (CDCl₃) δ: 8.09 (1H, d), 8.05 (1H, t), 7.79 (1H, d), 7.53 (1H, d), 7.31 (1H, t), 6.75 (1H, d), 3.57 (2H, q), 1.30 (3H, t).

Present compound 146: ¹H-NMR (CDCl₃) δ: 8.08 (1H, d), 8.05 (1H, t), 7.79 (1H, d), 7.53 (1H, d), 7.31 (1H, t), 6.74 (1H, d), 3.52-3.49 (2H, m), 1.81-1.72 (2H, m), 1.03 (3H, t).

Present compound 147: ¹H-NMR (CDCl₃) δ: 8.07 (1H, d) 7.74 (1H, s), 7.66 (1H, d), 7.36 (1H, t), 7.26-7.24 (1H, m), 6.76 (1H, d), 3.56 (2H, q), 2.71 (2H, q), 1.30-1.26 (6H, m).

Present compound 148: ¹H-NMR (CDCl₃) δ: 8.06 (1H, d), 7.74 (1H, s), 7.67 (1H, d), 7.36 (1H, t), 7.26-7.24 (1H, m), 6.75 (1H, d), 3.51-3.47 (2H, m), 2.71 (2H, q), 1.80-1.70 (2H, m), 1.28 (3H, t), 1.02 (3H, t).

Present compound 149: ¹H-NMR (CDCl₃) δ: 8.09 (1H, d), 7.64 (1H, d), 7.62-7.58 (1H, m), 7.41 (1H, m), 7.10 (1H, m), 6.75 (1H, d), 3.57 (2H, q), 1.30 (3H, t).

Present compound 150: ¹H-NMR (CDCl₃) δ: 8.08 (1H, d), 7.64 (1H, m), 7.61-7.59 (1H, m), 7.41 (1H, m), 7.10 (1H, m), 6.74 (1H, d), 3.52-3.48 (2H, m), 1.82-1.72 (2H, m), 1.03 (3H, t).

Present compound 151: ¹H-NMR (CDCl₃) δ: 8.07 (1H, d), 7.63 (1H, d), 7.55 (1H, s), 7.42-7.33 (3H, m), 7.12 (1H, t), 7.04 (3H, d), 6.72 (1H, d), 3.55 (2H, q), 1.29 (3H, t).

Present compound 152: ¹H-NMR (CDCl₃) δ: 8.05 (1H, d), 7.63 (1H, d), 7.55 (1H, s), 7.42-7.33 (3H, m), 7.12 (1H, t), 7.05-7.03 (3H, m), 6.71 (1H, d), 3.51-3.47 (2H, m), 1.80-1.71 (2H, m), 1.02 (3H, t).

Present compound 159: ¹H-NMR (CDCl₃) δ: 8.22 (1H, s), 8.10 (1H, d), 7.97 (1H, d), 7.81 (1H, d), 7.51 (1H, t), 6.82 (1H, d), 6.36 (1H, s), 3.57 (2H, q), 2.97-2.91 (1H, m), 1.30 (3H, t), 0.93-0.88 (2H, m), 0.69-0.65 (2H, m).

Present compound 160: ¹H-NMR (CDCl₃) δ: 8.23 (1H, s), 8.10 (1H, d), 7.98 (1H, d), 7.81 (1H, d), 7.51 (1H, t), 6.82 (1H, d), 6.35 (1H, s), 3.40 (3H, s), 2.97-2.91 (1H, m), 0.93-0.88 (2H, m), 0.69-0.65 (2H, m).

Present compound 161: ¹H-NMR (CDCl₃) δ: 8.23 (1H, d), 8.09 (1H, d), 7.97 (1H, d), 7.81 (1H, d), 7.51 (1H, t), 6.81 (1H, d), 6.37 (1H, s), 3.53-3.48 (2H, m), 2.98-2.91 (1H, m), 1.82-1.72 (2H, m), 1.03 (3H, t), 0.93-0.88 (2H, m), 0.70-0.66 (2H, m).

Present compound 162: ¹H-NMR (CDCl₃) δ: 8.20 (1H, t), 8.08 (1H, d), 7.96 (1H, m), 7.80 (1H, m), 7.50 (1H, t), 6.86-6.78 (2H, m), 6.65 (1H, d), 6.37 (1H, s), 6.25 (1H, d), 2.97-2.90 (1H, m), 0.92-0.88 (2H, m), 0.69-0.65 (2H, m).

Present compound 163: ¹H-NMR (CDCl₃) δ: 8.12 (1H, t), 8.09 (1H, d), 7.92-7.89 (3H, m), 7.84 (1H, m), 7.65 (1H, m), 7.61-7.56 (1H, m), 7.55-7.50 (2H, m), 7.46 (1H, t), 6.81 (1H, d), 3.56 (2H, q), 1.30 (3H, t).

Present compound 164: ¹H-NMR (CDCl₃) δ: 7.89-7.86 (1H, m), 7.81 (1H, dt), 7.63 (1H, dt), 7.48 (1H, t), 6.48 (1H, d), 6.34 (1H, br s), 4.88 (2H, s), 2.96-2.88 (1H, m), 0.90-0.86 (2H, m), 0.67-0.62 (2H, m).

Present compound 165: ³H-NMR (CDCl₃) δ: 8.40 (1H, s), 6.11 (1H, d), 8.04 (1H, d), 7.95-7.93 (2H, m), 7.69 (2H, d), 7.59 (1H, t), 7.41 (2H, t), 7.19 (1H, t), 6.84 (1H, d), 3.54-3.50 (2H, m), 1.83-1.73 (2H, m), 1.04 (3H, t).

Present compound 166: ¹H-NMR (CDCl₃) δ: 8.36 (1H, s), 8.09 (1H, d), 8.02-8.00 (2H, m), 7.93 (1H, d), 7.68 (2H, d), 7.56 (1H, t), 7.40 (2H, t), 7.18 (1H, t), 6.86-6.79 (2H, m), 6.66 (1H, d), 6.26 (1H, d).

Present compound 183: ¹H-NMR (CDCl₃) δ: 8.04 (1H, d), 7.81 (2H, dt), 7.46-7.32 (5H, m), 7.04 (2H, dt), 6.69 (1H, d), 5.12 (2H, s), 3.54 (2H, q), 1.28 (3H, t).

Present compound 184: ¹H-NMR (CDCl₃) δ: 8.11 (1H, s), 8.06-8.05 (1H, m), 7.73 (1H, d), 7.49 (2H, d), 7.40 (2H, t), 7.33 (1H, t), 6.98 (1H, d), 6.68-6.67 (1H, m), 5.22 (2H, s), 3.55 (2H, q), 1.29 (3H, t).

Present compound 196: ¹H-NMR (CDCl₃) δ: 8.38 (1H, s), 8.12 (1H, d), 8.04 (1H, d), 7.94-7.92 (2H, m), 7.70-7.68 (2H, m), 7.58 (1H, t), 7.40 (2H, t), 7.18 (1H, t), 6.84 (1H, d), 3.59 (2H, q), 1.31 (3H, t).

Preparation Example 1-2

The compounds that were prepared according to the Preparation example 1 and their physical properties are indicated below.

A compound represented by formula (pE1-2)

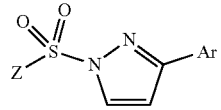

(pE1-2)

wherein Z and Ar represent any combination that are indicated in [Table pE7].

TABLE 13

Table pE7

| Present compound | Z | Ar |
|---|---|---|
| 101 | Et | naphthyl |
| 102 | Et | benzo[1,3]dioxol-5-yl |
| 103 | Et | 5,6,7,8-tetrahydronaphthalen-2-yl |
| 104 | Et | 2,2-difluorobenzo[1,3]dioxol-5-yl |
| 105 | Et | 2,3-dihydro-1H-inden-5-yl |
| 106 | Et | 2,3-dihydrobenzofuran-5-yl |

TABLE 13-continued

Table pE7

| Present compound | Z | Ar |
|---|---|---|
| 107 | Et | benzofurazan-5-yl |
| 108 | Et | benzothiazol-6-yl |
| 109 | NMe2 | 2,2-difluoro-benzo[1,3]dioxol-5-yl |

Present compound 101: $^1$H-NMR (CDCl$_3$) δ: 8.33 (1H, s), 8.13 (1H, d), 8.04 (1H, dd), 7.93-7.84 (3H, m), 7.54-7.50 (2H, m), 6.91 (1H, d), 3.60 (2H, q), 1.32 (3H, t).

Present compound 102: $^1$H-NMR (CDCl$_3$) δ: 8.04 (1H, d), 7.40 (1H, d), 7.34 (1H, dd), 6.87 (1H, d), 6.66 (1H, d), 6.01 (2H, s), 3.54 (2H, q), 1.29 (3H, t).

Present compound 103: $^1$H-NMR (CDCl$_3$) δ: 8.04 (1H, d), 7.60 (1H, s), 7.56 (1H, dd), 7.13 (1H, d), 6.72 (1H, d), 3.54 (2H, q), 2.83-2.78 (4H, m), 1.85-1.79 (4H, m), 1.27 (3H, t).

Present compound 104: $^1$H-NMR (CDCl$_3$) δ: 8.08 (1H, d), 7.64 (1H, d), 7.58 (1H, dd), 7.12 (1H, d), 6.70 (1H, d), 3.56 (2H, q), 1.31 (3H, t).

Present compound 105: $^1$H-NMR (CDCl$_1$) δ: 8.04 (1H, d), 7.76 (1H, s), 7.64-7.61 (1H, m), 7.28 (1H, d), 6.72 (1H, d), 3.54 (2H, q, 2.94 (4H, q), 2.14-2.07 (2H, m), 1.27 (3H, t).

Present compound 106: $^1$H-NMR (CDCl$_3$) δ: 8.03 (1H, d), 7.77 (1H, s), 7.60 (1H, d), 6.83 (1H, d), 6.66 (1H, d), 4.62 (2H, t), 3.53 (2H, q), 3.25 (2H, t), 1.28 (3H, t).

Present compound 107: $^1$H-NMR (CDCl$_3$) δ: 8.22 (1H, t), 8.17 (1H, d), 8.15 (1H, dd), 7.92 (1H, dd), 6.91 (1H, d), 3.61 (2H, q), 1.35 (3H, t).

Present compound 108: $^1$H-NMR (CDCl$_3$) δ: 9.05 (1H, s), 8.53 (1H, d), 8.19 (1H, d), 8.12 (1H, d), 8.02 (1H, dd), 6.84 (1H, d), 3.59 (2H, q), 1.32 (3H, t).

Present compound 109: $^1$H-NMR (CDCl$_3$) δ: 8.01 (1H, d), 7.61 (1H, m), 7.57-7.54 (1H, m), 7.11 (1H, d), 6.64 (1H, d), 3.00 (6H, s).

Preparation Example 1-3

The compounds that were prepared according to the Preparation example 1 and their physical properties are indicated below.

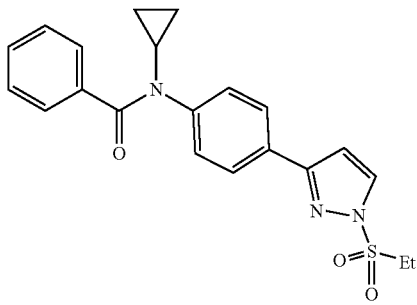

Present compound 190: $^1$H-NMR (CDCl$_3$) δ: 8.07 (1H, d), 7.68-7.63 (2H, m), 7.40 (2H, d), 7.34-7.23 (4H, m), 7.08 (1H, d), 6.66 (1H, d), 3.56 (2H, q), 3.31-3.26 (1H, m), 1.30 (3H, t), 0.87 (2H, q), 0.60 (2H, m).

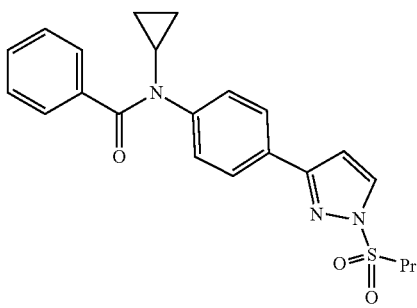 [SMILES: CCS(=O)(=O)n1ccc(-c2ccc(N(C(=O)c3ccccc3)C3CC3)cc2)n1]

Present compound 191: $^1$H-NMR (CDCl$_3$) δ: 8.05 (1H, d), 7.67 (1H, d), 7.63-7.62 (1H, m), 7.41-7.39 (2H, m), 7.32 (1H, t), 7.28-7.21 (3H, m), 7.09 (1H, d), 6.65 (1H, d), 3.51-3.47 (2H, m), 3.31-3.26 (1H, m), 1.81-1.72 (2H, m), 1.04 (3H, t), 0.87 (2H, dd), 0.62-0.58 (2H, m).

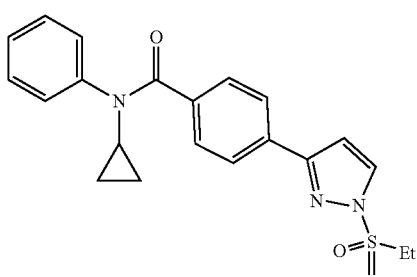

Present compound 192: $^1$H-NMR (CDCl$_3$) δ: 8.04 (1H, d), 7.88 (1H, t), 7.79 (1H, dt), 7.29-7.22 (4H, m), 7.18-7.15 (1H, m), 7.08-7.07 (2H, m), 6.63 (1H, d), 3.55 (2H, q), 3.35-3.29 (1H, m), 1.27 (3H, q), 0.91-0.86 (2H, m), 0.61-0.57 (2H, m).

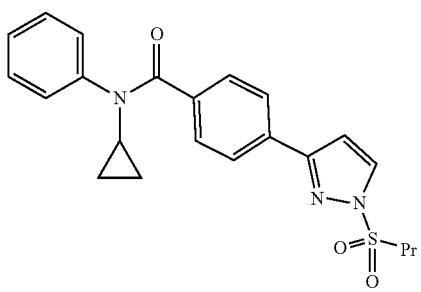

Present compound 193: $^1$H-NMR (CDCl$_3$) δ: 8.03 (1H, d), 7.88 (1H, s), 7.79 (1H, t), 7.29-7.22 (4H, m), 7.17 (1H, t), 7.08-7.06 (2H, m), 6.62 (1H, d), 3.50-3.46 (2H, m), 3.35-3.29 (1H, m), 1.79-1.69 (2H, m), 1.03 (3H, t), 0.89 (2H, dd), 0.61-0.57 (2H, m).

Preparation Example 2

A mixture of the intermediate compound 5-1 0.41 g, the intermediate compound 6-1 0.43 g, sodium carbonate 0.22 g, [1,1'-bis(diphenylphosphino)ferrocene]palladium (II) dichloride 0.11 g, toluene 15 mL, ethanol 15 mL and water 7.5 mL was stirred under reflux for 5 hours. The resulting mixtures were concentrated under reduced pressure, and the residues were subjected to silica gel column chromatography to obtain Present compound 116 represented by the below-mentioned formula 0.36 g.

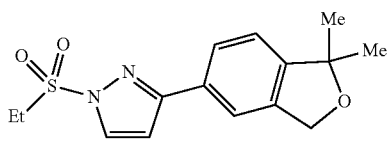 [SMILES: CCS(=O)(=O)n1ccc(-c2ccc3c(c2)COC3(C)C)n1]

Present compound 116: $^1$H-NMR (CDCl$_3$) δ: 8.08 (1H, d), 7.77 (1H, d), 7.74 (1H, s), 7.19 (1H, d), 6.75 (1H, d), 5.11 (2H, s), 3.56 (2H, q), 1.52 (6H, s), 1.28 (3H, t).

Preparation Example 2-1

The compounds that were prepared according to the Preparation example 2 and their physical properties are indicated below.

A compound represented by formula (pE1-1)

(pE1-1)

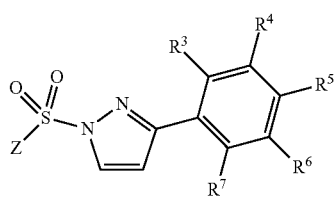

wherein Z, R$^3$, R$^4$, R$^5$, R$^6$ and R$^7$ represents any combination that are indicated in [Table pE8].

TABLE pE8

[Table 14]

| Present compound | Z | R$^3$ | R$^4$ | R$^5$ | R$^6$ | R$^7$ |
|---|---|---|---|---|---|---|
| 110 | Et | F | H | Cl | H | H |
| 111 | Et | H | H | CHF$_2$ | H | H |
| 112 | Et | H | Cl | CF$_3$ | H | H |
| 113 | Et | OMe | H | Cl | H | H |
| 114 | Et | H | F | F | H | F |

Present compound 110: $^1$H-NMR (CDCl$_3$) δ: 8.10 (1H, d), 8.05 (1H, t), 7.28-7.14 (2H, m), 6.88 (1H, d), 3.56 (2H, q), 1.30 (3H, t).

Present compound 111: $^1$H-NMR (CDCl$_3$) δ: 8.11 (1H, d), 7.97 (2H, d), 7.59 (2H, d), 6.80 (1H, d), 6.69 (1H, t), 3.58 (2H, q), 1.31 (3H, t).

Present compound 112: $^1$H-NMR (CDCl$_3$) δ: 8.13 (1H, d), 8.05 (1H, s), 7.84 (1H, d), 7.76 (1H, d), 6.80 (1H, d), 3.59 (2H, q), 1.32 (3H, t).

Present compound 113: $^1$H-NMR (CDCl$_3$) δ: 8.04 (1H, d), 7.98 (1H, d), 7.02 (1H, dd), 6.98-6.97 (2H, m), 3.92 (3H, s), 3.54 (2H, q), 1.29 (3H, t).

Present compound 114: $^1$H-NMR (CDCl$_3$) δ: 8.10 (1H, d), 7.99-7.92 (1H, m), 7.07-6.99 (1H, m), 6.88 (1H, dd), 3.57 (2H, q), 1.31 (3H, t).

Preparation Example 2-2

The compounds that were prepared according to the Preparation example 2 and their physical properties are indicated below.

A compound represented by formula (pE2-2)

(pE2-2)

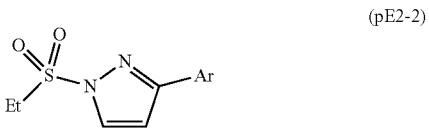

wherein Ar represents a group indicated in [Table pE9].

TABLE 15

Table pE9

| Present compound | Ar |
|---|---|
| 115 | ![benzoxazole] |

Present compound 115: $^1$H-NMR (CDCl$_3$) δ: 8.25 (1H, d), 8.14 (1H, s), 8.11 (1H, d), 8.01 (1H, dd), 7.65 (1H, dd), 6.81 (1H, d), 3.59 (2H, q), 1.32 (3H, t).

Preparation Example 3

To a mixture of 3-(4-chlorophenyl)-1H-pyrazole 0.23 g and THF 5 mL was added a compound represented by formula (ad):

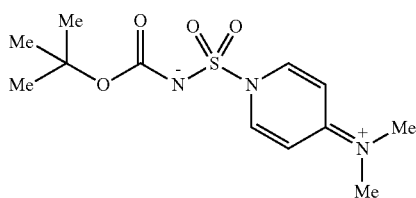

0.47 g at 0° C., and the mixture was stirred at room temperature for 3 hours. The resulting mixtures was acidified by adding hydrochloric acid to the mixture, and the mixtures were stirred at room temperature for 30 minutes. The resulting mixtures were extracted with MTBE, and the resulting organic layers were concentrated under reduced pressure. The resulting residues were washed with a mixed solvent of chloroform and hexane to obtain the present compound 57 represented by the below-mentioned formula 0.29 g.

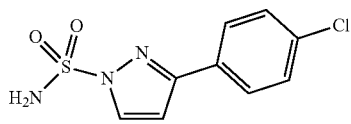 [SMILES: NS(=O)(=O)n1ccc(-c2ccc(Cl)cc2)n1]

Present compound 57: $^1$H-NMR (CDCl$_3$) δ: 7.70 (2H, d), 7.61 (1H, d), 7.37 (2H, d), 6.60 (1H, d).

Preparation Example 4

A mixture of 1,3-difluoro-5-iodobenzene 0.2 g, the intermediate compound 7-1 0.26 g, palladium (II) acetate 0.1 g, XPhos (dicyclohexyl(2',4',6'-triisopropyl-[1,1'-biphenyl]-2-yl)phosphine 0.2 g, sodium carbonate 0.15 g, and toluene 5 mL was stirred at 150° C. for 5 hours. The resulting mixtures were concentrated under reduced pressure. The resulting residues were subjected to silica gel column chromatography to obtain the present compound 118 represented by the below-mentioned formula 0.05 g.

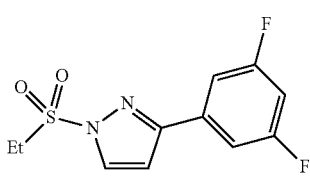 [SMILES: CCS(=O)(=O)n1ccc(-c2cc(F)cc(F)c2)n1]

Present compound 118: $^1$H-NMR (CDCl$_3$) δ: 8.10 (1H, d), 7.44-7.37 (2H, m), 6.88-6.81 (1H, m), 6.73 (1H, d), 3.58 (2H, q), 1.31 (3H, t).

Preparation Example 4-1

The compounds that were prepared according to the Preparation example 4 and their physical properties are indicated below.

A compound represented by formula (pE1-1)

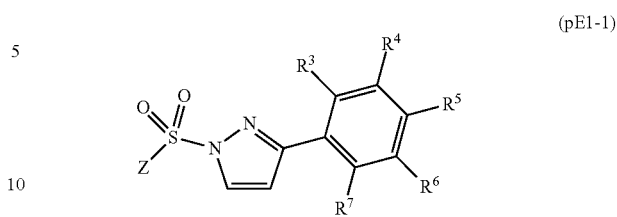

wherein Z, $R^3$, $R^4$, $R^5$, $R^6$ and $R^7$ represent any combination indicated in [Table pE8].

TABLE pE8

[Table 16]

| Present compound | Z | $R^3$ | $R^4$ | $R^5$ | $R^6$ | $R^7$ |
|---|---|---|---|---|---|---|
| 131 | Et | H | OCF$_3$ | H | H | H |
| 132 | Pr | H | OCF$_3$ | H | H | H |
| 153 | Et | H | OCH$_2$c-Pr | H | H | H |
| 154 | Pr | H | OCH$_2$c-Pr | H | H | H |
| 155 | Et | H | OPr | H | H | H |
| 156 | Pr | H | OPr | H | H | H |
| 157 | Et | H | Oi-Pr | H | H | H |
| 158 | Pr | H | Oi-Pr | H | H | H |

Present compound 131: $^1$H-NMR (CDCl$_3$) δ: 8.10 (1H, d), 7.80 (1H, d), 7.74 (1H, s), 7.47 (1H, t), 7.27-7.25 (1H, m), 6.76 (1H, d), 3.58 (2H, q), 1.31 (3H, t).

Present compound 132: $^1$H-NMR (CDCl$_3$) δ: 8.09 (1H, d), 7.80 (1H, dt), 7.74 (1H, s), 7.47 (1H, t), 7.27-7.25 (1H, m), 6.76 (1H, d), 3.53-3.49 (2H, m), 1.82-1.73 (2H, m), 1.04 (3H, t).

Present compound 153: $^1$H-NMR (CDCl$_3$) δ: 8.06 (1H, d), 7.44-7.40 (2H, m), 7.33 (1H, t), 6.96-6.94 (1H, m), 6.74 (1H, d), 3.88 (2H, d), 3.56 (2H, q), 1.31-1.24 (4H, m), 0.69-0.64 (2H, m), 0.40-0.36 (2H, m).

Present compound 154: $^1$H-NMR (CDCl$_3$) δ: 8.05 (1H, d), 7.45-7.40 (2H, m), 7.34 (1H, t), 6.97-6.94 (1H, m), 6.73 (1H, d), 3.88 (2H, d), 3.51-3.47 (2H, m), 1.80-1.68 (2H, m), 1.31-1.24 (1H, m), 1.02 (3H, t), 0.69-0.64 (2H, m), 0.40-0.36 (2H, m).

Present compound 155: $^1$H-NMR (CDCl$_3$) δ: 8.07 (1H, d), 7.45-7.40 (2H, m), 7.34 (1H, t), 6.96-6.93 (1H, m), 6.74 (1H, d), 3.99 (2H, t), 3.56 (2H, q), 1.88-1.79 (2H, m), 1.31-1.26 (3H, m), 1.06 (3H, t).

Present compound 156: $^1$H-NMR (CDCl$_3$) δ: 8.05 (1H, d), 7.43 (2H, d), 7.34 (1H, t), 6.96-6.93 (1H, m), 6.74 (1H, d), 3.99 (2H, t), 3.49 (2H, t), 1.88-1.70 (4H, m), 1.08-1.00 (6H, m).

Present compound 157: $^1$H-NMR (CDCl$_3$) δ: 8.06 (1H, d), 7.43-7.41 (2H, m), 7.33 (1H, t), 6.95-6.92 (1H, m), 6.73 (1H, d), 4.67-4.61 (1H, m), 3.56 (2H, q), 1.36 (6H, d), 1.28 (3H, t).

Present compound 158: $^1$H-NMR (CDCl$_3$) δ: 8.05 (1H, d), 7.43-7.41 (2H, m), 7.33 (1H, t), 6.95-6.92 (1H, m), 6.73 (1H, d), 4.67-4.61 (1H, m), 3.51-3.47 (2H, m), 1.78-1.70 (2H, m), 1.36 (6H, d), 1.02 (3H, t).

Preparation Example 5

A mixture of the intermediate compound 1-49 0.2 g, potassium carbonate 0.22 g, 4-methylbenzylbromide 0.16 mL and acetone 5 mL was stirred at 70° C. for 4 hours. The resulting mixture was concentrated under reduced pressure and the resulting residues were subjected to silica gel column chromatography to obtain the present compound 167 represented by the below-mentioned formula 0.2 g.

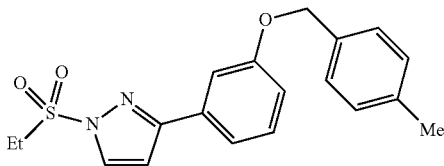 [SMILES: CCS(=O)(=O)n1ccc(-c2cccc(OCc3ccc(C)cc3)c2)n1]

Present compound 167: $^1$H-NMR (CDCl$_3$) δ: 8.07 (1H, d), 7.53 (1H, t), 7.46-7.43 (1H, m), 7.37-7.33 (3H, m), 7.21 (2H, d), 7.01 (1H, dq), 6.73 (1H, d), 5.09 (2H, s), 3.56 (2H, q), 2.37 (3H, s), 1.29 (3H, t).

The compounds that were prepared according to the Preparation example 5 and their physical properties are indicated below.

A compound represented by formula (pE1-1)

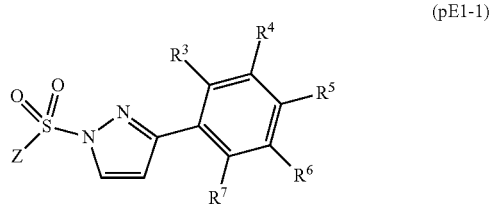

wherein Z, R$^3$, R$^4$, R$^5$, R$^6$ and R$^2$ represent any combination indicated in [Table pE11].

Present compound 168: $^1$H-NMR (CDCl$_3$) δ: 8.06 (1H, d), 7.61-7.58 (1H, m), 7.56-7.55 (1H, m), 7.49-7.47 (1H, m), 7.43-7.41 (1H, m), 7.37 (1H, t), 7.31-7.28 (2H, m), 7.04-7.01 (1H, m), 6.74 (1H, d), 5.24 (2H, s), 3.52-3.48 (2H, m), 1.81-1.71 (2H, m), 1.03 (3H, t).

Present compound 169: $^1$H-NMR (CDCl$_3$) δ: 8.06 (1H, d), 7.52-7.49 (2H, m), 7.37 (1H, t), 7.05-7.02 (1H, m), 6.74 (1H, d), 4.77 (2H, d), 3.52-3.48 (2H, m), 2.54 (1H, t), 1.80-1.71 (2H, m), 1.02 (3H, t).

Present compound 170: $^1$H-NMR (CDCl$_3$) δ: 8.06 (1H, d), 7.47-7.43 (2H, m), 7.35 (1H, t), 6.98-6.95 (1H, m), 6.73 (1H, d), 6.13-6.04 (1H, m), 5.45 (1H, dq), 5.31 (1H, dq), 4.61 (2H, dt), 3.51-3.47 (2H, m), 1.80-1.71 (2H, m), 1.02 (3H, t).

Present compound 171: $^1$H-NMR (CDCl$_3$) δ: 8.06 (1H, d), 7.56-7.55 (1H, m), 7.48-7.42 (2H, m), 7.37 (1H, t), 7.29-7.21 (3H, m), 7.05-7.02 (1H, m), 6.74 (1H, d), 5.11 (2H, s), 3.52-3.48 (2H, m), 2.41 (3H, s), 1.80-1.71 (2H, m), 1.02 (3H, t).

Present compound 172: $^1$H-NMR (CDCl$_3$) δ: 8.07 (1H, d), 7.74-7.71 (2H, m), 7.65 (1M, td), 7.58-7.57 (1H, m), 7.51-7.43 (2H, m), 7.38 (1H, t), 7.06-7.03 (1H, m), 6.75 (1H, d), 5.33 (2H, s), 3.53-3.49 (2H, m), 1.81-1.72 (2H, m), 1.03 (3H, t).

Present compound 173: $^1$H-NMR (CDCl$_3$) δ: 8.06 (1H, d), 7.54-7.53 (1H, m), 7.45 (1H, dt), 7.40-7.33 (3H, m), 7.28-7.26 (2H, m), 7.04-7.01 (1H, m), 6.73 (1H, d), 5.09 (2H, s), 3.51-3.47 (2H, m), 2.98-2.88 (1H, m), 1.80-1.71 (2H, m), 1.26 (6H, d), 1.02 (3H, t).

Present compound 174: $^1$H-NMR (CDCl$_3$) δ: 8.06 (1H, d), 7.58 (1H, s), 7.50 (1H, d), 7.41-7.37 (3H, m), 7.30-7.25 (2H, m), 7.07 (1H, dd), 6.75 (1H, d), 5.36 (2H, s), 3.52-3.48 (2H, m), 1.80-1.71 (2H, m), 1.03 (3H, t).

TABLE 17

Table pE11

| Present compound | Z | R$^3$ | R$^4$ | R$^5$ | R$^6$ | R$^7$ |
| --- | --- | --- | --- | --- | --- | --- |
| 168 | Pr | H | OCH$_2$ (2-Cl—Ph) | H | H | H |
| 169 | Pr | H | ≡–O—• | H | H | H |
| 170 | Pr | H | allyl-O—• | H | H | H |
| 171 | Pr | H | OCH$_2$ (2-Me—Ph) | H | H | H |
| 172 | Pr | H | OCH$_2$ (2-CN—Ph) | H | H | H |
| 173 | Pr | H | OCH$_2$ (4-i-Pr—Ph) | H | H | H |
| 174 | Pr | H | OCH$_2$ (4-Cl—Ph) | H | H | H |
| 175 | Pr | H | OCH$_2$ (4-CF$_3$O—Ph) | H | H | H |
| 176 | Pr | H | OCH$_2$ (2-CN—Ph) | H | H | H |
| 177 | Pr | H | OCH$_2$ (3-CN—Ph) | H | H | H |
| 178 | Pr | H | OCH$_2$ (3-Cl—Ph) | H | H | H |
| 179 | Pr | H | OCH$_2$ (4-Me—Ph) | H | H | H |
| 180 | Pr | H | OCH$_2$ (2,3,4,5,6-F$_5$—Ph) | H | H | H |
| 181 | Pr | H | OCH$_2$ (3,4,5-F$_3$—Ph) | H | H | H |
| 182 | Pr | H | OCH$_2$ (3-F-4-Br—Ph) | H | H | H |
| 185 | Pr | H | H | OCH$_2$Ph | H | H |
| 186 | Pr | H | H | ≡–O—• | H | H |
| 187 | Pr | H | H | OCH$_2$ (4-Me—Ph) | H | H |
| 188 | Pr | H | H | OCH$_2$ (3-Me—Ph) | H | H |
| 189 | Pr | H | H | OCH$_2$ (2-Me—Ph) | H | H |

Present compound 175: $^1$H-NMR (CDCl$_3$) δ: 8.06 (1H, d), 7.55-7.54 (1H, m), 7.52-7.48 (2H, m), 7.46 (1H, dt), 7.37 (1H, t), 7.26-7.24 (2H, m), 7.03-7.00 (1H, m), 6.74 (1H, d), 5.13 (2H, s), 3.51-3.47 (2H, m), 1.80-1.71 (2H, m), 1.02 (3H, t).

Present compound 176: $^1$H-NMR (CDCl$_3$) δ: 8.07 (1H, d), 7.79 (1H, s), 7.70 (1H, d), 7.64 (1H, d), 7.55-7.50 (2H, m), 7.47 (1H, d), 7.38 (1H, t), 7.02-6.99 (1H, m), 6.75 (1H, d), 5.17 (2H, s), 3.52-3.48 (2H, m), 1.81-1.72 (2H, m), 1.03 (3H, t).

Present compound 177: $^1$H-NMR (CDCl$_3$) δ: 8.07 (1H, d), 7.70 (21H, d), 7.60-7.54 (3H, m), 7.47 (1H, d), 7.37 (1H, t), 7.01-6.98 (1H, m), 6.74 (1H, d), 5.20 (2H, s), 3.51-3.47 (2H, m), 1.81-1.71 (2H, m), 1.03 (31H, t).

Present compound 178: $^1$H-NMR (CDCl$_3$) δ: 8.06 (1H, d), 7.54 (1H, s), 7.48-7.45 (2H, m), 7.38-7.31 (4H, m), 7.02-6.99 (1H, m), 6.74 (1H, d), 5.11 (2H, s), 3.52-3.48 (2H, m), 1.80-1.71 (2H, m), 1.02 (3H, t).

Present compound 179: $^1$H-NMR (CDCl$_3$) δ: 8.06 (1H, d), 7.54-7.52 (1H, m), 7.46-7.43 (1H, m), 7.36-7.33 (3H, m), 7.21 (2H, d), 7.03-7.00 (1H, m), 6.73 (1H, d), 5.09 (2H, s), 3.51-3.47 (2H, m), 2.37 (3H, s), 1.80-1.70 (2H, m), 1.02 (3H, t).

Present compound 180: $^1$H-NMR (CDCl$_3$) δ: 8.07 (1H, d), 7.55-7.54 (1H, m), 7.51-7.48 (1H, m), 7.38 (1H, t), 7.02-6.99 (1H, m), 6.74 (1H, d), 5.21 (2H, s), 3.52-3.48 (2H, m), 1.81-1.71 (2H, m), 1.03 (3H, t).

Present compound 181: $^1$H-NMR (CDCl$_3$) δ: 8.07 (1H, d), 7.53-7.52 (1H, m), 7.46 (1H, d), 7.37 (1H, t), 7.10 (2H, t), 6.98 (1H, dd), 6.74 (1H, d), 5.07 (2H, s), 3.51-3.48 (2H, m), 1.81-1.71 (2H, m), 1.03 (3H, t).

Present compound 182: $^1$H-NMR (CDCl$_3$) δ: 8.07 (1H, d), 7.59-7.52 (214, m), 7.47-7.45 (1H, m), 7.36 (1H, t), 7.28-7.25 (1H, m), 7.13 (1H, dd), 7.00-6.97 (1H, m), 6.74 (1H, d), 5.10 (2H, s), 3.51-3.47 (2H, m), 1.80-1.71 (2H, m), 1.02 (3H, t).

Present compound 185: $^1$H-NMR (CDCl$_3$) δ: 8.03 (1H, d), 7.83-7.79 (2H, m), 7.46-7.32 (5H, m), 7.06-7.02 (2H, m), 6.68 (1H, d), 5.12 (2H, s), 3.50-3.46 (2H, m), 1.79-1.70 (2H, m), 1.02 (3H, t).

Present compound 186: $^1$H-NMR (CDCl$_3$) δ: 8.04 (1H, d), 7.84 (1H, t), 7.82 (1H, t), 7.05 (1H, t), 7.03 (1H, t), 6.69 (1H, d), 4.74 (2H, d), 3.50-3.46 (2H, m), 2.54 (1H, t), 1.80-1.70 (2H, m), 1.02 (3H, t).

Present compound 187: $^1$H-NMR (CDCl$_3$) δ: 8.03 (1H, d), 7.82 (1H, t), 7.79 (1H, t), 7.33 (2H, d), 7.20 (2H, d), 7.04 (1H, t), 7.01 (1H, t), 6.68 (1H, d), 5.07 (2H, s), 3.49-3.45 (2H, m), 2.37 (3H, s), 1.79-1.70 (2H, m), 1.02 (3H, t).

Present compound 188: $^1$H-NMR (CDCl$_3$) δ: 8.03 (1H, d), 7.82 (1H, t), 7.80 (1H, t), 7.30-7.23 (3H, m), 7.15 (1H, d), 7.05 (1H, t), 7.01 (1H, dd), 6.68 (1H, d), 5.08 (2H, s), 3.49-3.46 (2H, m), 2.38 (3H, s), 1.80-1.70 (2H, m), 1.05-0.98 (3H, m).

Present compound 189: $^1$H-NMR (CDCl$_3$) δ: 8.04 (1H, d), 7.84 (1H, t), 7.81 (1H, t), 7.41 (1H, d), 7.30-7.21 (3H, m), 7.06 (1H, t), 7.04 (1H, t), 6.69 (1H, d), 5.09 (2H, s), 3.50-3.46 (2H, m), 2.39 (3H, s), 1.80-1.70 (2H, m), 1.02 (3H, t).

Preparation Example 6

A mixture of the intermediate compound 12-2 0.3 g, potassium carbonate 1.4 g, methyl iodide 0.32 mL and dimethyl formamide 5 mL was stirred at room temperature for 12 hours. The resulting mixtures were concentrated under reduced pressure, and the resulting residues were subjected to silica gel column chromatography to obtain the present compound 194 represented by formula 0.2 g.

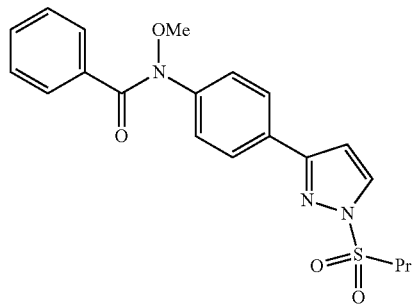

Present compound 194: $^1$H-NMR (CDCl$_3$) δ: 8.07 (1H, d), 8.03 (1H, s), 7.77 (1H, d), 7.69-7.67 (2H, m), 7.51-7.37 (54, m), 6.74 (1H, d), 3.70 (3H, s), 3.52-3.48 (2H, m), 1.81-1.72 (2H, m), 1.04 (3H, t).

Preparation Example 7

A mixture of the present compound 196 0.2 g, cesium carbonate 0.55 g, methyl iodide 0.10 mL, and dimethyl formamide 5 mL was stirred at room temperature for 2 hours. The resulting mixture was concentrated under reduced pressure, and the resulting residues were subjected to silica gel column chromatography to obtain the present compound 195 represented by the below-mentioned formula 0.1 g.

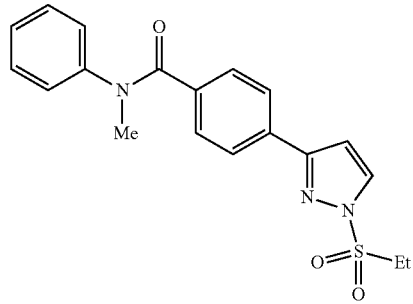 [SMILES: CCS(=O)(=O)n1ccc(-c2ccc(C(=O)N(C)c3ccccc3)cc2)n1]

Present compound 195: $^1$H-NMR (CDCl$_3$) δ: 8.03 (1H, d), 7.86 (1H, s), 7.79 (1H, dt), 7.26-7.20 (4H, m), 7.15 (1H, dd), 7.08 (2H, d), 6.59 (1H, d), 3.54 (21, q), 3.53 (3H, s), 1.27 (3H, t).

The compounds 1 to 196 are collectively referred to as "Present compound Q".

As used herein, "Pyrro" represents pyrrolidin-1-yl group.

In a compound represented by formula (III):

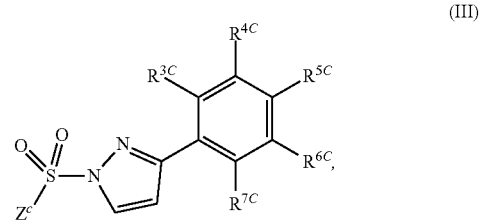

the compounds wherein a combination of $R^{3c}$, $R^{4c}$, $R^{5c}$, $R^{6c}$, $R^{7c}$ and $Z^c$ represents any combinations of the below-mentioned Substituent Numbers R1 to 24535 (hereinafter, the compounds with Substituent Numbers R1 to R4535 are referred to as "Present compounds R1 to R4535" respectively, and "Present compounds R1 to R4535" are collectively referred to as "Present compound R" may be obtained according to the above-mentioned processes.

Here "Substituent Number R1 to R4435" represents a combination of $R^{3c}$, $R^{4c}$, $R^{5c}$, $R^{6c}$, $R^{7c}$ and $Z^c$ in the compound represented by formula (III), and hereinafter is indicated as [Substituent Number; $R^{3C},R^{4C},R^{5C},R^{6C},R^{7C},Z^C$].

For example, Substituent Number R5 represents a combination wherein $R^{3c}$, $R^{4c}$, $R^{6c}$ and $R^{7c}$ represent a hydrogen atom, and $R^{5c}$ represents a methyl group and $Z^c$ represents a methyl group.

For example, the present compound R5 represents a compound represented by formula (III) wherein the substituent number is R5, and also represents the below-mentioned compound represented by formula (III) wherein $R^{3c}$, $R^{4c}$, $R^{6c}$ and $R^{7c}$ represent a hydrogen atom, $R^{5c}$ represents a methyl group, and $Z^c$ represents a methyl group.

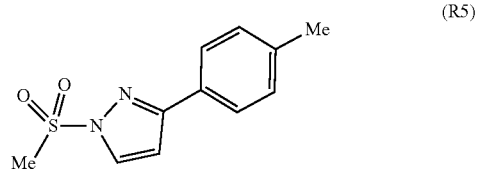 [SMILES: Cc1ccc(-c2ccn(S(C)(=O)=O)n2)cc1]

(R5)

[Substituent Number; $R^{3C},R^{4C},R^{5C},R^{6C},R^{7C},Z^C$]:[R1;H,H,F,H,H,Me],[R2;H,H,Cl,H,H,Me],[R3;H,H,Br,H,H,Me],[R4;H,H,I,H,H,Me],[R5;H,H,Me,H,H,Me],[R6; H,H,CHF$_2$,H,H,Me],[R7;H,H,CF$_3$,H,H,Me],[R8;H,H,NO$_2$,H,H,Me],[R9;H,H,F,H,H,Et],[R10;H,H,Cl,H,H,Et],[R11;H,H,Br,H,H,Et],[R12;H,H,I,H,H,Et],[R13;H,H,Me,H,H,Et],[R14;H,H,CHF$_2$,H,H,Et],[R15;H,H,CF$_3$,H,H,Et],[R16;H,H,NO$_2$,H,H,Et],[R17;H,H,F,H,H,Pr], [R18;H,H,Cl,H,H,Pr],[R19;H,H,Br,H,H,Pr],[R20;H,H,I,H,H,Pr], [R21;H,H,Me,H,H,Pr],[R22;H,H,CHF$_2$,H,H,Pr],[R23;H,H,CF$_3$,H,H, Pr],[R24;H,H,NO$_2$,H,H,Pr],[R25;H,H,F,H,H,Bu],[R26;H,H,Cl,H,H,Bu],[R27;H,H,Br,H,H,Bu],[R28;H,H,I,H,H,Bu],[R29;H,H,Me,H,H,Bu],[R30;H,H,CHF$_2$,H,H,Bu],[R31;H,H,CF$_3$,H,H,Bu],[R32;H,H,NO$_2$,H,H,Bu],[R33;H,H,F,H,H,c-Pr],[R34;H,H,Cl,H,H,c-Pr],[R35;H,H,Br,H,H,c-Pr],[R36;H,H,I,H,H,c-Pr],[R37;H,H,Me,H,H,c-Pr],[R$^{3B}$;H,H,CHF$_2$,H,H,c-Pr],[R39;H,H,CF$_3$,H,H,c-Pr],[R40;H,H,NO$_2$,H,H,c-Pr],[R41;H,H,F,H,H,CH$_2$CF$_3$],[R42;H,H,Cl,H,H,CH$_2$CF$_3$],[R43;H,H, Br,H,H,CH$_2$CF$_3$],[R44;H,H,I,H,H,CH$_2$CF$_3$],[R45;H,H,Me,H,H,CH$_2$CF$_3$],[R46;H,H,CHF$_2$,H,H,CH$_2$CF$_3$],[R47;H,H,CF$_3$,H,H,CH$_2$CF$_3$],[R$^{4B}$;H,H, NO$_2$,H,H,CH$_2$CF$_3$],[R49;H,H,F,H,H,CH$_2$CHF$_2$],[R50;H,H,Cl,H,H,CH$_2$CHF$_2$],[R51;H,H,Br,H,H,CH$_2$CHF$_2$],[R52;H,H,I,H,H,CH$_2$CHF$_2$],[R53;H, H,Me,H,H,CH$_2$CHF$_2$],[R54;H,H,CHF$_2$,H,H,CH$_2$CHF$_2$],[R55;H,H,CF$_3$,H,H,CH$_2$CHF$_2$],[R56;H,H,NO$_2$,H,H,CH$_2$CHF$_2$],[R57;H,H,F,H,H,CF$_2$CH$_3$],[R58;H,H,Cl,H,H,CF$_2$CH$_3$],[R59;H,H,Br,H,H,CF$_2$CH$_3$],[R60;H,H,I,H,H,CF$_2$CH$_3$],[R61;H,H,Me,H,H,CF$_2$CH$_3$],[R62;H,H,CHF$_2$,H,H,CF$_2$CH$_3$],[R63;H,H,CF$_3$,H,H,CF$_2$CH$_3$],[R64;H,H,NO$_2$,H,H,CF$_2$CH$_3$],[R65;H,H,F,H, H,NMe$_2$],[R66;H,H,Cl,H,H,NMe$_2$],[R67;H,H,Br,H,H,NMe$_2$],[R68;H,H,I,H,H,NMe$_2$],[R69;H,H,Me,H,H,NMe$_2$],[R70;H,H,CHF$_2$,H,H,NMe$_2$],[R71;H,EH,CF$_3$,H,H,NMe$_2$],[R72;H,H,NO$_2$,H,H,NMe$_2$],[R73;H,H,F,H,H, Pyrro],[R74;H,H,Cl,H,H,Pyrro],[R75;H,H,Br,H,H,Pyrro],[R76;H,H,I,H,H,Pyrro],[R77;H,H,Me,H,H,Pyrro],[R78;H,H,CHF$_2$,H,H,Pyrro],[R79;H,H,CF$_3$,H,H,Pyrro],[R80;H,H,NO$_2$,H,H,Pyrro],[R81;H,F,F,H,H,Me],[R82;H,F,Cl,H,H,Me],[R83;H,F,Br,H,H,Me],[R84;H,F,I,H,H,Me],[R85;H,F,Me,H,H,Me],[R86;H,F,CHF$_2$,H,H,Me],[R87;H,F,CF$_3$,H,H,Me],[R88;H,F,NO$_2$,H,H,Me],[R89;H,F,F,H,H,Et],[R90;H,F,Cl,H,H,Et],[R91;H,F,Br,H,H,Et],[R92;H,F,I,H,H,Et],[R93;H,F,Me,H,H,Et],[R94;H,F,CHF$_2$,H,H,Et],[R95;H,F,CF$_3$,H,H,Et],[R96;H,F,NO$_2$,H,H,Et],[R97;H,F,F,H,H,Pr],[R98;H,F,Cl,H,H,Pr],[R99;H,F,Br,H,H,Pr],[R100;H,F,I,H,H,Pr],[R101;H,F,Me,H,H,Pr],[R102;H,F,CHF$_2$,H,H,Pr],[R103;H,F,CF$_3$,H,H,Pr],[R104;H,F,NO$_2$,H,H,Pr],[R105;H,F,F,H,H,Bu],[R106;H,F,Cl,H,H,Bu],[R107;H,F,Br,H,H,Bu],[R108;H,F,I,H,H,Bu],[R109;H,F,Me,H,H,Bu],[R110;H,F,CCHF$_2$,H,H,Bu],[R111;H,F,CF$_3$,H,H,Bu],[R112;H,F,NO$_2$,H,H,Bu],[R113;H,F,F,H,H,c-Pr],[R114;H,F,Cl,H,H,c-Pr],[R115;H,F,Br,H,H,c-Pr],[R116;H,F,I,H,H,c-Pr],[R117;H,F,Me,H,H,c-Pr],[R118;H,F,CHF$_2$,H,H,c-Pr],[R119;H,F,CF$_3$,H,H,c-Pr],[R120;H,F,NO$_2$,H,H,c-Pr],[R121;H,F,F,H,H,CH$_2$CF$_3$],[R122;H,F,Cl,H,H,CH$_2$CF$_3$],[R123;H,F,Br,H,H,CH$_2$CF$_3$],[R124;H,F,I,H,H,CH$_2$CF$_3$],[R125;H,F,Me,H,H,CH$_2$CF$_3$],[R126;H,F,CHF$_2$,H,H,CH$_2$CF$_3$],[R127;H,F,CF$_3$,H,H,CH$_2$CF$_3$],[R128;H,F,NO$_2$,H,H,CH$_2$CF$_3$],[R129;H,F,F,H,H,CH$_2$CHF$_2$],[R130;H,F, Cl,H,H,CH$_2$CHF$_2$],[R131;H,F,Br,H,H,CH$_2$CHF$_2$],[R132;H,F,I,H,H,CH$_2$HF$_2$],[R133;H,F,Me,H,H,CH$_2$CHF$_2$],[R134;H,F,CHF$_2$,H,H,CH$_2$CHF$_2$], [R135;H,F,CF$_3$,H,H,CH$_2$CHF$_2$],[R136;H,F,NO$_2$,H,H,CH$_2$CHF$_2$],[R137;H,F,F,H,H,CF$_2$CH$_3$],[R138;H,F,Cl,H,H,CF$_2$CH$_3$],[R139;H,F,Br,H,H,CF$_2$CH$_3$],[R140;H,F,I,H,H,CF$_2$CH$_3$],[R141;H,F,Me,H,H,CF$_2$CH$_3$],[R142;H,F,CHF$_2$,H,H,CF$_2$CH$_3$],[R143;H,F,CF$_3$,H,H,CF$_2$CH$_3$],[R144;H,F,NO$_2$,H,H,CF$_2$CH$_3$],[R145;H,F,F,H,H,NMe$_2$],[R146;H,F,Cl,H,H,NMe$_2$],[R147;H,F,Br,H,H,NMe$_2$],[R148;H,F,I,H,H,NMe$_2$],[R149;H,F,Me,H,H,NMe$_2$],[R150;H,F,CHF$_2$,H,H,NMe$_2$],[R151;H,F,CF$_3$,H,H,NMe$_2$],[R152;H,F,NO$_2$,H,H,NMe$_2$],[R153;H,F,F, H,H,Pyrro],[R154;H,F,Cl,H,H,Pyrro],[R155;H,F,Br,H,H,Pyrro], [R156;H,F,I,H,H,Pyrro],[R157;H,F,Me,H,H,Pyrro],[R158;H,F,CH F$_2$,H,H,Pyrro],[R159;H,F,CF$_3$,H,H,Pyrro],[R160;H,F,NO$_2$,H,H,Pyrro],[R161;H,Cl,F,H,H,Me],[R162;H,Cl,Cl,H,H,Me],[R163;H,Cl,Br,H,H,Me],[R164;H,Cl,I,H,H,Me],[R165;H,Cl,Mie,H,H,Me],[R166;H,Cl,CHF$_2$,H,H,Me],[R167;H,Cl,CF$_3$,H,H,Me],[R168;H,Cl,NO$_2$,H,H, Me],[R169;H,Cl,F,H,H,Et],[R170;H,Cl,Cl,H,H,Et],[R171;H,Cl,Br,H,H,Et],[R172;H,Cl,I,H,H,Et],[R173;H,Cl,Me,H,H,Et],[R174; H,Cl,CHF$_2$,H,H,Et],[R175;H,Cl,CF$_3$,H,H,Et],[R176;H,Cl,NO$_2$,H,H, Et],[R177;H,Cl,F,H,H,Pr],[R178;H,Cl,Cl,H,H,Pr],[R179;H,Cl,Br,H,H,Pr],[R180;H,Cl,I,H,H,Pr],[R181;H,Cl,Me,H,H,Pr],[R182; H,Cl,CHF$_2$,H,H,Pr],[R183;H,Cl,CF$_3$,H,H,Pr],[R184;H,Cl,NO$_2$,H,H,Pr],[R185;H,Cl,F,H,H,Bu],[R186;H,Cl,Cl,H,H,Bu],[R187; H,Cl,Br,H,H,Bu],[R188;H,Cl,I,H,H,Bu],[R189;H,Cl,Me,H,H,Bu],[R190; H,Cl,CHF$_2$,H,H,Bu],[R191;H,Cl,CF$_3$,H,H,Bu],[R192;H,Cl,NO$_2$,H,H, Bu],[R193;H,Cl,F,H,H,c-Pr],[R194;H,Cl,Cl,H,H,c-Pr],[R195;H,Cl,Br,H,H,c-Pr],[R196;H,Cl,I,H,H,c-Pr],[R197;H,Cl,Me,H,H,c-Pr],[R198;H,Cl,CHF$_2$,H,H,c-Pr],[R199;H,Cl,CF$_3$,H,H,c-Pr],[R200;H,Cl,NO$_2$,H,H,c-Pr],[R201;H,Cl,F,H,H,CH$_2$CF$_3$],[R202;H,Cl,Cl,H,H,CH$_2$CF$_3$],[R203;H,Cl,Br,H,H,CH$_2$CF$_3$],[R204;H,Cl,I,H,H,CH$_2$CF$_3$],[R205;H,Cl,Me, H,H,CH$_2$CF$_3$],[R206;H,Cl,CHF$_2$,H,H,CH$_2$CF$_3$],[R207;H,Cl,CF$_3$,H,H,CH$_2$CF$_3$],[R208; H,Cl,NO$_2$,H,H,CH$_2$CF$_3$],[R209;H,Cl,F,H,H,CH$_2$CHF$_2$],[R210;H,Cl,Cl,H,H,CH$_2$CHF$_2$],[R211;H,Cl,Br,H,H,CH$_2$CHF$_2$],[R212;H, Cl,I,H,H,CH$_2$CHF$_2$],[R213;H,Cl,Me,H,H,CH$_2$CHF$_2$],[R214;H,Cl,CHF$_2$,H,H,CH$_2$CHF$_2$],[R215; H,Cl,CF$_3$,H,H,CH$_2$CHF$_2$],[R216;H,Cl,NO$_2$,H,H,CCH$_2$CHF$_2$],[R217;H,Cl,F,H,H,CF$_2$CH$_3$],[R218;H,Cl,Cl, H,H,CF₂CH₃],[R219;H,Cl,Br,H,H,CF₂CH₃],[R220;H,Cl,I, H,H,CF₂CH₃],[R221;H,Cl,Me,FH,H,CF₂CH₃],[R222;H,Cl, CHF₂,H,H,CF₂CH₃],[R223;H,Cl,CF₃,H,H,CF₂CH₃],[R224; H,Cl,NO₂,H,H,CF₂CH₃],[R225;H,Cl,F,H,H,NMe₂], [R226; H,Cl,Cl,H,H,NMe₂],[R227;H,Cl,Br,H,H,NMe₂],[R228;H, Cl, I,H,H,NMe₂],[R229;H,Cl,Me,H,H,NMe₂],[R230;H,Cl, CHF₂,H,H,NMe₂],[R231;H,Cl,CF₃,H,H,NMe₂],[R232;H, Cl,NO₂,H,H,NMe₂],[R233;H, Cl,F,H,H,Pyrro],[R234;H,Cl, Cl,H,H,Pyrro],[R235;H,Cl,Br,H,H, Pyrro],[R236;H,Cl,I,H, H,Pyrro],[R237;H,Cl,Me,H,H,Pyrro],[R238;H,Cl,CHF₂,H, H,Pyrro],[R239;H,Cl,CF₃,H,H,Pyrro],[R240;H,Cl,NO₂,H, H,Pyrro],[R241;H,Br,F,H,H,Me],[R242;H,Br,Cl,H,H,Me], [R243;H,Br,Br,H,H,Me],[R244;H,Br,I,H,H,Me],[R245;H, Br,Me,H,H,Me],[R246;H,Br,CHF₂,H,H,Me],[R247;H,Br, CF₃,H,H,Me],[R248;H,Br,NO₂,H,H,Me],[R249;H,Br,F,H, H,Et],[R250;H,Br,Cl,H,H,Et],[R251;H,Br,Br,H,H,Et], [R252;H,Br,I,H,H,Et],[R253;H,Br,Me, H,H,Et],[R254;H, Br,CHF₂,H,H,Et],[R255;H,Br,CF₃,H,H,Et],[R256;H,Br, NO₂,H,H,Et],[R257;H,Br,F,H,H,Pr],[R258;H,Br,Cl,H,H, Pr],[R259;H,Br,Br,H,H,Pr],[R260;H,Br,I,H,H,Pr],[R261;H, Br,Me,H,H,Pr],[R262;H,Br,CHF₂,H,H,Pr],[R263;H,Br,CF₃, H,H,Pr],[R264;H,Br,NO₂,H,H,Pr],[R265;H,Br,F,H,H,Bu], [R266;H,Br,Cl,H,H, Bu],[R267;H,Br,Br,H,H,Bu],[R268;H, Br,I,H,H,Bu],[R269;H,Br,Me,H,H,Bu],[R270;H,Br,CHF₂, H,H,Bu],[R271;H,Br,CF₃,H,H,Bu],[R272;H,Br,NO₂,H,H, Bu],[R273;H,Br,F,H,H,c-Pr],[R274;H,Br,Cl,H,H,c-Pr], [R275;H,Br,Br,H,H,c-Pr],[R276;H,Br,I,H,H,c-Pr],[R277;H, Br,Me,H,H,c-Pr],[R278;H,Br,CHF₂,H,H,c-Pr],[R279;H,Br, CF₃,H,H,c-Pr],[R280;H,Br,NO₂,H,H,c-Pr],[R281;H,Br,F,H, H,CH₂CF₃],[R282;H,Br,Cl,H,H,CH₂CF₃],[R283;H,Br,Br, H,H,CH₂CF₃],[R284;H,Br,I,H,H,CH₂CF₃],[R285;H,Br,Me, H,H,CH₂CF₃],[R286;H,Br,CHF₂,H,H,CH₂CF₃],[R287;H, Br,CF₃,H,H,CH₂CF₃],[R288;H,Br,NO₂,H,H,CH₂CF₃], [R289;H,Br,F,H,H,CH₂CHF₂],[R290;H,Br,Cl,H,H, CH₂CHF₂],[R291;H,Br,Br,H,H,CH₂CHF₂],[R292;H, Br,I, H,H,CH₂CHF₂],[R293;H,Br,Me,H,H,CH₂CHF₂],[R294;H, Br,CHF₂,H,H,CH₂CHF₂],[R295;H,Br,CF₃,H,H,CH₂CHF₂],
[8296;H,Br,NO₂,H,H,CH₂CHF₂],[R297;H,Br,F,H,H, CF₂CH₃],[R298;H,Br,Cl,H,H,CF₂CH₃], [R299;H,Br,Br,H, H,CF₂CH₃],[R300;H,Br,I,H,H,CF₂CH₃],
[R301;H,Br,Me,H,H,CF₂CH₃],[R302;H,Br,CHF₂,H,H, CF₂CH₃],[R303;H,Br,CF₃,H,H,CF₂CH₃],[R304;H,Br,NOs, H,H,CF₂CH₃],[R305;H,Br,F,H,H,NMe₂],[R306;H,Br,Cl,H, H,NMe₂],[R307;H,Br,Br,H,H,NMe₂],[R308;H,Br,I,H,H, NMe₂],[R309;H,Br,Me,H,H,NMe₂],[R310;H,Br,CHF₂, H,H,NMe₂];[R311;H,Br,CF₃,H,H,NMe₂],[R312;H,Br,NO₂, H,H,NMe₂], [R313;H,Br,F,H,H,Pyrro],[R314;H,Br,Cl,H,H, Pyrro],[R315;H,Br,Br,H,H,Pyrro],[R316;H,Br,I,H,H, Pyrro],[R317;H,Br,Me,H,H,Pyrro],[R318;H,Br,CHF₂,H,H, Pyrro],[R319;H,Br,CF₃,H,H,Pyrro],[R320;H,Br,NO₂,H,H, Pyrro],[R321;H,Me,F,H,H,Me],[R322;H,Me,Cl,H,H,Me], [R323;H,Me,Br,H,H,Me],[R324;H,Me,I,H,H,Me],[R325;H, Me,Me,H,H,Me],[R326;H,Me,CHF₂,H,H,Me],[R327;H, Me,CF₃,H,H,Me],[R328;H,Me,NO₂,H,H,Me],[R329;H,Me, F,H,H,Et],[R330;H,Me,Cl,H,H,Et],[R331;H,Me,Br,H,H, Et],[R332;H,Me,I,H,H,Et],[R333; H,Me,Me,H,H,Et], [R334;H,Me,CHF₂,H,H,Et],[R335;H,Me,CF₃,H,H, Et], [R336;H,Me,NO₂,H,H,Et],[R337;H,Me,F,H,H,Pr],[R338; H,Me, Cl,H,H,Pr],[R339;H,Me,Br,H,H,Pr],[R340;H,Me,I, H,H,Pr],[R341;H,Me,Me,H,H,Pr],[R342;H,Me,CHF₂,H,H, Pr],[R343;H,Me,CF₃,H,H,Pr],[R344;H,Me,NO₂,H,H,Pr], [R345;H,Me,F,H,H,Bu],[R346;H,Me,Cl,H,H,Bu],[R347;H, Me,Br,H,H,Bu],[R348;H,Me,I,H,H,Bu],[R349;H,Me,Me,H, H,Bu],[R350;H,Me,CHF₂,H,H,Bu],[R351;H,Me,CF₃,H, H,Bu],[R352;H,Me,NO₂,H,H,Bu],[R353;H,Me,F,H,H,c-Pr],[R354;H,Me,Cl,H,H,c-Pr],[R355;H,Me,Br,H,H,c-Pr], [R356;H,Me,I,H,H,c-Pr],[R357;H,Me,Me,H,H,c-Pr],[R358; H,Me,CHF₂,H,H,c-Pr],[R359;H,Me,CF₃,H,H,c-Pr],[R360; H,Me,NO₂,H,H,c-Pr],[R361;H,Me,F,H,H,CH₂CF₃],[R362; H,Me,Cl,H,H,CH₂CF₃],[R363;H,Me,Br,H,H,CH₂CF₃], [R364;H,Me,I,H,H,CH₂CF₃],[R365;H,Me,Me, H,H, CH₂CF₃],[R366;H,Me,CHF₂,H,H,CH₂CF₃],[R367;H,Me, CCF₃,H,H,CH₂CF₃],[R368;[H,Me,NO₂,H,H,CH₂CF₃], [R369;H,Me,F,H,H,CH₂CHF₂],[R370;H,Me,Cl,H,H, CH₂CHF₂],[R371;H,Me,Br,H,H,CH₂CHF₂],[R372;H, Me,I, H,H,CH₂CHF₂],[R373;H,Me,Me,H,H,CH₂CHF₂],[R374;H, Me,CHF₂,H,H,CH₂CHF₂],[R375;H,Me,CF₃,H,H, CHCHF₂],[R376;H,Me,NO₂,H,H, CH₂CHF₂],[R377;H,Me, F,H,H,H,CF₂CH₃],[R378;H,Me,Cl,H,H,CF₂CH₃],[R379;H, Me,Br,H,H,CF₂CH₃],[R380;H,Me,I,H,H,CF₂CH₃],[R381; H,Me,Me,H,H,CF₂CH₃],[R382;H,Me,CHF₂,H,H,CF₂CH₃], [R383;H,Me,CF₃,H, H,CF₂CH₃],[R384;H,Me,NO₂,H,H, CF₂CH₃],[R385;H,Me,F,H,H,NMe₂],[R386;H,Me,Cl,H,H, NMe₂],[R387;H,Me,Br,H,H,NMe₂],[R388;H,Me,I,H,H, NMe₂],[R389;H,Me,Me,H,H,NMe₂],[R390;H,Me,CHFZ, H,H,NMe₂],[R391;H,Me,CF₃,H,H,NMe₂],[R392;H,Me, NO₂,H,H,NMe₂],[R393;H,Me,F,H,H,Pyrro],[R394;H,Me, Cl,H,H,Pyrro],[R395;H,Me,Br,H,H,Pyrro],[R396;H,Me,I, H,H,Pyrro],[R397;H,Me,Me,H,H,Pyrro],[R398;H,Me, CHF₂,H,H,Pyrro],[R399;H,Me,CF₃,H,H,Pyrro],[R400;H, Me,NO₂,H,H,Pyrro],[R401;H,CHF₂,F,H,H,Me],[R402;H, CHF₂,Cl,H,H,Me],[R403;H,CHF₂,Br,H,H,Me],[R404;H, CHF₂,I,H,H,Me],[R405;H,CHF₂,Me,H,H,Me],[R406;H, CHF₂,CHF₂,H,H,Me],[R407;H,CHF₂,CF₃,H, H,Me], [R408;H,CHF₂,NO₂,H,H,Me],[R409;H,CHF₂,F,H,H,Et], [R410; H,CHF₂,Cl,H,H,Et],[R411;H,CHF₂,Br,H,H,Et], [R412;H,CHF₂,I,H,H,Et],[R413;H,CHF₂,Me,H,H,Et], [R414;H,CHF₂,CHF₂,H,H,Et],[R415;H,CHF₂,CF₃,H,H,Et], [R416;H,CHF₂,NO₂,H,H,Et],[R417;H,CHF₂,F, H,H,Pr], [R418;H,CHF₂,Cl,H,H,Pr],[R419;H,CHF₂,Br,H,H,Pr], [R420;H,CHF₂,I,H,H,Pr],[R421;H,CHF₂,Me,H,H,Pr], [R422;H,CHF₂,CHF₂,H,H,Pr],[R423;H,CHF₂,CF₃,H,H,Pr], [R424;H,CHF₂,NO₂,H,H,Pr],[R425;H,CHF₂,F,H,H,Bu], [R426;H,CHF₂,Cl,H,H,Bu],[R427;H,CHF₂,Br,H,H,Bu], [R428;H,CHF₂,I,H,H,Bu],[R429;H,CHF₂,Me,H,H,Bu], [R430;H,CHF₂,CHF₂,H,H,Bu],[R431;H,CHF₂,CF₃,H,H, BU],[R432;H,CHF₂,NO₂,H,H,Bu],[R433;H,CHF₂,F,H,H,c-Pr],[R434;H,CHF₂,Cl,H,H,c-Pr],[R435;H,CHF₂,Br,H,H,c-Pr],[R436;H,CH F₂,I,H,H,c-Pr],[R437;H,CHF₂,Me,H,H,c-Pr],[R438;H,CHF₂,CHF₂,H,H,c-Pr],[R439;H,CHF₂,CF₃,H, H,c-Pr],[R440;H,CHF₂,NO₂,H,H,c-Pr],[R441;H,CHF₂,F, H,CH₂CF₃],[R442;H,CHF₂,Cl,H,H,CH₂CF₃],[R443;H, CHF₂,Br,H,H,CH₂CF₃],[R444;H,CHF₂,I,H,H,CH₂CF₃], [R445;H, CHF₂,Me,H,H,CH₂CF₃],[R446;H,CHF₂,CHF₂,H, H,CH₂CF₃],[R447;H,CHF₂,CF₃,H,H,CH₂CF₃],[R448;H, CHF₂,NO₂,H,H,CH₂CF₃],[R449;H,CHF₂,F, H,H, CH₂CHF₂],[R450;H,CHF₂,Cl,H,H,CH₂CHF₂],
[R451;H,CHF₂,Br,H,H,CH₂CHF₂],[R452;H,CHF₂,I,H,H, CH₂CHF₂],[R453;H,CHF₂,Me,H,H,CH₂CHF₂],[R454;H, CHF₂,CHF₂,H,H,CH₂CHF₂],[R455;H,CHF₂,CF₃,H,H, CH₂CHF₂],[R456;H,CHF₂,NO₂,H,H,CH₂CHF₂],[R457; H,CHF₂,F,H,H,CF₂CH₃],[R458;H,CHF₂,Cl,H,H,CF₂CH₃], [R459;H,CHF₂,Br,H,H,CF₂CH₃],[R460;H,CHF₂,I,H,H, CF₂CH₃],[R461;H,CHF₂,Me,H, H,CF₂CH₃],[R462;H, CHF₂,CHF₂,H,H,CF₂CH₃],[R463;H,CHF₂,CF₃,H,H, CF₂CH₃],[R464;H,CHF₂,NO₂,H,H,CF₂CH₃],[R465;H, CHF₂,F,H,H,NMe₂],[R466;H,CHF₂,Cl,H,H,NMe₂],[R467; H,CHF₂,Br,H,H,NMe₂],[R468;H,CHF₂,I,H,H,NMe₂], [R469;H,CHF₂,Me,H,H,NMe₂],[R470;H,CHF₂,CHF₂,H,H, NMe₂],[R471;H,CHF₂,CF₃,H,H,NMe₂],[R472;H,CHF₂, NO₂,H,H,NMe₂],[R473;H,CHF₂,F,H,H,Pyrro],[R474;H, CHF₂,Cl,H,H,Pyrro],[R475;H,CHF₂,Br,H,H,Pyrro],[R476; H,CHF₂,I,H,H,Pyrro],[R477;H,CHF₂,Me,H,H,Pyrro], [R478;H,CHF₂,CHF₂,H,H,Pyrro],[R479;H,CHF₂, CF₃,H,

[R480;H,CHF$_2$,NO$_2$,H,H,Pyrro],[R481;H,CF$_3$,F,H,H,Me],[R482;H,CF$_3$,Cl,H,H,Me],[R483;H,CF$_3$,Br,H,H,Me],[R484;H,CF$_3$,I,H,H,Me],[R485;H,CF$_3$,Me,H,H,Me],[R486;H,CF$_3$,CHF$_2$,H,H,Me],[R487;H,CF$_3$,CF$_3$,H,H,Me],[R488;H,CF$_3$,NO$_2$,H,H,Me],[R489;H,CF$_3$,F,H,H,Et],[R490;H,CF$_3$,Cl,H,H,Et],[R491;H,CF$_3$,Br,H,H,Et],[R492;H,CF$_3$,I,H,H,Et],[R493;H,CF$_3$,Me,H,H,Et],[R494;H,CF$_3$,CHF$_2$,H,H,Et],[R495;H,CF$_3$,CF$_3$,H,H,Et],[R496;H,CF$_3$,NO$_2$,H,H,Et],[R497;H,CF$_3$,F,H,H,Pr],[R498;H,CF$_3$,Cl,H,H,Pr],[R499;H,CF$_3$,Br,H,H,Pr],[R500;H,CF$_3$,I,H,H,Pr],[R501;H,CF$_3$,Me,H,H,Pr],[R502;H,CF$_3$,CHF$_2$,H,H,Pr],[R503;H,CF$_3$,CF$_3$,H,H,Pr],[R504;H,CF$_3$,NO$_2$,H,H,Pr],[R505;H,CF$_3$,F,H,H,Bu],[R506;H,CF$_3$,Cl,H,H,Bu],[R507;H,CF$_3$,Br,H,H,Bu],[R508;H,CF$_3$,I,H,H,Bu],[R509;H,CF$_3$,Me,H,H,Bu],[R510;H,CF$_3$,CHF$_2$,H,H,Bu],[R511;H,CF$_3$,CF$_3$,H,H,Bu],[R512;H,CF$_3$,NO$_2$,H,H,Bu],[R513;H,CF$_3$,F,H,H,c-Pr],[R514;H,CF$_3$,Cl,H,H,c-Pr],[R515;H,CF$_3$,Br,H,H,c-Pr],[R516;H,CF$_3$,I,H,H,c-Pr],[R517;H,CF$_3$,Me,H,H,c-Pr],[R518;H,CF$_3$,CHF$_2$,H,H,c-Pr],[R519;H,CF$_3$,CF$_3$,H,H,c-Pr],[R520;H,CF$_3$,NO$_2$,H,H,c-Pr],[R521;H,CF$_3$,F,H,H,CH$_2$CF$_3$],[R522;H,CF$_3$,Cl,H,H,CH$_2$CF$_3$],[R523;H,CF$_3$,Br,H,H,CH$_2$CF$_3$],[R524;H,CF$_3$,I,H,H,CH$_2$CF$_3$],[R525;H,CF$_3$,Me,H,H,CH$_2$CF$_3$],[R526;H,CF$_3$,CHF$_2$,H,H,CH$_2$CF$_3$],[R527;H,CF$_3$,CF$_3$,H,H,CH$_2$CF$_3$],[R528;H,CF$_3$,NO$_2$,H,H,CH$_2$CF$_3$],[R529;H,CF$_3$,F,H,H,CH$_2$CHF$_2$],[R530;H,CF$_3$,Cl,H,H,CH$_2$CHF$_2$],[R531;H,CF$_3$,Br,H,H,CH$_2$CHF$_2$],[R532;H,CF$_3$,I,H,H,CH$_2$CHF$_2$],[R533;H,CF$_3$,Me,H,H,CH$_2$CHF$_2$],[R534;H,CF$_3$,CHF$_2$,H,H,CH$_2$CHF$_2$],[R535;H,CF$_3$,CF$_3$,H,H,CH$_2$CHF$_2$],[R536;H,CF$_3$,NO$_2$,H,H,CH$_2$CHF$_2$],[R537;H,CF$_3$,F,H,H,CF$_2$CH$_3$],[R538;H,CF$_3$,Cl,H,H,CF$_2$CH$_3$],[R539;H,CF$_3$,Br,H,H,CF$_2$CH$_3$],[R540;H,CF$_3$,I,H,H,CF$_2$CH$_3$],[R541;H,CF$_3$,Me,H,H,CF$_2$CH$_3$],[R542;H,CF$_3$,CHF$_2$,H,H,CF$_2$CH$_3$],[R543;H,CF$_3$,CF$_3$,H,H,CF$_2$CH$_3$],[R544;H,CF$_3$,NO$_2$,H,H,CF$_2$CH$_3$],[R545;H,CF$_3$,F,H,H,NMe$_2$],[R546;H,CF$_3$,Cl,H,H,NMe$_2$],[R547;H,CF$_3$,Br,H,H,NMe$_2$],[R548;H,CF$_3$,I,H,H,NMe$_2$],[R549;H,CF$_3$,Me,H,H,NMe$_2$],[R550;H,CF$_3$,CHF$_2$,H,H,NMe$_2$],[R551;H,CF$_3$,CF$_3$,H,H,NMe$_2$],[R552;H,CF$_3$,NO$_2$,H,H,NMe$_2$],[R553;H,CF$_3$,F,H,H,Pyrro],[R554;H,CF$_3$,Cl,H,H,Pyrro],[R555;H,CF$_3$,Br,H,H,Pyrro],[R556;H,CF$_3$,I,H,H,Pyrro],[R557;H,CF$_3$,Me,H,H,Pyrro],[R558;H,CF$_3$,CHF$_2$,H,H,Pyrro],[R559;H,CF$_3$,CF$_3$,H,H,Pyrro],[R560;H,CF$_3$,NO$_2$,H,H,Pyrro],[R561;H,NO$_2$,F,H,H,Me],[R562;H,NO$_2$,Cl,H,H,Me],[R$^{56B}$;H,NO$_2$,Br,H,H,Me],[R564;H,NO$_2$,I,H,H,Me],[R565;H,NO$_2$,Me,H,H,Me],[R566;H,NO$_2$,CHF$_2$,H,H,Me],[R567;H,NO$_2$,CF$_3$,H,H,Me],[R568;H,NO$_2$,NO$_2$,H,H,Me],[R569;H,NO$_2$,F,H,H,Et],[R570;H,NO$_2$,Cl,H,H,Et],[R571;H,NO$_2$,Br,H,H,Et],[R572;H,NO$_2$,I,H,H,Et],[R573;H,NO$_2$,Me,H,H,Et],[R574;H,NO$_2$,CHF$_2$,H,H,Et],[R575;H,NO$_2$,CF$_3$,H,H,Et],[R576;H,NO$_2$,NO$_2$,H,H,Et],[R577;H,NO$_2$,F,H,H,Pr],[R578;H,NO$_2$,Cl,H,H,Pr],[R579;H,N$_2$,Br,H,H,Pr],[R580;H,NO$_2$,I,H,H,Pr],[R561;H,NO$_2$,Me,H,H,Pr],[R582;H,NO$_2$,CHF$_2$,H,H,Pr],[R583;H,NO$_2$,CF$_3$,H,H,Pr],[R584;H,NO$_2$,NO$_2$,H,H,Pr],[R585;H,NO$_2$,F,H,H,Bu],[R586;H,NO$_2$,Cl,H,H,Bu],[R587;H,NO$_2$,Br,H,H,Bu],[R588;H,NO$_2$,I,H,H,Bu],[R589;H,NO$_2$,Me,H,H,Bu],[R590;H,NO$_2$,CHF$_2$,H,H,Bu],[R591;H,NO$_2$,CF$_3$,H,H,Bu],[R592;H,NO$_2$,NO$_2$,H,H,Bu],[R593;H,NO$_2$,F,H,H,c-Pr],[R594;H,NO$_2$,Cl,H,H,c-Pr],[R595;H,NO$_2$,Br,H,H,c-Pr],[R596;H,NO$_2$,I,H,H,c-Pr],[R597;H,NO$_2$,Me,H,H,c-Pr],[R598;H,NO$_2$,CHF$_2$,H,H,c-Pr],[R599;H,NO$_2$,CF$_3$,H,H,c-Pr],[R600;H,NO$_2$,NO$_2$,H,H,c-Pr],
[R601;H,NO$_2$,F,H,H,CH$_2$CF$_3$],[R602;H,NO$_2$,Cl,H,H,CH$_2$CF$_3$],[R603;H,NO$_2$,Br,H,H,CH$_2$CF$_3$],[R604;H,NO$_2$,I,H,H,CH$_2$CF$_3$],[R605;H,NO$_2$,Me,H,H,CH$_2$CF$_3$],[R606;H,NO$_2$,CHF$_2$,H,H,CH$_2$CF$_3$],[R607;H,NO$_2$,CF$_3$,H,H,CH$_2$CF$_3$],[R608;H,NO$_2$,NO$_2$,H,H,CH$_2$CF$_3$],[R609;H,NO$_2$,F,H,H,CH$_2$CHF$_2$],[R610;H,NO$_2$,Cl,H,H,CH$_2$CHF$_2$],[R611;H,NO$_2$,Br,H,H,CH$_2$CHF$_2$],[R612;H,NO$_2$,I,H,H,CH$_2$CHF$_2$],[R613;H,NO$_2$,Me,H,H,CH$_2$CHF$_2$],[R614;H,NO$_2$,CHF$_2$,H,H,CH$_2$CHF$_2$],[R615;H,NO$_2$,CF$_3$,H,H,CH$_2$CHF$_2$],[R616;H,NO$_2$,NO$_2$,H,H,CH$_2$CHF$_2$],[R617;H,NO$_2$,F,H,H,CF$_2$CH$_3$],[R618;H,NO$_2$,Cl,H,H,CF$_2$CH$_3$],[R619;H,NO$_2$,Br,H,H,CF$_2$CH$_3$],[R620;H,NO$_2$,I,H,H,CF$_2$CH$_3$],[R621;H,NO$_2$,Me,H,H,CF$_2$CH$_3$],[R622;H,NO$_2$,CHF$_2$,H,H,CF$_2$CH$_3$],[R623;H,NO$_2$,CF$_3$,H,H,CF$_2$CH$_3$],[R624;H,NO$_2$,NO$_2$,H,H,CF$_2$CH$_3$],[R625;H,NO$_2$,F,H,H,NMe$_2$],[R626;H,NO$_2$,Cl,H,H,NMe$_2$],[R627;H,NO$_2$,Br,H,H,NMe$_2$],[R628;H,NO$_2$,I,H,H,NMe$_2$],[R629;H,NO$_2$,Me,H,H,NMe$_2$],[R630;H,NO$_2$,CHF$_2$,H,H,NMe$_2$],[R631;H,NO$_2$,CF$_3$,E,H,NMe$_2$],[R632;H,NO$_2$,NO$_2$,H,H,NMe$_2$],[R633;H,NO$_2$,F,H,H,Pyrro],[R634;H,NO$_2$,Cl,H,H,Pyrro],[R635;H,NO$_2$,Br,H,H,Pyrro],[R636;H,NO$_2$,I,H,H,Pyrro],[R637;H,NO$_2$,Me,H,H,Pyrro],[R638;H,NO$_2$,CHF$_2$,H,H,Pyrro],[R639;H,NO$_2$,CF$_3$,H,H,Pyrro],[R640;H,NO$_2$,NO$_2$,H,H,Pyrro],[R641;H,F,F,F,H,Me],[R642;H,F,Cl,F,H,Me],[R643;H,F,Br,F,H,Me],[R644;H,F,I,F,H,Me],[R645;H,F,Me,F,H,Me],[R646;H,F,CHF$_2$,F,H,Me],[R647;H,F,CF$_3$,F,H,Me],[R648;H,NO$_2$,F,H,H,Me],[R649;H,F,F,F,H,Et],[R650;H,F,Cl,F,H,Et],[R650;H,F,Cl,F,H,Et],[R651;H,F,Br,F,H,Et],[R652;H,F,I,F,H,Et],[R653;H,F,Me,F,H,Et],[R654;H,F,CHF$_2$,F,H,Et],[R655;H,F,CF$_3$,F,H,Et],[R656;H,F,NO$_2$,F,H,Et],[R657;H,F,F,F,H,Pr],[R658;H,F,Cl,F,H,Pr],[R659;H,F,Br,F,H,Pr],[R660;H,F,I,F,H,Pr],[R661;H,F,Me,F,H,Pr],[R662;H,F,CHF$_2$,F,H,Pr],[R663;H,F,CF$_3$,F,H,Pr],[R664;H,F,NO$_2$,F,H,Pr],[R665;H,F,F,F,H,Bu],[R666;H,F,Cl,F,H,Bu],[R667;H,F,Br,F,H,Bu],[R668;H,F,I,F,H,Bu],[R669;H,F,Me,F,H,Bu],[R670;H,F,CHF$_2$,F,H,Bu],[R671;H,F,CF$_3$,F,H,Bu],[R672;H,F,NO$_2$,F,H,Bu],[R673;H,F,F,F,H,c-Pr],[R674;H,F,Cl,F,H,c-Pr],[R675;H,F,Br,F,H,c-Pr],[R676;H,F,I,F,H,c-Pr],[R677;H,F,Me,F,H,c-Pr],[R678;H,F,CHF$_2$,F,H,c-Pr],[R679;H,F,CF$_3$,F,H,c-Pr],[R680;H,F,NO$_2$,F,H,c-Pr],[R681;H,F,F,F,H,CH$_2$CF$_3$],[R682;H,F,Cl,F,H,CH$_2$CF$_3$],[R683;H,F,Br,F,H,CH$_2$CF$_3$],[R684;H,F,I,F,H,CH$_2$CF$_3$],[R685;H,F,Me,F,H,CH$_2$CF$_3$],[R686;H,F,CHF$_2$,F,H,CH$_2$CF$_3$],[R687;H,F,CF$_3$,F,H,CH$_2$CF$_3$],[R688;H,F,NO$_2$,F,H,CH$_2$CF$_3$],[R689;H,F,F,F,H,CH$_2$CHF$_2$],[R690;H,F,Cl,F,H,CH$_2$CHF$_2$],[R691;H,F,Br,F,H,CH$_2$CHF$_2$],[R692;H,F,I,F,H,CH$_2$CHF$_2$],[R693;H,F,Me,F,H,CH$_2$CHF$_2$],[R694;H,F,CHF$_2$,F,H,CH$_2$CHF$_2$],[R695;H,F,CF$_3$,F,H,CH$_2$CHF$_2$],[R696;H,F,NO$_2$,F,H,CH$_2$CHF$_2$],[R697;H,F,F,F,H,CF$_2$CH$_3$],[R698;H,F,Cl,F,H,CF$_2$CH$_3$],[R699;H,F,Br,F,H,CF$_2$CH$_3$],[R700;H,F,I,F,H,CF$_2$CH$_3$],[R701;H,F,Me,F,H,CF$_2$CH$_3$],[R702;H,F,CHF$_2$,F,H,CF$_2$CH$_3$],[R703;H,F,CF$_3$,F,H,CF$_2$CH$_3$],[R704;H,F,NO$_2$,F,H,CF$_2$CH$_3$],[R705;H,F,F,F,H,NMe$_2$],[R706;H,F,Cl,F,H,NMe$_2$],[R707;H,F,Br,F,H,NMe$_2$],[R708;H,F,I,F,H,NMe$_2$],[R709;H,F,Me,F,H,NMe$_2$],[R710;H,F,CHF$_2$,F,H,NMe$_2$],[R711;H,F,CF$_3$,F,H,NMe$_2$],[R712;H,F,NO2,F,H,NMe$_2$],[R713;H,F,F,F,H,Pyrro],[R714;H,F,Cl,F,H,Pyrro],[R715;H,F,Br,F,H,Pyrro],[R716;H,F,I,F,H,Pyrro],[R717;H,F,Me,F,H,Pyrro],[R718;H,F,CHF$_2$,F,H,Pyrro],[R719;H,F,CF$_3$,F,H,Pyrro],[R720;H,F,NO$_2$,F,H,Pyrro],[R721;H,Cl,F,F,H,Me],[R722;H,Cl,Cl,F,H,Me],[R723;H,Cl,Br,F,H,Me],[R724;H,Cl,I,F,H,Me],[R725;H,Cl,Me,F,H,Me],[R726;H,Cl,CHF$_2$,F,H,Me],[R727;H,Cl,CF$_3$,F,H,Me],[R728;H,Cl,NO$_2$,F,H,Me],[R729;H,Cl,F,F,H,Et],[R730;H,Cl,Cl,F,H,Et],[R731;H,Cl,Br,F,H,Et],[R732;H,Cl,I,F,H,Et],[R733;H,Cl,Me,F,H,Et],[R734;H,Cl,CHF$_2$,F,H,Et],[R735;H,Cl,CF$_3$,F,H,Et],[R736;H,Cl,NO$_2$,F,H,Et],[R737;H,Cl,F,F,H,Pr],[R738;H,Cl,Cl,F,H,Pr],[R739;H,Cl,Br,F,H,Pr],[R740;H,Cl,I,F,H,Pr],[R741;H,Cl,Me,F,H,Pr],[R742;H,Cl,CHF$_2$,F,H,Pr],[R743;H,Cl,CF$_3$,F,H,Pr],[R744;H,Cl,NO$_2$,F,H,Pr],[R745;H,Cl,F,F,H,Bu],[R746;H,Cl,Cl,F,H,Bu],[R747;H,Cl,Br,F,H,Bu],[R748;H,Cl,I,F,H,Bu],[R749;H,Cl,Me,F,H,Bu],[R750;H,Cl,CHF$_2$,F,H,Bu],

[R751;H,Cl,CF₃,F,H,Bu],[R752;H,Cl,NO₂,F,H,Bu],[R753; H,Cl,F, F,H,c-Pr],[R754;H,Cl,Cl,F,H,c-Pr],[R755;H,Cl,Br, F,H,c-Pr],[R756;H,Cl,I,F,H,c-Pr],[R757;H,Cl,Me,F,H,c-Pr], [R758;H,Cl,CHF₂,F,H,c-Pr],[R759;H,Cl,CF₃,F,H,c-Pr], [R760;H,Cl,NO₂,F,H,c-Pr],[R761;H,Cl,F,F,H,CH₂CF₃], [R762;H,Cl,Cl,F,H,CH₂CF₃],[R763;H,Cl,Br,F,H,CH₂CF₃], [R764;H,Cl,I,F,H,CH₂CF₃],[R765;H,Cl,Me, F,H,CH₂CF₃], [R766;H,Cl,CHF₂,F,H,CH₂CF₃],[R767;H,Cl,CF₃,F,H, CH₂CF₃],[R768;H,C,NO₂,F,H,CH₂CF₃],[R769;H,Cl,F,F,H, CH₂CHF₂],[R770;H,Cl,Cl,F,H,CH₂CHF₂],[R771;H,Cl,Br, F,H,CH₂CHF₂],[R772;H, Cl,I,F,H,CH₂CHF₂],[R773;H,Cl, Me,F,H,CH₂CHF₂],[R774;H,Cl,CHF2,F,H,CH₂CHF₂], [R775;H,Cl,CF₃,F,H,CH₂CHF₂],[R776;H,Cl,NO₂,F,H, CH₂CHF₂],[R777;H,Cl,F,F,H,CF₂CH₃],[R778;H,Cl,Cl,F,H, CF₂CH₃],[R779;H,Cl,Br,F,H,CF₂CH₃],[R780;H,Cl,I,F,H, CF₂CH₃],[R781;H,Cl,Me,F,H,CF₂CH₃],[R782;H,Cl,CHF₂, F,H,CF₂CH₃],[R783;H,Cl,CF₃,F, H,CF₂CH₃],[R784;H,Cl, NO₂,F,H,CF₂CH₃],[R785;H,Cl,F,F,H,NMe₂], [R786;H,Cl, Cl,F,H,NMe₂],[R787;H,Cl,Br,F,H,NMe₂],[R788;H,Cl, I,F, H,NMe₂],[R789;H,Cl,Me,F,H,NMe₂],[R790;H,Cl,CHF₂,F, H,NMe₂],[R791;H,Cl,CF₃,F,H,NMe₂],[R792;H,Cl,NO₂,F, H,NMe₂],[R793;H, Cl,F,F,H,Pyrro],[R794;H,Cl,Cl,F,H, Pyrro],[R795;H,Cl,Br,F,H, Pyrro],[R796;H,Cl,I,F,H,Pyrro], [R797;H,Cl,DMe,F,H,Pyrro],[R798;H,Cl,CHF₂,F,H,Pyrro], [R799;H,Cl,CF₃,F,H,Pyrro],[R800;H,Cl,NO₂,F,H,Pyrro], [R801;H,Br,F,F,H,Me],[R802;H,Br,Cl,F,H,Me],[R803;H, Br,Br,F,H,Me],[R804;H,Br,I,F,H,Me],[R805;H,Br,Me,F,H, Me],[R806;H,Br,CHF₂,F,H,Me],[R807;H,Br,CF₃,F,H,Me], [R808;H,Br,NO₂,F,H,Me],[R809;H,Br,F,F,H,Et],[R810,H, Br,Cl,F,H,Et],[R811;H,Br,Br,F,H,Et],[R812;H,Br,I,F,H,Et], [R813;H,Br,Me, F,H,Et],[R814;H,Br,CHF₂,F,H,Et],[R815; H,Br,CF₃,F,H,Et],[R816;H,Br,NO₂,F,H,Et],[R817;H,Br,F, H,Pr],[R818;H,Br,Cl,F,H,Pr],[R819;H,Br,Br,F,H,Pr],[R820; H,Br,I,F,H,Pr],[R821;H,Br,Me,F,H,Pr],[R822;H,Br,CHF₂,F, H,Pr],[R823;H,Br,CF₃,F,H,Pr],[R824;H,Br,NO₂,F,H,Pr], [R825;H,Br,F,F,H,Bu],[R826;H,Br,Cl,F,H, Bu],[R827;H,Br, Br,F,H,Bu],[R828;H,Br,I,F,H,Bu],[R829;H,Br,Me,F,H,Bu], [R830;H,Br,CHF₂,F,H,Bu],[R831;H,Br,CF₃,F,H,Bu], [R832;H,Br,NO₂,F,H,Bu],[R833;H,Br,F,F,H,c-Pr],[R834;H, Br,Cl,F,H,c-Pr],[R835;H,Br,Br,F,H,c-Pr],[R836;H,Br,I,F,H, c-Pr],[R837;H,Br,Me,F,H,c-Pr],[R838;H,Br,CHF₂,F,H,c-Pr],[R839;H,Br,CF₃,F,H,c-Pr],[R840;H,Br,NO₂,F,H,c-Pr], [R841;H,Br,F,F,H,CH₂CF₃],[R842;H,Br,Cl,F,H,CH₂CF₃], [R843;H,Br,Br,F,H,CH₂CF₃],[R844;H,Br,I,F,H,CH₂CF₃], [R845;H,Br,Me, F,H,CH₂CF₃],[R846;H,Br,CHF₂,F,H, CH₂CF₃],[R847;H,Br,CF₃,F,H,CH2CF3],[R848;H,Br,NO₂, F,H,CH₂CF₃],[R849;H,Br,F,F,H,CH₂CHF₂],[R850;H,Br,Cl, F,H,CH₂CHF₂],[R851;H,Br,Br,F,H,CH₂CHF₂],[R852;H,Br, I,F,H,CH₂CHF₂],[R853;H,Br,Me,F,H,CH₂CHF₂],[R854;H, Br,CHF₂,F,H,CH₂CHF₂],[R855;H,Br,CF₃,F,H,CH₂CHF₂], [R856;H,Br,NO₂,F,H,CH₂CHF₂],[R857;H,Br,F,F,H, CF₂CH₃],[R858;H,Br,Cl,F,H,CF₂CH₃], [R859;H,Br,Br,F,H, CF₂CH₃],[R860;H,Br,I,F,H,CF₂CH₃],[R861;H,Br,Me,F,H, CF₂CH₃],[R862;H,Br,CHF₂,F,H,CF₂CH₃],[R863;H,Br, CF₃,F,H,CF₂CH₃],[R864;H,Br,NO₂,F,H,CF₂CH₃],[R865;H, Br,F,F,H,NMe₂], [R866;H,Br,Cl,F,H,NMe₂],[R867;H,Br,Br, F,H,NNMe₂],[R868;H,Br, I,F,H,NMe₂],[R869;H,Br,Me,F, H,NMe₂],[R870;H,Br,CHF₂,F,H,NMe₂],[R871;H,Br,CF₃,F, H,NMe₂],[R872;H,Br,NO₂,F,H,NMe₂],[R873;H, Br,F,F,H, Pyrro],[R874;H,Br,Cl,F,H,Pyrro],[R875;H,Br,Br,F,H, Pyrro],[R876;H,Br,I,F,H,Pyrro],[R877;H,Br,Me,F,H,Pyrro], [R878;H,Br,CHF₂,F,H,Pyrro],[R879;H,Br,CF₃,F,H,Pyrro], [R880;H,Br,NO₂,F,H,Pyrro],[R881;H,Me,F,F,H,Me],[R882; H,Me,Cl,F,H,Me],[R883;H,Me,Br,F,H,Me],[R884;H,Me,I, F,H,Me],[R885;H,Me,Me,F,H,Me],[R886;H,Me,CHF₂,F,H, Me],[R887;H,Me,CF₃,F,H,Me],[R888;H,Me,NO₂,F,H,Me], [R889;H,Me,F,F,H,Et],[R890;H,Me,Cl,F,H,Et],[R891;H, Me,Br,F,H,Et],[R892;H,Me,I,F,H,Et],[R893;H,Me,Me, F,H, Et],[R894;H,Me,CHF₂,F,H,Et],[R895;H,Me,CF₃,F,H,Et], [R896;H,Me,NO₂,F,H,Et],[R897;H,Me,F,F,H,Pr],[R898;H, Me,Cl,F,H,Pr],[R899;H,Me,Br,F,H,Pr],[R900;H,Me,F,H, Pr],
[R901;H,Me,Me,F,H,Pr],[R902;H,Me,CHF₂,F,H,Pr],[R903; H,Me,CF3,F,H,Pr],[R904;H,Me,NO₂,F,H,Pr],[R905;H,Me, F,F,H,Bu],[R906;H,Me,Cl,F,H,Bu],[R907;H,Me,Br,F,H, Bu],[R908;H,Me,I,F,H,Bu],[R909;H,Me,Me,F,H,Bu], [R910;H,Me,CHF₂,F,H,Bu],[R903;H,Me,CF₃,F,H,Bu], [R912;H,Me,NO₂,F,H,Bu],[R913;H,Me,F,F,H,c-Pr],[R914; H,Me,Cl,F,H,c-Pr],[R915;H,Me,Br,F,H,c-Pr],[R916;H,Me, I,F,H,c-Pr],[R917;H,Me,Me,F,H,c-Pr],[R918;H,Me,CHF₂, F,H,c-Pr],[R919;H,Me,CF₃,F,H,c-Pr],[R920;H,Me,NO₂,F, H,c-Pr],[R921;H,Me,F,F,H,CH₂CF₃],[R922;H,Me,Cl,F,H, CH₂CF₃],[R923;H,Me,Br,F,H,CH₂CF₃],[R924;H,Me,I,F,H, CH₂CF₃],[R925;H,Me,Me, F,H,CH₂CF₃],[R926;H,Me, CHF₂,F,H,CH₂CF₃],[R927;H,Me,CF₃,F,H,CH₂CF₃],[R928; H,Me,NO₂,F,H,CH₂CF₃],[R929;H,Me,F,F,H,CH₂CHF₂], [R930;H,Me,Cl,F,H,CH₂CHF₂],[R931;H,Me,Br,F,H, CH₂CHF₂],[R932;H, Me,I,F,H,CH₂CHF₂],[R933;H,Me, Me,F,H,CH₂CHF₂],[R934;H,Me,CHF₂,F,H,CH₂CHF₂], [R935;H,Me,CF₃,F,H,CH₂CHF₂],[R936;H,Me,NO₂,F,H, CH₂CHF₂],[R937;H,Me,E,F,H,CF₂CH₃],[R938;H,Me,Cl,F, H,CF₂CH₃],[R939;H,Me,Br,F,H,CF₂CH₃],[R940;H,Me,I, H,CF₂CH₃],[R941;H,Me,Me,F,H,CF₂CH₃],[R942;H,Me, CHF₂,F,H,CF₂CH₃],[R943;H,Me,CF₃,F, H,CF₂CH₃], [R944;H,Me,NO₂,F,H,CF₂CH₃],[R945;H,Me,F,F,H,NMe₂], [R946;H,Me,Cl,F,H,NMe₂],[R947;H,Me,Br,F,H,NMe₂], [R948;H,Me,I,F,H,NMe₂],[R949;H,Me,Me,F,H,NMe₂], [R950;H,Me,CHF₂,F,H,NMe₂],[R951;H,Me,CF₃,F,H, NMe₂],[R952;H,Me,NO₂,F,H,NMe₂],[R953;H,Me,F,F,H, Pyrro],[R954;H,Me,Cl,F,H,Pyrro],[R955;H,Me,Br,F,H, Pyrro],[R956;H,Me,I,F,H,Pyrro],[R957;H,Me,Me,F,H, Pyrro],[R958;H,Me,CHF₂,F,H,Pyrro],[R959;H,Me,CF₃,F, H,Pyrro],[R960;H,Me,NO₂,F,H,Pyrro],[R961;H,CHF₂,F,F, H,Me],[R962;H,CHF₂,Cl,F,H,Me],[R963;H,CHF₂,Br,F,H, Me],[R964;H,CHF₂,I,F,H,Me],[R965;H,CHF₂,Me,F,H,Me], [R966;H,CHF₂,CHF₂,F,H,Me],[R967;H,CHF₂,CF₃,F, H,Me],[R968;H,CHF₂,NO₂,F,H,Me],[R969;H,CHF₂,F,F,H, Et],[R970; H,CHF₂,Cl,F,H,Et],[R971;H,CHF₂,Br,F,H,Et], [R972;H,CHF₂,I,F,H,Et],[R973;H,CHF₂,Me,F,H,Et],[R974; H,CHF₂,CHF₂,F,H,Et],[R975;H,CHF₂,CF₃,F,H,Et],[R976; H,CHF₂,NO₂,F,H,Et],[R977;H,CHF₂,F, F,H,Pr],[R978;H, CHF₂,Cl,F,H,Pr],[R979;H,CHF₂,Br,F,H,Pr],[R980;H,CHF₂, I,F,H,Pr],[R981;H,CHF₂,Me,F,H,Pr],[R982;H,CHF₂,CHF₂, F,H,Pr],[R983;H,CHF₂,CF₃,F,H,Pr],[R984;H,CHF₂,NO₂,F, H,Pr], [R985;H,CHF₂,F,F,H,Bu],[R986;H,CHF₂,Cl,F,H, Bu],[R987;H,CHF₂,Br,F,H,Bu],[R988;H,CHF₂,I,F,H,Bu], [R989;H,CHF₂,Me,F,H,Bu],[R990;H,CHF₂,CHF₂,F,H,Bu], [R991;H,CHF₂,CF₃,F,H,Bu],[R992;H,CHF₂,NO₂,F,H,Bu], [R993;H,CHF₂,F,F,H,c-Pr],[R994;H,CHF₂,Cl,F,H,c-Pr], [R995;H,CHF₂,Br,F,H,c-Pr],[R996;H,CHF₂,I,F,H,c-Pr], [R997;H,CHF₂,Me,F,H,c-Pr],[R998;H,CHF₂,CHF₂,F,H,c-Pr],[R999;H,CHF₂,CF₃,F,H,c-Pr],[R1000;H,CHF₂,NO₂,F, H,c-Pr],[R1001;H,CHF₂,F,F,H,CH₂CF₃],[R1002;H,CHF₂, Cl,F,H,CH₂CF₃], [R1003;H,CHF₂,Br,F,H,CH₂CF₃], [R1004;H,CHF₂,I,F,H,CH₂CF₃],[R1005;H,CHF₂,Me,F,H, CH₂CF₃],[R1006;H,CHF₂,CHF₂,F,H,CH₂CF₃],[R1007;H, CHF₂,CF₃,F,H,CH₂CF₃],[R1008;H,CHF₂,NO₂,F,H, CH₂CF₃],[R1009;H,CHF₂,F,F,H,CH₂CHF₂],[R1010;H, CHF₂,Cl,F,H,CH₂CHF₂],[R1011;H,CHF₂,Br,F,H, CH₂CHF₂],[R1012;H,CHF₂,I,F,H,CH₂CHF₂],[R1013;H, CHF₂,Me,F,H,CH₂CHF₂],[R1014;H,CHF₂,CHF₂,F,H, CH₂CHF₂],[R1015;H, CHF₂,CF₃,F,H,CH₂CHF₂],[R1016; H,CHF₂,NO₂,F,H,CH₂CHF₂],[R1017;H,CHF₂,F,F,H, CF₂CH₃],[R1018;H,CHF₂,Cl,F,H,CF₂CH₃],[R1019;H, CHF₂,Br,F,H,CF₂CH₃],[R1020;H,CHF₂,I,F,H,CF₂CH₃],
[R1021;H,CHF₂,Me,F,H,CF₂CH₃],[R1022;H,CHF₂,CHF₂,
F,H,CF₂CH₃],[R1023;H,CHF₂,CF₃,F,H,CF₂CH₃],[R1024;
H,CHF₂,NO₂,F,H,CF₂CH₃],[R1025;H,CHF₂,F,F, H,NMe₂],
[R1026;H,CHF₂,Cl,F,H,NMe₂],[R1027;H,CHF₂,Br,F,H,
NMe₂],[R1028;H,CHF₂,I,F,H,NMe₂],[R1029;H,CHF₂,Me,
F,H,NMe₂],[R1030;H,CHF₂,CHF₂,F,H,NMe₂],[R1031;H,
CHF₂,CF₃,F,H,NMe₂],[R1032;H, CHF₂,NO₂,F,H,NMe₂],
[R1033;H,CHF₂,F,F,H,Pyrro],[R1034;H,CHF₂, Cl,F,H,
Pyrro],[R1035;H,CHF₂,Br,F,H,Pyrro],[R1036;H,CHF₂,I,F,
H,Pyrro],[R1037;H,CHF₂,Me,F,H,Pyrro],[R1038;H,CHF₂,
CHF₂,F,H,Pyrro],[R1039;H,CHF₂,CF₃,F,H,Pyrro],[R1040;
H,CHF₂,NO₂,F,H,Pyrro],[R1041;H,CF₃,F,F,H,Me],[R1042;
H,CF₃,Cl,F,H,Me],[R1043;H,CF₃,Br,F,H,Me],[R1044;H,
CF₃,I,F,H,Me],[R1045;H,CF₃,Me,F,H,Me],[R1046;H,CF₃,
CHF₂,F,H,Me],[R1047;H,CF₃,CF₃,F,H,Me],[R1048;H,CF₃,
NO₂,F,H,Me],[R1049;H,CF₃,F,F,H,Et],[R1050;H,CF₃,Cl,
F,H,Et],
[R1051;H,CF₃,Br,F,H,Et],[R1052;H,CF₃,I,F,H,Et],[R1053;
H,CF₃, Me,F,H,Et],[R1054;H,CF₃,CHF₂,F,H,Et],[R1055;H,
CF₃,CF₃,F,H,Et],[R1056;H,CF₃,NO₂,F,H,Et],[R1057;H,
CF₃,F,F,H,Pr],[R1058;H,CF₃,Cl,F,H,Pr],[R1059;H,CF₃,Br,
F,H,Pr],[R1060;H,CF₃,I,F,H,Pr],[R1061;H,CF₃,Me,F,H,Pr],
[R1062;H,CF₃,CHF₂,F,H,Pr],[R1063;H, CF₃,CF₃,F,H,Pr],
[R1064;H,CF₃,NO₂,F,H,Pr],[R1065;H,CF₃,F,F,H, Bu],
[R1066;H,CF₃,C,F,H,Bu],[R1067;H,CF₃,Br,F,H,Bu],
[R1068; H,CF₃,I,F,H,Bu],[R1069;H,CF₃,Me,F,H,Bu],
[R1070;H,CF₃,CHF₂,F, H,Bu],[R1071;H,CF₃,CF₃,F,H,Bu],
[R1072;H,CF₃,NO₂,F,H,Bu],[R1073;H,CF₃,F,F,H,c-Pr],
[R1074;H,CF₃,Cl,F,H,c-Pr],[R1075;H,CF₃,Br,F,H,c-Pr],
[R1076;H,CF₃,I,F,H,c-Pr],[R1077;H,CF₃,Me,F,H,c-Pr],
[R1078;H,CF₃,CHF₂,F,H,c-Pr],[R1079;H,CF₃,CF₃,F,H,c-
Pr],[R1080;H,CF₃,NO₂,F,H,c-Pr],[R1081;H,CF₃,F,F,H,
CH₂CF₃],[R1082;H,CF₃,Cl,F,H,CH₂CF₃],[R1083;H,CF₃,
Br,F,H,CH₂CF₃],[R1084;H,CF₃,I,F,H,CH₂CF₃],[R1085;H,
CF₃,Me,F,H,CH₂CF₃],[R1086;H,CF₃,CHF₂,F,H,CH₂CF₃],
[R1087;H,CF₃,CF₃,F,H,CH₂CF₃],[R1088;H,CF₃,NO₂,F,H,
CH₂CF₃],[R1089;H,CF₃,F, F,H,CH₂CHF₂],[R1090;H,CF₃,
Cl,F,H,CH₂CHF₂],[R1091;H,CF₃,Br,F,H,CH₂CHF₂],
[R1092;H,CF₃,I,F,H,CH₂CHF₂],[R1093;H,CF₃,Me,F,H,
CH₂CHF₂],[R1094;H,CF₃,CHF₂,F,H,CH₂CHF₂],[R1095;
H,CF₃,CF₃,F,H,CH₂CHF₂],[R1096;H,CF₃,NO₂,F,H,
CH₂CHF₂],[R1097;H,CF₃,F,F,H,CF₂CH₃],[R1098;H,CF₃,
Cl,F,H,CF₂CH₃],[R1099;H,CF₃,Br,F,H,CF₂CH₃],[R1100;
H,CF₃,I,F,H,CF₂CH₃],[R1101;H,CF₃,Me,F,H,CF₂CH₃],
[R1102;H, CF₃,CHF₂,F,H,CF₂CH₃],[R1103;H,CF₃,CF₃,
H,CF₂CH₃],[R1104;H,CF₃,NO₂,F,H,CF₂CH₃],[R1105;H,
CF₃,F,F,H,NMe₂], [R1106;H,CF₃,Cl,F,H,NMe₂],[R1107;H,
CF₃,Br,F,H,NMe₂],[R1108;H,CF₃,I,F,H,NMe₂],[R1109;H,
CF₃,Me,F,H,NMe₂],[R1110;H,CF₃,CHF₂,F,H,NMe₂],
[R1111;H,CF₃,CF₃,F,H,NMe₂],[R1112;H,CF₃,NO₂,F,H,
NMe₂],[R1113;H,CF₃,F, F,H,Pyrro],[R1114;H,CF₃,Cl,F,H,
Pyrro],[R1115;H,CF₃,Br,F,H,Pyrro],[R1116;H,CF₃,I,F,H,
Pyrro],[R1117;H,CF₃,Me,F,H,Pyrro], [R1118;H,CF₃,CHF₂,
F,H,Pyrro],[R1119;H,CF₃,CF₃,F,H,Pyrro],[R1120;H,CF₃,
NO₂,F,H,Pyrro],[R1121;H,NO₂,F,F,H,Me],[R1122;H,NO₂,
Cl,F,H,Me],[R1123;H,NO₂,Br,F,H,Me],[R1124;H,NO₂,I,F,
H,Me],[R1125;H,NO₂,Me,F,H,Me],[R1126;H,NO₂,CHF₂,F,
H,Me],[R1127;H,NO₂,CF₃,F,H,Me],[R1128;H,NO₂,NO₂,F,
H,Me],[R1129;H,NO₂,F,F,H,Et],[R1130;H,NO₂,Cl,F,H,Et],
[R1131;H,NO₂,Br,F,H,Et],[R1132;H, NO₂,I,F,H,Et],
[R1133;H,NO₂,Me,F,H,Et],[R1134;H,NO₂,CHF₂,F,H, Et],
[R1135;H,NO₂,CF₃,F,H,Et],[R1136;H,NO₂,NO₂,F,H,Et],
[R1137;H,NO₂,F,F,H,Pr],[R1138;H,NO₂,Cl,F,H,Pr],
[R1139;H,NO₂,Br,F,H,Pr],[R1140;H,NO₂,I,F,H,Pr],[R1141;
H,NO₂,Me,F,H,Pr],[R1142; H,N₂,CHF₂,F,H,Pr],[R1143;H,
NO₂,CF₃,F,H,Pr],[R1144;H,NO₂,NO₂, F,H,Pr],[R145;H,
NO₂,F,F,H,Bu],[R1146;H,NO₂,Cl,F,H,Bu],[R1147;H,NO₂,
Br,F,H,Bu],[R1148;H,NO₂,I,F,H,Bu],[R1149;H,NO₂,Me,F,
H,Bu],[R1150;H,NO₂,CHF₂,F,H,Bu],[R1151;H,NO₂,CF₃,F,
H,Bu],[R1152;H,NO₂,NO₂,F,H,Bu],[R1153;H,NO₂,F,F,H,
c-Pr],[R1154;H,NO₂,Cl,F,H,c-Pr],[R1155;H,NO₂,Br,F,H,c-
Pr],[R1156;H,NO₂,I,F,H,c-Pr],[R1157;H,NO₂,Me,F,H,c-
Pr],[R1158;H,NO₂,CHF₂,F,H,c-Pr],[R1159;H,NO₂,CF₃,F,
H,c-Pr],[R160;H,NO₂,NO₂,F,H,c-Pr],[R1161;H,NO₂,F,F,H,
CH₂CF₃],[R1162;H,NO₂,Cl,F,H,CH₂CF₃],[R1163;H,NO₂,
Br,F,H,CH₂CF₃],[R1164;H,NO₂,I,F,H,CH₂CF₃],[R1165;H,
NO₂,Me,F,H,CH₂CF₃],[R1166;H,NO₂,CHF₂,F,H,CH₂CF₃],
[R1167;H,NO₂,CF₃,F,H,CH₂CF₃],[R1168;H,NO₂,NO₂,F,H,
CH₂CF₃],[R1169;H,NO₂,F, F,H,CH₂CHF₂],[R1170;H,NO₂,
Cl,F,H,CH₂CHF₂],[R1171;H,NO₂,Br,F,H,CH₂CHF₂],
[R1172;H,NO₂,I,F,H,CH₂CHF₂],[R1173;H,NO₂,Me,F,H,
CH₂CHF₂],[R1174;H,NO₂,CHF₂,F,H,CH₂CHF₂],[R1175;
H,NO₂,CF₃,F,H,CH₂CHF₂],[R1176;H,NO₂,NO₂,F,H,
CH₂CHF₂],[R1177;H,NO₂,F,F,H,CF₂CH₃],[R1178;H,NO₂,
Cl,F,H,CF₂CH₃],[R1179;H,NO₂,Br,F,H,CF₂CH₃],[R1180;
H,NO₂,I,F,H,CF₂CH₃],[R1181;H,NO₂,Me,F,H,CF₂CH₃],
[R1182;H,NO₂,CHF₂,F,H,CF₂CH₃],[R1183;H,NO₂,CF₃,F,
H,CF₂CH₃],[R1184;H,NO₂,NO₂,F,H,CF₂CH₃],[R1185;H,
NO₂,F,F,H,NMe₂],[R1186;H,NO₂,Cl,F,H,NMe₂],[R1187;H,
NO₂,Br,F,H,NMe₂],[R1188;H,NO₂,I,F,H,NMe₂], [R1189;
H,NO₂,Me,F,H,NMe₂],[R1190;H,NO₂,CHF₂,F,H,NMe₂],
[R1191;H,NO₂,CF₃,F,H,NMe₂],[R1192;H,NO₂,NO₂,F,H,
NMe₂],[R1193;H,NO₂, F,F,H,Pyrro],[R1194;H,NO₂,Cl,F,H,
Pyrro],[R1195;H,NO₂,Br,F,H,Pyrro],[R1196;H,NO₂,I,F,H,
Pyrro],[R1197;H,NO₂,Me,F,H,Pyrro],[R1198;H,NO₂,
CHF₂,F,H,Pyrro],[R1199;H,NO₂,CF₃,F,H,Pyrro],[R1200;H,
NO₂,NO₂,F,H,Pyrro],
[R1201;H,F,F,Me,H,Me],[R1202;H,F,Cl,Me,H,Me],
[R1203;H,F,Br, Me,H,Me],[R1204;H,F,I,Me,H,Me],
[R1205;H,F,Me,Me,H,Me],[R1206;H,F,CHF₂,Me,H,Me],
[R1207;H,F,CF₃,Me,H,Me],[R1208;H,F,NO₂,Me,H,Me],
[R1209;H,F,F,Me,H,Et],[R1210;H,F,Cl,Me,H,Et],[R1211;
H,F,Br,Me,H,Et],[R1212;H,F,I,Me,H,Et],[R1213;H,F,Me,
Me,H,Et],[R1214;H,F,CHF₂,Me,H,Et],[R1215;H,F,CF₃,
Me,H,Et],[R1216; H,F,NO₂,Me,H,Et],[R1217;H,F,F,IMe,H,
Pr],[R1218;H,F,Cl,Me,H,Pr],[R1219;H,F,Br,Me,H,Pr],
[R1220;H,F,I,Me,H,Pr],[R1221;H,F, Me,Me,H,Pr],[R1222;
H,F,CHF₂,Me,H,Pr],[R1223;H,F,CF₃,Me,H,Pr],[R1224;H,
F,NO₂,Me,H,Pr],[R1225;H,F,F,Me,H,Bu],[R1226;H,F,
Cl,Me,H,Bu],[R1227;H,F,Br,Me,H,Bu],[R1228;H,F,I,Me,
H,Bu],[R1229;H,F,Me,Me,H,Bu],[R1230;H,F,CHF₂,Me,H,
Bu],[R1231;H,F,CF₃,Me,H,Bu],[R1232;H,F,NO₂,Me,H,
Bu],[R1233;H,F,F,Me,H,c-Pr],[R1234;H,F,Cl,Me,H,c-Pr],
[R1235;H,F,Br,Me,H,c-Pr],[R1236;H,F,I,Me,H,c-Pr],
[R1237;H,F,Me,Me,H,c-Pr],[R1238;H,F,CHF₂,Me,H,c-Pr],
[R1239;H,F,CF₃,Me,H,c-Pr],[R1240;H,F,NO₂,Me,H,c-Pr],
[R1241;H,F,F,Me,H,CH₂CF₃],[R1242;H,F,Cl,Me,H,
CH₂CF₃],[R1243;H,F,Br,Me,H,CH₂CF₃],[R1244;H,F,I,Me,
H,CH₂CF₃],[R1245;H,F,Me,Me,H,CH₂CF₃],[R1246;H,F,
CHF₂,Me,H,CH₂CF₃],[R1247;H,F,CF₃, Me,H,CH₂CF₃],
[R1248;H,F,NO₂,Me,H,CH₂CF₃],[R1249;H,F,F,Me,H,
CH₂CHF₂],[R1250;H,F,Cl,Me,H,CH₂CHF₂],[R1251;H,F,
Br,Me,H,CH₂CHF₂],[R1252;H,F,I,Me,H,CH₂CHF₂],
[R1253;H,F,Me,Me,H,CH₂CHF₂], [R1254;H,F,CHF₂,Me,
H,CH₂CHF₂],[R1255;H,F,CF₃,Me,H,CH₂CHF₂],[R1256;
H,F,NO₂,Me,H,CH₂CHF₂],[R1257;H,F,F,Me,H,CF₂CH₃],
[R1258;H,F,Cl,Me,H,CF₂CH₃],[R1259;H,F,Br,Me,H,
CF₂CH₃],[R1260;H,F,I,Me,H,CF₂CH₃],[R1261;H,F,Me,
Me,H,CF₂CH₃],[R1262;H,F,CHF₂,Me,H, CF₂CH₃],
[R1263;H,F,CF₃,Me,H,CF₂CH₃],[R1264;H,F,NO₂,Me,H,
CF₂CH3],[R1265;H,F,F,Me,H,NMe₂],[R1266;H,F,Cl,Me,
H,NMe₂],[R1267; H,F,Br,Me,H,NMe₂],[R1268;H,F,I,Me,
H,NMe₂],[R1269;H,F,Me,Me, H,NMe₂],[R1270;H,F,CHF₂, Me,H,NMe₂],[R1271;H,F,CF₃,Me,H,NMe₂],[R1272;H,F, NO₂,Me,H,NMe₂],[R1273;H,F,F,Me,H,Pyrro],[R1274; H,F, Cl,Me,H,Pyrro],[R1275;H,F,Br,Me,H,Pyrro],[R1276;H,F,I, Me,H,Pyrro],[R1277;H,F,Me,Me,H,Pyrro],[R1278;H,F, CHF₂,Me,H,Pyrro],[R1279;H,F,CF₃,Me,H,Pyrro],[R1280; H,F,NO₂,Me,H,Pyrro],[R1281;H,Cl,F,Me,H,Me],[R1282; H,Cl,Cl,Me,H,Me],[R1283;H,Cl,Br,Me,H,Me],[R1284;H, Cl,I,Me,H,Me],[R1285;H,Cl,Me,Me,H,Me],[R1286;H,Cl, CHF₂,Ne,H,Me],[R1287;H,Cl,CF₃,Me,H,Me],[R1288; H,Cl,NO₂,Me,H,Me],[R1289;H,Cl,F,Me,H,Et],[R1290;H, Cl,Me,Me,H,Et],[R1291;H,Cl,Br,Me,H,Et],[R1292;H,Cl,I, Me,H,Et],[R1293; H,Cl,Me,Me,H,Et],[R1294;H,Cl,CHF₂, Me,H,Et],[R1295;H,Cl,CF₃,Me,H,Et],[R1296;H,Cl,NO₂, Me,H,Et],[R1297;H,Cl,F,Me,H,Pr][R1298;H,Cl,Cl,Me,H, Pr],[R1299;H,Cl,Br,Me,H,Pr],[R1300;H,Cl, I,Me,H,Pr], [R1301;H,Cl,Me,Me,H,Pr],[R1302;H,Cl,CHF₂,Me,H,Pr], [R1303;H,Cl,CF₃,Me,H,Pr],[R1304;H,Cl,NO₂,Me,H,Pr], [R1305; H,Cl,F,Me,H,Bu],[R1306;H,Cl,Cl,Me,H,Bu], [R1307;H,Cl,Br,Me,H,Bu],[R1308;H,Cl,I,Me,H,Bu], [R1309;H,Cl,Me,Me,H,Bu],[R1310; H,Cl,CHF₂,Me,H,Bu], [R1311;H,Cl,CF₃,Me,H,Bu],[R1312;H,Cl,NO₂, Me,H,Bu], [R1313;H,Cl,F,Me,H,c-Pr],[R1314;H,Cl,Cl,Me,H,c-Pr], [R1315;H,Cl,Br,Me,H,c-Pr],[R1316;H,Cl,I,Me,H,c-Pr], [R1317;H,Cl,Me,Me,H,c-Pr],[R1318;H,Cl,CHF₂,Me,H,c-Pr],[R1319;H,Cl,CF₃,Me,H,c-Pr],[R1320;H,Cl,NO₂,Me,H, c-Pr],[R1321;H,Cl,F,Me,H,CH₂CF₃],[R1322;H,Cl,Cl,Me, H,CH₂CF₃],[R1323;H,Cl,Br,Me,H,CH₂CF₃],[R1324;H,Cl, I,Me,H,CH₂CF₃],[R1325; H,Cl,Me,Me,H,CH₂CF₃], [R1326;H,Cl,CHF₂,Me,H,CH₂CF₃],[R1327;H,Cl,CF₃,Me, H,CH₂CF₃],[R1328;H,Cl,NO₂,Me,H,CH₂CF₃],[R1329;H, Cl,F,Me,H,CH₂CHF₂],[R1330;H,Cl,Cl,Me,H,CH₂CHF₂], [R1331;H,Cl,Br,Me,H,CH₂CHF₂],[R1332;H,Cl,I,Me,H, CH₂CHF₂],[R1333;H,Cl,Me,Me,H,CH₂CHF₂],[R1334;H, Cl,CHF₂,Me,H,CH₂CHF₂],[R1335;H,Cl,CF₃,Me,H, CH₂CHF₂],[R1336;H,Cl,NO₂,Me,H,CH₂CHF₂],[R1337;H, Cl,F,Me,H,CF₂CH₃],[R1338;H,Cl,Cl,Me,H,CF₂CH₃], [R1339;H,Cl,Br,Me,H,CF₂CH₃],[R1340;H,Cl,I,Me,H, CF₂CH₃],[R1341;H,Cl,Me,Me,H,CF₂CH₃], [R1342;H,Cl, CHF₂,Me,H,CF₂CH₃],[R1343;H,Cl,CF₃,Me,H,CF₂CH₃], [R1344;H,Cl,NO₂,Me,H,CF₂CH₃],[R1345;H,Cl,F,Me,H, NMe₂],[R1346;H,Cl,Cl,Me,H,NMe₂],[R1347;H,Cl,Br,Me, H,NMe₂],[R1348;H,Cl,I,Me,H,NMe₂],[R1349;H,Cl,DMe, Me,H,NMe₂],[R1350;H,Cl,CHF₂,Me,H,NMe₂], [R1351;H,Cl,CF₃,Me,H,NMe₂],[R1352;H,Cl,NO₂,Me,H, NMe₂],[R1353;H,Cl,F,Me,H,Pyrro],[R1354;H,Cl,Cl,Me,H, Pyrro],[R1355;H,Cl, Br,Me,H,Pyrro],[R1356H,Cl,I,Me,H, Pyrro],[R1357;H,Cl,Me,Me, H,Pyrro],[R1358;H,Cl,CHF₂, Me,H,Pyrro],[R1359;H,Cl,CF₃,Me,H, Pyrro],[R1360;H,Cl, NO₂,Me,H,Pyrro],[R1361;H,Br,F,Me,H,Me],[R1362;H,Br, Cl,Me,H,Me],[R1363;H,Br,Br,Me,H,Me],[R1364;H,Br, I,Me,H,Me],[R1365;H,Br,Me,Me,H,Me],[R1366;H,Br, CHF₂,Me,H,Me],[R1367;H,Br,CF₃,Me,H,Me],[R1368;H, Br,NO₂,Me,H,Me],[R1369; H,Br,F,Me,H,Et],[R1370;H,Br, Cl,Me,H,Et],[R1371;H,Br,Br,Me,H,Et],[R1372;H,Br,I,Me, H,Et],[R1373;H,Br,Me,Me,H,Et],[R1374; H,Br,CHF₂,Me, H,Et],[R1375;H,Br,CF₃,Me,H,Et],[R1376;H,Br,NO₂, Me,H,Et],[R1377;H,Br,F,Me,H,Pr],[R1378;H,Br,Cl,Me,H, Pr],[R1379;H,Br,Br,Me,H,Pr],[R1380;H,Br,I,Me,H,Pr], [R1381;H,Br,Me, Me,H,Pr],[R1382;H,Br,CHF₃,Me,H,Pr], [R1383;H,Br,CF₃,Me,H,Pr],[R1384;H,Br,NO₂,Me,H,Pr], [R1385;H,Br,F,Me,H,Bu],[R1386;H,Br,Cl,Me,H,Bu], [R1387;H,Br,Br,Me,H,Bu],[R1388;H,Br,I,Me,H,Bu], [R1389;H,Br,Me,Me,H,Bu],[R1390;H,Br,CHF₂,Me,H,Bu], [R1391; H,Br,CF₃,Me,H,Bu],[R1392;H,Br,NO₂,Me,H,Bu], [R1393;H,Br,F,Me,H,c-Pr],[R1394;H,Br,Cl,Me,H,c-Pr], [R1395;H,Br,Br,Me,H,c-Pr],[R1396;H,Br,I,Me,H,c-Pr], [R1397;H,Br,Me,Me,H,c-Pr],[R1398;H,Br,CHF₂,Me,H,c-Pr],[R1399;H,Br,CF₃,Me,H,c-Pr],[R1400;H,Br,NO₂,Me,H, c-Pr],[R1401;H,Br,F,Me,H,CH₂CF₃],[R1402;H,Br,Cl,Me, H,CH₂CF₃],[R1403;H,Br,Br,Me,H,CH₂CF₃],[R1404;H,Br, I,Me,H,CH₂CF₃],[R1405;H,Br,Me,Me,H,CH₂CF₃],[R1406; H,Br,CHF₂,Me,H,CH₂CF₃],[R1407;H,Br,CF₃,Me,H, CH₂CF₃],[R1408;H,Br,NO₂,Me,H,CH₂CF₃],[R1409;H,Br, F,Me,H,CH₂CHF₂],[R1410;H,Br,Cl,Me,H,CH₂CHF₂], [R1411;H,Br,Br,Me,H,CH₂CHF₂],[R1412;H,Br,I,Me,H, CH₂CHF₂],[R1413;H,Br,Me,Me,H,CH₂CHF₂],[R1414;H, Br,CHF₂,Me,H,CH₂CHF₂],[R1415;H,Br,CF₃,Me,H, CH₂CHF₂],[R1416;H,Br,NO₂,Me,H,CH₂CHF₂],[R1417;H, Br,F,Me,H,CF₂CH₃],[R1418;H,Br,Cl,Me,H,CF₂CH₃], [R1419;H,Br,Br,Me,H,CF₂CH],[R1420;H,Br,I,Me,H, CF₂CH₃],[R1421;H,Br,Me,Me,H,CF₂CH₃], [R1422;H,Br, CHF₂,Me,H,CF₂CH₃],[R1423;H,Br,CF₃,Me,H,CF₂CH₃], [R1424;H,Br,NO₂,Me,H,CF₂CH₃],[R1425;H,Br,F,Me,H, NMe₂],[R1426;H,Br,Cl,Me,H,NMe₂],[R1427;H,Br,Br,Me, H,NMe₂],[R1428;H,Br,I,Me,H,NMe₂],[R1429;H,Br,Me, Me,H,NMe₂],[R1430;H,Br,CHF₂,Me,H,NMe₂],[R1431;H, Br,CF₃,Me,H,NMe₂],[R1432;H,Br,NO₂,Me,H,NMe₂], [R1433;H,Br,F,Me,H,Pyrro],[R1434;H,Br,Cl,Me,H,Pyrro], [R1435;H,Br,Br,Me,H,Pyrro],[R1436;H,Br,I,Me,H,Pyrro], [R1437;H,Br,Me,Me,H,Pyrro],[R1438;H,Br,CHF₂,Me,H, Pyrro],[R1439;H,Br,CF₃,Me,H,Pyrro],[R1440;H,Br,NO₂, Me,H,Pyrro],[R1441;H,Me,F,Me,H,Me],[R1442;H,Me,Cl, Me,H,Me],[R1443;H,Me,Br,Me,H,Me],[R1444;H,Me,T, Me,H,Me],[R1445;H,Me,Me,Me,H,Me],[R1446;H,Me, CHF₂,Me, H,Me],[R1447;H,Me,CF₃,Me,H,Me],[R1448;H, Me,NO₂,Me,H,Me],[R1449;H,Me,F,Me,H,Et],[R1450;H, Me,Cl,Me,H,Et],[R1451;H,Me,Br, Me,H,Et],[R1452;H,Me, I,Me,H,Et],[R1453;H,Me,Me,Me,H,Et],[R1454;H,Me, CHF₂,Me,H,Et],[R1455;H,Me,CF₃,Me,H,Et],[R1456;H, Me,NO₂,Me,H,Et],[R1457;H,Me,F,Me,H,Pr],[R1458;H, Me,Cl,Me,H,Pr],[R1459;H,Me,Br,Me,H,Pr],[R1460;H,Me, I,Me,H,Pr],[R1461;H,Me,Me,Me,H,Pr],[R1462;H,Me, CHF₂,Me,H,Pr],[R1463;H,Me,CF₃,Me, H,Pr],[R1464;H, Me,NO₂,Me,H,Pr],[R1465;H,Me,F,Me,H,Bu],[R1466;H, Me,Cl,Me,H,Bu],[R1467;H,Me,Br,Me,H,Bu],[R1468;H, Me,I,Me,H,Bu],[R1469;H,Me,Me,Me,H,Bu],[R1470;H, Me,CHF₂,Me,H,Bu],[R1471;H,Me,CF₃,Me,H,Bu],[R1472; H,Me,NO₂,Me,H,Bu],[R1473;H,Me,F,Me,H,c-Pr],[R1474; H,Me,Cl,Me,H,c-Pr],[R1475;H,Me,Br,Me,H,c-Pr],[R1476; H,Me,I,Me,H,c-Pr],[R1477;H,Me,Me,Me,H,c-Pr],[R1478; H,Me,CHF₂,Me,H,c-Pr],[R1479;H,Me,CF₃,Me,H,c-Pr], [R1480;H,Me,NO₂,Me,H,c-Pr],[R1481;H,Me,F,Me,H, CH₂CF₃],[R1482;H,Me,Cl,Me,H,CH₂CF₃],[R1483;H,Me, Br,Me,H,CH₂CF₃],[R1484;H,Me,I,Me,H,CH₂CF₃],[R1485; H,Me,Me,Me,H,CH₂CF₃],[R1486;H,Me,CHF₂,Me,H, CH₂CF₃],[R1487;H,Me,CF₃,Me,H,CH₂CF₃],[R1488;H, Me,NO₂,Me,H,CH₂CF₃],[R1489;H,Me,F,Me,H, CH₂CHF₂],[R1490;H,Me,Cl,Me,H,CH₂CHF₂],[R1491;H, Me,Br,Me,H,CH₂CHF₂],[R1492;H,Me,I,Me,H,CH₂CHF₂], [R1493;H,Me,Me,Me,H,CH₂CHF₂],[R1494;H,Me,CCHF₂, Me,H,CH₂CHF₂],[R1495;H,Me,CF₃,Me,H,CH₂CHF₂], [R1496;H,Me,NO₂,Me,H,CH₂CHF₂],[R1497;H,Me,F,Me, H,CF₂CH₃],[R1498;H,Me,Cl,Me,H,CF₂CH₃],[R1499;H, Me,Br,Me,H,CF₂CH₃],[R1500;H,Me,I,Me,H,CF₂CH₃], [R1501;H,Me,Me,Me,H,CF₂CH₃],[R1502;H,Me,CHF₂,Me, H,CF₂CH₃],[R1503;H,Me,CF₃,Me,H,CF₂CH₃],[R1504;H, Me,NO₂,Me,H,CF₂CH₃],[R150 S;H,Me,F,Me,H,NMe₂], [R1506;H,Me,Cl,Me,H,NMe₂],[R1507;H,Me,Br,Me,H, NMe₂],[R1508;H,Me,I,Me,H,NMe₂],[R1509;H,Me,Me, Me,H,NMe₂],[R1510;H,Me,CHF₂,Me,H,NMe₂],[R1511;H, Me,CF₃,Me,H,NMe₂], [R1512;H,Me,NO₂,Me,H,NMe₂], [R1513;H,Me,F,Me,H,Pyrro],[R1514; H,Me,Cl,Me,H, Pyrro],[R1515;H,Me,Br,Me,H,Pyrro],[R1516;H,Me,I,Me, H,Pyrro],[R1517;H,Me,Me,Me,H,Pyrro],[R1518;H,Me, CHF₂, Me,H,Pyrro],[R1519;H,Me,CF₃,Me,H,Pyrro], [R1520;H,Me,NO₂,Me, H,Pyrro],[R1521;H,CHF₂,F,Me,H, Me],[R1522;H,CHF₂,Cl,Me,H,Me],[R1523;H,CHF₂,Br, Me,H,Me],[R1524;H,CHF₂,I,Me,H,Me],[R1525; H,CHF₂, Me,Me,H,Me],[R1526;H,CHF₂,CHF₂,Me,H,Me],[R1527; H,CHF₂,CF₃,Me,H,Me],[R1528;EH,CHF₂,NO₂,Me,H,Me], [R1529;LH,CHF₂,F,Me, H,Et],[R1530;H,CHF₂,Cl,Me,H, Et],[R1531;H,CHF₂,Br,Me,H,Et],[R1532;H,CHF₂,I,Me,I, Et],[R1533;H,CHF₂,Me,Me,H,Et],[R1534;H, CHF₂,CHF₂, Me,H,Et],[R1535;H,CHF₂,CF₃,Me,H,Et],[R1536;H,CHF₂, NO₂,Me,H,Et],[R1537;H,CHF₂,F,Me,H,Pr],[R1538;H, CHF₂,Cl,Me,H, Pr],[R1539;H,CHF₂,Br,Me,H,Pr],[R1540; H,CHF₂,I,Me,H,Pr],[R1541;H,CHF₂,Me,Me,H,Pr],[R1542; H,CHF₂. CHF₂,Me,H,Pr],[R1543;H,CHF₂,CF₃,Me,H,Pr], [R1544;H,CHF₂,NO₂,Me,H,Pr],[R1545;H,CHF₂,F, Me,H, Bu],[R1546;H,CHF₂,Cl,Me,H,Bu],[R1547;H,CHF₂,Br,Me, H,Bu],[R1548;H,CHF₂,I,Me,H,Bu],[R1549;H,CHF₂,Me, Me,H,Bu],[R1550;H,CHF₂,CHF₂,Me,H,Bu],[R1551;H, CHF₂,CF₃,Me,H,Bu],[R1552;H,CHF₂,NO₂,Me,H,Bu], [R1553;H,CHF₂,F,Me,H,c-Pr],[R1554;H,CHF₂,Cl,Me,H,c-Pr],[R1555;H,CHF₂,Br,Me,H,c-Pr],[R1556;H,CHF₂,I,Me, H,c-Pr],[R1557;H,CHF₂,Me,Me,H,c-Pr],[R1558;H,CHF₂, CHF₂,Me,H,c-Pr],[R1559;H,CHF₂,CF₃,Me,H,c-Pr], [R1560;H,CHF₂,NO₂,Me,H,c-Pr],[R1561;H,CHF₂,F,Me,H, CH₂CF₃],[R1562;H,CHF₂,Cl,Me,H,CH₂CF₃],[R1563;H, CHF₂,Br,Me,H,CH₂CF₃],[R1564;H,CHF₂,I,Me,H, CH₂CF₃], [R1565;H,CHF₂,Me,Me,H,CH₂CF₃],[R1566;H, CHF₂,CHF₂,Me,H,CH₂CF₃][R1567;H,CHF₂,CF₃,Me,H, CH₂CF₃],[R1568;H,CHF₂,NO₂,Me,H,CH₂CF₃],[R1569;H, CHF₂,F,Me,H,CH₂CHF₂],[R1570; B,CHF₂,Cl,Me,H, CH₂CHF₂],[R1571;H,CHF₂,Br,Me,H,CH₂CHF₂],[R1572; H,CHF₂,I,Me,H,CH₂CHF₂],[R1573;H,CHF₂,Me,Me,H, CH₂CHF₂],[R1574;H,CHF₂,CHF₂,Me,H,CH₂C HF₂], [R1575;H,CHF₂,CF₃,Me,H,CH₂CHF₂],[R1576;H,CHF₂, NO₂,Me,H,CH₂CHF₂],[R1577;H,CHF₂,F,Me,H,CF₂CH₃], [R1578;H,CHF₂,Cl,Me,H,CF₂CH₃],[R1579;H,CHF₂,Br, Me,H,CF₂CH₃],[R1580;H,CHF₂,I,Me,H,CF₂CH₃],[R1581; H,CHF₂,Me,Me,H,CF₂CH₃],[R1582;H,CHF₂,CHF₂,Me,H, CF₂CH₃],[R1583;H,CHF₂,CF₃,Me,H,CF₂CH₃],[R1584;H, CHF₂,NO₂,Me,H,CF₂CH₃],[R1585;H,CHF₂,F,Me,H, NMe₂],[R1586;H,CHF₂,Cl,Me,H,NMe₂], [R1587;H,CHF₂, Br,Me,H,NMe₂],[R1588;H,CHF₂,I,Me,H,NMe₂],[R1589; H,CHF₂,Me,Me,H,NMe₂],[R1590;H,CHF₂,CHF₂,Me,H, NMe₂], H,CHF₂,CF₃,Me,H,NMe₂],[R1592;H, [R1591; CHF₂,NO₂,Me,H,NMe₂],[R1593;H,CHF₂,F,Me,H,Pyrro], [R1594;H,CHF₂,Cl,Me,H,Pyrro],[R1595;H,CHF₂,Br,Me,H, Pyrro],[R1596;H,CHF₂,I,Me,H,Pyrro],[R1597;H,CHF₂,Me, Me,H,Pyrro],[R1598;H,CHF₂,CHF₂,Me,H,Pyrro],[R1599; H,CHF₂,CF₃,Me,H,Pyrro],[R1600;H,CHF₂,NO₂,Me,H, Pyrro],[R1601;H,CF₃,F, Me,H,Me],[R1602;H,CF₃,Cl,Me, H,Me],[R1603;H,CF₃,Br,Me,H,Me], [R1604;H,CF₃,I,Me, H,Me],[R1605;H,CF₃,Me,Me,H,Me],[R1606;H,CF₃,CHF₂, Me,H,Me],[R1607;H,CF₃,CF₃,Me,H,Me],[R1608;H,CF₃, NO₂,Me,H,Me],[R1609;H,CF₃,F,Me,H,Et],[R1610;H,CF₃, Cl,Me,H,Et],[R1611;H,CF₃,Br,Me,H,Et],[R1612;H,CF₃,I, Me,H,Et],[R1613;H,CF₃, Me,Me,H,Et],[R1614;H,CF₃, CHF₂,Me,H,Et],[R1615;H,CF₃,CF₃,Me,H,Et],[R1616;H, CF₃,NO₂,Me,H,Et],[R1617;H,CF₃,F,Me,H,Pr],[R1618;H, CF₃,Cl,Me,H,Pr],[R1619;H,CF₃,Br,Me,H,Pr],[R1620;H, CF₃,I, Me,H,Pr],[R1621;H,CF₃,Me,Me,H,Pr],[R1622;H, CF₃,CHF₂,Me,H,Pr],[R1623;H,CF₃,CF₃,Me,H,Pr],[R1624; H,CF₃,NO₂,Me,H,Pr],[R1625; H,CF₃,F,Me,H,Bu],[R1626; H,CF₃,Cl,Me,H,Bu],[R1627;H,CF₃,Br,Me,H,Bu],[R1628; H,CF₃,I,Me,H,Bu],[R1629;H,CF₃,Me,Me,H,Bu],[R1630;H, CF₃,CHF₂,Me,H,Bu],[R1631;H,CF₃,CF₃,Me,H,Bu], [R1632;H,CF₃,NO₂,Me,H,Bu],[R1633;H,CF₃,F,Me,H,c-Pr],[R1634;H,CF₃,Cl,Me,H,c-Pr],[R1635;H,CF₃,Br,Me,H, c-Pr],[R1636;H,CF₃,I,Me,H,c-Pr],[R1637;H,CF₃,Me,Me,H, c-Pr],[R1638;H,CF₃,CHF₂,Me,H,c-Pr],[R1639;H,CF₃,CF₃, Me,H,c-Pr],[R1640;H,CF₃,NO₂,Me,H,c-Pr],[R1641;H,CF₃, F,Me,H,CH₂CF₃],[R1642;H,CF₃,Cl,Me,H,CH₂CF₃], [R1643;H,CF₃,Br,Me,H,CH₂CF₃],[R1644;H,CF₃,I,Me,H, CH₂CF₃],[R1645;H,CF₃,Me,Me,H,CH₂CF₃],[R1646;H, CF₃,CHF₂,Me,H,CH₂CF₃],[R1647;H,CF₃,CF₃,Me,H, CH₂CF₃],[R1648;H,CF₃,NO₂,Me,H,CH₂CF₃],[R1649;H, CF₃,F,Me,H,CH₂CHF₂],[R1650;H,CF₃,Cl,Me,H, CH₂CHF₂], [R1651;H,CF₃,Br,Me,H,CH₂CHF₂],[R1652;H,CF₃,I,Me,H, CH₂CHF₂],[R1653;H,CF₃,Me,Me,H,CH₂CHF₂],[R1654;H, CF₃,CHF₂,Me,H,CH₂CHF₂], [R1655;H,CF₃,CF₃,Me,H, CH₂CHF₂],[R1656;H,CF₃,NO₂,Me,H,CH₂CHF₂], [R1657; H,CF₃,F,Me,H,CF₂CH₃],[R1658;H,CF₃,Cl,Me,H,CF₂CH₃], [R1659;H,CF₃,Br,Me,H,CF₂CH₃],[R1660;H,CF₃,I,Me,H, CF₂CH₃],[R1661;H,CF₃,Me,Me,H,CF₂CH₃],[R1662;H, CF₃,CHF₂,Me,H,CF₂CH₃],[R1663;H, CF₃,CF₃,Me,H, CF₂CH₃],[R1664;H,CF₃,NO₂,Me,H,CF₂CH₃],[R1665;H, CF₃,F,Me,H,NMe₂],[R1666;H,CF₃,Cl,Me,H,NMe₂], [R1667;H,CF₃,Br,Me,H,NMe₂],[R1668;H,CF₃,I,Me,H, NMe₂],[R1669;H,CF₃,Me,Me,H,NMe₂],[R1670;H,CF₃, CHF₂,Me,H,NMe₂],[R1671;H,CF₃,CF₃,Me,H,NMe₂], [R1672;H,CF₃,NO₂,Me,H,NMe₂],[R1673;H,CF₃,F,Me,H, Pyrro],[R1674;H,CF₃,Cl,Me,H,Pyrro],[R1675;H,CF₃,Br, Me,H,Pyrro],[R1676;H, CF₃,I,Me,H,Pyrro],[R1677;H,CF₃, Me,Me,H,Pyrro],[R1678;H,CF₃,CHF₂,Me,H,Pyrro], [R1679;H,CF₃,CF₃,Me,H,Pyrro],[R1680;H,CF₃,NO₂,Me, H,Pyrro],[R1681;H,NO₂,F,Me,H,Me],[R1682;H,NO₂,Cl, Me,H,Me],[R1683;H,NO₂,Br,Me,H,Me],[R1684;H,NO₂,I, Me,H,Me],[R1685; H,NO₂,Me,Me,H,Me],[R1686;H,NO₂, CHF₂,Me,H,Me],[R687;H,NO₂,CF₃,Me,H,Me],[R1688;H, NO₂,NO₂,Me,H,Me],[R1689;H,NO₂,F,Me,H,Et],[R1690;H, NO₂,Cl,Me,H,Et],[R1691;H,NO₂,Br,Me,H,Et],[R1692;H, NO₂,I,Me,H,Et],[R1693;H,NO₂,Me,Me,H,Et],[R1694;H, NO₂,CHF₂,Me,H,Et],[R1695;H,NO₂,CF₃,Me,H,Et], [R1696;H,NO₂,NO₂,Me,H,Et], [R1697;H,NO₂,F,Me,H,Pr], [R1698;H,NO₂,Cl,Me,H,Pr],[R1699;H,NO₂,Br,Me,H,Pr], [R1700;H,NO₂,I,Me,H,Pr],[R1701;H,NO₂,Me,Me,H, Pr], [R1702;H,NO₂,CHF₂,Me,H,Pr],[R1703;H,NO₂,CF₃,Me,H, Pr],[R1704;H,NO₂,NO₂,Me,H,Pr],[R1705;H,NO₂,F,Me,H, Bu],[R1706;H,NO₂, Cl,Me,H,Bu],[R1707;H,NO₂,Br,Me,H, Bu],[R1708;H,NO₂,I,Me,H,Bu],[R1709;H,NO₂,Me,Me,H, Bu],[R1710;H,NO₂,CHF₂,Me,H,Bu],[R1711;H,NO₂,CF₃, Me,H,Bu],[R1712;H,NO₂,NO₂,Me,H,Bu],[R1713;H,NO₂, F,Me,H,c-Pr],[R1714;H,NO₂,Cl,Me,H,c-Pr],[R1715;H, NO₂,Br,Me,H,c-Pr],[R1716;H,NO₂,I,Me,H,c-Pr],[R1717; H,NO₂,Me,Me,H,c-Pr],[R1718;H,NO₂,CHF₂,Me,H,c-Pr], [R1719;H,NO₂,CF₃,Me,H,c-Pr],[R1720;H,NO₂,NO₂,Me,H, c-Pr], [R1721;H,NO₂,F,Me,H,CH₂CF₃],[R1722;H,NO₂,Cl, Me,H,CH₂CF], [R1723;H,NO₂,Br,Me,H,CH₂CF₃],[R1724; H,NO₂,I,Me,H,CH₂CF₃],[R1725;H,NO₂,Me,Me,H, CH₂CF₃],[R1726;H,NO₂,CHF₂,Me,H,CH₂CF₃],[R1727;H, NO₂,CF₃,Me,H,CH₂CF₃],[R1728;H,NO₂,NO₂,Me,H, CH₂CF₃],[R1729; H,NO₂,F,Me,H,CH₂CHF₂],[R1730;H, NO₂,Cl,Me,H,CH₂CHF₂],[R1731;H,NO₂,Br,Me,H, CH₂CHF₂],[R1732;H,NO₂,I,Me,H,CH₂CHF₂],[R1733;H, NO₂,Me,Me,H,CH₂CHF₂],[R1734;H,NO₂,CHF₂,Me,H, CH₂HF₂],[R1735;H, NO₂,CF₃,Me,H,CH₂CHF₂],[R1736;H, NO₂,NO₂,Me,H,CH₂CH₂CHF₂],[R1737;H,NO₂,F,Me,H, CF₂CH₃],[R1738;H,NO₂,Cl,Me,H,CF₂CH₃],[R1239;H, NO₂,Br,Me,H,CF₂CH₃],[R1740;H,NO₂,I,Me,H,CF₂CH₃], [R1741;H,NO₂,Me, Me,H,CF₂CH₃],[R1742;H,NO₂,CHF₂, Me,H,CF₂CH₃],[R1743;H,NO₂,CF₃, Me,H,CF₂CH₃], [R1744;H,NO₂,NO₂,Me,H,CF₂CH₃],[R1745;H,NO₂,F,Me, H,NMe₂],[R1746;H,NO₂,Cl,Me,H,NMe₂],[R1747;H,NO₂, Br,Me,H,NMe₂],[R1748;H,NO₂,I,Me,H,NMe₂],[R1749;H, NO$_2$,Me,Me,H,NMe$_2$],[R1750;H,NO$_2$,CHF$_2$,Me,H,NMe$_2$],
[R1751;H,NO$_2$,CF$_3$,Me,H,NMe$_2$],[R1752;H, NO$_2$,NO$_2$,Me,
H,NMe$_2$],[R1753;H,NO$_2$,F,Me,H,Pyrro],[R1754;H,NO$_2$,Cl,
Me,H,Pyrro],[R1755;H,NO$_2$,Rr,Me,H,Pyrro],[R1756;H,
NO$_2$,I,Me,H,Pyrro],[R1757;H,NO$_2$,Me,Me,H,Pyrro],
[R1758;H,NO$_2$,CHF$_2$,Me,H,Pyrro],[R1759;H,NO$_2$,CF$_3$,
Me,H,Pyrro],[R1760;H,NO$_2$,NO$_2$,Me,H,Pyrro],[R1761;H,
H,F,H,H,i-Pr],[R1762;H,F,F,H,H,i-Pr],[R1763;H,Cl,F,H,H,
i-Pr],[R1764;H,Me,F,H,H,i-Pr],[R1765;H,CHF$_2$,F,H,H,i-
Pr],[R1766;H,CF$_3$,F,H,H,i-Pr],[R1767;H,NO$_2$,F,H,H,i-Pr],
[R1768;H,H,F,F,H,i-Pr],[R1769;H,F,F,F,H,i-Pr],[R1770;H,
Cl,F,F,H,i-Pr],[R1771;H,Me,F,F,H,i-Pr],[R1772;H,CHF$_2$,F,
F,H,i-Pr],[R1773;H,CF$_3$,F,F,H,i-Pr],[R1774;H,NO$_2$,F,F,H,i-
Pr],[R1775;H,H,F,Me,H,i-Pr],[R1776;H,F,F,Me,H,i-Pr],
[R1777;H,Cl,F,Me,H,i-Pr],[R1778;H,Me,F,Me,H,i-Pr],
[R1779;H,CHF$_2$,F,Me,H,i-Pr],[R1780;H,CF$_3$,F,Me,H,i-Pr],
[R1781;H,NO$_2$,F,Me,H,i-Pr],[R1782;H,H,Cl,H,H,i-Pr],
[R1783;H,F,Cl,H,H,i-Pr],[R1784;H,Cl,Cl,H,H,i-Pr],
[R1785;H,Me,Cl,H,H,i-Pr],[R1786;H,CHF$_2$,Cl,H,H,i-Pr],
[R1287;H,CF$_3$,Cl,H,H,i-Pr],[R1788;H,NO$_2$,Cl,H,H,i-Pr],
[R1789;H,H,Cl,F,H,i-Pr],[R1790;H,F,Cl,F,H,i-Pr],[R1791;
H,Cl,Cl,F,H,i-Pr],[R1792;H,Me,Cl,F,H,i-Pr],[R1793;H,
CHF$_2$,Cl,F,H,i-Pr],[R1794;H,CF$_3$,Cl,F,H,i-Pr],[R1795;H,
N$_2$,C,F,H,i-Pr],[R1796;H,H,Cl,Me,H,i-Pr],[R1797;H,F,Cl,
Me,H,i-Pr],[R1798;H,Cl,Cl,Me,H,i-Pr],[R1799;H,Me,Cl,
Me,H,i-Pr],[R1800;H,CHF$_2$,Cl,Me,H,i-Pr],
[R1801;H,CF$_3$,Cl,Me,H,i-Pr],[R1802;H,NO$_2$,Cl,Me,H,i-
Pr],[R1803;H,H,Br,H,H,i-Pr],[R1804;H,F,Br,H,H,i-Pr],
[R1805;H,Cl,Br,H,H,i-Pr],[R1806;H,Me,Br,H,H,i-Pr],
[R1807;H,CHF$_2$,Br,H,H,i-Pr],[R1808;H,CF$_3$,Br,H,H,i-Pr],
[R1809;H,NO$_2$,Br,H,H,i-Pr],[R1810;H,H,Br,F,H,i-Pr],
[R1811;H,F,Br,F,H,i-Pr],[R1812;H,Cl,Br,F,H,i-Pr],[R1813;
H,Me,Br,F,H,i-Pr],[R1814;H,CHF$_2$,Br,F,H,i-Pr],[R1815;H,
CF$_3$,Br,F,H,i-Pr],[R1816;H,NO$_2$,Br,F,H,i-Pr],[R1817;H,H,
Br,Me,H,i-Pr],[R1818;H,F,Br,Me,H,i-Pr],[R1819;H,Cl,Br,
Me,H,i-Pr],[R1820;H,Me,Br,Me,H,i-Pr],[R1821;H,CHF$_2$,
Br,Me,H,i-Pr],[R1822;H,CF$_3$,Br,Me,H,i-Pr],[R1823;H,
NO$_2$,Br,Me,H,i-Pr],[R1824;H,H,I,H,H,i-Pr],[R1825;H,F,I,
H,H,i-Pr],[R1826;H,Cl,I,H,H,i-Pr],[R1827;H,Me,I,H,H,i-
Pr],[R1828;H,CHF$_2$,I,H,H,i-Pr],[R1829;H,CF$_3$,I,H,H,i-Pr],
[R1830;H,NO$_2$,I,H,H,i-Pr],[R1831;H,H,I,F,H,i-Pr],[R1832;
H,F,I,F,I,FH,i-Pr],[R1833;H,Cl,I,F,H,i-Pr],[R1834;H,Me,I,
F,H,i-Pr],[R1835;H,CHF$_2$,I,F,H,i-Pr],[R1836;H,CF$_3$,I,F,H,i-
Pr],[R1837;H,NO$_2$,I,F,H,i-Pr],[R1838;H,H,I,Me,H,i-Pr],
[R1839;H,F,I,Me,H,i-Pr],[R1840;H,Cl,I,Me,H,i-Pr],
[R1841;H,Me,I,Me,H,i-Pr],[R1842;H,CHF$_2$,I,Me,H,i-Pr],
[R1843;H,CF$_3$,I,Me,H,i-Pr],[R1844;H,NO$_2$,I,Me,H,i-Pr],
[R1845;H,H,Me,H,H,i-Pr],[R1846;H,F,Me,H,H,i-Pr],
[R1847;H,Cl,Me,H,H,i-Pr],[R1848;H,Me,Me,H,H,i-Pr],
[R1849;H,CHF$_2$,Me,H,H,i-Pr],[R1850;H,CF$_3$,Me,H,H,i-
Pr],[R1851;H,NO$_2$,Me,H,H,i-Pr],[R1852;H,H,Me,F,H,i-Pr],
[R1853;H,F,Me,F,H,i-Pr],[R1854;H,Cl,Me,F,H,i-Pr],
[R1855;H,Me,Me,F,H,i-Pr],[R1856;H,CHF$_2$,Me,F,H,i-Pr],
[R1857;H,CF$_3$,Me,F,H,i-Pr],[R1858;H,NO$_2$,Me,F,H,i-Pr],
[R1859;H,H,Me,Me,H,i-Pr],[R1860;H,F,Me,Me,H,i-Pr],
[R1861;H,Cl,Me,Me,H,i-Pr],[R1862;H,Me,Me,Me,H,i-Pr],
[R1863;H,CHF$_2$,Me,Me,H,i-Pr],[R1864;H,CF$_3$,Me,Me,i-
Pr],[R1865;H,NO$_2$,Me,Me,H,i-Pr],[R1866;H,H,CHF$_2$,H,H,
i-Pr],[R1867;H,F,CHF$_2$,H,H,i-Pr],[R1868;H,Cl,CHF$_2$,H,H,
i-Pr],[R1869;H,Me,CHF$_2$,H,H,i-Pr],[R1870;H,CHF$_2$,CHF$_2$,
H,H,i-Pr],[R1871;H,CF$_3$,CHF$_2$,H,H,i-Pr],[R1872;H,NO$_2$,
CHF$_2$,H,H,i-Pr],[R1873;H,H,CHF$_2$,F,H,i-Pr],[R1874;H,F,
CHF$_2$,F,H,i-Pr],[R1875;H,Cl,CHF$_2$,F,H,i-Pr],[R1876;H,
Me,CHF$_2$,F,H,i-Pr],[R1877;H,CHF$_2$,CHF$_2$,F,H,i-Pr],
[R1878;H,CF$_3$,CHF$_2$,F,H,i-Pr],[R1879;H,NO$_2$,CHF$_2$,F,H,i-
Pr],[R1880;H,H,CHF$_2$,Me,H,i-Pr],[R1881;H,F,CHF$_2$,Me,
H,i-Pr],[R1882;H,Cl,CHF$_2$,Me,H,i-Pr],[R1883;H,Me,
CHF$_2$,Me,H,i-Pr],[R1884;H,CHF$_2$,CHF$_2$,Me,H,i-Pr],
[R1885;H,CF$_3$,CHF$_2$,Me,H,i-Pr],[R1886;H,NO$_2$,CHF$_2$,Me,
H,i-Pr],[R1887;H,H,CF$_3$,H,H,i-Pr],[R1888;H,F,CF$_3$,H,H,i-
Pr],[R1889;H,C,CF$_3$,H,H,i-Pr],[R1890;H,Me,CF$_3$,H,H,i-
Pr],[R1891;H,CHF$_2$,CF$_3$,H,H,i-Pr],[R1892;H,CF$_3$,CF$_3$,H,
H,i-Pr],[R1893;H,NO$_2$,CF$_3$,H,H,i-Pr],[R1894;H,H,CF$_3$,F,
H,i-Pr],[R1895;H,F,CF$_3$,F,H,i-Pr],[R1896;H,Cl,CF$_3$,F,H,i-
Pr],[R1897;H,Me,CF$_3$,F,H,i-Pr],[R1898;H,CHF$_2$,CF$_3$,F,H,i-
Pr],[R1899;H,CF$_3$,CF$_3$,F,H,i-Pr],[R1900;H,NO$_2$,CF$_3$,F,H,i-
Pr],[R1901;H,H,CF$_3$,Me,H,i-Pr],[R1902;H,F,CF$_3$,Me,H,i-
Pr],[R1903;H,Cl,CF$_3$,Me,H,i-Pr],[R1904;H,Me,CF$_3$,Me,H,
i-Pr],[R1905;H,CHF$_2$,CF$_3$,Me,H,i-Pr],[R1906;H,CF$_3$,CF$_3$,
Me,H,i-Pr],[R1907;H,NO$_2$,CF$_3$,Me,H,i-Pr],[R1908;H,H,
NO$_2$,H,H,i-Pr],[R1909;H,F,NO$_2$,H,H,i-Pr],[R1910;H,Cl,
NO$_2$,H,H,i-Pr],[R1911;H,Me,NO$_2$,H,H,i-Pr],[R1912;H,
CHF$_2$,NO$_2$,H,H,i-Pr],[R1913;H,CF$_3$,NO$_2$,H,H,i-Pr],
[R1914;H,NO$_2$,NO$_2$,H,H,i-Pr],[R1915;H,H,NO$_2$,F,H,i-Pr],
[R1916;H,F,NO$_2$,F,H,i-Pr],[R1917;H,Cl,NO$_2$,F,H,i-Pr],
[R1918;H,Me,NO$_2$,F,H,i-Pr],[R1919;H,CHF$_2$,NO$_2$,F,H,i-
Pr],[R1920;H,CF$_3$,NO$_2$,F,H,i-Pr],[R1921;H,NO$_2$,NO$_2$,F,H,
i-Pr],[R1922;H,H,NO$_2$,Me,H,i-Pr],[R1923;H,F,NO$_2$,Me,H,
i-Pr],[R1924;H,Cl,NO$_2$,Me,H,i-Pr],[R1925;H,Me,NO$_2$,Me,
H,i-Pr],[R1926;H,CHF$_2$,NO$_2$,Me,H,i-Pr],[R1927;H,CF$_3$,
NO$_2$,Me,H,i-Pr],[R1928;H,NO$_2$,NO$_2$,Me,H,i-Pr],[R1929;
H,Br,Cl,H,H,Me],[R1930;H,Br,Br,H,H,Me],[R1931;H,
Br,I,H,H,Me],[R1932;H,Br,Me,H,H,Me],[R1933;H,Br,
CHF$_2$,H,H,Me],[R1934;H,Br,CF$_3$,H,H,Me],[R1935;H,Br,
H,H,H,Me],[R1936;H,Br,F,H,H,Et],[R1937;H,Br,Cl,H,H,
Et],[R1938;H,Br,Br,H,H,Et],[R1939;H,Br,I,H,H,Et],
[R1940;H,Br,Me,H,H,Et],[R1941;H,Br,CHF$_2$,H,H,Et],
[R1942;H,Br,CF$_3$,H,H,Et],[R1943;H,Br,H,H,H,Er],[R1944;
H,Br,F,H,H,Pr],[R1945;H,Br,Cl,H,H,Pr],[R1946;H,Br,Br,
H,H,Pr],[R1947;H,Br,I,H,H,Pr],[R1948;H,Br,Me,H,H,Pr],
[R1949;H,Br,CHF$_2$,H,H,Pr],[R1950;H,Br,CF$_3$,H,H,Pr],
[R1951;H,Br,H,H,H,Pr],[R1952;H,Br,F,H,H,Bu],[R1953;H,
Br,Cl,H,H,Bu],[R1954;H,Br,Br,H,H,Bu],[R1955;H,Br,I,H,
H,Bu],[R1956;H,Br,Me,H,H,Bu],[R1957;H,Br,CHF$_2$,H,H,
Bu],[R1958;H,Br,CF$_3$,H,H,Bu],[R1959;H,Br,H,H,H,Bu],
[R1960;H,Br,F,H,H,c-Pr],[R1961;H,Br,Cl,H,H,c-Pr],
[R1962;H,Br,Br,H,H,c-Pr],[R1963;H,Br,I,H,H,c-Pr],
[R1964;H,Br,Me,H,H,c-Pr],[R1965;H,Br,CHF$_2$,H,H,c-Pr],
[R1966;H,Br,CF$_3$,H,H,c-Pr],[R1967;H,Br,H,H,H,c-Pr],
[R1968;H,Br,F,H,H,CH$_2$CF$_3$],[R1969;H,Br,Cl,H,H,
CH$_2$CF$_3$],[R1970;H,Br,Br,H,H,CH$_2$CF$_3$],[R1971;H,Br,I,H,
H,CH$_2$CF$_3$],[R1972;H,Br,Me,H,H,CH$_2$CF$_3$],[R1973;H,Br,
CHF$_2$,H,H,CH$_2$CF$_3$],[R1974;H,Br,CF$_3$,H,H,CH$_2$CF$_3$],
[R1975;H,Br,H,H,H,CH$_2$CF$_3$],[R1976;H,Br,F,H,H,
CH$_2$CHF$_2$],[R1977;H,Br,Cl,H,H,CH$_2$CHF$_2$],[R1978;H,Br,
Br,H,H,CH$_2$CHF$_2$],[R1979;H,Br,I,H,H,CH$_2$CHF$_2$],[R1980;
H,Br,Me,H,H,CH$_2$CHF$_2$],[R1981;H,Br,CHF$_2$,H,H,
CH$_2$CHF$_2$],[R1982;H,Br,CF$_3$,H,H,CH$_2$CHF$_2$],[R1983;H,
Br,H,H,H,CH$_2$CHF$_2$],[R1984;H,Br,F,H,H,CF$_2$CH$_3$],
[R1985;H,Br, Cl,H,H,CF$_2$CH$_3$],[R1986;H,Br,Br,H,H,
CF$_2$CH$_3$],[R1987;H,Br,I,H,H, CF$_2$CH$_3$],[R1988;H,Br,Me,
H,H,CF$_2$CH$_3$],[R1989;H,Br,CHF$_2$,H,H,CF$_2$CH$_3$],[R1990;
H,Br,CF$_3$,H,H,CF$_2$CH$_3$],[R1991;H,Br,H,H,H,CF$_2$CH$_3$],
[R192;H,Br,F,H,H,NMe$_2$],[R1993;H,Br,Cl,H,H,NMe$_2$],
[R1994;H,Br,Br,H,H,NMe$_2$],[R1995;H,Br,I,H,H,NMe$_2$],
[R1996;H,Br,Me,H,H,NMe$_2$], [R1997;H,Br,CHF$_2$,H,H,
NMe$_2$],[R1998;H,Br,CF$_3$,H,H,NMe$_2$],[R1999; H,Br,H,H,H,
NMe$_2$],[R2000;H,Br,F,H,H,Pyrro],[R2001;H,Br,Cl,H,
H,Pyrro],[R2002;H,Br,Br,H,H,Pyrro],[R2003;H,Br,I,H,H,
Pyrro],[R2004;H,Br,Me,H,H,Pyrro],[R2005;H,Br,CHF$_2$,H,
H,Pyrro],[R2006;H,Br,CF$_3$,H,H,Pyrro],[R2007;H,Br,H,H,
H,Pyrro],[R2008;H,I, Cl,H,H,Me],[R2009;H,I,Br,H,H,Me],
[R2010;H,I,I,H,H,Me],[R2011;H,I,Me,H,H,Me],[R2012;H,
I,CHF$_2$,H,H,Me],[R2013;H,I,CF$_3$,H,H,Me],[R2014;H,I,H, H,H,Me],[R2015;H,I,F,H,H,Et],[R2016;H,I,Cl,H,H,Et], [R2017;H,I,Br,H,H,Et],[R2018;H,I,I,H,H,Et],[R2019;H,I, Me,H,H,Et],[R2020;H,I,CHF₂,H,H,Et],[R2021;H,I,CF₃,H, H, Et],[R2022;H,I,H,H,H,Et],[R2023;H,I,F,H,H,Pr], [R2024;H,I,Cl,H,H,Pr],[R2025;H,I,Br,H,H,Pr],[R2026;H,I, I,H,H,Pr],[R2027; H,I,Me,H,H,Pr],[R2028;H,I,CHF₂,H, Pr],[R2029;H,I,CF₃,H,H,Pr],[R2030;H,I,H,H,H,Pr], [R2031;H,I,F,H,H,Bu],[R2032;H,I,Cl, H,H,Bu],[R2033;H, I,Br,H,H,Bu],[R2034;H,I,I,H,H,Bu],[R2035;H,I,Me,H,H, Bu],[R2036;H,I,CHF₂,H,H,Bu],[R2037;H,I,CF₃,H,H,Bu], [R2038;H,I,H,H,H,Bu],[R2039;H,I,F,H,H,c-Pr],[R2040;H, I,Cl,H,H,c-Pr],[R2041;H,I,Br,H,H,c-Pr],[R2042;H,I,I,H,H, c-Pr],[R2043;H,I,Me,H,H,c-Pr],[R2044;H,I,CHF₂,H,H,c-Pr],[R2045;H,I,CF₃,H,H,c-Pr],[R2046;H,I,H,H,H,c-Pr], [R2047;H,I,F,H,H,CH₂CF₃],[R2048;H,I,Cl,H,H,CH₂CF₃], [R2049;H,I,Br,H,H,CH₂CF₃],[R2050;H,I,I,H,H,CH₂CF₃], [R2051;H,I,Me, H,H,CH₂CF₃],[R2052;H,I,CHF₂,H,H, CH₂CF₃],[R2053;H,I,CF₃,H,H,CH₂CF₃],[R2054;H,I,H,H, H,CH₂CF₃],[R2055;H,I,F,H,H,CH₂CHF₂],[R2056;H,I,Cl, H,H,CH₂CHF₂],[R2057;H,I,Br,H,H,CH₂CHF₂],[R2058;H, I,I,H,H,CH₂CHF₂],[R2059;H,I,Me,H,H,CH₂CHF₂], [R2060;H,I,CHF₂,H,H,CH₂CHF₂],[R2061;H,I,CF₃,H,H, CH₂CHF₂],[R2062;H,I,H,H,H,CH₂CHF₂],[R2063;H,I,F,H, H,CF₂CH₃],[R2064;H,I,Cl,H,H,CF₂CH₃],[R2065;H,I,Br,H, H,CF₂CH₃],[R2066;H,I,I,H,H,CF₂CH₃],[R2067;H,I,Me,H, H,CF₂CH₃],[R2068;H,I,CHF₂,H,H,CF₂CH₃],[R2069;H,I, CF₃,H,H,CF₂CH₃],[R2070;H,I,H,H,H,CF₂CH₃],[R2071;H, I,F,H,H,NMe₂],[R2072;H,I,Cl,H,H,NMe₂],[R2073;H,I,Br, H,H,NMe₂],[R2074;H,I,I,H,H,NMe₂],[R2075;H,I,Me,H,H, NMe₂],[R2076;H,I,CHF₂,H,H,NMe₂],[R2077;H,I,CF₃,H, H,NMe₂],[R2078;H,I,H,H,H,NMe₂],[R2079;H,I,F,H, H,Pyrro],[R2080;H,I,Cl,H,H,Pyrro],[R2081;H,I,Br,H,H, Pyrro], [R2082;H,I,I,H,H,Pyrro],[R2083;H,I,Me,H,H, Pyrro],[R2084;H,I,CHF₂,H,H,Pyrro],[R2085;H,I,CF₃,H,H, Pyrro],[R2086;H,I,H,H,H,Pyrro],[R2087;H,OMe,Cl,H,H, Me],[R2088;H,OMe,Br,H,H,Me],[R2089;H,OMe,I,H,H, Me],[R2090;H,OMe,Me,H,H,Me],[R2091;H,OMe,CHF₂, H,H,Me],[R2092;H,OMe,CF₃,H,H,Me],[R2093;H,OMe,H, H,H,Me], [R2094;H,Me,F,H,H,Et],[R2095;H,OMe,Cl,H,H, Et],[R2096;H,OMe,Br,H,H,Et],[R2097;H,OMe,I,H,H,Et], [R2098;H,OMe,Me,H,H,Et], [R2099;H,OMe,CHF₂,H,H, Et],[R2100;H,OMe,CF₃,H,H,Et], [R2101;H,OMe,H,H,H,Et],[R2102;H,OMe,F,H,H,Pr], [R2103;H,OMe, Cl,H,H,Pr],[R2104;H,OMe,Br,H,H,Pr], [R2105;H,OMe,I,H,H,Pr],[R2106;H,OMe,Me,H,H,Pr], [R2107;H,OMe,CHF₂,H,H,Pr],[R2108;H,OMe,CF₃,H,H, Pr],[R2109;H,OMe,H,H,H,Pr],[R2110;H,OMe,F,H,H,Bu], [R2111;H,CMe,Cl,H,H,Bu],[R2112;H,OMe,Br,H,H,Bu], [R2113;H, OMe,I,H,H,Bu],[R2114;H,OMe,Me,H,H,Bu], [R2115;H,OMe,CHF₂,H,H,Bu],[R2116;H,OMe,CF₃,H,H, Bu],[R2117;H,OMe,H,H,H,Bu],[R2118; H,OMe,F,H,H,c-Pr],[R2119;H,OMe,Cl,H,H,c-Pr],[R2120;H,cMe,Br,H,H,c-Pr],[R2121;H,OMe,I,H,H,c-Pr],[R2122;H,OMe,Me,H,H,c-Pr],[R2123;H,OMe,CHF₂,H,H,c-Pr],[R2124;H,OMe,CF₃, H,H,c-Pr],[R2125;H,OMe,H,H,H,c-Pr],[R2126;H,OMe,F, H,H,CH₂CF₃],[R2127;H,OMe,Cl,H,H,CH₂CF₃],[R2128;H, OMe,Br,H,H,CH₂CF₃],[R2129;H,OMe,I,H,H,CH₂CF₃], [R2130;H,OMe,Me,H,H,CH₂CF₃],[R2131;H,OMe,CHF₂, H,H,CH₂CF₃],[R2132;H,OMe,CF₃,H,H,CH₂CF₃],[R2133; H,OMe,H,H,H,CH₂CF₃],[R2134;H,OMe,F,H,H, CH₂CHF₂],[R2135;H,OMe,Cl,H,H,CH₂CHF₂],[R2136;H, OMe,Br,H,H,CH₂CHF₂],[R2137;H,OMe,I,H,H,CH₂CHF₂], [R2138;H,OMe,Me,H, H,CH₂CHF₂],[R2139;H,OMe, CHF₂,H,H,CH₂CHF₂],[R2140;H,OMe,CF₃,H,H, CH₂CHF₂],[R2141;H,OMe,H,H,H,CH₂CHF₂],[R2142;H, OMe,F,H,H,CF₂CH₃],[R2143;H,OMe,Cl,H,H,CF₂CH₃], [R2144;H,OMe,Br,H,H,CF₂CH₃],[R2145;H,OMe,I,H,H, CF₂CH₃],[R2146;H,OMe,Me,H,H,CF₂CH₃],[R2147;H, OMe,CHF₂,H,H,CF₂CH₃],[R2148;H,OMe,CF₃,H,H, CF₂CH₃],[R2149;H,OMe,H,H,H,CF₂CH₃],[R2150;H,OMe, F,H,H,NMe₂],[R2151;H,OMe, Cl,H,H,H,NMe₂],[R2152;H, OMe,Br,H,H,H,NMe₂],[R2153;H,OMe,I,H,H,NMe₂],[R2154; H,OMe,Me,H,H,H,NMe₂],[R2155;H,OMe,CHF₂,H,H,NMe₂], [R2156;H,OMe,CF₃,H,H,NMe₂],[R2157;H,OMe,H,H,H, NMe₂],[R2158;H, OMe,F,H,H,Pyrro],[R2159;H,OMe,Cl,H, H,Pyrro],[R2160;H,OMe,Br,H,H,Pyrro],[R2161;H,OMe,I, H,H,Pyrro],[R2162;H,OMe,Me,H,H,Pyrro],[R2163;H, OMe,CHF₂,H,H,Pyrro],[R2164;H,OMe,CF₃,H,H,Pyrro], [R2165;H,OMe,H,H,H,Pyrro],[R2166;H,OEt,C,H,H,Me], [R2167;H,OEt,Br,H,H,Me],[R2168;H,OEt,I,H,H,Me], [R2169;H,OEt,Me,H,H,Me],[R2170;H,OEt,CHF₂,H,H, Me],[R2171;H,OEt,CF₃,H,H,Me],[R2172;H,OEt,H,H,H, Me],[R2173;H,OEt,F,H,H,Et],[R2174;H,OEt,Cl,H,H,Et], [R2175;H,OEt,Br,H,H,Et],[R2176;H,OEt,I,H,H,Et], [R2177;H,OEt,Me,H,H,Et].[R2178;H,OEt,CHF₂,H,H,Et], [R2179;H,OEt,CF₃,H,H,Et],[R2180;H,OEt,H,H,H,Et], [R2181;H,OEt,F,H,H,Pr],[R2182;H,OEt,Cl,H,H,Pr], [R2183;H,OEt,Br,H,H,Pr],[R2184;H,OEt,I,H,H,Pr], [R2185;H,OEt,Me,H,H,Pr],[R2186;H,OEt,CHF₂,H,H, Pr], [R2187;H,OEt,CF₃,H,H,Pr],[R2188;H,OEt,H,H,H,Pr], [R2189; H,OEt,F,H,H,Bu],[R2190;H,OEt,Cl,H,H,Bu], [R2191;H,OEt,Br,H,H,Bu],[R2192;H,OEt,I,H,H,Bu], [R2193;H,OEt,Me,H,H,Bu],[R2194; H,OEt,CHF₂,H,H,Bu], [R2195;H,OEt,CF₃,H,H,Bu],[R2196;H,OEt,H, H,H,Bu], [R2197;H,OEt,F,H,H,c-Pr],[R2198;H,OEt,Cl,H,H,c-Pr], [R2199;H,OEt,Br,H,H,c-Pr],[R2200;H,OEt,I,H,H,c-Pr], [R2201;H,OEt,Me,H,H,c-Pr],[R2202;H,OEt,CHF₂,H,H,c-Pr],[R2203;H,OEt,CF₃,H,H,c-Pr],[R2204;H,OEt,H,H,H,c-Pr],[R2205;H,OEt,F,H,H,CH₂CF₃],[R2206;H,OEt,Cl,H,H, CH₂CF₃],[R2207;H,OEt,Br,H,H,CH₂CF₃],[R2208;H,OEt,I, H,H,CH₂CF₃],[R2209;H,OEt,Me,H,H,CH₂CF₃],[R2210;H, OEt,CHF₂,H,H,CH₂CF₃],[R2211;H,OEt,CF₃,H,H, CH₂CF₃],[R2212;H,OEt,H,H,H,CH₂CF₃],[R2213;H,OEt,F, H,H,CH₂CHF₂],[R2214;H,OEt,Cl,H,H,CH₂CHF₂],[R2215; H,OEt,Br,H,H,CH₂CHF₂],[R2216;H,OEt,I,H,H, CH₂CHF₂],[R2217;H,OEt,Me,H, H,CH₂CHF₂],[R2218;H, OEt,CHF₂,H,H,CH₂CHF₂],[R2219;H,OEt,CF₃,H, H,CH₂CHF₂],[R2220;H,OEt,H,H,H,CH₂CHF₂],[R2221;H, OEt,F,H,H,CF₂CH₃],[R2222;H,OEt,Cl,H,H,CF₂CH₃], [R2223;H,OEt,Br,H,H,CF₂CH₃],[R2224;H,OEt,I,H,H, CF₂CH₃],[R2225;H,OEt,Me,H,H,CF₂CH₃],[R2226;H,OEt, CHF₂,H,H,CF₂CH₃],[R2227;H,OEt,CF₃,H,H,CF₂CH₃], [R2228; H,OEt,H,H,H,CF₂CH₃],[R2229;H,OEt,F,H,H, NMe₂],[R2210;H,OEt, Cl,H,H,NMe₂],[R2211;H,OEt,Br,H, H,NMe₂],[R2212;H,OEt,I,H,H,NMe₂],[R2213;H,OEt,Me, H,H,NMe₂],[R2214;H,OEt,CHF₂~H,H,NMe₂],[R2215;H, OEt,CF₃,H,H,NMe₂],[R2216;H,OEt,H,H,H,NMe₂], [R2217;H, OEt,F,H,H,Pyrro],[R2218;H,OEt,Cl,H,H,Pyrro], [R2219;H,OEt,Br,H,H,Pyrro],[R2240;H,OEt,I,H,H,Pyrro], [R2241;H,OEt,Me,H,H,Pyrro],[R2242;H,OEt,CHF₂,H,H, Pyrro],[R2243;H,OEt,CF₃,H,H,Pyrro],[R2244;H,OEt,H,H, H,Pyrro],[R2245;H,Oi-Pr,Cl,H,H,Me],[R2246;H,Oi-Pr,Br, H,H,Me],[R2247;H,Oi-Pr,I,H,H,Me],[R2248;H,Oi-Pr,Me, H,H,Me],[R2249;H,Oi-Pr,CHF₂,H,H,Me],[R2250;H,Oi-Pr, CF₃,H,H,Me], [R2251;H,Oi-Pr,H,H,H,Me],[R2252;H,Oi-Pr,F,H,H,Et], [R2253;H,Oi-Pr,Cl,H,H,Et],[R2254;H,Oi-Pr,Br,H,H,Et], [R2255;H,Oi-Pr,I,H,H,Et],[R2256;H,Oi-Pr,Me,H,H,Et], [R2257;H,Oi-Pr,CHF₂,H,H,Et],[R2258;H,Oi-Pr,CF₃,H,H, Et],[R2259;H,Oi-Pr,H,H,H,Et],[R2260;H,Oi-Pr,F,H,H,Pr], [R2261;H,Oi-Pr,Cl,H,H,Pr],[R2262;H,Oi-Pr,Br,H,H,Pr], [R2263;H,Oi-Pr,I,H,H,Pr],[R2264;H,Oi-Pr,Me,H,H,Pr], [R2265;H,Oi-Pr,CHF₂,H,H Pr],[R2266;H,Oi-Pr,CF₃,H,H, Pr],[R2267;H,Oi-Pr,H,H,H,Pr],[R2268;H,Oi-Pr,F,H,H,Bu],

[R2269;H,Oi-Pr,Cl,H,H,Bu],[R2270;H,Oi-Pr,Br,H,H,Bu],
[R2271;H,Oi-Pr,I,H,H,Bu],[R2272;H,Oi-Pr,Me,H,H,Bu],
[R2273;H,Oi-Pr,CHF$_2$,H,H,Bu],[R2274;H,Oi-Pr,CF$_3$,H,H,Bu],[R2275;H,Oi-Pr,H,H,H,Bu],[R2276;H,Oi-Pr,F,H,H,c-Pr],[R2277;H,Oi-Pr,Cl,H,H,c-Pr],[R2278;H,Oi-Pr,Br,H,H,c-Pr],[R2279;H,Oi-Pr,I,H,H,c-Pr],[R2280;H,Oi-Pr,Me,H,H,c-Pr],[R2281;H,Oi-Pr,CHF$_2$,H,H,c-Pr],[R2282;H,Oi-Pr,CF$_3$,H,H,c-Pr],[R2283;H,Oi-Pr,H,H,H,c-Pr],[R2284;H,Oi-Pr,F,H,H,CH$_2$CF$_3$],[R2285;H,Oi-Pr,Cl,H,H,CH$_2$CF$_3$],[R2286;H,Oi-Pr,Br,H,H,CH$_2$CF$_3$],[R2287;H,Oi-Pr,I,H,H,CH$_2$CF$_3$],[R2288;H,Oi-Pr,Me,H,H,CH$_2$CF$_3$],[R2289;H,Oi-Pr,CCHF$_2$,H,H,CH$_2$CF$_3$],[R2290;H,Oi-Pr,CF$_3$,H,H,CH$_2$CF$_3$],[R2291;H,Oi-Pr,H,H,H,CH$_2$CF$_3$],[R2292;H,Oi-Pr,F,H,H,CH$_2$CHF$_2$],[R2293;H,Oi-Pr,Cl,H,H,CH$_2$CHF$_2$],[R2294;H,Oi-Pr,Br,fH,H,CH$_2$CHF$_2$],[R2295;H,Oi-Pr,I,H,H,CH$_2$CHF$_2$],[R2296;H,Oi-Pr,Me,H,H,CH$_2$CHF$_2$],[R2297;H,Oi-Pr,CHF$_2$,H,H,CH$_2$CHF$_2$],[R2298;H,Oi-Pr,CF$_3$,H,H,CH$_2$CHF$_2$],[R2299;H,Oi-Pr,H,H,H,CH$_2$CHF$_2$],[R2300;H,Oi-Pr,F,H,H,CF$_2$CH$_3$],[R2301;H,Oi-Pr,Cl,H,H,CF$_2$CH$_3$],[R2302;H,Oi-Pr,Br,H,H,CF$_2$CH$_3$],[R2303;H,Oi-Pr,I,H,H,CF$_2$CH$_3$],[R2304;H,Oi-Pr,Me,H,H,CF$_2$CH$_3$],[R2305;H,Oi-Pr,CHF$_2$,H,H,CF$_2$CH$_3$],[R2306;H,Oi-Pr,CCF$_3$,H,H,CF$_2$CH$_3$],[R2307;H,Oi-Pr,H,H,H,CF$_2$CH$_3$],[R2308;H,Oi-Pr,F,H,H,NMe$_2$],[R2309;H,Oi-Pr,Cl,H,H,NMe$_2$],[R2310;H,Oi-Pr,Br,H,H,NMe$_2$],[R2311;H,Oi-Pr,I,H,H,NMe$_2$],[R2312;H,Oi-Pr,DMe,H,H,NMe$_2$],[R2313;H,Oi-Pr,CHF$_2$,H,H,NMe$_2$],[R2314;H,Oi-Pr,CF$_3$,H,H,NMe$_2$],[R2315;H,Oi-Pr,H,H,H,NMe$_2$],[R2316;H,Oi-Pr,F,H,H,Pyrro],[R2317;H,Oi-Pr,Cl,H,H,Pyrro],[R2318;H,Oi-Pr,Br,H,H,Pyrro],[R2319;H,Oi-Pr,I,H,H,Pyrro],[R2320;H,Oi-Pr,Me,H,Pyrro],[R2321;H,Oi-Pr,CHF$_2$,H,H,Pyrro],[R2322;H,Oi-Pr,CF$_3$,H,H,Pyrro],[R2323;H,Oi-Pr,H,H,H,Pyrro],[R2324;H,OBu,Cl,H,H,Me],[R2325;H,OBu,Br,H,H,Me],[R2326;H,OBu,I,H,H,Me],[R2327;H,OBu,Me,H,H,Me],[R2328;H,OBu,CHF$_2$,H,H,Me],[R2329;H,OBu,CF$_3$,H,HH,Me],[R2330;H,OBu,H, H,H,Me],[R2331;H,OBu,F,H,H,Et],[R2332;H,OBu,Cl,H,H,Et],[R2333;H,OBu,Br,H,H,Et],[R2334;H,OBu,I,H,H,Et],[R2335;H,OBu,Me, H,H,Et],[R2336;H,OBu,CHF$_2$,H,H,Et],[R2337;H,OBu,CF$_3$,H,H,Et], [R2338;H,OBu,H,H,H,Et],[R2339;H,OBu,F,H,H,Pr],[R2340;H,OBu, Cl,H,H,Pr],[R2341;H,OBu,Br,H,H,Pr],[R2342;H,OBu,I,H,H,Pr],[R2343;H,OBu,Me,H,H,Pr],[R2344;H,OBu,CHF$_2$,H,H,Pr],[R2345;H,OBu,CF$_3$,H,H,Pr],[R2346;H,OBu,H,H,H,Pr],[R2347;H,OBu,F,H,H,Bu],[R2348;H,OBu,Cl,H,H,Bu],[R2349;H,OBu,Br,H,H,Bu],[R2350;H, OBu,I,H,H,Bu],[R2351;H,OBu,Me,H,H,Bu],[R2352;H,OBu,CHF$_2$,H,H,Bu],[R2353;H,OBu,CF$_3$,H,H,Bu],[R2354;H,OBu,H,H,H,Bu],[R2355; H,OBu,F,H,H,c-Pr],[R2356;H,OBu,Cl,H,H,c-Pr],[R2357;H,OBu,Br,H,H,c-Pr],[R2358;H,OBu,I,H,H,c-Pr],[R2359;H,OBu,Me,H,H,c-Pr],[R2360;H,OBu,CHF$_2$,H,H,c-Pr],[R2361;H,OBu,CF$_3$,H,H,c-Pr],[R2362;H,OBu,H,H,H,c-Pr],[R2363;H,OBu,BF,H,H,CH$_2$CF$_3$],[R2364;H,OBu,Cl,H,H,CH$_2$CF$_3$],[R2365;H,OBu,Br,H,H,CH$_2$CF$_3$],[R2366;H,OBu,I,H,H,CH$_2$CF$_3$],[R2367;H,OBu,Me,H,H,CH$_2$CF$_3$],[R2368;H,OBu,CHF$_2$,H,H,CH$_2$CF$_3$],[R2369;H,OBu,CF$_3$,H,H,CH$_2$CF$_3$],[R2370;H,OBu,H,H,H,CH$_2$CF$_3$],[R2371;H,OBu,F,H,H,CH$_2$CHF$_2$],[R2372;H,OBu,Cl,H,H,CH$_2$CHF$_2$],[R2373;H,OBu,Br,H,H,CH$_2$CHF$_2$],[R2374;H,OBu,I,H,H,CH$_2$CHF$_2$],[R2375;H, OBu,Me,H, H,CH$_2$CHF$_2$],[R2376;H,OBu,CHF$_2$,H,H,CH$_2$CHF$_2$],[R2377;H,OBu,CF$_3$,H, H,CH$_2$CHF$_2$],[R2378; H,OBu,H,H,H,CH$_2$CHF$_2$],[R2379;H,OBu,F,H,H,CF$_2$CH$_3$],[R2380;H,OBu,Cl,H,H,CF$_2$CH$_3$],[R2381;H,OBu,Br,H,H,CF$_2$CH$_3$],[R2382;H,OBu,I,H,H,CF$_2$CH$_3$],[R2383;H,OBu,Me,H,H,CF$_2$CH$_3$],[R2384;H,OBu,CHF$_2$,H,H,CF$_2$CH$_3$],[R2385;H,OBu,CF$_3$,H,H,CF$_2$CH$_3$],[R2386; H,OBu,H,H,H,CF$_2$CH$_3$],[R2387;H,OBu,F,H,H,NMe$_2$],[R2388;H,OBu,Cl,H,H,NMe$_2$],[R2389;H,OBu,Br,H,H,NMe$_2$],[R2390;H,OBu,I,H,H,NMe$_2$],[R2391;H,OBu,Me,H,H,NMe$_2$],[R2392;H,OBu,CHF$_2$,H,H,NMe$_2$],[R2393;H,OBu,CF$_3$,H,H,NMe$_2$],[R2394;H,OBu,H,H,H,NMe$_2$],[R2395;H,OBu,F,H,H,Pyrro],[R2396;H,OBu,Cl,H,H,Pyrro],[R2397;H,OBu,Br,H,H,Pyrro],[R2398;H,OBu,I,H,H,Pyrro],[R2399;H,OBu,Me,H,H,Pyrro],[R2400;H,OBu,CHF$_2$,H,H,Pyrro],[R2401;H,OBu,CF$_3$,H,H,Pyrro],[R2402;H,OBu,H,H,H,Pyrro],[R2403;H,Ot-Bu,Cl,H,H,Me],[R2404;H,Ot-Bu,Br,H,H,Me],[R2405;H,Ot-Bu,I,H,H,Me],[R2406;H,Ot-Bu,Me,H,H,Me],[R2407;H,Ot-Bu,CHF$_2$,H,H,Me],[R2408;H,Ot-Bu,CF$_3$,H,H,Me],[R2409;H,Ot-Bu,H,H,H,Me],[R2410;H,Ot-Bu,F,H,H,Et],[R2411;H,Ot-Bu,Cl,H,H,Et],[R2412;H,Ot-Bu,Br,H,H,Et],[R2413;H,Ot-Bu,I,H,H,Et],[R2414;H,Ot-Bu,Me,H,H,Et],[R2415;H,Ot-Bu,CHF$_2$,H,H,Et],[R2416;H,Ot-Bu,CF$_3$,H,H,Et],[R2417;H,Ot-Bu,H,H,H,Et],[R2418;H,Ot-Bu,F,H,H,Pr],[R2419;H,Ot-Bu,Cl,H,H,Pr],[R2420;H,Qt-Bu,Br,H,H,Pr],[R2421;H,Ot-Bu,I,H,H,Pr],[R2422;H,Ot-Bu,Me,H,H,Pr],[R2423;H,Ot-Bu,CHF$_2$,H,H,Pr],[R2424;H,Ot-Bu,CF$_3$,H,F,Pr],[R2425;H,Ot-Bu,H,H,H,Pr],[R2426;H,Ot-Bu,F,H,H,Bu],[R2427;H,Ot-Bu,Cl,H,H,Bu],[R2428;H,Ot-Bu,Br,H,H,Bu],[R2429;H,Ot-Bu,I,H,H,Bu],[R2430;H,Ot-Bu,Me,H,H,Bu],[R2431;H,Ot-Bu,CHF$_2$,H,H,Bu],[R2432;H,Ot-Bu,CF$_3$,H,H,Bu],[R2433;H,Ot-Bu,H,H,H,Bu],[R2434;H,Ot-Bu,F,H,H,c-Pr],[R2435;H,Ot-Bu,Cl,H,H,c-Pr],[R2436;H,Ot-Bu,Br,H,H,c-Pr],[R2437;H,Ot-Bu,I,H,H,c-Pr],[R2438;H,Ot-Bu,Me,H,H,c-Pr],[R2439;H,Ot-Bu,CHF$_2$,H,H,c-Pr],[R2440;H,Ot-Bu,CFs,H,H,c-Pr],[R2441;H,Ot-Bu,H,H,H,c-Pr],[R2442;H,Ot-Bu,F,H,H,CH$_2$CF$_3$],[R2443;H,Ot-Bu,Cl,H,H,CH$_2$CF$_3$],[R2444;H,Ot-Bu,Br,H,H,CH$_2$CF$_3$],[R2445;H,Ot-Bu,I,H,H,CH$_2$CF$_3$],[R2446;H,Ot-Bu,Me,H,H,CH$_2$CF$_3$],[R2447;H,Ot-Bu,CHF$_2$,H,H,CH$_2$CF$_3$],[R2448;H,Ot-Bu,CF$_3$,H,H,CH$_2$CF$_3$],[R2449;H,Ot-Bu,H,H,H,CH$_2$CF$_3$],[R2450;H,Ot-Bu,F,H,H,CH$_2$CHF$_2$],[R2451;H,Ot-Bu,Cl,H,H,CH$_2$CHF$_2$],[R2452;H,Ot-Bu,Br,H,H,CH$_2$CHF$_2$],[R2453;H,Ot-Bu,I,H,H,CH$_2$CHF$_2$],[R2454;H,Ot-Bu,Me,H,H,CH$_2$CHF$_2$],[R2455;H,Ot-Bu,CCHF$_2$,H,H,CH$_2$CHF$_2$],[R2456;H,Ot-Bu,CF$_3$,H,H,CH$_2$CHF$_2$],[R2457;H,Ot-Bu,H,H,H,CH$_2$CHF$_2$],[R2458;H,Ot-Bu,F,H,H,CF$_2$CH$_3$],[R2459;H,Ot-Bu,C,H,H,CF$_2$CH$_3$],[R2460;H,Ot-Bu,Br,H,H,CF$_2$CH$_3$],[R2461;H,Ot-Bu,I,H,H,CF$_2$CH$_3$],[R2462;H,Ot-Bu,Me,H,H,CF$_2$CH$_3$],[R2463;H,Ot-Bu,CHF$_2$,H,H,CF$_2$CH$_3$],[R2464;H,Ot-Bu,CF$_3$,H H,CF$_2$CH$_3$],[R2465;H,Ot-Bu,H,H,H,CF$_2$CH$_3$],[R2466;H,Ot-Bu,F,H,H,NMe$_2$],[R2467;H,Ot-Bu,Cl,H,H,NMe$_2$],[R2468;H,Ot-Bu,Br,H,H,NMe$_2$],[R2469;H,Ot-Bu,I,H,H,NMe$_2$],[R2470;H,Ot-Bu,Me,H,H,NMe$_2$],[R2471;H,Ot-Bu,CHF$_2$,H,H,NMe$_2$],[R2472;H,Ot-Bu,CF$_3$,H,H,NMe$_2$],[R2473;H,Ot-Bu,H,H,H,NMe$_2$],[R2474;H,Ot-Bu,F,H,H,Pyrro],[R2475;H,Ot-Bu,Cl,H,H,Pyrro],[R2476;H,Ot-Bu,Br,H,H,Pyrro],[R2477;H,Ot-Bu,I,H,H,Pyrro],[R2478;H,Ot-Bu,Me,H,H,Pyrro],[R2479;H,Ot-Bu,CHF$_2$,H,H,Pyrro],[R2480;H,Ot-Bu,CF$_3$,H,H,Pyrro],[R2481;H,Ot-Bu,H,H,H,Pyrro],[R2482;H,i-Pr,Cl,H,H,Me],[R2483;H,i-Pr,Br,H,H,Me],[R2484;H,i-Pr,I,H,H,Me],[R2485;H,i-Pr,Me,H,H,Me],[R2486;H,i-Pr,CHF$_2$,H,H,Me],[R2487;H,i-Pr,CF$_3$,H,H,Me],[R2488;H,i-Pr,H,H,H,Me],[R2489;H,i-Pr,F,H,H,Et],[R2490;H,i-Pr,Cl,H,H,Et],[R2491;H,i-Pr,Br,H,H,Et],[R2492;H,i-Pr,I,H,H,Et],[R2493;H,i-Pr,Me,H,H,Et],[R2494;H,i-Pr,CHF$_2$,H,H,Et],[R2495;H,i-Pr,CF$_3$,H,H,Et],[R2496;H,i-Pr,H,H,H,Et],[R2497;H,i-Pr,F,H,H,Pr],[R2498;H,i-Pr,Cl,H,H,Pr],[R2499;H,i-Pr,Br,H,H,Pr],[R2500;H,i-Pr,I,H,H,Pr],[R2501;H,i-Pr,Me,H,H,Pr],[R2502;H,i-Pr,CHF$_2$,H,H,Pr],[R2503;H,i-Pr,CF$_3$,H,H,Pr],[R2504;H,i-Pr,H,H,H,Pr],[R2505;H,i-Pr,F,H,H,Bu],[R2506;H,i-Pr,Cl,H,H,Bu],[R2507;H,i-Pr,Br,H,H,Bu],[R2508;H,i-Pr,I,H,H,Bu],[R2509;H,i-Pr,Me,H,H,Bu],[R2510;H,i-Pr,CHF$_2$,H,H,Bu],

[R2511;H,i-Pr,CF₃,H,H,Bu],[R2512;H,i-Pr,H,H,H,Bu],
[R2513;H,i-Pr,F,H,H,c-Pr],[R2514;H,i-Pr,Cl,H,H,c-Pr],
[R2515;H,i-Pr,Br,H,H,c-Pr],[R2516;H,i-Pr,I,H,H,c-Pr],
[R2517;H,i-Pr,Me,H,H,c-Pr],[R2518;H,i-Pr,CHF₂,H,H,c-Pr],[R2519;H,i-Pr,CF₃,H,H,c-Pr],[R2520;H,i-Pr,H,H,H,c-Pr],[R2521;H,i-Pr,F,H,H,CH₂CF₃],[R2522;H,i-Pr,Cl,H,H,CH₂CF₃],[R2523;H,i-Pr,Br,H,H,CH₂CF₃],[R2524;H,i-Pr,I,H,H,CH₂CF₃],[R2525;H,i-Pr,Me,H,H,CH₂CF₃],[R2526;H,i-Pr,CHF₂,H,H,CH₂CF₃],[R2527;H,i-Pr,CF₃,H,H,CH₂CF₃],
[R2528;H,i-Pr,H,H,H,CH₂CF₃],[R2529;H,i-Pr,F,H,H,CH₂CHF₂],[R2530;H,i-Pr,Cl,H,H,CH₂CHF₂],[R2531;H,i-Pr,Br,H,H,CH₂CHF₂],[R2532;H,i-Pr,I,H,H,CH₂CHF₂],
[R2533;H,i-Pr,Me,H,H,CH₂CHF₂],[R2534;H,i-Pr,CHF₂,H,H,CH₂CHF₂],[R2535;H,i-Pr,CF₃,H,H,CH₂CHF₂],[R2536;H,i-Pr,HH,H,CH₂CHF₂],[R2537;H,i-Pr,F,H,H,CF₂CH₃],
[R2538;H,i-Pr,Cl,H,H,CF₂CH₃],[R2539;H,i-Pr,Br,H,H,CF₂CH₃],[R2540;H,i-Pr,I,H,H,CF₂CH₃],[R2541;H,i-Pr,Me,H,H,CF₂CH₃],[R2542;H,i-Pr,CHF₂,H,H,CF₂CH₃],[R2543;H,i-Pr,CF₃,H,H,CF₂CH₃],[R2544;H,i-Pr,H,H,H,CF₂CH₃],
[R2545;H,i-Pr,F,H,H,NMe₂],[R2546;H,i-Pr,Cl,H,H,NMe₂],
[R2547;H,i-Pr,Br,H,H,NMe₂],[R2548;H,i-Pr,I,H,H,NMe₂],
[R2549;H,i-Pr,Me,H,H,NMe₂],[R2550;H,i-Pr,CHF₂,H,H,NMe₂],
[R2551;H,i-Pr,CF₃,H,H,NMe₂],[R2552;H,i-Pr,H,H,H,NMe₂],[R2553;H,i-Pr,F,H,H,Pyrro],[R2554;H,i-Pr,Cl,H,H,Pyrro],[R2555;H,i-Pr,Br,H,H,Pyrro],[R2556;H,i-Pr,I,H,H,Pyrro],[R2557;H,i-Pr,Me,H,H,Pyrro],[R2558;H,i-Pr,CHF₂,H,H,Pyrro],[R2559;H,i-Pr,CF₃,H,H,Pyrro],[R2560;H,i-Pr,H,H,H,Pyrro],[R2561;H,OCH₂CHCH₂,Cl,H,H,Me],
[R2562;H,OCH₂CHCH₂,Br,H,H,Me],[R2563;H,OCH₂CHCH₂,I,H,H,Me],[R2564;H,OCH₂CHCH₂,Me,H,H,Me],[R2565;H,OCH₂CHCH₂,CHF₂,H,H,Me],[R2566;H,OCH₂CHCH₂,CF₃,H,H,Me],[R2567;H,OCH₂CHCH₂,H,H,H,Me],[R2568;H,OCH₂CHCH₂,F,H,H,Et],[R2569;H,OCH₂CHCH₂,Cl,H,H,Et],[R2570;H,OCH₂CHCH₂,Br,H,H,Et],[R2571;H,OCH₂CHCH₂,I,H,H,Et],[R2572;H,OCH₂CHCH₂,Me,H,H,Et],[R2573;H,OCH₂CHCH₂,CHF₂,H,H,Et],[R2574;H,OCH₂CHCH₂,CF₃,H,H,Et],[R2575;H,OCH₂CHCH₂,H,H,H,Et],[R2576;H,OCH₂CHCH₂,F,H,H,Pr],[R2577;H,OCH₂CHCH₂,Cl,H,H,Pr],[R2578;H,OCH₂CHCH₂,Br,H,H,Pr],[R2579;H,OCH₂CHCH₂,I,H,H,Pr],[R2580;H,OCH₂CHCH₂,Me,H,H,Pr],[R2581;H,OCH₂CHCH₂,CHF₂,H,H,Pr],[R2582;H,OCH₂CHCH₂,CF₃,H,H,Pr],[R2583;H,OCH₂CHCH₂,H,H,H,Pr],[R2584;H,OCH₂CHCH₂,F,H,H,Bu],[R2585;H,OCH₂CHCH₂,Cl,H,H,Bu],[R2586;H,OCH₂CHCH₂,Br,H,H,Bu],[R2587;H,OCH₂CHCH₂,I,H,H,Bu],[R2588;H,OCH₂CH CH₂,Me,H,H,Bu],[R2589;H,OCH₂CHCH₂,CHF₂,H,H,Bu],[R2590;H,OCH₂CHCH₂,CF₃,H,H,Bu],[R2591;H,OCH₂CHCH₂,H,H,H,Bu],[R2592;H,OCH₂CHCH₂,F,H,H,c-Pr],[R2593;H,OCH₂CHCH₂,Cl,H,H,c-Pr],[R2594;H,OCH₂CHCH₂,Br,H,H,c-Pr],[R2595;H,OCH₂CHCH₂,I,H,H,c-Pr],[R2596;H,OCH₂CHCH₂,Me,H,H,c-Pr],[R2597;H,OCH₂CHCH₂,CHF₂,H,H,c-Pr],[R2598;H,OCH₂CHCH₂,CF₃,H,H,c-Pr],
[R2599;H,OCH₂CHCH₂,H,H,H,c-Pr],[R2600;H,OCH₂CHCH₂,F,H,H,CH₂CF₃],[R2601;H,OCH₂CHCH₂,Cl,H,H,CH₂CF₃],[R2602;H,OCH₂CHCH₂,Br,H,H,CH₂CF₃],
[R2603;H,OCH₂CHCH₂,I,H,H,CH₂CF₃],[R2604;H,OCH₂CHCH₂,Me,H,H,CH₂CF₃],[R2605;H,OCH₂CHCH₂,CHF₂,H,H,CH₂CF₃],[R2606;H,OCH₂CHCH₂,CF₃,H,H,CH₂CF₃],[R2607;H,OCH₂CHCH₂,H,H,H,CH₂CF₃],
[R2608;H,OCH₂CHCH₂,F,H,H,CH₂CHF₂],[R2609;H,OCH₂CHCH₂,Cl,H,H,CH₂CHF₂],[R2610;H,OCH₂CHCH₂,Br,H,H,CH₂CHF₂],[R2611;H,OCH₂CHCH₂,I,H,H,CH₂CHF₂],[R2612;H,OCH₂CHCH₂,Me,H,H,CH₂CHF₂],[R2613;H,OCH₂CHCH₂,CHF₂,H,H,CH₂CHF₂],[R2614;H,OCH₂CHCH₂,CF₃,H,H,CH₂CHF₂],[R2615;H,OCH₂CHCH₂,H,H,H,CH₂CHF₂],[R2616;H,OCH₂CHCH₂,F,H,H,CF₂CH₃],[R2617;H,OCH₂CHCH₂,Cl,H,H,CF₂CH₃],[R2618;H,OCH₂CHCH₂,Br,H,H,CF₂CH₃],
[R2619;H,OCH₂CHCH₂,I,H,H,CF₂CH₃],[R2620;H,OCH₂CHCH₂,Me,H,H,CF₂CH₃],[R2621;H,OCH₂CHCH₂,CHF₂,H,H,CF₂CH₃],[R2622;H,OCH₂CHCH₂,CF₃,H,H,CF₂CH₃],[R2623;H,OCH₂CHCH₂,H,H,H,CF₂CH₃],
[R2624;H,OCH₂CHCH₂,F,H,H,NMe₂],[R2625;H,OCH₂CHCH₂,Cl,H,H,NMe₂],[R2626;H,OCH₂CHCH₂,Br,H,H,NMe₂],[R2627;H,OCH₂CHCH₂,I,H,H,NMe₂],
[R2628;H,OCH₂CHCH₂,Me,H,H,NMe₂],[R2629;H,OCH₂CHCH₂,CHF₂,H,H,NMe₂],[R2630;H,OCH₂CHCH₂,CF₃,H,H,NMe₂],[R2631;H,OCH₂CHCH₂,H,H,H,NMe₂],
[R2632;H,OCH₂CHCH₂,F,H,H,Pyrro],[R2633;H,OCH₂CHCH₂,Cl,H,H,Pyrro],[R2634;H,OCH₂CHCH₂,Br,H,H,Pyrro],[R2635;H,OCH₂CHCH₂,I,H,H,Pyrro],[R2636;H,OCH₂CHCH₂,Me,H,H,Pyrro],[R2637;H,OCH₂CHCH₂,CHF₂,H,H,Pyrro],[R2638;H,OCH₂CHCH₂,CF₃,H,H,Pyrro],[R2639;H,OCH₂CHCH₂,H,H,H,Pyrro],[R2640;H,OCH₂CCH,Cl,H,H,Me],[R2641;H,OCH₂CCH,Br,H,H,Me],
[R2642;H,OCH₂CCH,I,H,H,Me],[R2643;H,OCH₂CCH,Me,H,H,Me],[R2644;H,OCH₂CCH,CHF₂,H,H,Me],
[R2645;H,OCH₂CCH,CF₃,H,H,Me],[R2646;H,OCH₂CCH,H,H,H,Me],[R2647;H,OCH₂CCH,F,H,H,Et],
[R2648;H,OCH₂CCH,Cl,H,H,Et],[R2649;H,OCH₂CCH,Br,H,H,Et],[R2650;H,OCH₂CCH,I,H,H,Et],[R2651;H,OCH₂CCH,Me,H,H,Et],[R2652;H,OCH₂CCH,CHF₂,H,H,Et],[R2653;H,OCH₂CCH,CF₃,H,H,Et],[R2654;H,OCH₂CCH,H,H,H,Et],[R2655;H,OCH₂CCH,F,H,H,Pr],
[R2656;H,OCH₂CCH,Cl,H,H,Pr],[R2657;H,OCH₂CCH,Br,H,H,Pr],[R2658;H,OCH₂CCH,I,H,H,Pr],[R2659;H,OCH₂CCH,Me,H,H,Pr],[R2660;H,OCH₂CCH,CHF₂,H,H,Pr],[R2661;H,OCH₂CCH,CF₃,H,H,Pr],[R2662;H,OCH₂CCH,H,H,H,Pr],[R2663;H,OCH₂CCH,F,H,H,Bu],
[R2664;H,OCH₂CCH,Cl,H,H,Bu],[R2665;H,OCH₂CCH,Br,H,H,Bu],[R2666;H,OCH₂CCH,I,H,H,Bu],[R2667;H,OCH₂CCH,Me,H,H,Bu],[R2668;H,OCH₂CCH,CHF₂,H,H,Bu],[R2669;H,OCH₂CCH,CF₃,H,H,Bu],[R2670;H,OCH₂CCH,H,H,H,Bu],[R2671;H,OCH₂CCH,F,H,H,c-Pr],
[R2672;H,OCH₂CCH,Cl,H,H,c-Pr],[R2673;H,OCH₂CCH,Br,H,H,c-Pr],[R2674;H,OCH₂CCH,I,H,H,c-Pr],[R2675;H,OCH₂CCH,Me,H,H,c-Pr],[R2676;H,OCH₂CCH,CHF₂,H,H,c-Pr],[R2677;H,OCH₂CCH,CF₃,H,H,c-Pr],[R2678;H,OCH₂CCH,H,H,H,c-Pr],[R2679;H,OCH₂CCH,F,H,H,CH₂CF₃],[R2680;H,OCH₂CCH,Cl,H,H,CH₂CF₃],[R2681;H,OCH₂CCH,Br,H,H,CH₂CF₃],[R2682;H,OCH₂CCH,I,H,H,CH₂CF₃],[R2683;H,OCH₂CCH,Me,H,H,CH₂CF₃],
[R2684;H,OCH₂CCH,CHF₂,H,H,CH₂CF₃],[R2685;H,OCH₂CCH,CF₃,H,H,CH₂CF₃],[R2686;H,OCH₂CCH,H,H,H,CH₂CF₃],[R2687;H,OCH₂CCH,F,H,H,CH₂CHF₂],
[R2688;H,OCH₂CCH,Cl,H,H,CH₂CHF₂],[R2689;H,OCH₂CCH,Br,H,H,CH₂CHF₂],[R2690;H,OCH₂CCH,I,H,H,CH₂CHF₂],[R2691;H,OCH₂CCH,Me,H,H,CH₂CHF₂],
[R2692;H,OCH₂CCH,CHF₂,H,H,CH₂CHF₂],[R2693;H,OCH₂CCH,CF₃,H,H,CH₂CHF₂],[R2694;H,OCH₂CCH,H,H,H,CH₂CHF₂],[R2695;H,OCH₂CCH,F,H,H,CF₂CH₃],
[R2696;H,OCH₂CCH,C,H,H,CF₂CH₃],[R2697;H,OCH₂CCH,Br,H,H,CF₂CH₃],[R2698;H,OCH₂CCH,I,H,H,CF₂CH₃],[R2699;H,OCH₂CCH,Me,H,H,CF₂CH₃],[R2700;H,OCH₂CCH,CHF₂,H,H,CF₂CH₃],
[R2701;H,OCH₂CCH,CF₃,H,H,CF₂CH₃],[R2702;H,OCH₂CCH,H,H,H,CF₂CH₃],[R2703;H,OCH₂CCH,F,H,H,NMe₂],[R2704;H,OCH₂CCH,Cl,H,H,NMe₂],[R2705;H,OCH₂CCH,Br,H,H,NMe₂],[R2706;H,OCH₂CCH,I,H,H,NMe₂],[R2707;H,OCH₂CCH,Me,H,H,NMe₂],[R2708;H,OCH₂CCH,CHF₂,H,H,NMe₂],[R2709;H,OCH₂CCH,CF₃,H,H,NMe₂],[R2710;H,OCH₂CCH,H,H,H,NMe₂],[R2711;

H,OCH₂CCH,F,H,H,Pyrro],[R2712;H,OCH₂CCH,Cl,H,H,Pyrro],[R2713;H,OCH₂CCH,Br,H,H,Pyrro],[R2714;H,OCH₂CCH,I,H,H,Pyrro],[R2715;H,OCH₂CCH,Me,H,H,Pyrro],[R2716;H,OCH₂CCH,CHF₂,H,H,Pyrro],[R2717;H,OCH₂CCH,CF₃,H,H,Pyrro],[R2718;H,OCH₂CCH,H,H,H,Pyrro],[R2719;H,OPh,Cl,H,H,Me],[R2720;H,OPh,Br,H,H,Me],[R2721;H,OPh,I,H,H,Me],[R2722;H,OPh,Me,H,H,Me],[R2723;H,OPh,CHF₂,H,H,Me],[R2724;H,OPh,CF₃,H,H,Me],[R2725;H,OPh,H,H,H,Me],[R2726;H,OPh,F,H,H,Et],[R2727;H,OPh,Cl,H,H,Et],[R2728;H, OPh,Br,H,H,Et],[R2729;H,OPh,I,H,H,Et],[R2730;H,OPh,Me,H,H,Et],[R2731;H,OPh,CHF₂,H,H,Et],[R2732;H,OPh,CF₃,H,H,Et],[R2733;H,OPh,H,H,H,Et],[R2734;H,OPh,F,H,H,Pr],[R2735;H,OPh,Cl,H, H,Pr],[R2736;H,OPh,Br,H,H,Pr],[R2737;H,OPh,I,H,H,Pr],[R2738;H,OPh,Me,H,H,Pr],[R2739;H,OPh,CHF₂,H,H,Pr],[R2740;H,OPh,CF₃,H,H,Pr],[R2741;H,OPh,H,H,H,Pr],[R2742;H,OPh,F,H,H,Bu],[R2743;H,OPh,Cl,H,H,Bu],[R2744;H,OPh,Br,H,H,Bu],[R2745;H,OPh,I,H,H,Bu],[R2746;H,OPh,Me,H,H,Bu],[R2747;H,OPh,CHF₂,H,H,Bu], [R2748;H,OPh,CF₃,H,H,Bu],[R2749;H,OPh,H,H,H,Bu],[R2750;H,OPh,F,H,H,c-Pr],[R2751;H,OPh,Cl,H,H,c-Pr],[R2752;H,OPh,Br,H,H,c-Pr],[R2753;H,OPh,I,H,H,c-Pr],[R2754;H,OPh,Me,H,H,c-Pr],[R2755;H,OPh,CHF₂,H,H,c-Pr],[R2756;H,OPh,CF₃,H,H,c-Pr],[R2757;H,OPh,H,H,H,c-Pr],[R2758;H,OPh,F,H,H,CH₂CF₃],[R2759;H,OPh,Cl,H,H,CH₂CF₃],[R2760;H,OPh,Br,H,H,CH₂CF₃],[R2761;H,OPh,I,H,H,CH₂CF₃],[R2762;H,OPh,Ne,H,H,CH₂CF₃],[R2763;H,OPh,CHF₂,H,H,CH₂CF₃],[R2764;H,OPh,CF₃,H,H,CH₂CF₃],[R2765;H,OPh,H,H,H,CH₂CF₃],[R2766;H,OPh,F,H,H,CH₂CHF₂],[R2767;H,OPh,Cl,H,H,CH₂CHF₂],[R2768;H,OPh,Br,H,H,CH₂CHF₂],[R2769;H,OPh,I,H,H,CH₂CHF₂],[R2770;H,OPh,Me,H, H,CH₂CHF₂],[R2771;H,OPh,CHF₂,H,H,CH₂CHF₂],[R2772;H,OPh,CF₃,H, H,CH₂CHF₂],[R2773;H,OPh,H,H,H,CH₂CHF₂],[R2774;H,OPh,F,H,H,CF₂CH₃],[R2775;H,OPh,Cl,H,H,CF₂CH₃],[R2776;H,OPh,Br,H,H,CF₂CH₃],[R2777;H,OPh,I,H,H,CF₂CH₃],[R2778;H,OPh,[Me,H,H,CF₂CH₃],[R2779;H,OPh,CHF₂,H,H,CF₂CH₃],[R2710;H,OPh,CF₃,H,H,CF₂CH₃],[R2711; H,OPh,H,H,H,CF₂CH₃],[R2712;H,OPh,F,H,H,NMe₂],[R2713;H,OPh,Cl,H,H,NMe₂],[R2714;H,OPh,Br,H,H,NMe₂],[R2715;H,OPh,I,H,H,NMe₂],[R2716;H,OPh,Me,H,H,NMe₂],[R2717;H,OPh,CHF₂,H,H,NMe₂],[R2788;H,OPh,CF₃,H,H,NMe₂],[R2719;H,OPh,H,H,H,NMe₂],[R2790;H,OPh,F,H,H,Pyrro],[R2791;H,OPh,Cl,H,H,Pyrro],[R2792;H,OPh,Br, H,H,Pyrro],[R2793;H,OPh,I,H,H,Pyrro],[R2794;H,OPh,Me,H,H,Pyrro],[R2795;H,OPh,CHF₂,H,H,Pyrro],[R2796;H,OPh,CF₃,H,H,Pyrro],[R2797;H,OPh,H,H,H,Pyrro],[R2798;H,OCH₂Ph,Cl,H,H,Me],[R2799;H,OCH₂Ph,Br,H,H,Me],[R2800;H,OCH₂Ph,I,H,H,Me],[R2801;H, OCH₂Ph,Me,H,H,Me],[R2802;H,OCH₂Ph,CHF₂,H,H,Me],[R2803;H,OCH₂Ph,CF₃,H,H,Me],[R2804;H,OCH₂Ph,H,H,H,Me],[R2805;H,OCH₂Ph,F,H,H,Et],[R2806;H,OCH₂Ph,Cl,H,H,Et],[R2807;H,OCH₂Ph,Br,H,H,Et],[R2808;H,OCH₂Ph,I,H,H,Et],[R2809;H,OCH₂Ph,Me,H,H,Et],[R2810;H,OCH₂Ph,CHF₂,H,H,Et],[R2811;H,OCH₂Ph,CCF₃,H,H,Et],[R2812;H,OCH₂₂Ph,H,H,H,Et],[R2813;H,OCH₂Ph,F,H,H,Pr],[R2814;H,OCH₂Ph,Cl,H,H,Pr],[R2815;H,OCH₂Ph,Br,H,H,Pr],[R2816;H,OCH₂Ph,I,H, H,Pr],[R2817;H,OCH₂Ph,Me,H,H,Pr],[R2818;H,OCH₂Ph,CHF₂,H,H,Pr],[R2819;H,OCH₂Ph,CF₃,H,H,Pr],[R2820;H,OCH₂Ph,H,H,H,Pr],[R2821;H,OCH₂Ph,F,H,H,Bu],[R2822;H,OCH₂Ph,Cl,H,H,Bu],[R2823;H,OCH₂Ph,Br,H,H,Bu],[R2824;H,OCH₂Ph,I,H,H,Bu],[R2825;H,OCH₂Ph,Me,H,H,Bu],[R2826;H,OCH₂Ph,CHF₂,H,H,Bu],[R2827;H,OCH₂Ph,CF₃,H,H,Bu],[R2828;H,OCH₂Ph,H,H,H,Bu],[R2829;H,OCH₂Ph,F,H,H,c-Pr],[R2830;H,OCH₂Ph,Cl,H,H,c-Pr],[R2831;H,OCH₂Ph,Br,H,H,c-Pr],[R2832;H,OCH₂Ph,I,H,H,c-Pr],[R2833;H,OCH₂Ph,Me,H,H,c-Pr],[R2834;H,OCH₂Ph,CHF₂,H,H,c-Pr],[R2835;H,OCH₂Ph,CF₃,H,H,c-Pr],[R2836;H,OCH₂Ph,H,H,H,c-Pr],[R2837;H,OCH₂Ph,F,H,H,CH₂CF₃],[R2838; H,OCH₂Ph,Cl,I,H,CH₂CF₃],[R2839;H,OCH₂Ph,Br,H,H,CH₂CF₃],[R2840;H,OCH₂Ph,I,H,H,CH₂CF₃],[R2841;H,OCH₂Ph,Me,H,H,CH₂CF₃],[R2842;H,OCH₂Ph,CHF₂,H,H,CH₂CF₃],[R2843;I,OCH₂Ph,CF₃,H,H,CH₂CF₃],[R2844;H,OCH₂Ph,H,H,H,CH₂CF₃],[R2845;H,OCH₂Ph,F,H,H,CH₂CHF₂],[R2846;H,OCH₂Ph,Cl,H, H,CH₂CHF₂],[R2847;H,OCH₂Ph,Br,H,H,CH₂CHF₂],[R2848;H,OCH₂Ph,I, H,H,CH₂CHF₂],[R2849;H,OCH₂Ph,Me,H,H,CH₂CHF₂],[R2850;H,OCH₂Ph, CHF₂,H,H,CH₂CHF₂],[R2851;H,OCHZPh,CF₃,H,H,CH₂CHF₂],[R2852;H,OCH₂Ph,H,H,H,CH₂CHF₂],[R2853;H,OCH₂Ph,F,H,H,CF₂CH₃],[R2854;H,OCH₂Ph,Cl,H,H,CF₂CH₃],[R2855;H,OCH₂Ph,Br,H,H,CF₂CH₃],[R2856;H,OCH₂Ph,I,H,H,CF₂CH₃],[R2857;H,OCH₂Ph,Me,H,H,CF₂CH₃],[R2858;H,OCH₂Ph,CHF₂,H,H,CF₂CH₃],[R2859;H,OCH₂Ph,CF₃,H,H,CF₂CH₃],[R2860;H,OCH₂Ph,H,H,H,CF₂CH₃],[R2861;H,OCH₂Ph,F,H,H,NMe₂],[R2862;H,OCH₂Ph,Cl,H,H,NMe₂],[R2863;H,OCH₂Ph,Br,H,H,NMe₂],[R2864;H,OCH₂Ph,I,H,H,NMe₂],[R2865;H,OCH₂Ph,Me,H,H,NMe₂],[R2866;H,OCH₂Ph,CHF₂,H,H,NMe₂],[R2867;H,OCH₂Ph,CF₃,H,H,NMe₂],[R2868;H,OCH₂Ph,H,H,H,NMe₂],[R2869;H,OCH₂Ph,F,H,FH,Pyrro],[R2870;H,OCH₂Ph,Cl,H,H,Pyrro],[R2871;H,OCH₂Ph,Br,H,H,Pyrro],[R2872;H,OCH₂Ph,I,H,H,Pyrro],[R2873;H,OCH₂Ph,Me,H,H,Pyrro],[R2874;H,OCH₂Ph,CHF₂,H,H,Pyrro],[R2875;H,OCH₂Ph,CF₂,H,H,Pyrro],[R2876;H,OCH₂Ph,H,H,H,Pyrro],[R2877;H,OCH₂(2-Cl-Ph),Cl,H,H,Me],[R2878;H,OCH₂(2-Cl-Ph),Br,H,H,Me],[R2879;H,OCH₂(2-Cl-Ph),I,H,H,Me],[R2880;H,OCH₂ (2-Cl-Ph),Me,H,H,Me],[R2881;H,OCH₂(2-Cl-Ph),CHF₂,H,H,Me,[R2882;H,OCH₂(2-Cl-Ph),CF₃,H,H,Me],[R2883;H,OCH₂(2-Cl-Ph),H,H,H,Me],[R2884;H,OCH₂(2-Cl-Ph),F,H,H,Et],[R2885;H,OCH₂(2-Cl-Ph),Cl,H,H,Et],[R2886;H,OCH₂(2-Cl-Ph),Br,H,H,Et],[R2887;H,OCH₂(2-Cl-Ph),I,H,H,Et],[R2888;H,OCH₂(2-Cl-Ph),Me,H,H,Et],[R2889;H,OCH₂(2-Cl-Ph),CHF₂,H,H,Et],[R2890;H,OCH₂(2-Cl-Ph),CF₃,H,H,Et],[R2891;H,OCH₂(2-Cl-Ph),H,H,H,Et],[R2892;H,OCH₂(2-Cl-Ph),F,H,H,Pr],[R2893;H,OCH₂(2-Cl-Ph),Cl,H,H,Pr],[R2894;H,OCH₂(2-Cl-Ph),Br,H,H,Pr],[R2895;H,OCH₂(2-Cl-Ph),I,H,H,Pr],[R2896;H,OCH₂(2-Cl-Ph),Me,H,H,Pr],[R2897;H,OCH₂(2-Cl-Ph),CHF₂,H,H,Pr],[R2898;H,OCH₂(2-Cl-Ph),CF₃,H,H,Pr],[R2899;H,OCH₂(2-Cl-Ph),H,H,H,Pr],[R2900;H,OCH₂(2-Cl-Ph),F,H,H,Bu],[R2901;H,OCH₂(2-Cl-Ph),Cl,H,H,Bu],[R2902;H,OCH₂(2-Cl-Ph),Br,H,H,Bu],[R2903;H,OCH₂(2-Cl-Ph),I,H,H,Bu],[R2904;H,OCH₂(2-Cl-Ph),Me,H,H,Bu],[R2905;H,OCH₂(2-Cl-Ph),CHF₂,H,H,Bu],[R2906;H,OCH₂(2-Cl-Ph),CF₃,H,H,Bu],[R2907;H,OCH₂(2-Cl-Ph),H,H,H,Bu],[R2908;H,OCH₂(2-Cl-Ph),F,H,H,c-Pr],[R2909;H,OCH₂(2-Cl-Ph),Cl,H,H,c-Pr],[R2910;H,OCH₂(2-Cl-Ph),Br,H,H,c-Pr],[R2911;H,OCH₂(2-Cl-Ph),I,H,H,c-Pr],[R2912;H,OCH₂(2-Cl-Ph),Me,H,H,c-Pr],[R2913;H,OCH₂(2-Cl-Ph),CHF₂,H,H,c-Pr],[R2914;H,OCH₂(2-Cl-Ph),CF₃,H,H,c-Pr],[R2915;H,OCH₂(2-Cl-Ph),H,H,H,c-Pr],[R2916;H,OCH₂(2-Cl-Ph),F,H,H,CH₂CF₃],[R2917;H,OCH₂(2-Cl-Ph),Cl,H,H,CH₂CF₃],[R2918;H,OCH₂(2-Cl-Ph),Br,H,H,CH₂CF₃],[R2919;H,OCH₂(2-Cl-Ph),I,H,H,CH₂CF₃],[R2920;H,OCH₂(2-Cl-Ph),Me,H,H,CH₂CF₃],[R2921;H,OCH₂(2-Cl-Ph),CHF₂,H,H,CH₂CF₃],[R2922;H,OCH₂ (2-Cl-Ph),CF₃,H,H,CH₂CF₃],[R2923;H,OCH₂(2-Cl-Ph),H,H,H,CH₂CF₃],[R2924;H,OCH₂(2-Cl-Ph),F,H,H,CH₂CHF₂],[R2925;H,OCH₂(2-Cl-Ph),Cl,H,H,CH₂CHF₂],[R2926;H,OCH₂(2-Cl-Ph),Br,H,H,CH₂CHF₂],[R2927;H,OCH₂(2-Cl-Ph),I,H,H,CH₂CHF₂],[R2928;H,OCH₂(2-Cl-Ph),Me,H,H,CH₂CHF₂],

[R2929;H,OCH₂(2-Cl-Ph),CHF₂,H,H,CH₂CHF₂],[R2930; H,OCH₂(2-Cl-Ph),CF₃,H,H,CHCHF₂],[R2931;H,OCH₂ (2-Cl-Ph),H,H,H,CH₂CHF₂],[R2932;H,OCH₂(2-Cl-Ph),F, H,H,CF₂CH₃],[R2933;H,OCH₂(2-Cl-Ph),Cl,H,H,CF₂CH₃], [R2934;H,OCH₂(2-Cl-Ph),Br,H,H,CF₂CH₃],[R2935;H, OCH₂(2-Cl-Ph),I,H,H,CF₂CH₃],[R2936;H,OCH₂ (2-Cl-Ph),Me,H,H,CF₂CH₃],[R2937;H,OCH₂ (2-Cl-Ph),CHF₂,H, H,CF₂CH₃],[R2938;H,OCH₂ (2-Cl-Ph),CF₃,H,H,CF₂CH₃], [R2939;H,OCH₂ (2-Cl-Ph),H,H,H,CF₂CH₃],[R2940;H, OCH₂(2-Cl-Ph),F,H,H,NMe₂],[R2941;H,OCH₂(2-Cl-Ph), Cl,H,H,NMe₂],[R2942;H,OCH₂(2-Cl-Ph),Br,H,H,NMe₂], [R2943;H,OCH₂(2-Cl-Ph),I,H,H,NMe₂],[R2944;H,OCH₂ (2-Cl-Ph),Me,H,H,NMe₂],[R2945;H,OCH₂(2-Cl-Ph), CHF₂,H,H,NMe₂],[R2946;H,OCH₂(2-Cl-Ph),CF₃,H,H, NMe₂],[R2947;H,OCH₂(2-Cl-Ph),H,H,H,NMe₂],[R2948; H,OCH₂(2-Cl-Ph),F,H,H,Pyrro],[R2949;H,OCH₂(2-Cl-Ph), Cl,H,H,Pyrro],[R2950;H,OCH₂(2-Cl-Ph),Br,H,H,Pyrro], [R2951;H,OCH₂(2-Cl-Ph),I,H,H,Pyrro],[R2952;H,OCH₂ (2-Cl-Ph),Me,H,H,Pyrro],[R2953;H,OCH₂(2-Cl-Ph),CHF₂, H,H,Pyrro],[R2954;H,OCH₂(2-Cl-Ph),CF₃,H,H,Pyrro], [R2955;H,OCH₂(2-Cl-Ph),H,H,H,Pyrro],[R2956;H,OCH₂ (3-Cl-Ph),Cl,H,H,Me],[R2957;H,OCH₂(3-Cl-Ph),Br,H,H, Me],[R2958;H,OCH₂(3-Cl-Ph),I,H,H,Me],[R2959;H,OCH₂ (3-Cl-Ph),Me,H,H,Me],[R2960;H,OCH₂(3-Cl-Ph),CHF₂,H, H,Me], [R2961;H,OCH₂(3-Cl-Ph),CF₃,H,H,Me],[R2962;H, OCH₂(3-Cl-Ph),H,H,H,Me],[R2963;H,OCH₂(3-Cl-Ph),F,H, H,Et],[R2964;H,OCH₂(3-Cl-Ph),Cl,H,H,Et],[R2965;H, OCH₂(3-Cl-Ph),Br,H,H,Et],[R2966;H,OCH₂(3-Cl-Ph),I,H, H,Et],[R2967;H,OCH₂(3-Cl-Ph),Me,H,H,Et],[R2968;H, OCH₂(3-Cl-Ph),CHF₂,H,H,Et],[R2969;H,OCH₂(3-Cl-Ph), CF₃,H,H,Et],[R2970;H,OCH₂(3-Cl-Ph),H,H,H,Et],[R2971; H,OCH₂(3-Cl-Ph),F,H,H,Pr],[R2972;H,OCH₂(3-Cl-Ph),Cl, H,H,Pr],[R2973;H,OCH₂(3-Cl-Ph),Br,H,H,Pr],[R2974;H, OCH₂(3-Cl-Ph),I,H,H,Pr],[R2975;H,OCH₂(3-Cl-Ph),Me,H, H,Pr],[R2976;H,OCH₂(3-Cl-Ph),CHF₂,H,H,Pr],[R2977;H, OCH₂(3-Cl-Ph),CF₃,H,H,Pr],[R2978;H,OCH₂(3-Cl-Ph),H, H,H,Pr],[R2979;H,OCH₂(3-Cl-Ph),F,H,H,Bu],[R2910;H, OCH₂(3-Cl-Ph),Cl,H,H,Bu],[R2911;H,OCH₂(3-Cl-Ph),Br, H,H,Bu],[R2912;H,OCH₂(3-Cl-Ph),I,H,H,Bu],[R2913;H, OCH₂(3-Cl-Ph),Me,H,H,Bu],[R2914;H,OCH₂(3-Cl-Ph), CHF₂,H,H,Bu],[R2915;H,OCH₂(3-Cl-Ph),CF₃,H,H,Bu], [R2916;H,OCH₂(3-Cl-Ph),H,H,H,Bu],[R2917;H,OCH₂(3-Cl-Ph),F,H,H,c-Pr],[R2918;H,OCH₂(3-Cl-Ph),Cl,H,H,c-Pr],[R2919;H,OCH₂(3-Cl-Ph),Br,H,H,c-Pr],[R2990;H, OCH₂(3-Cl-Ph),I,H,H,c-Pr],[R2991;H,OCH₂(3-Cl-Ph),Me, H,H,c-Pr],[R2992;H,OCH₂(3-Cl-Ph),CHF₂,H,H,c-Pr], [R2993;H,OCH₂(3-Cl-Ph),CF₃,H,H,c-Pr],[R2994;H,OCH₂ (3-Cl-Ph),H,H,H,c-Pr],[R2995;H,OCH₂(3-Cl-Ph),F,H,H, CH₂CF₃],[R2996;H,OCH₂(3-Cl-Ph),Cl,H,H,CH₂CF₃], [R2997;H,OCH₂(3-Cl-Ph),Br,H,H,CH₂CF₃],[R2998;H, OCH₂(3-Cl-Ph),I,H,H,CH₂CF₃],[R2999;H,OCH₂(3-Cl-Ph), Me,H,H,CH₂CF₃],[R3000;H,OCH₂(3-Cl-Ph),CHF₂,H,H, CH₂CF₃], [R3001;H,OCH₂(3-Cl-Ph),CF₃,H,H,CH₂CF₃],[R3002;H, OCH₂(3-Cl-Ph),H,H,H,CH₂CF₃],[R3003;H,OCH₂(3-Cl-Ph),F,H,H,CH₂CHF₂],[R3004;H,OCH₂(3-Cl-Ph),Cl,H,H, CH₂CHF₂],[R3005;H,OCH₂(3-Cl-Ph),Br,H,H,CH₂CHF₂], [R3006;H,OCH₂(3-Cl-Ph),I,H,H,CH₂CHF₂],[R3007;H, OCH₂(3-Cl-Ph),Me,H,H,CH₂CHF₂],[R3008;H,OCH₂(3-Cl-Ph),CHF₂,H,H,CH₂CHF₂],[R3009;H,OCH₂(3-Cl-Ph),CF₃, H,H,CH₂CHF₂],[R3010;H,OCH₂(3-Cl-Ph),H,H,H, CH₂CHF₂],[R3011;H,OCH₂(3-Cl-Ph),F,H,H,CF₂CH₃], [R3012;H,OCH₂(3-Cl-Ph),Cl,H,H,CF₂CH₃],[R3013;H, OCH₂(3-Cl-Ph),Br,H,H,CF₂CH₃],[R3014;H,OCH₁(3-Cl-Ph),I,H,H,CF₂CH₃],[R3015;H,OCH₂(3-Cl-Ph),Me,H,H, CF₂CH₃],[R3016;H,OCH₂(3-Cl-Ph),CHF₂,H,H,CF₂CH₃], [R3017;H,OCH₂(3-Cl-Ph),CF₃,H,H,CF₂CH₃],[R3018;H, OCH₂(3-Cl-Ph),H,H,H,CF₂CH₃],[R3019;H,OCH₂(3-Cl-Ph),F,H,H,NMe₂],[R3020;H,OCH₂(3-Cl-Ph),Cl,H,H, NMe₂],[R3021;H,OCH₂(3-Cl-Ph),Br,H,H,NMe₂],[R3022; H,OCH₂(3-Cl-Ph),I,H,H,NMe₂],[R3023;H,OCH₂(3-Cl-Ph), Me,H,H,NMe₂],[R3024;H,OCH₂(3-Cl-Ph),CHF₂,H,H, NMe₂],[R3025;H,OCH₂(3-Cl-Ph),CF₃,H,H,NMe₂],[R3026; H,OCH₂(3-Cl-Ph),H,H,H,NMe₂],[R3027;H,OCH₂(3-Cl-Ph),F,H,H,Pyrro],[R3028;H,OCH₂(3-Cl-Ph),Cl,H,H,Pyrro], [R3029;H,OCH₂(3-Cl-Ph),Br,H,H,Pyrro],[R3030;H,OCH₂ (3-Cl-Ph),I,H,H,Pyrro],[R3031;H,OCH₂(3-Cl-Ph),Me,H,H, Pyrro],[R3032;H,OCH₂(3-Cl-Ph),CHF₂,H,H,Pyrro], [R3033;H,OCH₂(3-Cl-Ph),CF₃,H,H,Pyrro],[R3034;H, OCH₂(3-Cl-Ph),H,H,H,Pyrro],[R3035;H,OCH₂(4-Cl-Ph), Cl,H,H,Me],[R3036;H,OCH₂(4-Cl-Ph),Br,H,H,Me], [R3037;H,OCH₂(4-Cl-Ph),H,H,Me],[R3038;H,OCH₂(4-Cl-Ph),Me,H,H,Me],[R3039;H,OCH₂(4-Cl-Ph),CHF₂,H,H, Me],[R3040;H,OCH₂(4-Cl-Ph),CF₃,H,H,Me],[R3041;H, OCH₂(4-Cl-Ph),H,H,H,Me],[R3042;H,OCH₂(4-Cl-Ph),F,H, H,Et],[R3043;H,OCH₂(4-Cl-Ph),Cl,H,H,Et],[R3044;H, OCH₂(4-Cl-Ph),Br,H,H,Et],[R3045;H,OCH₂(4-Cl-Ph),I,H, H,Et],[R3046;H,OCH₂(4-Cl-Ph),Me,H,H,Et],[R3047;H, OCH₂(4-Cl-Ph),CHF₂,H,H,Et],[R3048;H,OCH₂(4-Cl-Ph), CF₃,H,H,Et],[R3049;H,OCH₂(4-Cl-Ph),H,H,H,Et],[R3010; H,OCH₂(4-Cl-Ph),F,H,H,Pr],[R3011;H,OCH₂(4-Cl-Ph),Cl, H,H,Pr],[R3012;H,OCH₂(4-Cl-Ph),Br,H,H,Pr],[R3013;H, OCH₂(4-Cl-Ph),I,H,H,Pr],[R3014;H,OCH₂(4-Cl-Ph),Me,H, H,Pr],[R3015;H,OCH₂(4-Cl-Ph),CHF₂,H,H,Pr],[R3016;H, OCH₂(4-Cl-Ph),CF₃,H,H,Pr],[R3017;H,OCH₂(4-Cl-Ph),H, H,H,Pr],[R3018;H,OCH₂(4-Cl-Ph),F,H,H,Bu],[R3019;H, OCH₂(4-Cl-Ph),Cl,H,H,Bu],[R3060;H,OCH₂(4-Cl-Ph),Br, H,H,Bu],[R3061;H,OCH₂(4-Cl-Ph),I,H,H,Bu],[R3062;H, OCH₂(4-Cl-Ph),Me,H,H,Bu],[R3063;H,OCH₂(4-Cl-Ph), CHF₂,H,H,Bu],[R3064;H,OCH₂(4-Cl-Ph),CF₃,H,H,Bu], [R3065;H,OCH₂(4-Cl-Ph),H,H,H,Bu],[R3066;H,OCH₂(4-Cl-Ph),F,H,H,c-Pr],[R3067;H,OCH₂(4-Cl-Ph),Cl,H,H,c-Pr],[R3068;H,OCH₂(4-Cl-Ph),Br,H,H,c-Pr],[R3069;H, OCH₂(4-Cl-Ph),I,H,H,c-Pr],[R3070;H,OCH₂(4-Cl-Ph),Me, H,H,c-Pr],[R3071;H,OCH₂(4-Cl-Ph),CHF₂,H,H,c-Pr], [R3072;H,OCH₂(4-Cl-Ph),CF₃,H,H,c-Pr],[R3073;H,OCH₂ (4-Cl-Ph),H,H,H,c-Pr],[R3074;H,OCH₂(4-Cl-Ph),F,H,H, CH₂CF₃],[R3075;H,OCH₂(4-Cl-Ph),Cl,H,H,CH₂CF₃], [R3076;H,OCH₂(4-Cl-Ph),Br,H,H,CH₂CF₃],[R3077;H, OCH₂(4-Cl-Ph),I,H,H,CH₂CF₃],[R3078;H,OCH₂(4-Cl-Ph), Me,H,H,CH₂CF₃],[R3079;H,OCH₂(4-Cl-Ph),CHF₂,H,H, CH₂CF₃],[R3080;H,OCH₂(4-Cl-Ph),CF₃,H,H,CH₂CF₃], [R3081;H,OCH₂(4-Cl-Ph),H,H,H,CH₂CF₃],[R3082;H, OCH₂(4-Cl-Ph),F,H,H,CH₂CHF₂],[R3083;H,OCH₂(4-Cl-Ph),Cl,H,H,CH₂CHF₂],[R3084;H,OCH₂(4-Cl-Ph),Br,H,H, CH₂CHF₂],[R3085;H,OCH₂(4-Cl-Ph),I,H,H,CH₂CHF₂], [R3086;H,OCH₂(4-Cl-Ph),Me,H,H,CH₂CHF₂],[R3087;H, OCH₂(4-Cl-Ph),CHF₂,H,H,CH₂CHF₂],[R3088;H,OCH₂(4-Cl-Ph),CF₃,H,H,CH₂CHF₂],[R3089;H,OCH₂(4-Cl-Ph),H, H,H,CH₂CHF₂],[R3090;H,OCH₂(4-Cl-Ph),F,H,H, CF₂CH₃],[R3091;H,OCH₂(4-Cl-Ph),Cl,H,H,CF₂CH₃], [R3092;H,OCH₂(4-Cl-Ph),Br,H,H,CF₂CH₃],[R3093;H, OCH₂(4-Cl-Ph),I,H,H,CF₂CH₃],[R3094;H,OCH₂(4-Cl-Ph), Me,H,H,CF₂CH₃],[R3095;H,OCH₂(4-Cl-Ph),CHF₂,H,H, CF₂CH₃],[R3096;H,OCH₂(4-Cl-Ph),CF₃,H,H,CF₂CH₃], [R3097;H,OCH₂(4-Cl-Ph),H,H,H,CF₂CH₃],[R3098;H, OCH₂(4-Cl-Ph),F,H,H,NMe₂],[R3099;H,OCH₂(4-Cl-Ph), Cl,H,H,NMe₂],[R3100;H,OCH₂(4-Cl-Ph),Br,H,H,NMe₂], [R3101;H,OCH₂(4-Cl-Ph),I,H,H,NMe₂],[R3102;H,OCH₂ (4-Cl-Ph),Me,H,H,NMe₂],[R3103;H,OCH₂(4-Cl-Ph), CHF₂,H,H,NMe₂],[R3104;H,OCH₂(4-Cl-Ph),CF₃,H,H, NMe₂],[R3105;H,OCH₂(4-Cl-Ph),H,H,H,NMe₂],[R3106; H,OCH₂(4-Cl-Ph),F,H,H,Pyrro],[R3107;H,OCH₂(4-Cl-Ph), Cl,H,H,Pyrro],[R3108;H,OCH₂(4-Cl-Ph),Br,H,H,Pyrro],

[R3109;H,OCH₂(4-Cl-Ph),I,H,H,Pyrro],[R3110;H,OCH₂(4-Cl-Ph),Me,H,H,Pyrro],[R3111;H,OCH₂(4-Cl-Ph),CHF₂,H,H,Pyrro],[R3112;H,OCH₂(4-Cl-Ph),CF₃,H,H,Pyrro],[R3113;H,OCH₂(4-Cl-Ph),H,H,H,Pyrro],[R3114;H,OCH₂(2-Me-Ph),Cl,H,H,Me],[R3115;H,OCH₂(2-Me-Ph),Br,H,H,Me],[R3116;H,OCH₂(2-Me-Ph),I,H,H,Me],[R3117;H,OCH₂(2-Me-Ph),Me,H,H,Me],[R3118;H,CCH₂(2-Me-Ph),CHF₂,H,H,Me],[R3119;H,OCH₂(2-Me-Ph),CF₃,H,H,Me],[R3120;H,OCH₂(2-Me-Ph),H,H,H,Me],[R3121;H,OCH₂(2-Me-Ph),F,H,H,Et],[R3122;H,OCH₂(2-Me-Ph),Cl,H,H,Et],[R3123;H,OCH₂(2-Me-Ph),Br,H,H,Et],[R3124;H,OCH₂(2-Me-Ph),I,H,H,Et],[R3125;H,OCH₂(2-Me-Ph),Me,H,H,Et],[R3126;H,OCH₂(2-Me-Ph),CHF₂,H,H,Et],[R3127;H,OCH₂(2-Me-Ph),CF₃,H,H,Et],[R3128;H,OCH₂(2-Me-Ph),H,H,H,Et],[R3129;H,OCH₂(2-Me-Ph),F,H,H,Pr],[R313;H,OCH₂(2-Me-Ph),Cl,H,H,Pr],[R3131;H,OCH₂(2-Me-Ph),Br,H,H,Pr],[R3132;H,OCH₂(2-Me-Ph),I,H,H,Pr],[R3133;H,OCH₂(2-Me-Ph),Me,H,H,Pr],[R3134;H,OCH₂(2-Me-Ph),CHF₂,H,H,Pr],[R3135;H,OCH₂(2-Me-Ph),CF₃,H,H,Pr],[R3136;H,OCH₂(2-Me-Ph),H,H,H,Pr],[R3137;H,OCH₂(2-Me-Ph),F,H,H,Bu],[R3138;H,OCH₂(2-Me-Ph),Cl,H,H,Bu],[R3139;H,OCH₂(2-Me-Ph),Br,H,H,Bu],[R3140;H,OCH₂(2-Me-Ph),C,H,H,Bu],[R3141;H,OCH₂(2-Me-Ph)Me,H,H,Bu],[R3142;H,OCH₂(2-Me-Ph),CHF₂,H,H,Bu],[R3143;H,OCH₂(2-Me-Ph),CF₃,H,H,Bu],[R3144;H,OCH₂(2-Me-Ph),H,H,H,Bu],[R3145;H,OCH₂(2-Me-Ph),F,H,H,c-Pr],[R3146;H,OCH₂(2-Me-Ph),Cl,H,H,c-Pr],[R3147;H,OCH₂(2-Me-Ph),Br,H,H,c-Pr],[R3148;H,OCH₂(2-Me-Ph),I,H,H,c-Pr],[R3149;H,OCH₂(2-Me-Ph),Me,H,H,c-Pr],[R3150;H,OCH₂(2-Me-Ph),CHF₂,H,H,c-Pr],[R3151;H,OCH₂(2-Me-Ph),CF₃,H,H,c-Pr],[R3152;H,CCH₂(2-Me-Ph),H,H,H,c-Pr],[R3153;H,OCH₂(2-Me-Ph),F,H,H,CH₂CF₃],[R3154;H,OCH₂(2-Me-Ph),Cl,H,H,CH₂CF₃],[R3155;H,OCH₂(2-Me-Ph),Br,H,H,CH₂CF₃],[R3156;H,OCH₂(2-Me-Ph),I,H,H,CH₂CF₃],[R3157;H,OCH₂(2-Me-Ph),Me,H,H,CH₂CF₃],[R3158;H,OCH₂(2-Me-Ph),CHF₂,H,H,CH₂CF₃],[R3159;H,OCH₂(2-Me-Ph),CF₃,H,H,CH₂CF₃],[R3160;H,OCH₂(2-Me-Ph),H,H,H,CH₂CF₃],[R3161;H,OCH₂(2-Me-Ph),F,H,H,CH₂CHF₂],[R3162;H,OCH₂(2-Me-Ph),Cl,H,H,CH₂CHF₂],[R3163;H,OCH₂(2-Me-Ph),Br,H,H,CH₂CHF₂],[R3164;H,OCH₂(2-Me-Ph),I,H,H,CH₂CHF₂],[R3165;H,OCH₂(2-Me-Ph),Me,H,H,CH₂CHF₂],[R3166;H,OCH₂(2-Me-Ph),CHF₂,H,H,CH₂CHF₂],[R3167;H,OCH₂(2-Me-Ph),CF₃,H,H,CH₂CHF₂],[R3168;H,OCH₂(2-Me-Ph),H,H,H,CH₂CHF₂],[R3169;H,OCH₂(2-Me-Ph),F,H,H,CF₂CH₃],[R3170;H,OCH₂(2-Me-Ph),Cl,H,H,CF₂CH₃],[R3171;H,OCH₂(2-Me-Ph),Br,H,H,CF₂CH₃],[R3122;H,OCH₂(2-Me-Ph),I,H,H,CF₂CH₃],[R3173;H,OCH₂(2-Me-Ph),Me,H,H,CF₂CH₃],[R3174;H,OCH₂(2-Me-Ph),CHF₂,H,H,CF₂CH₃],[R3175;H,OCH₂(2-Me-Ph),CF₃,H,H,CF₂CH₃],[R3176;H,OCH₂(2-Me-Ph),H,H,H,CF₂CH₃],[R3177;H,OCH₂(2-Me-Ph),F,H,H,NMe₂],[R3178;H,OCH₂(2-Me-Ph),Cl,H,H,NMe₂],[R3179;H,OCH₂(2-Me-Ph),Br,H,H,NMe₂],[R3180;H,OCH₂(2-Me-Ph),I,H,H,NMe₂],[R3181;H,OCH₂(2-Me-Ph),Me,H,H,NMe₂],[R3182;H,OCH₂(2-Me-Ph),CHF₂,H,H,NMe₂],[R3183;H,OCH₂(2-Me-Ph),CF₃,H,H,NMe₂],[R3184;H,OCH₂(2-Me-Ph),H,H,H,NMe₂],[R3185;H,OCH₂(2-Me-Ph),F,H,H,Pyrro],[R3186;H,OCH₂(2-Me-Ph),Cl,H,H,Pyrro],[R3187;H,OCH₂(2-Me-Ph),Br,H,H,Pyrro],[R3188;H,OCH₂(2-Me-Ph),I,H,H,Pyrro],[R3189;H,OCH₂(2-Me-Ph),Me,H,H,Pyrro],[R3190;H,OCH₂(2-Me-Ph),CHF₂,H,H,Pyrro],[R3191;H,OCH₂(2-Me-Ph),CF₃,H,H,Pyrro],[R3192;H,OCH₂(2-Me-Ph),H,H,H,Pyrro],[R3193;H,OCH₂(3-Me-Ph),Cl,H,H,Me],[R3194;H,OCH₂(3-Me-Ph),Br,H,H,Me],[R3195;H,OCH₂(3-Me-Ph),I,H,H,Me],[R3196;H,OCH₂(3-Me-Ph),Me H,H,Me],[R3197;H,OCH₂(3-Me-Ph),CHF₂,H,H,Me],[R3198;H,OCH₂(3-Me-Ph),CF₃,H,H,Me],[R3199;H,OCH₂(3-Me-Ph),H,H,H,Me],[R3200;H,OCH₂(3-Me-Ph),F,H,H,Et],[R3201;H,OCH₂(3-Me-Ph),Cl,H,H,Et],[R3202;H,OCH₂(3-Me-Ph),Br,H,H,Et],[R3203;H,OCH₂(3-Me-Ph),I,H,H,Et],[R3204;H,OCH₂(3-Me-Ph),Me,H,H,Et],[R3205;H,OCH₂(3-Me-Ph),CHF₂,H,H,Et],[R3206;H,OCH₂(3-Me-Ph),CF₃,H,H,Et],[R3207;H,OCH₂(3-Me-Ph),H,H,H,Et],[R3208;H,OCH₂(3-Me-Ph),F,H,H,Pr],[R3209;H,OCH₂(3-Me-Ph),Cl,H,H,Pr],[R3210;H,OCH₂(3-Me-Ph),Br,H,H,Pr],[R3211;H,OCH₂(3-Me-Ph),I,H,H,Pr],[R3212;H,OCH₂(3-Me-Ph),Me,H,H,Pr],[R3213;H,OCH₂(3-Me-Ph),CHF₂,H,H,Pr],[R3214;H,OCH₂(3-Me-Ph),CF₃,H,H,Pr],[R3215;H,OCH₂(3-Me-Ph),H,H,H,Pr],[R3216;H,OCH₂(3-Me-Ph),F,H,H,Bu],[R3217;H,OCH₂(3-Me-Ph),Cl,H,H,Bu],[R3218;H,OCH₂(3-Me-Ph),Br,H,H,Bu],[R3219;H,OCH₂(3-Me-Ph),I,H,H,Bu],[R3220;H,OCH₂(3-Me-Ph),Me,H,H,Bu],[R3221;H,OCH₂(3-Me-Ph),CHF₂,H,H,Bu],[R3222;H,OCH₂(3-Me-Ph),CF₃,H,H,Bu],[R3223;H,CCH₂(3-Me-Ph),H,H,H,Bu],[R3224;H,OCH₂(3-Me-Ph),F,H,H,c-Pr],[R3225;H,OCH₂(3-Me-Ph),Cl,H,H,c-Pr],[R3226;H,OCH₂(3-Me-Ph),Br,H,H,c-Pr],[R3227;H,OCH₂(3-Me-Ph),I,H,H,c-Pr],[R3228;H,OCH₂(3-Me-Ph),Me,H,H,c-Pr],[R3229;H,OCH₂(3-Me-Ph),CHF₂,H,H,c-Pr],[R3230;H,OCH₂(3-Me-Ph),CF₃,H,H,c-Pr],[R3231;H,OCH₂(3-Me-Ph),H,H,H,c-Pr],[R3232;H,OCH₂(3-Me-Ph),F,H,H,CH₂CF₃],[R3233;H,OCH₂(3-Me-Ph),Cl,H,H,CH₂CF₃],[R3234;H,OCH₂(3-Me-Ph),Br,H,H,CH₂CF₃],[R3235;H,OCH₂(3-Me-Ph),I,H,H,CH₂CF₃],[R3236;H,OCH₂(3-Me-Ph),Me,H,H,CH₂CF₃],[R3237;H,OCH₂(3-Me-Ph),CHF₂,H,H,CH₂CF₃],[R3238;H,OCH₂(3-Me-Ph),CF₃,H,H,CH₂CF₃],[R3239;H,OCH₂(3-Me-Ph),H,H,H,CH₂CF₃],[R3240;H,OCH₂(3-Me-Ph),F,H,H,CH₂CHF₂],[R3241;H,OCH₂(3-Me-Ph),Cl,H,H,CH₂CHF₂],[R3242;H,OCH₂(3-Me-Ph),Br,H,H,CH₂CHF₂],[R3243;H,OCH₂(3-Me-Ph),I,H,H,CH₂CHF₂],[R3244;H,OCH₂(3-Me-Ph),Me,H,H,CH₂CHF₂],[R3245;H,OCH₂(3-Me-Ph),CHF₂,H,H,CH₂CHF₂],[R3246;H,OCH₂(3-Me-Ph),CF₃,H,H,CH₂CHF₂],[R3247;H,OCH₂(3-Me-Ph),H,H,H,CH₂CHF₂],[R3248;H,OCH₂(3-Me-Ph),F,H,H,CF₂CH₃],[R3249;H,OCH₂(3-Me-Ph),Cl,H,H,CF₂CH₃],[R3250;H,OCH₂(3-Me-Ph),Br,H,H,CF₂CH₃],[R3251;H,OCH₂(3-Me-Ph),I,H,H,CF₂CH₃],[R3252;H,OCH₂(3-Me-Ph),Me,H,H,CF₂CH₃],[R3253;H,OCH₂(3-Me-Ph),CHF₂,H,H,CF₂CH₃],[R3254;H,OCH₂(3-Me-Ph),CF₃,H,H,CF₂CH₃],[R3255;H,OCH₂(3-Me-Ph),H,H,H,CF₂CH₃],[R3256;H,OCH₂(3-Me-Ph),F,H,H,NMe₂],[R3257;H,OCH₂(3-Me-Ph),Cl,H,H,NMe₂],[R3258;H,OCH₂(3-Me-Ph),Br,H,H,NMe₂],[R3259;H,OCH₂(3-Me-Ph),I,H,H,NMe₂],[R3260;H,OCH₂(3-Me-Ph),Me,H,H,NMe₂],[R3261;H,OCH₂(3-Me-Ph),CHF₂,H,H,NMe₂],[R3262;H,OCH₂(3-Me-Ph),CF₃,H,H,NMe₂],[R3263;H,OCH₂(3-Me-Ph),H,H,H,NMe₂],[R3264;H,OCH₂(3-Me-Ph),F,H,H,Pyrro],[R3265;H,OCH₂(3-Me-Ph),Cl,H,H,Pyrro],[R3266;H,OCH₂(3-Me-Ph),Br,H,H,Pyrro],[R3267;H,OCH₂(3-Me-Ph),I,H,H,Pyrro],[R3268;H,OCH₂(3-Me-Ph),Me,H,H,Pyrro],[R3269;H,OCH₂(3-Me-Ph),CHF₂,H,H,Pyrro],[R3270;H,OCH₂(3-Me-Ph),CF₃,H,H,Pyrro],[R3271;H,OCH₂(3-Me-Ph),H,H,H,Pyrro],[R3272;H,OCH₂(4-Me-Ph),Cl,H,H,Me],[R3273;H,OCH₂(4-Me-Ph),Br,H,H,Me],[R3274;H,OCH₂(4-Me-Ph),I,H,H,Me],[R3275;H,OCH₂(4-Me-Ph),Me,H,H,Me],[R3276;H,OCH₂(4-Me-Ph),CHF₂,H,H,Me],[R3277;H,OCH₂(4-Me-Ph),CF₃,H,H,Me],[R3278;H,OCH₂(4-Me-Ph),H,H,H,Me],[R3279;H,OCH₂(4-Me-Ph),F,H,H,Et],[R3280;H,OCH₂(4-Me-Ph),Cl,H,H,Et],[R3281;H,OCH₂(4-Me-Ph),Br,H,H,Et],[R3282;H,OCH₂(4-Me-Ph),I,H,H,Et],[R3283;H,OCH₂(4-Me-Ph),Me,H,H,Et],[R3284;H,OCH₂(4-Me-Ph),CHF₂,H,H,Et],[R3285;H,OCH₂(4-Me-Ph),CF₃,H,H,Et],[R3286;H,OCH₂(4-Me-Ph),H,H,H,Et],[R3287;H,OCH₂(4-Me-Ph),F,H,H, Pr],[R3288;H,OCH₂(4-Me-Ph),Cl,H,H,Pr],[R3289;H, OCH₂(4-Me-Ph),Br,H,H,Pr],[R3290;H,OCH₂(4-Me-Ph),I, H,H,Pr],[R3291;H,OCH₂(4-Me-Ph),Me,H,H,Pr],[R3292;H, OCH₂(4-Me-Ph),CHF₂,H,H,Pr],[R3293;H,OCH₂(4-Me-Ph),CF₃,H,H,Pr],[R3294;H,OCH₂(4-Me-Ph),H,H,H,Pr], [R3295;H,OCH₂(4-Me-Ph),F,H,H,Bu],[R3296;H,OCH₂(4-Me-Ph),Cl,H,H,Bu],[R3297;H,OCH₂(4-Me-Ph),Br,H,H, Bu],[R3298;H,OCH₂(4-Me-Ph),I,H,H,Bu],[R3299;H,OCH₂ (4-Me-Ph),Me,H,H,Bu],[R3300;H,OCH₂(4-Me-Ph),CHF₂, H,H,Bu],
[R3301;H,OCH₂(4-Me-Ph),CF₃,H,H,Bu],[R3302;H,OCH₂ (4-Me-Ph),H,H,H,Bu],[R3303;H,OCH₂(4-Me-Ph),F,H,H,c-Pr],[R3304;H,OCH₂(4-Me-Ph),Cl,H,H,c-Pr],[R3305;H, OCH₂(4-Me-Ph),Br,H,H,c-Pr],[R3306;H,OCH₂(4-Me-Ph), I,H,H,c-Pr],[R3307;H,OCH₂(4-Me-Ph),Me,H,H,c-Pr], [R3308;H,OCH₂(4-Me-Ph),CHF₂,H,H,c-Pr],[R3309;H, OCH₂(4-Me-Ph),CF₃,H,H,c-Pr],[R3310;H,OCH₂(4-Me-Ph),H,H,H,c-Pr],[R3311;H,OCH₂(4-Me-Ph),F,H,H, CH₂CF₃],[R3312;H,OCH₂(4-Me-Ph),Cl,H,H,CH₂CF₃], [R3313;H,OCH₂(4-Me-Ph),Br,H,H,CH₂CF₃],[R3314;H, OCH₂(4-Me-Ph),I,H,H,CH₂CF₃],[R3315;H,OCH₂(4-Me-Ph),Me,H,H,CH₂CF₃],[R3316;H,OCH₂(4-Me-Ph),CHF₂,H, H,CH₂CF₃],[R3317;H,OCH₂(4-Me-Ph),CF₃,H,H,CH₂CF₃], [R3318;H,OCH₂(4-Me-Ph),H,H,H,CH₂CF₃],[R3319;H, OCH₂(4-Me-Ph),F,H,H,CH₂CHF₂],[R3320;H,OCH₂(4-Me-Ph),Cl,H,H,CH₂CHF₂],[R3321;H,OCH₂(4-Me-Ph),Br,H,H, CH₂CHF₂],[R3322;H,OCH₂(4-Me-Ph),I,H,H,CH₂CHF₂], [R3323;H,OCH₂(4-Me-Ph),Me,H,H,CH₂CHF₂],[R3324;H, OCH₂(4-Me-Ph),CHF₂,H,H,CH₂CHF₂],[R3325;H,OCH₂ (4-Me-Ph),CF₃,H,H,CH₂CHF₂],[R3326;H,OCH₂(4-Me-Ph),H,H,H,CH₂CHF₂],[R3327;H,OCH₂(4-Me-Ph),F,H,H, CF₂CH₃],[R3328;H,OCH₂(4-Me-Ph),Cl,H,H,CF₂CH₃], [R3329;H,OCH₂(4-Me-Ph),Br,H,H,CF₂CH₃],[R3330;H, OCH₂(4-Me-Ph),I,H,H,CF₂CH₃],[R3331;H,OCH₂(4-Me-Ph),Me,H,H,CF₂CH₃],[R3332;H,OCH₂(4-Me-Ph),CHF₂,H, H,CF₂CH₃],[R3333;H,OCH₂(4-Me-Ph),CF₃,H,H,CF₂CH₃], [R3334;H,OCH₂(4-Me-Ph),H,H,H,CF₂CH₃],[R3335;H, OCH₂(4-Me-Ph),F,H,H,NMe₂],[R3336;H,OCH₂(4-Me-Ph), Cl,H,H,NMe₂],[R3337;H,OCH₂(4-Me-Ph),Br,H,H,NMe₂], [R3338;H,OCH₂(4-Me-Ph),I,H,H,NMe₂],[R3339;H,OCH₂ (4-Me-Ph),Me,H,H,NMe₂],[R3340;H,OCH₂(4-Me-Ph), CHF₂,H,H,NMe₂],[R3341;H,OCH₂(4-Me-Ph),CF₃,H,H, NMe₂],[R3342;H,OCH₂(4-Me-Ph),H,H,H,NMe₂],[R3343; H,OCH₂(4-Me-Ph),F,H,H,Pyrro],[R3344;H,OCH₂(4-Me-Ph),Cl,H,H,Pyrro],[R3345;H,OCH₂(4-Me-Ph),Br,H,H, Pyrro],[R3346;H,OCH₂(4-Me-Ph),I,H,H,Pyrro],[R3347;H, OCH₂(4-Me-Ph),Me,H,H,Pyrro],[R3348;H,OCH₂(4-Me-Ph),CHF₂,H,H,Pyrro],[R3349;H,OCH₂(4-Me-Ph),CF₃,H,H, Pyrro],[R3350;H,OCH₂(4-Me-Ph),H,H,H,Pyrro],[R3351;H, OCH₂(2-CN-Ph),Cl,H,H,Me],[R3352;H,CCH₂(2-CN-Ph), Br,H,H,Me],[R3353;H,OCH₂(2-CN-Ph),I,H,H,Me], [R3354;H,OCH₂(2-CN-Ph),Me,H,H,Me],[R3355;H,OCH₂ (2-CN-Ph),CHF₂,H,H,Me],[R3356;H,OCH₂(2-CN-Ph), CF₃,H,H,Me],[R3357;H,OCH₂(2-CN-Ph),H,H,H,Me], [R3358;H,OCH₂(2-CN-Ph),F,H,H,Et],[R3359;H,OCH₂(2-CN-Ph),Cl,H,H,Et],[R3360;H,OCH₂(2-CN-Ph),Br,H,H,Et], [R3361;H,OCH₂(2-CN-Ph),I,H,H,Et],[R3362;H,OCH₂(2-CN-Ph),Me,H,H,Et],[R3363;H,OCH₂(2-CN-Ph),CHF₂,H, H,Et],[R3364;H,OCH₂(2-CN-Ph),CF₃,H,H,Et],[R3365;H, OCH₂(2-CN-Ph),H,H,H,Et],[R3366;H,OCH₂(2-CN-Ph),F, H,H,Pr],[R3367;H,OCH₂(2-CN-Ph),Cl,H,H,Pr],[R3368;H, OCH₂(2-CN-Ph),Br,H,H,Pr],[R3369;H,OCH₂(2-CN-Ph),I, H,H,Pr],[R3370;H,OCH₂(2-CN-Ph),Me,H,H,Pr],[R3371;H, OCH₂(2-CN-Ph),CHF₂,H,H,Pr],[R3372;H,OCH₂(2-CN-Ph),CF₃,H,H,Pr],[R3373;HF₁,OCH₂(2-CN-Ph),H,H,H,Pr], [R3374;H,OCH₂(2-CN-Ph),F,H,H,Bu],[R3375;H,OCH₂(2-CN-Ph),Cl,H,H,Bu],[R3376;H,OCH₂(2-CN-Ph),Br,H,H, Bu],[R3377;H,OCH₂(2-CN-Ph),I,H,H,Bu],[R3378;H, OCH₂(2-CN-Ph),Me,H,H,Bu],[R3379;H,OCH₂(2-CN-Ph), CHF₂,H,H,Bu],[R3380;H,OCH₂(2-CN-Ph),CF₃,H,H,Bu], [R3381;H,OCH₂ (2-CN-Ph),H,H,H,Bu],[R3382;H,OCH₂ (2-CN-Ph),F,H,H,c-Pr],[R3383;H,OCH₂(2-CN-Ph),Cl,H,H, c-Pr],[R3384;H,OCH₂(2-CN-Ph),Br,H,H,c-Pr],[R3385;H, OCH₂(2-CN-Ph),I,H,H,c-Pr],[R3386;H,OCH₂(2-CN-Ph), Me,H,H,c-Pr],[R3387;H,OCH₂(2-CN-Ph),CHF₂,H,H,c-Pr], [R3388;H,OCH₂(2-CN-Ph),CF₃,H,H,c-Pr],[R3389;H, OCH₂(2-CN-Ph),H,H,H,c-Pr],[R3390;H,OCH₂(2-CN-Ph), F,H,H,CH₂CF₃],[R3391;H,OCH₂(2-CN-Ph),Cl,H,H, CH₂CF₃],[R3392;H,OCH₂(2-CN-Ph),Br,H,H,CH₂CF₃], [R3393;H,OCH₂(2-CN-Ph),I,H,H,CH₂CF₃],[R3394;H, OCH₂ (2-CN-Ph),Me,H,H,CH₂CF₃],[R3395;H,OCH₂(2-CN-Ph),CHF₂,H,H,CH₂CF₃],[R3396;H,OCH₂ (2-CN-Ph), CF₃,H,H,CH₂CF₃],[R3397;H,OCH₂ (2-CN-Ph),H,H,H, CH₂CF₃],[R3398;H,OCH₂ (2-CN-Ph),F,H,H,CH₂CHF₂], [R3399;H,OCH₂(2-CN-Ph),Cl,H,H,CH₂CHF₂],[R3400;H, OCH₂(2-CN-Ph),Br,H,H,CH₂CHF₂],[R3401;H,OCH₂ (2-CN-Ph),I,H,H,CH₂CHF₂],[R3402;H,OCH₂ (2-CN-Ph), Me,H,H,CH₂CHF₂],[R3403;H,OCH₂(2-CN-Ph),CHF₂,H, H,CH₂CHF₂],[R3404;H,OCH₂ (2-CN-Ph),CF₃,H,H, CH₂CHF₂],[R3405;H,OCH₂ (2-CN-Ph),H,H,H,CH₂CHF₂], [R3406;H,OCH₂ (2-CN-Ph),F,H,H,CF₂CH₃],[R3407;H, OCH₂ (2-CN-Ph),Cl,H,H,CF₂CH₃],[R3408;H,OCH₂ (2-CN-Ph),Br,H,H,CF₂CH₃],[R3409;H,OCH₂ (2-CN-Ph),I, H,H,CF₂CH₃],[R3410;H,OCH₂(2-CN-Ph),Me,H,H, CF₂CH₃],[R3411;H,OCH₂ (2-CN-Ph),CHF₂,H,H,CF₂CH₃], [R3412;H,OCH₂(2-CN-Ph),CF₃,H,H,CF₂CH₃],[R3413;H, OCH₂(2-CN-Ph),H,H,H,CF₂CH₃],[R3414;H,OCH₂(2-CN-Ph),F,H,H,NMe₂],[R3415;H,OCH₂(2-CN-Ph),Cl,H,H, NMe₂],[R3416;H,OCH₂(2-CN-Ph),Br,H,H,NMe₂],[R3417; H,OCH₂(2-CN-Ph),I,H,H,NMe₂],[R3418;H,OCH₂(2-CN-Ph),Me,H,H,NMe₂],[R3419;H,OCH₂(2-CN-Ph),CHF₂,H,H, NMe₂],[R3420;H,OCH₂(2-CN-Ph),CF₃,H,H,NMe₂], [R3421;H,OCH₂(2-CN-Ph),H,H,H,NMe₂],[R3422;H,OCH₂ (2-CN-Ph),F,H,H,Pyrro],[R3423;H,OCH₂(2-CN-Ph),Cl,H, H,Pyrro],[R3424;H,OCH₂ (2-CN-Ph),Br,H,H,Pyrro], [R3425;H,OCH₂(2-CN-Ph),I,H,H,Pyrro],[R3426;H,OCH₂ (2-CN-Ph),Me,H,H,Pyrro],[R3427;H,OCH₂ (2-CN-Ph), CHF₂,H,H,Pyrro],[R3428;H,OCH₂(2-CN-Ph),CF₃,H,H, Pyrro],[R3429;H,OCH₂(2-CN-Ph),H,H,H,Pyrro],[R3430; H,OCH₂(3-CN-Ph),Cl,H,H,Me],[R3431;H,OCH₂(3-CN-Ph),Br,H,H,Me],[R3432;H,OCH₂(3-CN-Ph),I,H,H,Me], [R3433;H,OCH₂(3-CN-Ph),Me,H,H,Me],[R3434;H,OCH₂ (3-CN-Ph),CHF₂,H,H,Me],[R3435;H,OCH₂(3-CN-Ph), CF₃,H,H,Me],[R3436;H,OCH₂(3-CN-Ph),H,H,H,Me], [R3437;H,OCH₂(3-CN-Ph),F,H,H,Et],[R3438;H,OCH₂(3-CN-Ph),Cl,H,H,Et],[R3439;H,OCH₂(3-CN-Ph),Br,H,H,Et], [R3440;H,OCH₂(3-CN-Ph),I,H,H,Et],[R3441;H,OCH₂(3-CN-Ph),Me,H,H,Et],[R3442;H,OCH₂(3-CN-Ph),CHF₂,H, H,Et],[R3443;H,OCH₂(3-CN-Ph),CF₃,H,H,Et],[R3444;H, OCH₂(3-CN-Ph),H,H,H,Et],[R3445;H,OCH₂(3-CN-Ph),F, H,H,Pr],[R3446;H,OCH₂(3-CN-Ph),Cl,H,H,Pr],[R3447;H, OCH₂(3-CN-Ph),Br,H,H,Pr],[R3448;H,OCH₂(3-CN-Ph),I, H,H,Pr],[R3449;H,OCH₂(3-CN-Ph),Me,H,H,Pr],[R3450;H, OCH₂(3-CN-Ph),CHF₂,H,H,Pr],
[R3451;H,OCH₂(3-CN-Ph),CF₃,H,H,Pr],[R3452;H,OCH₂ (3-CN-Ph),H,H,H,Pr],[R3453;H,OCH₂(3-CN-Ph),F,H,H, Bu],[R3454;H,OCH₂(3-CN-Ph),Cl,H,H,Bu],[R3455;H, OCH₂(3-CN-Ph),Br,H,H,Bu],[R3456;H,OCH₂(3-CN-Ph),I, H,H,Bu],[R3457;H,OCH₂(3-CN-Ph),Me,H,H,Bu],[R3458; H,OCH₂(3-CN-Ph),CHF₂,H,H,Bu],[R3459;H,OCH₂(3-CN-Ph),CF₃,H,H,Bu],[R3460;H,OCH₂(3-CN-Ph),H,H,H,Bu], [R3461;H,OCH₂(3-CN-Ph),F,H,H,c-Pr],[R3462;H,OCH₂ (3-CN-Ph),Cl,H,H,c-Pr],[R3463;H,OCH₂(3-CN-Ph),Br,H, H,c-Pr],[R3464;H,OCH₂(3-CN-Ph),I,H,H,c-Pr],[R3465;H, OCH₂(3-CN-Ph),Me,H,H,c-Pr],[R3466;H,OCH₂(3-CN-Ph),CHF₂,H,H,c-Pr],[R3467;H,OCH₂(3-CN-Ph),CF₃,H,H,c-Pr],[R3468;H,OCH₂(3-CN-Ph),H,H,H,c-Pr],[R3469;H,OCH₂(3-CN-Ph),F,H,H,CH₂CF₃],[R3470;H,OCH₂(3-CN-Ph),Cl,H,H,CH₂CF₃],[R3471;H,OCH₂(3-CN-Ph),Br,H,H,CH₂CF₃],[R3472;H,OCH₂(3-CN-Ph),I,H,H,CH₂CF₃],[R3473;H,OCH₂(3-CN-Ph),Me,H,H,CH₂CF₃],[R3474;H,OCH₂(3-CN-Ph),CHF₂,H,H,CH₂CF₃],[R3475;H,OCH₂(3-CN-Ph),CF₃,H,H,CH₂CF₃],[R3476;H,OCH₂(3-CN-Ph),H,H,H,CH₂CF₃],[R3477;H,OCH₂(3-CN-Ph),F,H,H,CH₂CHF₂],[R3478;H,OCH₂(3-CN-Ph),Cl,H,H,CH₂CHF₂],[R3479;H,OCH₂(3-CN-Ph),Br,H,H,CH₂CHF₂],[R3480;H,OCH₂(3-CN-Ph),I,H,H,CH₂CHF₂],[R3481;H,OCH₂(3-CN-Ph),Me,H,H,CH₂CHF₂],[R3482;H,OCH₂(3-CN-Ph),CHF₂,H,H,CH₂CHF₂],[R3483;H,OCH₂(3-CN-Ph),CF₃,H,H,CH₂CHF₂],[R3484;H,OCH₂(3-CN-Ph),H,H,H,CH₂CHF₂],[R3485;H,OCH₂(3-CN-Ph),F,H,H,CF:CH₃],[R3486;H,OCH₂(3-CN-Ph),Cl,H,H,CF₂CH₃],[R3487;H,OCH₂(3-CN-Ph),Br,H,H,CF₂CH₃],[R3488;H,OCH₂(3-CN-Ph),I,H,H,CF₂CH₃],[R3489;H,OCH₂(3-CN-Ph),Me,H,H,CF₂CH₃],[R3490;H,OCH₂(3-CN-Ph),CHF₂,H,H,CF₂CH₃],[R3491;H,OCH₂(3-CN-Ph),CF₃,H,H,CF₂CH₃],[R3492;H,OCH₂(3-CN-Ph),H,H,H,CF₂CH₃],[R3493;H,OCH₂(3-CN-Ph),F,H,H,NMe₂],[R3494;H,OCH₂(3-CN-Ph),Cl,H,H,NMe₂],[R3495;H,OCH₂(3-CN-Ph),Br,H,H,NMe₂],[R3496;H,OCH₂(3-CN-Ph),I,H,H,NMe₂],[R3497;H,OCH₂(3-CN-Ph),Me,H,H,NMe₂],[R3498;H,OCH₂(3-CN-Ph),CHF₂,H,H,NMe₂],[R3499;H,OCH₂(3-CN-Ph),CF₃,H,H,NMe₂],[R3500;H,OCH₂(3-CN-Ph),H,H,H,NMe₂],[R3501;H,OCH₂(3-CN-Ph),F,H,H,Pyrro],[R3502;H,OCH₂(3-CN-Ph),Cl,H,H,Pyrro],[R3503;H,OCH₂(3-CN-Ph),Br,H,H,Pyrro],[R3504;H,OCH₂(3-CN-Ph),I,H,H,Pyrro],[R3505;H,OCH₂(3-CN-Ph),Me,H,H,Pyrro],[R3506;H,OCH₂(3-CN-Ph),CHF₂,H,H,Pyrro],[R3507;H,OCH₂(3-CN-Ph),CF₃,H,H,Pyrro],[R3508;H,OCH₂(3-CN-Ph),H,H,H,Pyrro],[R3509;H,OCH₂(4-CN-Ph),Cl,H,H,Me],[R3510;H,OCH₂(4-CN-Ph),Br,H,H,Me],[R3511;H,OCH₂(4-CN-Ph),I,H,H,Me],[R3512;H,OCH₂(4-CN-Ph),Me,H,H,Me],[R3513;H,OCH₂(4-CN-Ph),CHF₂,H,H,Me],[R3514;H,OCH₂(4-CN-Ph),CF₃,H,H,Me],[R3515;H,OCH₂(4-CN-Ph),H,H,H,Me],[R3516;H,OCH₂(4-CN-Ph),F,H,H,Et],[R3517;H,OCH₂(4-CN-Ph),Cl,H,H,Et],[R3518;H,OCH₂(4-CN-Ph),Br,H,H,Et],[R3519;H,OCH₂(4-CN-Ph),I,H,H,Et],[R3520;H,OCH₂(4-CN-Ph),Me,H,H,Et],[R3521;H,OCH₂(4-CN-Ph),CHF₂,H,H,Et],[R3522;H,OCH₂(4-CN-Ph),CF₃,H,H,Et],[R3523;H,OCH₂(4-CN-Ph),H,H,H,Et],[R3524;H,OCH₂(4-CN-Ph),F,H,H,Pr],[R3525;H,OCH₂(4-CN-Ph),Cl,H,H,Pr],[R3526;H,OCH₂(4-CN-Ph),Br,H,H,Pr],[R3527;H,OCH₂(4-CN-Ph),I,H,H,Pr],[R3528;H,OCH₂(4-CN-Ph),Me,H,H,Pr],[R3529;H,OCH₂(4-CN-Ph),CHF₂,H,H,Pr],[R3530;H,OCH₂(4-CN-Ph),CF₃,H,H,Pr],[R3531;H,OCH₂(4-CN-Ph),H,H,H,Pr],[R3532;H,OCH₂(4-CN-Ph),F,H,H,Bu],[R3533;H,OCH₂(4-CN-Ph),Cl,H,H,Bu],[R3534;H,OCH₂(4-CN-Ph),Br,H,H,Bu],[R3535;H,OCH₂(4-CN-Ph),I,H,H,Bu],[R3536;H,OCH₂(4-CN-Ph),Me,H,H,Bu],[R3537;H,OCH₂(4-CN-Ph),CHF₂,H,H,Bu],[R3538;H,OCH₂(4-CN-Ph),CF₃,H,H,Bu],[R3539;H,OCH₂(4-CN-Ph),H,H,H,Bu],[R3540;H,OCH₂(4-CN-Ph),F,H,H,c-Pr],[R3541;H,OCH₂(4-CN-Ph),Cl,H,H,c-Pr],[R3542;H,OCH₂(4-CN-Ph),Br,H,H,c-Pr],[R3543;H,OCH₂(4-CN-Ph),I,H,H,c-Pr],[R3544;H,OCH₂(4-CN-Ph),Me,H,H,c-Pr],[R3545;H,OCH₂(4-CN-Ph),CHF₂,H,H,c-Pr],[R3546;H,OCH₂(4-CN-Ph),CF₃,H,H,c-Pr],[R3547;H,OCH₂(4-CN-Ph),H,H,H,c-Pr],[R3548;H,OCH₂(4-CN-Ph),F,H,H,CH₂CF₃],[R3549;H,OCH₂(4-CN-Ph),Cl,H,H,CH₂CF₃],[R3550;H,OCH₂(4-CN-Ph),Br,H,H,CH₂CF₃],[R3551;H,OCH₂(4-CN-Ph),I,H,H,CH₂CF₃],[R3552;H,OCH₂(4-CN-Ph),Me,H,H,CH₂CF₃],[R3553;H,OCH₂(4-CN-Ph),CHF₂,H,H,CH₂CF₃],[R3554;H,OCH₂(4-CN-Ph),CF₃,H,H,CH₂CF₃],[R3555;H,OCH₂(4-CN-Ph),H,H,H,CH₂CF₃],[R3556;H,OCH₂(4-CN-Ph),F,H,H,CH₂CHF₂],[R3557;H,OCH₂(4-CN-Ph),Cl,H,H,CH₂CHF₂],[R3558;H,OCH₂(4-CN-Ph),Br,H,H,CH₂CHF₂],[R3559;H,OCH₂(4-CN-Ph),I,H,H,CH₂CHF₂],[R3560;H,OCH₂(4-CN-Ph),Me,H,H,CH₂CHF₂],[R3561;H,OCH₂(4-CN-Ph),CHF₂,H,H,CH₂CHF₂],[R3562;H,OCH₂(4-CN-Ph),CF₃,H,H,CH₂CHF₂],[R3563;H,OCH₂(4-CN-Ph),H,H,H,CH₂CHF₂],[R3564;H,OCH₂(4-CN-Ph),F,H,H,CF₂CH₃],[R3565;H,OCH₂(4-CN-Ph),Cl,H,H,CF₂CH₃],[R3566;H,OCH₂(4-CN-Ph),Br,H,H,CF₂CH₃],[R3567;H,OCH₂(4-CN-Ph),I,H,H,CF₂CH₃],[R3568;H,OCH₂(4-CN-Ph),Me,H,H,CF₂CH₃],[R3569;H,OCH₂(4-CN-Ph),CHF₂,H,H,CF₂CH₃],[R3570;H,OCH₂(4-CN-Ph),CF₃,H,H,CF₂CH₃],[R3571;H,OCH₂(4-CN-Ph),H,H,H,CF₂CH₃],[R3572;H,OCH₂(4-CN-Ph),F,H,H,NMe₂],[R3573;H,OCH₂(4-CN-Ph),Cl,H,H,NMe₂],[R3574;H,OCH₂(4-CN-Ph),Br,H,H,NMe₂],[R3575;H,OCH₂(4-CN-Ph),I,H,H,NMe₂],[R3576;H,OCH₂(4-CN-Ph),Me,H,H,NMe₂],[R3577;H,OCH₂(4-CN-Ph),CHF₂,H,H,NMe₂],[R3578;H,OCH₂(4-CN-Ph),CF₃,H,H,NMe₂],[R3579;H,OCH₂(4-CN-Ph),H,H,H,NMe₂],[R3580;H,OCH₂(4-CN-Ph),F,H,H,Pyrro],[R3581;H,OCH₂(4-CN-Ph),Cl,H,H,Pyrro],[R3582;H,OCH₂(4-CN-Ph),Br,H,H,Pyrro],[R3583;H,OCH₂(4-CN-Ph),I,H,H,Pyrro],[R3584;H,OCH₂(4-CN-Ph),Me,H,H,Pyrro],[R3585;H,OCH₂(4-CN-Ph),CHF₂,H,H,Pyrro],[R3586;H,OCCH₂(4-CN-Ph),CF₃,H,H,Pyrro],[R3587;H,OCH₂(4-CN-Ph),H,H,H,Pyrro],[R3588;H,OCH₂(2-OCF₃-Ph),Cl,H,H,Me],[R3589;H,OCH₂(2-OCF₃-Ph),Br,H,H,Me],[R3590;H,OCH₂(2-OCF₃-Ph),I,H,H,Me],[R3591;H,OCH₂(2-OCF₃-Ph),Me,H,H,Me],[R3592;H,OCH₂(2-OCF₃-Ph),CHF₂,H,H,Me],[R3593;H,OCH₂(2-OCF₃-Ph),CF₃,H,H,Me],[R3594;H,OCH₂(2-OCF₃-Ph),H,H,H,Me],[R3595;H,OCH₂(2-OCF₃-Ph),F,H,H,Et],[R3596;H,OCH₂(2-OCF₃-Ph),Cl,H,H,Et],[R3597;H,OCH₂(2-OCF₃-Ph),Br,H,H,Et],[R3598;H,OCH₂(2-OCF₃-Ph),I,H,H,Et],[R3599;H,OCH₂(2-OCF₃-Ph),Me,H,H,Et],[R3600;H,OCH₂(2-OCF₃-Ph),CHF₂,H,H,Et],[R3601;H,OCH₂(2-OCF₃-Ph),CF₃,H,H,Et[ ],[R3602;H,OCH₂(2-OCF₃-Ph),H,H,H,Et],[R3603;H,OCH₂(2-OCF₃-Ph),F,H,H,Pr],[R3604;H,OCH₂(2-OCF₃-Ph),Cl,H,H,Pr],[R3605;H,OCH₂(2-OCF₃-Ph),Br,H,H,Pr],[R3606;H,OCH₂(2-OCF₃-Ph),I,H,H,Pr],[R3607;H,OCH₂(2-OCF₃-Ph),Me,H,H,Pr],[R3608;H,OCH₂(2-OCF₃-Ph),CHF₂,H,H,Pr],[R3609;H,OCH₂(2-OCF₃-Ph),CF₃,H,H,Pr],[R3610;H,OCH₂(2-OCF₃-Ph),H,H,H,Pr],[R3611;H,OCH₂(2-OCF₃-Ph),F,H,H,Bu],[R3612;H,OCH₂(2-OCF₃-Ph),Cl,H,H,Bu],[R3613;H,OCH₂(2-OCF₃-Ph),Br,H,H,Bu],[R3614;H,OCH₂(2-CF₃-Ph),I,H,H,Bu],[R3615;H,OCH₂(2-OCF₃-Ph),Me,H,H,Bu],[R3616;H,OCH₂(2-OCF₃-Ph),CHF₂,H,H,Bu],[R3617;H,OCH₂(2-OCF₃-Ph),CF₃,H,H,Bu],[R3618;H,OCH₂(2-OCF₃-Ph),H,H,H,Bu],[R3619;H,OCH₂(2-OCF₃-Ph),F,H,H,c-Pr],[R3620;H,OCH₂(2-OCF₃-Ph),Cl,H,H,c-Pr],[R3621;H,OCH₂(2-OCF₃-Ph),Br,H,H,c-Pr],[R3622;H,OCH₂(2-OCF₃-Ph),I,H,H,c-Pr],[R3623;H,OCH₂(2-OCF₃-Ph),Me,H,H,c-Pr],[R3624;H,OCH₂(2-OCF₃-Ph),CHF₂,H,H,c-Pr],[R3625;H,OCH₂(2-OCF₃-Ph),CF₃,H,H,c-Pr],[R3626;H,OCH₂(2-OCF₃-Ph),H,H,H,c-Pr],[R3627;H,OCH₂(2-OCF₃-Ph),F,H,H,CH₂CF₃],[R3628;H,OCH₂(2-OCF₃-Ph),Cl,H,H,CH₂CF₃],[R3629;H,OCH₂(2-OCF₃-Ph),Br,H,H,CH₂CF₃],[R3630;H,OCH₂(2-OCF₃-Ph),I,H,H,CH₂CF₃],[R3631;H,OCH₂(2-OCF₃-Ph),Me,H,H,CH₂CF₃],[R3632;H,OCH₂(2-OCF₃-Ph),CHF₂,H,H,CH₂CF₃],[R3633;H,OCH₂(2-OCF₃-Ph),CF₃,H,H,CH₂CF₃],[R3634;H,OCH₂(2-OCF₃-Ph),H,H,H,CH₂CF₃],[R3635;H,OCH₂(2-OCF₃-Ph),F,H,H,CH₂CHF₂],[R3636;H,OCH₂(2-OCF₃-Ph),Cl,H,H,CH₂CHF₂],[R3637;H,OCH₂(2-OCF₃-Ph),Br,H,H, CH₂CHF₂],[R3638;H,OCH₂ (2-OCF₃-Ph),I,H,H, CH₂CHF₂],[R3639;H,OCH₂(2-OCF₃-Ph),Me,H,H, CH₂CHF₂],[R3640;H,OCH₂(2-OCF₃-Ph),CHF₂,H,H, CH₂CHF₂],[R3641;H,OCH₂(2-OCF₃-Ph),CF₃,H,H, CH₂CHF₂],[R3642;H,OCH₂(2-OCF₃-Ph),H,H,H, CH₂CHF₂],[R3643;H,OCH₂(2-OCF₃-Ph),F,H,H,CF₂CH₃], [R3644;H,OCH₂ (2-OCF₃-Ph),Cl,H,H,CF₂CH₃],[R3645;H, OCH₂(2-OCF₃-Ph),Br,H,H,CF₂CH₃],[R3646;H,OCH₂(2-OCF₃-Ph),I,H,H,CF₂CH₃],[R3647;H,OCH₂ (2-OCF₃-Ph), Me,H,H,CF₂CH₃],[R3648;H,OCH₂(2-OCF₃-Ph),CHF₂,H, H,CF₂CH₃],[R3649;H,OCH₂ (2-OCF₃-Ph),CF₃,H,H, CF₂CH₃],[R3650;H,OCH₂ (2-OCF₃-Ph),H,H,H,CF₂CH₃], [R3651;H,OCH₂ (2-OCF₃-Ph),F,H,H,NMe₂],[R3652;H, OCH₂(2-OCF₃-Ph),Cl,H,H,NMe₂],[R3653;H,OCH₂(2-OCF₃-Ph),Br,H,H,NMe₂],[R3654;H,OCH₂(2-OCF₃-Ph),I, H,H,NMe₂],[R3655;H,OCH₂(2-OCF₃-Ph),Me,H,H,NMe₂], [R3656;H,OCH₂(2-OCF₃-Ph),CHF₂,H,H,NMe₂],[R3657; H,OCH₂(2-OCF₃-Ph),CF₃,H,H,NMe₂],[R3658;H,OCH₂ (2-OCF₃-Ph),H,H,H,NMe₂],[R3659;H,OCH₂(2-OCF₃-Ph), F,H,H,Pyrro],[R3660;H,OCH₂(2-OCF₃-Ph),Cl,H,H,Pyrro], [R3661;H,OCH₂(2-OCF₃-Ph),Br,H,H,Pyrro],[R3662;H, OCH₂(2-OCF₃-Ph),I,H,H,Pyrro],[R3663;H,OCH₂(2-OCF₃-Ph),Me,H,H,Pyrro],[R3664;H,OCH₂(2-OCF₃-Ph),CHF₂,H, H,Pyrro],[R3665;H,OCH₂ (2-OCF₃-Ph),CF₃,H,H,Pyrro], [R3666;H,OCH₂(2-OCF₃-Ph),H,H,H,Pyrrol], [R3657;H, OCH₂(3-OCF₃-Ph),Cl,H,H,Me],[R3668;H,OCH₂(3-OCF₃-Ph),Br,H,H,Me],[R3669;H,OCH₂(3-OCF₃-Ph),I,H,H,Me], [R3670;H,OCH₂(3-OCF₃-Ph),Me,H,H,Me],[R3671;H, OCH₂(3-OCF₃-Ph),CHF₂,H,H,Me],[R3672;H,OCH₂(3-OCF₃-Ph),CF₃,H,H,Me],[R3673;H,OCH₂(3-OCF₃-Ph),H, H,H,Me],[R3674;H,OCH₂(3-OCF₃-Ph),F,H,H,Et],[R3675; H,CCH₂(3-OCF₃-Ph),Cl,H,H,Et],[R3676;H,OCH₂(3-OCF₃-Ph),Br,H,H,Et],[R3677;H,OCH₂(3-OCF₃-Ph),I,H,H, Et],[R3678;H,OCH₂(3-OCF₂-Ph),Me,H,H,Et],[R3679;H, OCH₂(3-OCF₃-Ph),CHF₂,H,H,Et],[R3680;H,OCH₂(3-OCF₃-Ph),CF₃,H,H,Et],[R3681;H,OCH₂(3-OCF₃-Ph),H, H,Et],[R3682;H,OCH₂(3-OCF₃-Ph),F,H,H,Pr],[R3683;H, OCH₂(3-OCF₃-Ph),Cl,H,H,Pr],[R3684;H,OCH₂(3-OCF₃-Ph),Br,H,H,Pr],[R3685;H,OCH₂(3-OCF₃-Ph),I,H,H,Pr], [R3686;H,OCH₂(3-OCF₃-Ph),Me,H,H,Pr],[R3687;H,OCH₂ (3-OCF₃-Ph),CHF₂,H,H,Pr],[R3688;H,OCH₂(3-OCF₃-Ph), CF₃,H,H,Pr],[R3689;H,OCH₂(3-OCF₃-Ph),H,H,H,Pr], [R3690;H,OCH₂(3-OCF₃-Ph),F,H,H,Bu],[R3691;H,OCH₂ (3-OCF₃-Ph),Cl,H,H,Bu],[R3692;H,OCH₂(3-OCF₃-Ph),Br, H,H,Bu],[R3693;H,OCH₂(3-OCF₃-Ph),I,H,H,Bu],[R3694; H,OCH₂(3-OCF₃-Ph),Me,H,H,Bu],[R3695;H,OCH₂(3-OCF₃-Ph),CHF₂,H,H,Bu],[R3696;H,OCH₂(3-OCF₃-Ph), CF₃,H,H,Bu],[R3697;H,OCH₂(3-OCF₃-Ph),H,H,H,Bu], [R3698;H,OCH₂(3-OCF₃-Ph),F,H,H,c-Pr],[R3699;H,OCH₂ (3-OCF₃-Ph),Cl,H,H,c-Pr],[R3700;H,OCH₂(3-OCF₃-Ph), Br,H,H,c-Pr],[R3701;H,OCH₂(3-OCF₃-Ph),I,H,H,c-Pr], [R3702;H,OCH₂(3-OCF₃-Ph),Me,H,H,c-Pr],[R3703;H, OCH₂(3-OCF₃-Ph),CHF₂,H,H,c-Pr],[R3704;H,OCH₂(3-OCF₃-Ph),CF₃,H,H,c-Pr],[R3705;H,OCH₂(3-OCF₃-Ph),H, H,H,c-Pr],[R3706;H,OCH₂(3-OCF₃-Ph),F,H,H,CH₂CF₃], [R3707;H,OCH₂(3-OCF₃-Ph),Cl,H,H,CH₂CF₃],[R3708;H, OCH₂(3-OCF₃-Ph),Br,H,H,CH₂CF₃],[R3709;H,OCH₂(3-OCF₃-Ph),I,H,H,CH₂CF₃],[R3710;H,OCH₂(3-OCF₃-Ph), Me,H,H,CH₂CF₃],[R3711;H,OCH₂(3-OCF₃-Ph),CHF₂,H, H,CH₂CF₃],[R3712;H,OCH₂(3-OCF₃-Ph),CF₃,H,H, CH₂CF₃],[R3713;H,OCH₂(3-OCF₃-Ph),H,H,H,CH₂CF₃], [R3714;H,OCH₂(3-OCF₃-Ph),F,H,H,CH₂CHF₂],[R3715;H, OCH₂(3-OCF₃-Ph),Cl,H,H,CHCHF₂],[R3716;H,OCH₂(3-OCF₃-Ph),Br,H,H,CH₂CHF₂],[R3717;H,OCH₂(3-OCF₃-Ph),I,H,H,CH₂CHF₂],[R3718;H,OCH₂(3-OCF₃-Ph),Me,H, H,CH₂CHF₂],[R3719;H,OCH₂(3-OCF₃-Ph),CHF₂,H,H, CH₂CHF₂],[R3720;H,OCH₂(3-OCF₃-Ph),CF₃,H,H, CH₂CHF₂],[R3721;H,OCH₂(3-OCF₃-Ph),H,H,H, CH₂CHF₂],[R3722;H,OCH₂(3-OCF₃-Ph),F,H,H,CF₂CH₃], [R3723;H,OCH₂(3-OCF₃-Ph),Cl,H,H,CF₂CH₃],[R3724;H, OCH₂(3-OCF₃-Ph),Br,H,H,CF₂CH₃],[R3725;H,OCH₂(3-OCF₃-Ph),I,H,H,CF₂CH₃],[R3726;H,OCH₂(3-OCF₃-Ph), Me,H,H,CF₂CH₃],[R3727;H,OCH₂(3-OCF₃-Ph),CHF₂,H, H,CF₂CH₃],[R3728;H,OCH₂(3-OCF₃-Ph),CF₃,H,H, CF₂CH₃],[R3729;H,OCH₂(3-OCF₃-Ph),H,H,H,CF₂CH₃], [R3730;H,OCH₂(3-OCF₃-Ph),F,H,H,NMe₂],[R3731;H, OCH₂(3-OCF₃-Ph),Cl,H,H,NMe₂],[R3732;H,OCH₂(3-OCF₃-Ph),Br,H,H,NMe₂],[R3733;H,OCH₂(3-OCF₃-Ph),I, H,H,NMe₂],[R3734;H,CCH₂(3-OCF₃-Ph),Me,H,H,NMe₂], [R3735;H,OCH₂(3-OCF₃-Ph),CHF₂,H,H,NMe₂],[R3736; H,OCH₂(3-OCF₃-Ph),CF₃,H,H,NMe₂],[R3737;H,OCH₂(3-OCF₃-Ph),H,H,H,NMe₂],[R3738;H,OCH₂(3-OCF₃-Ph),F, H,H,Pyrro],[R3739;H,OCH₂(3-OCF₃-Ph),Cl,H,H,Pyrro], [R3740;H,OCH₂(3-OCF₃-Ph),Br,H,H,Pyrro],[R3741;H, OCH₂(3-OCF₃-Ph),I,H,H,Pyrro],[R3742;H,OCH₂(3-OCF₃-Ph),Me,H,H,Pyrro],[R3743;H,OCH₂(3-OCF₃-Ph),CHF₂,H, H,Pyrro],[R3744;H,OCH₂(3-OCF₃-Ph),CF₃,H,H,Pyrro], [R3745;H,OCH₂(3-OCF₃-Ph),H,H,H,Pyrro],[R3746;H, OCH₂(4-OCF₃-Ph),Cl,H,H,Me],[R3747;H,OCH₂(4-OCF₃-Ph),Br,H,H,Me],[R3748;H,OCH₂(4-OCF₃-Ph),I,H,H,Me], [R3749;H,OCH₂(4-OCF₃-Ph),Me,H,H,Me],[R3750;H, OCH₂(4-OCF₃-Ph),CHF₂,H,H,Me], [R3751;H,OCH₂(4-OCF₃-Ph),CF₃,H,H,Me],[R3752;H, OCH₂(4-OCF₃-Ph),H,H,H,Me],[R3753;H,OCH₂(4-OCF₃-Ph),F,H,H,Et],[R3754;H,OCH₂(4-OCF₃-Ph),Cl,H,H,Et], [R3755;H,OCH₂(4-OCF₃-Ph),Br,H,H,Et],[R3756;H,OCH₂ (4-OCF₃-Ph),I,H,H,Et],[R3757;H,OCH₂(4-OCF₃-Ph),Me, H,H,Et],[R3758;H,OCH₂(4-OCF₃-Ph),CHF₂,H,H,Et], [R3759;H,OCH₂(4-OCF₃-Ph),CF₃,H,H,Et],[R3760;H, OCH₂(4-OCF₃-Ph),H,H,H,Et],[R3761;H,OCH₂(4-OCF₃-Ph),F,H,H,Pr],[R3762;H,OCH₂(4-OCF₃-Ph),Cl,H,H,Pr], [R3763;H,OCH₂(4-OCF₃-Ph),Br,H,H,Pr],[R3764;H,OCH₂ (4-OCF₃-Ph),I,H,H,Pr],[R3765;H,OCH₂(4-OCF₃-Ph),Me, H,H,Pr],[R3766;H,OCH₂(4-OCF₃-Ph),CHF₂,H,H,Pr], [R3767;H,OCH₂(4-OCF₃-Ph),CF₃,H,H,Pr],[R3768;H, OCH₂(4-OCF₃-Ph),H,H,H,Pr],[R3769;H,OCH₂(4-OCF₃-Ph),F,H,H,Bu],[R3770;H,OCH₂(4-OCF₃-Ph),Cl,H,H,Bu], [R3771;H,OCH₂(4-OCF₃-Ph),Br,H,H,Bu],[R3772;H,OCH₂ (4-OCF₃-Ph),I,H,H,Bu],[R3773;H,OCH₂(4-OCF₃-Ph),Me, H,H,Bu],[R3774;H,OCH₂(4-OCF₃-Ph),CHF₂,H,H,Bu], [R3775;H,OCH₂(4-OCF₃-Ph),CF₃,H,H,Bu],[R3776;H, OCH₂(4-OCF₃-Ph),H,H,H,Bu],[R3777;H,OCH₂(4-OCF₃-Ph),F,H,H,c-Pr],[R3778;H,OCH₂(4-OCF₃-Ph),Cl,H,H,c-Pr],[R3779;H,OCH₂(4-OCF₃-Ph),Br,H,H,c-Pr],[R3780;H, OCH₂(4-OCF₃-Ph),I,H,H,c-Pr],[R3781;H,OCH₂(4-OCF₃-Ph),Me,H,H,c-Pr],[R3782;H,OCH₂(4-OCF₃-Ph),CHF₂,H, H,c-Pr],[R3783;H,OCH₂(4-OCF₃-Ph),CF₃,H,H,c-Pr], [R3784;H,OCH₂(4-OCF₃-Ph),H,H,H,c-Pr],[R3785;H, OCH₂(4-OCF₃-Ph),F,H,H,CH₂CF₃],[R3786;H,OCH₂(4-OCF₃-Ph),Cl,H,H,CH₂CF₃],[R3787;H,OCH₂(4-OCF-Ph), Br,H,H,CH₂CF₃],[R3788;H,OCH₂(4-OCF₃-Ph),I,H,H, CH₂CF₃],[R3789;H,OCH₂(4-OCF₃-Ph),Me,H,H,CH₂CF₃], [R3790;H,OCH₂(4-OCF₃-Ph),CHF₂,H,H,CH₂CF₃],[R3791; H,OCH₂(4-OCF₃-Ph),CF₃,H,H,CH₂CF₃],[R3792;H,OCH₂ (4-OCF₃-Ph),H,H,H,CH₂CF₃],[R3793;H,OCH₂(4-OCF₃-Ph),F,H,H,CH₂CHF₂],[R3794;H,OCH₂(4-OCF-Ph),Cl,H,H, CH₂CHF₂],[R3795;H,OCH₂(4-OCF-Ph),Br,H,H, CH₂CHF₂],[R3796;H,OCH₂(4-OCF-Ph),I,H,H, CH₂CHF₂],[R3797;H,OCH₂(4-OCF-Ph),Me,H,H, CH₂CHF₂],[R3798;H,OCH₂(4-OCF-Ph),CHF₂,H,H, CH₂CHF₂],[R3799;H,OCH₂(4-OCF-Ph),CF₃,H,H, CH₂CHF₂],[R3800;H,OCH₂(4-OCF-Ph),H,H,H, CH₂CHF₂],[R3801;H,OCH₂(4-OCF₃-Ph),F,H,H,CF₂CH₃], [R3802;H,OCH₂(4-OCF₃-Ph),Cl,H,H,CF₂CH₃],[R3803;H, OCH₂(4-OCF₃-Ph),Br,H,H,CF₂CH₃],[R3804;H,OCH₂(4-OCF₃-Ph),I,H,H,CF₂CH₃],[R3805;H,OCH₂(4-OCF₃-Ph),Me,H,H,CF₂CH₃],[R3806;H,OCH₂(4-OCF₃-Ph),CHF₂,H,H,CF₂CH₃],[R3807;H,OCH₂(4-OCF₃-Ph),CF₃,H,H,CF₂CH₃],[R3808;H,OCH₂(4-OCF₃-Ph),H,H,H,CF₂CH₃],[R3809;H,OCH₂(4-OCF₃-Ph),F,H,H,NMe₂,R3810;H,OCH₂(4-OCF₃-Ph),Cl,H,H,NMe₂],[R3811;H,OCH₂(4-OCF₃-Ph),Br,H,H,NMe₂],[R3812;H,OCH₂(4-OCF₃-Ph),I,H,H,NMe₂],[R3813;H,OCH₂(4-OCF₃-Ph),Me,H,H,NMe₂],[R3814;H,OCH₂(4-OCF₃-Ph),CHF₂,H,H,NMe₂],[R3815;H,OCH₂(4-OCF₃-Ph),CF₃,H,H,NMe₂],[R3816;H,OCH₂(4-OCF₃-Ph),H,H,H,NMe₂],[R3817;H,OCH₂(4-OCF₃-Ph),F,H,H,Pyrro],[R3818;H,OCH₂(4-OCF₃-Ph),Cl,H,H,Pyrro],[R3819;H,OCH₂(4-OCF₃-Ph),Br,H,H,Pyrro],[R3820;H,OCH₂(4-OCF₃-Ph),I,H,H,Pyrro],[R3821;H,OCH₂(4-OCF₃-Ph),Me,H,H,Pyrro],[R3822;H,OCH₂(4-OCF₃-Ph),CHF₂,H,H,Pyrro],[R3823;H,OCH₂(4-OCF₃-Ph),CF₃,H,H,Pyrro],[R3824;H,OCH₂(4-OCF₃-Ph),H,H,H,Pyrro],[R3825;H,OCH₂(3-F-4-Br-Ph),Cl,H,H,Me],[R3826;H,OCH₂(3-F-4-Br-Ph),Br,H,H,Me],[R3827;H,OCH₂(3-F-4-Br-Ph),I,H,H,Me],[R3828;H,OCH₂(3-F-4-Br-Ph),Me,H,H,Me],[R3829;H,OCH₂(3-F-4-Br-Ph),CHF₂,H,H,Me],[R3830;H,OCH₂(3-F-4-Br-Ph),CF₃,H,H,Me],[R3831;H,OCH₂(3-F-4-Br-Ph),H,H,H,Me],[R3832;H,OCH₂(3-F-4-Br-Ph),F,H,H,Et],[R3833;H,OCH₂(3-F-4-Br-Ph),Cl,H,H,Et],[R3834;H,OCH₂(3-F-4-Br-Ph),Br,H,H,Et],[R3835;H,OCH₂(3-F-4-Br-Ph),I,H,H,Et],[R3836;H,OCH₂(3-F-4-Br-Ph),Me,H,H,Et],[R3837;H,OCH₂(3-F-4-Br-Ph),CHF₂,H,H,Et],[R3838;H,OCH₂(3-F-4-Br-Ph),CF₃,H,H,Et],[R3839;H,OCH₂(3-F-4-Br-Ph),H,H,H,Et],[R3840;H,OCH₂(3-F-4-Br-Ph),F,H,H,Pr],[R3841;H,OCH₂(3-F-4-Br-Ph),Cl,H,H,Pr],[R3842;H,OCH₂(3-F-4-Br-Ph),Br,H,H,Pr],[R3843;H,OCH₂(3-F-4-Br-Ph),I,H,H,Pr],[R3844;H,OCH₂(3-F-4-Br-Ph),Me,H,H,Pr],[R3845;H,OCH₂(3-F-4-Br-Ph),CHF₂,H,H,Pr],[R3846;H,OCH₂(3-F-4-Br-Ph),CF₃,H,H,Pr],[R3847;H,OCH₂(3-F-4-Br-Ph),H,H,H,Pr],[R3848;H,OCH₂(3-F-4-Br-Ph),F,H,H,Bu],[R3849;H,OCH₂(3-F-4-Br-Ph),Cl,H,H,Bu],[R3850;H,OCH₂(3-F-4-Br-Ph),Br,H,H,Bu],[R3851;H,OCH₂(3-F-4-Br-Ph),I,H,H,Bu],[R3852;H,OCH₂(3-F-4-Br-Ph),Me,H,H,Bu],[R3853;H,OCH₂(3-F-4-Br-Ph),CHF₂,H,H,Bu],[R3854;H,OCH₂(3-F-4-Br-Ph),CF₃,H,H,Bu],[R3855;H,OCH₂(3-F-4-Br-Ph),H,H,H,Bu],[R3856;H,OCH₂(3-F-4-Br-Ph),F,H,H,c-Pr],[R3857;H,OCH₂(3-F-4-Br-Ph),Cl,H,H,c-Pr],[R3858;H,OCH₂(3-F-4-Br-Ph),Br,H,H,c-Pr],[R3859;H,OCH₂(3-F-4-Br-Ph),I,H,H,c-Pr],[R3860;H,OCH₂(3-F-4-Br-Ph),Me,H,H,c-Pr],[R3861;H,OCH₂(3-F-4-Br-Ph),CHF₂,H,H,c-Pr],[R3862;H,OCH₂(3-F-4-Br-Ph),CF₃,H,H,c-Pr],[R3863;H,OCH₂(3-F-4-Br-Ph),H,H,H,c-Pr],[R3864;H,OCH₂(3-F-4-Br-Ph),F,H,H,CH₂CF₃],[R3865;H,OCH₂(3-F-4-Br-Ph),Cl,H,H,CH₂CF₃],[R3866;H,OCH₂(3-F-4-Br-Ph),Br,H,H,CH₂CF₃],[R3867;H,OCH₂(3-F-4-Br-Ph),I,H,H,CH₂CF₃],[R3868;H,OCH₂(3-F-4-Br-Ph),Me,H,H,CH₂CF₃],[R3869;H,OCH₂(3-F-4-Br-Ph),CHF₂,H,H,CH₂CF₃],[R3870;H,OCH₂(3-F-4-Br-Ph),CF₃,H,H,CH₂CF₃],[R3871;H,OCH₂(3-F-4-Br-Ph),H,H,H,CH₂CF₃],[R3872;H,OCH₂(3-F-4-Br-Ph),F,H,H,CH₂CHF₂],[R3873;H,OCH₂(3-F-4-Br-Ph),Cl,H,H,CH₂CHF₂],[R3874;H,OCH₂(3-F-4-Br-Ph),Br,H,H,CH₂CHF₂],[R3875;H,OCH₂(3-F-4-Br-Ph),I,H,H,CH₂CHF₂],[R3876;H,OCH₂(3-F-4-Br-Ph),Me,H,H,CH₂CHF₂],[R3877;H,OCH₂(3-F-4-Br-Ph),CHF₂,H,H,CH₂CHF₂],[R3878;H,OCH₂(3-F-4-Br-Ph),CF₃,H,H,CH₂CHF₂],[R3879;H,OCH₂(3-F-4-Br-Ph),H,H,H,CH₂CHF₂],[R3880;H,OCH₂(3-F-4-Br-Ph),F,H,H,CF₂CH₃],[R3881;H,OCH₂(3-F-4-Br-Ph),Cl,H,H,CF₂CH₃],[R3882;H,OCH₂(3-F-4-Br-Ph),Br,H,H,CF₂CH₃],[R3883;H,OCH₂(3-F-4-Br-Ph),I,H,H,CF₂CH₃],[R3884;H,OCH₂(3-F-4-Br-Ph),Me,H,H,CF₂CH₃],[R3885;H,OCH₂(3-F-4-Br-Ph),CHF₂,H,CF₂CH₃],[R3886;H,OCH₂(3-F-4-Br-Ph),CF₃,H,H,CF₂CH₃],[R3887;H,OCH₂(3-F-4-Br-Ph),H,H,H,CF₂CH₃],[R3888;H,OCH₂(3-F-4-Br-Ph),F,H,H,NMe₂],[R3889;H,OCH₂(3-F-4-Br-Ph),Cl,H,H,NMe₂],[R3890;H,OCH₂(3-F-4-Br-Ph),Br,H,H,NMe₂],[R3891;H,OCH₂(3-F-4-Br-Ph),I,H,H,NMe₂],[R3892;H,OCH₂(3-F-4-Br-Ph),Me,H,H,NMe₂],[R3893;H,OCH₂(3-F-4-Br-Ph),CHF₂,H,H,NMe₂],[R3894;H,OCH₂(3-F-4-Br-Ph),CF₃,H,H,NMe₂],[R3895;H,OCH₂(3-F-4-Br-Ph),F,H,H,NMe₂],[R3896;H,OCH₂(3-F-4-Br-Ph),F,H,H,Pyrro],[R3897;H,OCH₂(3-F-4-Br-Ph),Cl,H,H,Pyrro],[R3898;H,OCH₂(3-F-4-Br-Ph),Br,H,H,Pyrro],[R3899;H,OCH₂(3-F-4-Br-Ph),I,H,H,Pyrro],[R3900;H,OCH₂(3-F-4-Br-Ph),Me,H,H,Pyrro],[R3901;H,OCH₂(3-F-4-Br-Ph),CHF₂,H,H,Pyrro],[R3902;H,OCH₂(3-F-4-Br-Ph),CF₃,H,H,Pyrro],[R3903;H,OCH₂(3-F-4-Br-Ph),H,H,H,Pyrro],[R3904;H,OCH₂(3-F-4-Br-Ph),Cl,H,H,Me],[R3905;H,OCH₂(3-F-4-Br-Ph),Br,H,H,Me],[R3906;H,OCH₂(3-F-4-Br-Ph),I,H,H,Me],[R3907;H,OCH₂(3-F-4-Br-Ph),Me,H,H,Me],[R3908;H,OCH₂(3-F-4-Br-Ph),CHF₂,H,H,Me],[R3909;H,OCH₂(3-F-4-Br-Ph),CF₃,H,H,Me],[R3910;H,OCH₂(3-F-4-Br-Ph),H,H,H,Me],[R3911;H,OCH₂(3-F-4-Br-Ph),F,H,H,Et],[R3912;H,OCH₂(3-F-4-Br-Ph),Cl,H,H,Et],[R3913;H,OCH₂(3-F-4-Br-Ph),Br,H,H,Et],[R3914;H,OCH₂(3-F-4-Br-Ph),I,H,H,Et],[R3915;H,OCH₂(3-F-4-Br-Ph),Me,H,H,Et],[R3916;H,OCH₂(3-F-4-Br-Ph),CHF₂,H,H,Et],[R3917;H,OCH₂(3-F-4-Br-Ph),CF₃,H,H,Et],[R3918;H,OCH₂(3-F-4-Br-Ph),H,H,H,Et],[R3919;H,OCH₂(3-F-4-Br-Ph),F,H,H,Pr],[R3920;H,OCH₂(3-F-4-Br-Ph),Cl,H,H,Pr],[R3921;H,OCH₂(3-F-4-Br-Ph),Br,H,H,Pr],[R3922;H,OCH₂(3-F-4-Br-Ph),I,H,H,Pr],[R3923;H,OCH₂(3-F-4-Br-Ph),Me,H,H,Pr],[R3924;H,OCH₂(3-F-4-Br-Ph),CHF₂,H,H,Pr],[R3925;H,OCH₂(3-F-4-Br-Ph),CF₃,H,H,Pr],[R3926;H,OCH₂(3-F-4-Br-Ph),H,H,H,Pr],[R3927;H,OCH₂(3-F-4-Br-Ph),F,H,H,Bu],[R3928;H,OCH₂(3-F-4-Br-Ph),Cl,H,H,Bu],[R3929;H,OCH₂(3-F-4-Br-Ph),Br,H,H,Bu],[R3930;H,OCH₂(3-F-4-Br-Ph),I,H,H,Bu],[R3931;H,OCH₂(3-F-4-Br-Ph),Me,H,H,Bu],[R3932;H,OCH₂(3-F-4-Br-Ph),CHF₃,H,H,Bu],[R3933;H,OCH₂(3-F-4-Br-Ph),CF₃,H,H,Bu],[R3934;H,OCH₂(3-F-4-Br-Ph),H,H,H,Bu],[R3935;H,OCH₂(3-F-4-Br-Ph),F,H,H,c-Pr],[R3936;H,OCH₂(3-F-4-Br-Ph),Cl,H,H,c-Pr],[R3937;H,OCH₂(3-F-4-Br-Ph),Br,H,H,c-Pr],[R3938;H,OCH₂(3-F-4-Br-Ph),I,H,H,c-Pr],[R3939;H,OCH₂(3-F-4-Br-Ph),Me,H,c-Pr],[R3940;H,CH₂(3-F-4-Br-Ph),CHF₂,H,H,c-Pr],[R3941;H,OCH₂(3-F-4-Br-Ph),CF₃,H,H,c-Pr],[R3942;H,OCH₂(3-F-4-Br-Ph),N,H,H,c-Pr],[R3943;H,OCH₂(3-F-4-Br-Ph),F,H,H,CH₂CF₃],[R3944;H,OCH₂(3-F-4-Br-Ph),Cl,H,H,CH₂CF₃],[R3945;H,OCH₂(3-F-4-Br-Ph),Br,H,H,CH₂CF₃],[R3946;H,OCH₂(3-F-4-Br-Ph),I,H,H,CH₂CF₃],[R3947;H,OCH₂(3-F-4-Br-Ph),Me,H,H,CCH₂CF₃],[R3948;H,OCH₂(3-F-4-Br-Ph),CHF₂,H,H,CH₂CF₃],[R3949;H,OCH₂(3-F-4-Br-Ph),CF₃,H,H,CH₂CF₃],[R3950;H,OCH₂(3-F-4-Br-Ph),H,H,H,CH₂CF₃],[R3951;H,OCH₂(3-F-4-Br-Ph),F,H,H,CH₂CHF₂], [R3952;H,OCH₂(3-F-4-Br-Ph),Cl,H,H,CH₂CHF₂],[R3953;H,OCH₂(3-F-4-Br-Ph),Br,H,H,CH₂CHF₂],[R3954;H,OCH₂(3-F-4-Br-Ph),I,H,H,CH₂CHF₂],[R3955;H,OCH₂(3-F-4-Br-Ph),Me,H,H,CH₂CHF₂],[R3956;H,OCH₂(3-F-4-Br-Ph),CHF₂,H,H,CH₂CHF₂],[R3957;H,OCH₂(3-F-4-Br-Ph),CF₃,H,H,CH₂CHF₂],[R3958;H,OCH₂(3-F-4-Br-Ph),H,H,H,CH₂CHF₂],[R3959;H,OCH₂(3-F-4-Br-Ph),F,H,H,CF₂CH₃],[R3960;H,OCH₂(3-F-4-Br-Ph),Cl,H,H,CF₂CH₃],[R3961;H,OCH₂(3-F-4-Br-Ph),Br,H,H,CF₂CH₃],[R3962;H,OCH₂(3-F-4-Br-Ph),I,H,H,CF₂CH₃],[R3963;H,OCH₂(3-F-4-Br-Ph),Me,H,H,CF₂CH₃],[R3964;H,OCH₂(3-F-4-Br-Ph),CHF₂,H,H,CF₂CH₃],[R3965;H,OCH₂(3-F-4-Br-Ph),CF₃,H,H,CF₂CH],[R3966;H,OCH₂(3-F-4-Br-Ph),H,H,H,CF₂CH₃],[R3967;H,OCH₂(3-F-4-Br-Ph),F,H,H,NMe₂],[R3968;H, OCH₂(3-F-4-Br-Ph),Cl,H,H,NMe₂],[R3969;H,OCH₂(3-F-4-Br-Ph),Br,H,H,NMe₂],[R3970;H,OCH₂(3-F-4-Br-Ph),I,H,H,NMe₂],[R3971;H,OCH₂(3-F-4-Br-Ph),Me,H,H,NMe₂],[R3972;H,OCH₂(3-F-4-Br-Ph),CHF₂,H,H,NMe₂],[R3973;H,OCH₂(3-F-4-Br-Ph),CF₃,H,H,NMe₂],[R3974;H,OCH₂(3-F-4-Br-Ph),H,H,H,NMe₂],[R3975;H,OCH₂(3-F-4-Br-Ph),F,H,H,Pyrro],[R3976;H,OCH₂(3-F-4-Br-Ph),Cl,H,H,Pyrro],[R3977;H,OCH₂(3-F-4-Br-Ph),Br,H,H,Pyrro],[R3978;H,OCH₂(3-F-4-Br-Ph),I,H,H,Pyrro],[R3979;H,OCH₂(3-F-4-Br-Ph),Me,H,H,Pyrro],[R3980;H,OCH₂(3-F-4-Br-Ph),CHF₂,H,H,Pyrro],[R3981;H,OCH₂(3-F-4-Br-Ph),CF₃,H,H,Pyrro],[R3982;H,OCH₂(3-F-4-Br-Ph),H,H,H,Pyrro],[R3983;H,OCH₂(4-Br-Ph),Cl,H,H,Me],[R3984;H,OCH₂(4-Br-Ph),Br,H,H,Me],[R3985;H,OCH₂(4-Br-Ph),I,H,H,Me],[R3986;H,OCH₂(4-Br-Ph),Me,H,H,Me],[R3987;H,OCH₂(4-Br-Ph),CHF₂,H,H,Me],[R3988;H,OCH₂(4-Br-Ph),CF₃,H,H,Me],[R3989;H,OCH₂(4-Br-Ph),H,H,H,Me],[R3990;H,OCH₂(4-Br-Ph),F,H,H,Et],[R3991;H,OCH₂(4-Br-Ph),Cl,H,H,Et],[R3992;H,OCH₂(4-Br-Ph),Br,H,H,Et],[R3993;H,OCH₂(4-Br-Ph),I,H,H,Et],[R3994;H,OCH₂(4-Br-Ph),Me,H,H,Et],[R3995;H,OCH₂(4-Br-Ph),CHF₂,H,H,Et],[R3996;H,OCH₂(4-Br-Ph),CF₃,H,H,Et],[R3997;H,OCH₂(4-Br-Ph),H,H,H,Et],[R3998;H,OCH₂(4-Br-Ph),F,H,H,Pr],[R3999;H,OCH₂(4-Br-Ph),Cl,H,H,Pr],[R4000;H,OCH₂(4-Br-Ph),Br,H,H,Pr],[R4001;H,OCH₂(4-Br-Ph),I,H,H,Pr],[R4002;H,OCH₂(4-Br-Ph),Me,H,H,Pr],[R4003;H,OCH₂(4-Br-Ph),CHF₂,H,H,Pr],[R4004;H,OCH₂(4-Br-Ph),CF₃,H,H,Pr],[R4005;H,OCH₂(4-Br-Ph),H,H,H,Pr],[R4006;H,OCH₂(4-Br-Ph),F,H,H,Bu],[R4007;H,OCH₂(4-Br-Ph),Cl,H,H,Bu],[R4008;H,OCH₂(4-Br-Ph),Br,H,H,Bu],[R4009;H,OCH₂(4-Br-Ph),I,H,H,Bu],[R4010;H,OCH₂(4-Br-Ph),Me,H,H,Bu],[R4011;H,OCH₂(4-Br-Ph),CHF₂,H,H,Bu],[R4012;H,OCH₂(4-Br-Ph),CF₃,H,H,Bu],[R4013;H,OCH₂(4-Br-Ph),H,H,H,Bu],[R4014;H,OCH₂(4-Br-Ph),F,H,H,c-Pr],[R4015;H,OCH₂(4-Br-Ph),Cl,H,H,c-Pr],[R4016;H,OCH₂(4-Br-Ph),Br,H,H,c-Pr],[R4017;H,OCH₂(4-Br-Ph),I,H,H,c-Pr],[R4018;H,OCH₂(4-Br-Ph),Me,H,H,c-Pr],[R4019;H,CCH₂(4-Br-Ph),CHF₂,H,H,c-Pr],[R4020;H,OCH₂(4-Br-Ph),CF₃,H,H,c-Pr],[R4021;H,OCH₂(4-Br-Ph),H,H,H,c-Pr],[R4022;H,OCH₂(4-Br-Ph),F,H,H,CH₂CF₃],[R4023;H,OCH₂(4-Br-Ph),Cl,H,H,CH₂CF₃],[R4024;H,OCH₂(4-Br-Ph),Br,H,H,CH₂CF₃],[R4025;H,OCH₂(4-Br-Ph),I,H,H,CH₂CF₃],[R4026;H,OCH₂(4-Br-Ph),Me,H,H,CH₂CF₃],[R4027;H,OCH₂(4-Br-Ph),CHF₂,H,H,CH₂CF₃],[R4028;H,OCH₂(4-Br-Ph),CF₃,H,H,CH₂CF₃],[R4029;H,OCH₂(4-Br-Ph),H,H,H,CH₂CF₃],[R4030;H,OCH₂(4-Br-Ph),F,H,H,CH₂CHF₂],[R4031;H,OCH₂(4-Br-Ph),Cl,H,H,CH₂CHF₂],[R4032;H,OCH₂(4-Br-Ph),Br,H,H,CH₂CHF₂],[R4033;H,OCH₂(4-Br-Ph),I,H,H,CH₂CHF₂],[R4034;H,OCH₂(4-Br-Ph),Me,H,H,CH₂CHF₂],[R4035;H,OCH₂(4-Br-Ph),CHF₂,H,H,CH₂CHF₂],[R4036;H,OCH₂(4-Br-Ph),CF₃,H,H,CH₂CHF₂],[R4037;H,OCH₂(4-Br-Ph),H,H,H,CH₂CHF₂],[R4038;H,OCH₂(4-Br-Ph),F,H,H,CF₂CH₃],[R4039;H,OCH₂(4-Br-Ph),Cl,H,H,CF₂CH₃],[R4040;H,OCH₂(4-Br-Ph),Br,H,H,CF₂CH₃],[R4041;H,OCH₂(4-Br-Ph),I,H,H,CF₂CH₃],[R4042;H,OCH₂(4-Br-Ph),Me,H,H,CF₂CH₃],[R4043;H,OCH₂(4-Br-Ph),CHF₂,H,H,CF₂CH₃],[R4044;H,OCH₂(4-Br-Ph),CF₃,H,H,CF₂CH₃],[R4045;H,OCH₂(4-Br-Ph),H,H,H,CF₂CH₃],[R4046;H,OCH₂(4-Br-Ph),F,H,H,NMe₂],[R4047;H,OCH₂(4-Br-Ph),Cl,H,H,NMe₂],[R4048;H,OCH₂(4-Br-Ph),Br,H,FH,NMe₂],[R4049;H,OCH₂(4-Br-Ph),I,H,H,NMe₂],[R4050;H,OCH₂(4-Br-Ph),Me,H,H,NMe₂],[R4051;H,OCH₂(4-Br-Ph),CHF₂,H,H,NMe₂],[R4052;H,OCH₂(4-Br-Ph),CF₃,H,H,NMe₂],[R4053;H,OCH₂(4-Br-Ph),H,H,H,NMe₂],[R4054;H,OCH₂(4-Br-Ph),F,H,H,Pyrro],[R4055;H,OCH₂(4-Br-Ph),Cl,H,H,Pyrro],[R4056;H,OCH₂(4-Br-Ph),Br,H,H,Pyrro],[R4057;H,OCH₂(4-Br-Ph),I,H,H,Pyrro],[R4058;H,OCH₂(4-Br-Ph),Me,H,H,Pyrro],[R4059;H,OCH₂(4-Br-Ph),CHF₂,H,H,Pyrro],[R4060;H,OCH₂(4-Br-Ph),CF₃,H,H,Pyrro],[R4061;H,OCH₂(4-Br-Ph),H,H,H,Pyrro],[R4062;H,OCH₂(3-Br-Ph),Cl,H,H,Me],[R4063;H,OCH₂(3-Br-Ph),Br,H,H,Me],[R4064;H,OCH₂(3-Br-Ph),I,H,H,Me],[R4065;H,OCH₂(3-Br-Ph),Me,H,H,Me],[R4066;H,OCH₂(3-Br-Ph),CHF₂,H,H,Me],[R4067;H,OCH₂(3-Br-Ph),CF₃,H,H,Me],[R4068;H,OCH₂(3-Br-Ph),H,H,H,Me],[R4069;H,OCH₂(3-Br-Ph),F,H,H,Et],[R4070;H,OCH₂(3-Br-Ph),Cl,H,H,Et],[R4071;H,OCH₂(3-Br-Ph),Br,H,H,Et],[R4072;H,OCH₂(3-Br-Ph),I,H,H,Et],[R4073;H,OCH₂(3-Br-Ph),Me,H,H,Et],[R4074;H,OCH₂(3-Br-Ph),CHF₂,H,H,Et],[R4075;H,OCH₂(3-Br-Ph),CF₃,H,H,Et],[R4076;H,OCH₂(3-Br-Ph),H,H,H,Et],[R4077;H,OCH₂(3-Br-Ph),F,H,H,Pr],[R4078;H,OCH₂(3-Br-Ph),Cl,H,H,Pr],[R4079;H,OCH₂(3-Br-Ph),Br,H,H,Pr],[R4080;H,OCH₂(3-Br-Ph),I,H,H,Pr],[R4081;H,OCH₂(3-Br-Ph),Me,H,H,Pr],[R4082;H,OCH₂(3-Br-Ph),CHF₂,H,H,Pr],[R4083;H,OCH₂(3-Br-Ph),CF₃,H,H,Pr],[R4084;H,OCH₂(3-Br-Ph),H,H,H,Pr],[R4085;H,OCH₂(3-Br-Ph),F,H,H,Bu],[R4086;H,OCH₂(3-Br-Ph),Cl,H,H,Bu],[R4087;H,OCH₂(3-Br-Ph),Br,H,H,Bu],[R4088;H,OCH₂(3-Br-Ph),I,H,H,Bu],[R4089;H,OCH₂(3-Br-Ph),Me,H,H,Bu],[R4090;H,OCH₂(3-Br-Ph),CHF₂,H,H,Bu],[R4091;H,OCH₂(3-Br-Ph),CF₃,H,H,Bu],[R4092;H,OCH₂(3-Br-Ph),H,H,H,Bu],[R4093;H,OCH₂(3-Br-Ph),F,H,H,c-Pr],[R4094;H,OCH₂(3-Br-Ph),Cl,H,H,c-Pr],[R4095;H,OCH₂(3-Br-Ph),Br,H,H,c-Pr],[R4096;H,OCH₂(3-Br-Ph),I,H,H,c-Pr],[R4097;H,OCH₂(3-Br-Ph),Me,H,H,c-Pr],[R4098;H,OCH₂(3-Br-Ph),CHF₂,H,H,c-Pr],[R4099;H,OCH₂(3-Br-Ph),CF₃,H,H,c-Pr],[R4100;H,OCH₂(3-Br-Ph),H,H,H,c-Pr],[R4101;H,OCH₂(3-Br-Ph),F,H,H,CH₂CF₃],[R4102;H,OCH₂(3-Br-Ph),Cl,H,H,CH₂CF₃],[R4103;H,OCH₂(3-Br-Ph),Br,H,H,CH₂CF₃],[R4104;H,OCH₂(3-Br-Ph),I,H,H,CH₂CF₃],[R4105;H,OCH₂(3-Br-Ph),Me,H,H,CH₂CF₃],[R4106;H,OCH₂(3-Br-Ph),CHF₂,H,H,CH₂CF₃],[R4107;H,OCH₂(3-Br-Ph),CF₃,H,H,CH₂CF₃],[R4108;H,OCH₂(3-Br-Ph),H,H,H,CH₂CF₃],[R4109;H,OCH₂(3-Br-Ph),F,H,H,CH₂CHF₂],[R4110;H,OCH₂(3-Br-Ph),Cl,H,H,CH₂CHF₂],[R4111;H,OCH₂(3-Br-Ph),Br,H,H,CH₂CHF₂],[R4112;H,OCH₂(3-Br-Ph),I,H,H,CH₂CHF₂],[R4113;H,OCH₂(3-Br-Ph),Me,H,H,CH₂CHF₂],[R4114;H,OCH₂(3-Br-Ph),CHF₂,H,H,CH₂CHF₂],[R4115;H,OCH₂(3-Br-Ph),CF₃,H,H,CH₂CHF₂],[R4116;H,OCH₂(3-Br-Ph),H,H,H,CH₂CHF₂],[R4117;H,OCH₂(3-Br-Ph),F,H,H,CF₂CH₃],[R4118;H,OCH₂(3-Br-Ph),Cl,H,H,CF₂CH₃],[R4119;H,OCH₂(3-Br-Ph),Br,H,H,CF₂CH₃],[R4120;H,OCH₂(3-Br-Ph),I,H,H,CF₂CH₃],[R4121;H,OCH₂(3-Br-Ph),Me,H,H,CF₂CH₃],[R4122;H,OCH₂(3-Br-Ph),CHF₂,H,H,CF₂CH₃],[R4123;H,OCH₂(3-Br-Ph),CF₃,H,H,CF₂CH₃],[R4124;H,OCH₂(3-Br-Ph),H,H,H,CF₂CH₃],[R4125;H,OCH₂(3-Br-Ph),F,H,H,NMe₂],[R4126;H,OCH₂(3-Br-Ph),Cl,H,H,NMe₂],[R4127;H,OCH₂(3-Br-Ph),Br,H,H,NMe₂],[R4128;H,OCH₂(3-Br-Ph),I,H,H,NMe₂],[R4129;H,OCH₂(3-Br-Ph),Me,H,H,NMe₂],[R4130;H,OCH₂(3-Br-Ph),CHF₂,H,H,NMe₂],[R4131;H,OCH₂(3-Br-Ph),CF₃,H,H,NMe₂],[R4132;H,OCH₂(3-Br-Ph),H,H,H,NMe₂],[R4133;H,OCH₂(3-Br-Ph),F,H,H,Pyrro],[R4134;H,OCH₂(3-Br-Ph),Cl,H,H,Pyrro],[R4135;H,OCH₂(3-Br-Ph),Br,H,H,Pyrro],[R4136;H,OCH₂(3-Br-Ph),I,H,H,Pyrro],[R4137;H,OCH₂(3-Br-Ph),Me,H,H,Pyrro],[R4138;H,OCH₂(3-Br-Ph),CHF₂,H,H,Pyrro],[R4139;H,OCH₂(3-Br-Ph),CF₃,F,H,Pyrro],[R4140;H,OCH₂(3-Br-Ph),H,H,H,Pyrro],[R4141;H,OCH₂(2-Br-Ph),Cl,H,H,Me],[R4142;H,OCH₂(2-Br-Ph),Br,H,H,Me],[R4143;H,OCH₂(2-Br-Ph),I,H,H,Me],[R4144;H,OCH₂(2-Br-Ph),Me,H,H,Me],[R4145;H,OCH₂(2-Br-Ph),CHF₂,H,H,Me],[R4146;H,OCH₂(2-Br-Ph),CF₃,H,H,Me],[R4147;H, OCH₂(2-Br-Ph),H,H,H,Me],[R4148;H,OCH₂(2-Br-Ph),F, H,H,Et],[R4149;H,OCH₂(2-Br-Ph),Cl,H,H,Et],[R4150;H, OCH₂(2-Br-Ph),Br,H,H,Et],[R4151;H,OCH₂(2-Br-Ph),I,H, H,Et],[R4152;H,OCH₂(2-Br-Ph),Me,H,H,Et],[R4153;H, OCH₂(2-Br-Ph),CHF₂,H,H,Et],[R4154;H,OCH₂(2-Br-Ph), CF₃,H,H,Et],[R4155;H,OCH₂(2-Br-Ph),H,H,H,Et],[R4156; H,OCH₂(2-Br-Ph),F,H,H,Pr],[R4157;H,OCH₂(2-Br-Ph),Cl, H,H,Pr],[R4158;H,OCH₂(2-Br-Ph),Br,H,H,Pr],[R4159;H, OCH₂(2-Br-Ph),I,H,H,Pr],[R4160;H,OCH₂(2-Br-Ph),Me, H,H,Pr],[R4161;H,OCH₂(2-Br-Ph),CHF₂,H,H,Pr],[R4162; H,OCH₂(2-Br-Ph),CF₃,H,H,Pr],[R4163;H,OCH₂(2-Br-Ph), H,H,H,Pr],[R4164;H,OCH₂(2-Br-Ph),F,H,H,Bu],[R4165;H, OCH₂(2-Br-Ph),Cl,H,H,Bu],[R4166;H,OCH₂(2-Br-Ph),Br, H,H,Bu],[R4167;H,OCH₂(2-Br-Ph),I,H,H,Bu],[R4168;H, OCH₂(2-Br-Ph),Me,H,H,Bu],[R4169;H,OCH₂(2-Br-Ph), CHF₂,H,H,Bu],[R4170;H,OCH₂(2-Br-Ph),CF₃,H,H,Bu], [R4171;H,OCH₂(2-Br-Ph),H,H,H,Bu],[R4172;H,OCH₂(2-Br-Ph),F,H,H,c-Pr],[R4173;H,OCH₂(2-Br-Ph),Cl,H,H,c-Pr],[R4174;H,OCH₂(2-Br-Ph),Br,H,H,c-Pr],[R4175;H, OCH₂(2-Br-Ph),I,H,H,c-Pr],[R4176;H,OCH₂(2-Br-Ph),Me, H,H,c-Pr],[R4177;H,OCH₂(2-Br-Ph),CHF₂,H,H,c-Pr], [R4178;H,OCH₂(2-Br-Ph),CF₃,H,H,c-Pr],[R4179;H,OCH₂ (2-Br-Ph),H,H,H,c-Pr],[R4180;H,OCH₂(2-Br-Ph),F,H,H, CH₂CF₃],[R4181;H,OCH₂ (2-Br-Ph),Cl,H,H,CH₂CF₃], [R4182;H,OCH₂ (2-Br-Ph),Br,H,H,CH₂CF₃],[R4183;H, OCH₂(2-Br-Ph),I,H,H,CH₂CF₃],[R4184;H,OCH₂(2-Br-Ph), Me,H,H,CH₂CF₃],[R4185;H,OCH₂(2-Br-Ph),CHF₂,H,H, CH₂CF₃],[R4186;H,OCH₂(2-Br-Ph),CF₃,H,H,CH₂CF₃], [R4187;H,OCH₂(2-Br-Ph),H,H,H,CH₂CF₃],[R4188;H, OCH₂ (2-Br-Ph),F,H,H,CH₂CHF₂],[R4189;H,OCH₂(2-Br-Ph),Cl,H,H,CH₂CHF₂],[R4190;H,OCH₂(2-Br-Ph),Br,H,H, CH₂CHF₂],[R4191;H,OCH₂(2-Br-Ph),I,H,H,CH₂CHF₂], [R4192;H,OCH₂(2-Br-Ph),Me,H,H,CH₂CHF₂],[R4193;H, OCH₂(2-Br-Ph),CHF₂,H,H,CH₂CHF₂],[R4194;H,OCH₂ (2-Br-Ph),CF₃,H,H,CH₂CHF₂],[R4195;H,OCH₂ (2-Br-Ph), H,H,H,CH₂CHF₂],[R4196;H,OCH₂(2-Br-Ph),F,H,H, CF₂CH₃],[R4197;H,OCH₂(2-Br-Ph),Cl,H,H,CF₂CH₃], [R4198;H,OCH₂(2-Br-Ph),Br,H,H,CF₂CH],[R4199;H, OCH₂ (2-Br-Ph),I,H,H,CF₂CH₃],[R4200;H,OCH₂(2-Br-Ph),Me,H,H,CF₂CH₃], [R4201;H,OCH₂(2-Br-Ph),CHF₂,H,H,CF₂CH],[R4202;H, OCH₂(2-Br-Ph),CF₃,H,H,CF₂CH₃],[R4203;H,OCH₂(2-Br-Ph),H,H,H,CF₂CH₃],[R4204;H,OCH₂(2-Br-Ph),F,H,H, NMe₂],[R4205;H,OCH₂(2-Br-Ph),Cl,H,H,NMe₂],[R4206; H,OCH₂(2-Br-Ph),Br,H,H,NMe₂],[R4207;H,OCH₂(2-Br-Ph),I,H,H,NMe₂],[R4208;H,OCH₂(2-Br-Ph),Me,H,H, NMe₂],[R4209;H,OCH₂(2-Br-Ph),CHF₂,H,H,NMe₂], [R4210;H,OCH₂(2-Br-Ph),CF₃,H,H,NMe₂],[R4211;H, OCH₂(2-Br-Ph),H,H,H,NMe₂],[R4212;H,OCH₂(2-Br-Ph), F,H,H,Pyrro],[R4213;H,OCH₂(2-Br-Ph),Cl,H,H,Pyrro], [R4214;H,OCH₂(2-Br-Ph),Br,H,H,Pyrro],[R4215;H,OCH₂ (2-Br-Ph),I,H,H,Pyrro],[R4216;H,OCH₂(2-Br-Ph),Me,H,H, Pyrro],[R4217;H,OCH₂(2-Br-Ph),CHF₂,H,H,Pyrro], [R4218;H,OCH₂(2-Br-Ph),CF₃,H,H,Pyrro],[R4219;H, OCH₂(2-Br-Ph),H,H,H,Pyrro],[R4220;H,OCH₂(3-Br-4-Br-Ph),Cl,H,H,Me],[R4221;H,OCH₂(3-Br-4-Br-Ph),Br,H,H, Me],[R4222;H,OCH₂(3-Br-4-Br-Ph),I,H,H,Me],[R4223;H, OCH₂(3-Br-4-Br-Ph),Me,H,H,Me],[R4224;H,OCH₂(3-Br-4-Br-Ph),CHF₂,H,H,Me],[R4225;H,OCH₂(3-Br-4-Br-Ph), CF₃,H,H,Me],[R4226;H,OCH₂(3-Br-4-Br-Ph),H,H,H,Me], [R4227;H,OCH₂(3-Br-4-Br-Ph),F,H,H,Et],[R4228;H,OCH₂ (3-Br-4-Br-Ph),Cl,H,H,Et],[R4229;H,OCH₂(3-Br-4-Br-Ph), Br,H,H,Et],[R4230;H,OCH₂(3-Br-4-Br-Ph),I,H,H,Et], [R4231;H,OCH₂(3-Br-4-Br-Ph),Me,H,H,Et],[R4232;H, OCH₂(3-Br-4-Br-Ph),CHF₂,H,H,Et],[R4233;H,OCH₂(3-Br-4-Br-Ph),CF₃,H,H,Et],[R4234;H,OCH₂(3-Br-4-Br-Ph),H, H,H,Et],[R4235;H,OCH₂(3-Br-4-Br-Ph),F,H,H,Pr],[R4236; H,OCH₂(3-Br-4-Br-Ph),Cl,H,H,Pr],[R4237;H,OCH₂(3-Br-4-Br-Ph),Br,H,H,Pr],[R4238;H,OCH₂(3-Br-4-Br-Ph),I,H,H, Pr],[R4239;H,OCH₂(3-Br-4-Br-Ph),Me,H,H,Pr],[R4240;H, OCH₂(3-Br-4-Br-Ph),CHF₂,H,H,Pr],[R4241;H,OCH₂(3-Br-4-Br-Ph),CF₃,H,H,Pr],[R4242;H,OCH₂(3-Br-4-Br-Ph),H, H,H,Pr],[R4243;H,OCH₂(3-Br-4-Br-Ph),F,H,H,Bu], [R4244;H,OCH₂(3-Br-4-Br-Ph),Cl,H,H,Bu],[R4245;H, OCH₂(3-Br-4-Br-Ph),Br,H,H,Bu],[R4246;H,OCH₂(3-Br-4-Br-Ph),I,H,H,Bu],[R4247;H,OCH₂(3-Br-4-Br-Ph),Me,H,H, Bu],[R4248;H,OCH₂(3-Br-4-Br-Ph),CHF₂,H,H,Bu], [R4249;H,OCH₂(3-Br-4-Br-Ph),CF₃,H,H,Bu],[R4250;H, OCH₂(3-Br-4-Br-Ph),H,H,H,Bu],[R4251;H,OCH₂(3-Br-4-Br-Ph),F,H,H,c-Pr],[R4252;H,OCH₂(3-Br-4-Br-Ph),Cl,H, H,c-Pr],[R4253;H,OCH₂(3-Br-4-Br-Ph),Br,H,H,c-Pr], [R4254;H,OCH₂(3-Br-4-Br-Ph),I,H,H,c-Pr],[R4255;H, OCH₂(3-Br-4-Br-Ph),Me,H,H,c-Pr],[R4256;H,OCH₂(3-Br-4-Br-Ph),CHF₂,H,H,c-Pr],[R4257;H,OCH₂(3-Br-4-Br-Ph), CF₃,H,H,c-Pr],[R4258;H,OCH₂(3-Br-4-Br-Ph),H,H,H,c-Pr],[R4259;H,OCH₂(3-Br-4-Br-Ph),F,H,H,CH₂CF₃], [R4260;H,OCH₂(3-Br-4-Br-Ph),Cl,H,H,CH₂CF₃],[R4261; H,OCH₂(3-Br-4-Br-Ph),Br,H,H,CH₂CF₃],[R4262;H,OCH₂ (3-Br-4-Br-Ph),I,H,H,CH₂CF₃],[R4263;H,OCH₂(3-Br-4-Br-Ph),Me,H,H,CH₂CF₃],[R4264;H,OCH₂(3-Br-4-Br-Ph), CHF₂,H,H,CH₂CF₃],[R4265;H,OCH₂(3-Br-4-Br-Ph),CF₃, H,H,CH₂CF₃],[R4266;H,OCH₂(3-Br-4-Br-Ph),H,H,H, CH₂CF₃],[R4267;H,OCH₂(3-Br-4-Br-Ph),F,H,H, CH₂CHF₂],[R4268;H,OCH₂(3-Br-4-Br-Ph),Cl,H,H, CH₂CHF₂],[R4269;H,OCH₂(3-Br-4-Br-Ph),Br,H,H, CH₂CHF₂],[R4270;H,OCH₂(3-Br-4-Br-Ph),I,H,H, CH₂CHF₂],[R4271;H,OCH₂(3-Br-4-Br-Ph),Me,H,H, CH₂CHF₂],[R4272;H,OCH₂(3-Br-4-Br-Ph),CHF₂,H,H, CH₂CHF₂],[R4273;H,OCH₂(3-Br-4-Br-Ph),CF₃,H,H, CH₂CHF₂],[R4274;H,OCH₂(3-Br-4-Br-Ph),H,H,H, CH₂CHF₂],[R4275;H,OCH₂(3-Br-4-Br-Ph),F,H,H, CF₂CH₃],[R4276;H,OCH₂(3-Br-4-Br-Ph),Cl,H,H, CF₂CH₃],[R4277;H,OCH₂(3-Br-4-Br-Ph),Br,H,H, CF₂CH₃],[R4278;H,OCH₂(3-Br-4-Br-Ph),I,H,H,CF₂CH₃], [R4279;H,OCH₂(3-Br-4-Br-Ph),Me,H,H,CF₂CH₃],[R4280; H,OCH₂(3-Br-4-Br-Ph),CHF₂,H,H,CF₂CH₃],[R4281;H, OCH₂(3-Br-4-Br-Ph),CF₃,H,H,CF₂CH₃],[R4282;H,OCH₂ (3-Br-4-Br-Ph),H,H,H,CF₂CH₃],[R4283;H,OCH₂(3-Br-4-Br-Ph),F,H,H,NMe₂],[R4284;H,OCH₂(3-Br-4-Br-Ph),Cl,H, H,NMe₂],[R4285;H,OCH₂(3-Br-4-Br-Ph),Br,H,H,NMe], [R4286;H,OCH₂(3-Br-4-Br-Ph),I,H,H,NMe₂],[R4287;H, OCH₂(3-Br-4-Br-Ph),Me,H,H,NMe₂],[R4288;H,OCH₂(3-Br-4-Br-Ph),CHF₂,H,H,NMe₂],[R4289;H,OCH₂(3-Br-4-Br-Ph),CF₃,H,H,NMe₂],[R4290;H,OCH₂(3-Br-4-Br-Ph),H, H,H,NMe₂],[R4291;H,OCH₂(3-Br-4-Br-Ph),F,H,H,Pyrro], [R4292;H,OCH₂(3-Br-4-Br-Ph),Cl,H,H,Pyrro],[R4293;H, OCH₂(3-Br-4-Br-Ph),Br,H,H,Pyrro],[R4294;H,OCH₂(3-Br-4-Br-Ph),I,H,H,Pyrro],[R4295;H,OCH₂(3-Br-4-Br-Ph),Me, H,H,Pyrro],[R4296;H,OCH₂(3-Br-4-Br-Ph),CHF₂,H,H, Pyrro],[R4297;H,OCH₂(3-Br-4-Br-Ph),CF₃,H,H,Pyrro], [R4298;H,OCH₂(3-Br-4-Br-Ph),H,H,H,Pyrro],[R4299;H, OCH₂(3-Br-4-Br-Ph),Cl,H,H,Me],[R4300;H,OCH₂(3-Br-4-Br-Ph),Br,H,H,Me],[R4301;H,OCH₂(3-Br-4-Br-Ph),I,H,H, Me],[R4302;H,OCH₂(3-Br-4-Br-Ph),Me,H,H,Me],[R4303; H,OCH₂(3-Br-4-Br-Ph),CHF₂,H,H,Me],[R4304;H,OCH₂ (3-Br-4-Br-Ph),CF₃,H,H,Me],[R4305;H,OCH₂(3-Br-4-Br-Ph),H,H,H,Me],[R4306;H,OCH₂(3-Br-4-Br-Ph),F,H,H,Et], [R4307;H,OCH₂(3-Br-4-Br-Ph),Cl,H,H,Et],[R4308;H, OCH₂(3-Br-4-Br-Ph),Br,H,H,Et],[R4309;H,OCH₂(3-Br-4-Br-Ph),I,H,H,Et],[R4310;H,OCH₂(3-Br-4-Br-Ph),Me,H,H, Et],[R4311;H,OCH₂(3-Br-4-Br-Ph),CHF₂,H,H,Et],[R4312; H,OCH₂(3-Br-4-Br-Ph),CF₃,H,H,Et],[R4313;H,OCH₂(3-Br-4-Br-Ph),H,H,H,Et],[R4314;H,OCH₂(3-Br-4-Br-Ph),F, H,H,Pr],[R4315;H,OCH₂(3-Br-4-Br-Ph),Cl,H,H,Pr],

[R4316;H,OCH₂(3-Br-4-Br-Ph),Br,H,H,Pr],[R4317;H,OCH₂(3-Br-4-Br-Ph),I,H,H,Pr],[R4318;H,OCH₂(3-Br-4-Br-Ph),Me,H,H,Pr],[R4319;H,OCH₂(3-Br-4-Br-Ph),CHF₂,H,H,Pr],[R4320;H,OCH₂(3-Br-4-Br-Ph),CF₃,H,H,Pr],[R4321;H,OCH₂(3-Br-4-Br-Ph),H,H,H,Pr],[R4322;H,OCH₂(3-Br-4-Br-Ph),F,H,H,Bu],[R4323;H,OCH₂(3-Br-4-Br-Ph),Cl,H,H,Bu],[R4324;H,OCH₂(3-Br-4-Br-Ph),Br,H,H,Bu],[R4325;H,OCH₂(3-Br-4-Br-Ph),I,H,H,Bu],[R4326;H,OCH₂(3-Br-4-Br-Ph),Me,H,H,Bu],[R4327;H,OCH₂(3-Br-4-Br-Ph),CHF₂,H,H,Bu],[R4328;H,OCH₂(3-Br-4-Br-Ph),CF₃,H,H,Bu],[R4329;H,OCH₂(3-Br-4-Br-Ph),H,H,H,Bu],[R4330;H,OCH₂(3-Br-4-Br-Ph),F,H,H,c-Pr],[R4331;H,OCH₂(3-Br-4-Br-Ph),Cl,H,H,c-Pr],[R4332;H,OCH₂(3-Br-4-Br-Ph),Br,H,H,c-Pr],[R4333;H,OCH₂(3-Br-4-Br-Ph),I,H,H,c-Pr],[R4334;H,OCH₂(3-Br-4-Br-Ph),Me,H,H,c-Pr],[R4335;H,OCH₂(3-Br-4-Br-Ph),CHF₂,H,H,c-Pr],[R4336;H,OCH₂(3-Br-4-Br-Ph),CF₃,H,H,c-Pr],[R4337;H,OCH₂(3-Br-4-Br-Ph),H,H,H,c-Pr],[R4338;H,OCH₂(3-Br-4-Br-Ph),F,H,H,CH₂CF₃],[R4339;H,OCH₂(3-Br-4-Br-Ph),Cl,H,H,CH₂CF₃],[R4340;H,OCH₂(3-Br-4-Br-Ph),Br,H,H,CH₂CF₃],[R4341;H,OCH₂(3-Br-4-Br-Ph),I,H,H,CH₂CF₃],[R4342;H,OCH₂(3-Br-4-Br-Ph),Me,H,H,CH₂CF₃],[R4343;H,OCH₂(3-Br-4-Br-Ph),CHF₂,H,H,CH₂CF₃],[R4344;H,OCH₂(3-Br-4-Br-Ph),CF₃,H,H,CH₂CF₃],[R4345;H,OCH₂(3-Br-4-Br-Ph),H,H,H,CH₂CF₃],[R4346;H,OCH₂(3-Br-4-Br-Ph),F,H,H,CH₂CHF₂],[R4347;H,OCH₂(3-Br-4-Br-Ph),Cl,H,H,CH₂CHF₂],[R4348;H,OCH₂(3-Br-4-Br-Ph),Br,H,H,CH₂CHF₂],[R4349;H,OCH₂(3-Br-4-Br-Ph),I,H,H,CH₂CHF₂],[R4350;H,OCH₂(3-Br-4-Br-Ph),Me,H,H,CH₂CHF₂],
[R4351;H,OCH₂(3-Br-4-Br-Ph),CHF₂,H,H,CH₂CHF₂],[R4352;H,OCH₂(3-Br-4-Br-Ph),CF₃,H,H,CH₂CHF₂],[R4353;H,OCH₂(3-Br-4-Br-Ph),H,H,H,CH₂CHF₂],[R4354;H,CCH₂(3-Br-4-Br-Ph),F,H,H,CF₂CH₃],[R4355;H,OCH₂(3-Br-4-Br-Ph),Cl,H,H,CF₂CH₃],[R4356;H,OCH₂(3-Br-4-Br-Ph),Br,H,H,CF₂CH₃],[R4357;H,OCH₂(3-Br-4-Br-Ph),I,H,H,CF₂CH₃],[R4358;H,OCH₂(3-Br-4-Br-Ph),Me,H,H,CF₂CH₃],[R4359;H,OCH₂(3-Br-4-Br-Ph),CHF₂,H,H,CF₂CH₃],[R4360;H,OCH₂(3-Br-4-Br-Ph),CF₃,H,H,CF₂CH₃],[R4361;H,OCH₂(3-Br-4-Br-Ph),H,H,H,CF₂CH₃],[R4362;H,OCH₂(3-Br-4-Br-Ph),F,H,H,NMe₂],[R4363;H,OCH₂(3-Br-4-Br-Ph),Cl,H,H,NMe₂],[R4364;H,OCH₂(3-Br-4-Br-Ph),Br,H,H,NMe₂],[R4365;H,OCH₂(3-Br-4-Br-Ph),I,H,H,NMe₂],[R4366;H,OCH₂(3-Br-4-Br-Ph),Me,H,H,NMe₂],[R4367;H,OCH₂(3-Br-4-Br-Ph),CHF₂,H,H,NMe₂],[R4368;H,OCH₂(3-Br-4-Br-Ph),CF₃,H,H,NMe₂],[R4369;H,OCH₂(3-Br-4-Br-Ph),H,H,H,NMe₂],[R4370;H,OCH₂(3-Br-4-Br-Ph),F,H,H,Pyrro],[R4371;H,OCH₂(3-Br-4-Br-Ph),Cl,H,H,Pyrro],[R4372;H,OCH₂(3-Br-4-Br-Ph),Br,H,H,Pyrro],[R4373;H,OCH₂(3-Br-4-Br-Ph),I,H,H,Pyrro],[R4374;H,OCH₂(3-Br-4-Br-Ph),Me,H,H,Pyrro],[R4375;H,OCH₂(3-Br-4-Br-Ph),CHF₂,H,H,Pyrro],[R4376;H,OCH₂(3-Br-4-Br-Ph),CF₂,H,H,Pyrro],[R4377;H,OCH₂(3-Br-4-Br-Ph),H,H,H,Pyrro],[R4378;H,OCH₂(3-Br-4-F-Ph),Cl,H,H,Me],[R4379;H,OCH₂(3-Br-4-F-Ph),Br,H,H,Me],[R4380;H,OCH₂(3-Br-4-F-Ph),I,H,H,Me],[R4381;H,OCH₂(3-Br-4-F-Ph),Me,H,H,Me],[R4382;H,OCH₂(3-Br-4-F-Ph),CHF₂,H,H,Me],[R4383;H,OCH₂(3-Br-4-F-Ph),CF₃,H,H,Me],[R4384;H,CH₂(3-Br-4-F-Ph),H,H,H,Me],[R4385;H,OCH₂(3-Br-4-F-Ph),F,H,H,Et],[R4386;H,OCH₂(3-Br-4-F-Ph),Cl,H,H,Et],[R4387;H,OCH₂(3-Br-4-F-Ph),Br,H,H,Et],[R4388;H,OCH₂(3-Br-4-F-Ph),I,H,H,Et],[R4389;H,OCH₂(3-Br-4-F-Ph),Me,H,H,Et],[R4390;H,OCH₂(3-Br-4-F-Ph),CHF₂,H,H,Et],[R4391;H,OCH₂(3-Br-4-F-Ph),CF₃,H,H,Et],[R4392;H,OCH₂(3-Br-4-F-Ph),H,H,H,Et],[R4393;H,OCH₂(3-Br-4-F-Ph),F,H,H,Pr],[R4394;H,OCH₂(3-Br-4-F-Ph),Cl,H,H,Pr],[R4395;H,OCH₂(3-Br-4-F-Ph),Br,H,H,Pr],[R4396;H,OCH₂(3-Br-4-F-Ph),I,H,H,Pr],[R4397;H,OCH₂(3-Br-4-F-Ph),Me,H,H,Pr],[R4398;H,OCH₂(3-Br-4-F-Ph),CHF₂,H,H,Pr],[R4399;H,OCH₂(3-Br-4-F-Ph),CF₃,H,H,Pr],[R4400;H,OCH₂(3-Br-4-F-Ph),H,H,H,Pr],[R4401;H,OCH₂(3-Br-4-F-Ph),F,H,H,Bu],[R4402;H,OCH₂(3-Br-4-F-Ph),Cl,H,H,Bu],[R4403;H,OCH₂(3-Br-4-F-Ph),Br,H,H,Bu],[R4404;H,OCH₂(3-Br-4-F-Ph),I,H,H,Bu],[R4405;H,OCH₂(3-Br-4-F-Ph),Me,H,H,Bu],[R4406;H,OCH₂(3-Br-4-F-Ph),CHF₂,H,H,Bu],[R4407;H,OCH₂(3-Br-4-F-Ph),CF₃,H,H,Bu],[R4408;H,OCH₂(3-Br-4-F-Ph),H,H,H,Bu],[R4409;H,OCH₂(3-Br-4-F-Ph),F,H,H,c-Pr],[R4410;H,OCH₂(3-Br-4-F-Ph),Cl,H,H,c-Pr],[R4411;H,OCH₂(3-Br-4-F-Ph),Br,H,H,c-Pr],[R4412;H,OCH₂(3-Br-4-F-Ph),I,H,H,c-Pr],[R4413;H,OCH₂(3-Br-4-F-Ph),Me,H,H,c-Pr],[R4414;H,OCH₂(3-Br-4-F-Ph),CHF₂,H,H,c-Pr],[R4415;H,OCH₂(3-Br-4-F-Ph),CF₃,H,H,c-Pr],[R4416;H,OCH₂(3-Br-4-F-Ph),H,H,H,c-Pr],[R4417;H,OCH₂(3-Br-4-F-Ph),F,H,H,CH₂CF₃],[R4418;H,OCH₂(3-Br-4-F-Ph),Cl,H,H,CH₂CF₃],[R4419;H,OCH₂(3-Br-4-F-Ph),Br,H,H,CH₂CF₃],[R4420;H,OCH₂(3-Br-4-F-Ph),I,H,H,CH₂CF₃],[R4421;H,OCH₂(3-Br-4-F-Ph),Me,H,H,CH₂CF₃],[R4422;H,OCH₂(3-Br-4-F-Ph),CHF₂,H,H,CH₂CF₃],[R4423;H,OCH₂(3-Br-4-F-Ph),CF₃,H,H,CH₂CF₃],[R4424;H,OCH₂(3-Br-4-F-Ph),H,H,H,CH₂CF₃],[R4425;H,OCH₂(3-Br-4-F-Ph),F,H,H,CH₂CHF₂],[R4426;H,OCH₂(3-Br-4-F-Ph),Cl,H,H,CH₂CHF₂],[R4427;H,OCH₂(3-Br-4-F-Ph),Br,H,H,CH₂CHF₂],[R4428;H,OCH₂(3-Br-4-F-Ph),I,H,H,CH₂CHF₂],[R4429;H,OCH₂(3-Br-4-F-Ph),Me,H,H,CH₂CHF₂],[R4430;H,OCH₂(3-Br-4-F-Ph),CHF₂,H,H,CH₂CHF₂],[R4431;H,OCH₂(3-Br-4-F-Ph),CF₃,H,H,CH₂CHF₂],[R4432;H,OCH₂(3-Br-4-F-Ph),H,H,H,CH₂CHF₂],[R4433;H,OCH₂(3-Br-4-F-Ph),F,H,H,CF₂CH₃],[R4434;H,OCH₂(3-Br-4-F-Ph),Cl,H,H,CF₂CH₃],[R4435;H,OCH₂(3-Br-4-F-Ph),Br,H,H,CF₂CH],[R4436;H,OCH₂(3-Br-4-F-Ph),I,H,H,CF₂CH₃],[R4437;H,OCH₂(3-Br-4-F-Ph),Me,H,H,CF₂CH₃],[R4438;H,OCH₂(3-Br-4-F-Ph),CHF₂,H,H,CF₂CH₃],[R4439;H,OCH₂(3-Br-4-F-Ph),CF₃,H,H,CF₂CH₃],[R4440;H,OCH₂(3-Br-4-F-Ph),H,H,H,CF₂CH₃],[R4441;H,OCH₂(3-Br-4-F-Ph),F,H,H,NMe₂],[R4442;H,OCH₂(3-Br-4-F-Ph),Cl,H,H,NMe₂],[R4443;H,OCH₂(3-Br-4-F-Ph),Br,H,H,NMe₂],[R4444;H,OCH₂(3-Br-4-F-Ph),I,H,H,NMe₂],[R4445;H,OCH₂(3-Br-4-F-Ph),Me,H,H,NMe₂],[R4446;H,CCH₂(3-Br-4-F-Ph),CHF₂,H,H,NMe₂],[R4447;H,OCH₂(3-Br-4-F-Ph),CF₃,H,H,NMe₂],[R4448;H,OCH₂(3-Br-4-F-Ph),H,H,H,NMe₂],[R4449;H,OCH₂(3-Br-4-F-Ph),F,H,H,Pyrro],[R4450;H,OCH₂(3-Br-4-F-Ph),Cl,H,H,Pyrro],[R4451;H,OCH₂(3-Br-4-F-Ph),Br,H,H,Pyrro],[R4452;H,OCH₂(3-Br-4-F-Ph),I,H,H,Pyrro],[R4453;H,OCH₂(3-Br-4-F-Ph),Me,H,H,Pyrro],[R4454;H,OCH₂(3-Br-4-F-Ph),CHF₂,H,H,Pyrro],[R4455;H,OCH₂(3-Br-4-F-Ph),CF₃,H,H,Pyrro],[R4456;H,OCH₂(3-Br-4-F-Ph),H,H,H,Pyrro],[R4457;H,OCH₂(3-Br-4-F-Ph),Cl,H,H,Me],[R4458;H,OCH₂(3-Br-4-F-Ph),Br,H,H,Me],[R4459;H,OCH₂(3-Br-4-F-Ph),I,H,H,Me],[R4460;H,OCH₂(3-Br-4-F-Ph),Me,H,H,Me],[R4461;H,OCH₂(3-Br-4-F-Ph),CHF₂,H,H,Me],[R4462;H,OCH₂(3-Br-4-F-Ph),CF₃,H,H,Me],[R4463;H,OCH₂(3-Br-4-F-Ph),H,H,H,Me],[R4464;H,OCH₂(3-Br-4-F-Ph),F,H,H,Et],[R4465;H,OCH₂(3-Br-4-F-Ph),Cl,H,H,Et],[R4466;H,OCH₂(3-Br-4-F-Ph),Br,H,H,Et],[R4467;H,OCH₂(3-Br-4-F-Ph),I,H,H,Et],[R4468;H,OCH₂(3-Br-4-F-Ph),Me,H,H,Et],[R4469;H,OCH₂(3-Br-4-F-Ph),CHF₂,H,H,Et],[R4470;H,OCH₂(3-Br-4-F-Ph),CF₃,H,H,Et],[R4471;H,OCH₂(3-Br-4-F-Ph),H,H,H,Et],[R4472;H,OCH₂(3-Br-4-F-Ph),F,H,H,Pr],[R4473;H,OCH₂(3-Br-4-F-Ph),Cl,H,H,Pr],[R4474;H,OCH₂(3-Br-4-F-Ph),Br,H,H,Pr],[R4475;H,OCH₂(3-Br-4-F-Ph),I,H,H,Pr],[R4476;H,OCH₂(3-Br-4-F-Ph),Me,H,H,Pr],[R4477;H,OCH₂(3-Br-4-F-Ph),CHF₂,H,H,Pr],[R4478;H,OCH₂(3-Br-4-F-Ph),CF₃,H,H,Pr],[R4479;H, OCH$_2$(3-Br-4-F-Ph),H,H,H,Pr],[R4480;H,OCH$_2$(3-Br-4-F-Ph),F,H,H,Bu],[R4481;H,OCH$_2$(3-Br-4-F-Ph),Cl,H,H,Bu],[R4482;H,OCH$_2$(3-Br-4-F-Ph),Br,H,H,Bu],[R4483;H,OCH$_2$(3-Br-4-F-Ph),I,H,H,Bu],[R4484;H,OCH$_2$(3-Br-4-F-Ph),Me,H,H,Bu],[R4485;H,OCH$_2$(3-Br-4-F-Ph),CHF$_2$,H,H,Bu],[R4486;H,OCH$_2$(3-Br-4-F-Ph),CF$_3$,H,H,Bu],[R4487;H,OCH$_2$(3-Br-4-F-Ph),H,H,H,Bu],[R4488;H,OCH$_2$(3-Br-4-F-Ph),F,H,H,c-Pr],[R4489;H,OCH$_2$(3-Br-4-F-Ph),Cl,H,H,c-Pr],[R4490;H,OCH$_2$(3-Br-4-F-Ph),Br,H,H,c-Pr],[R4491;H,OCH$_2$(3-Br-4-F-Ph),I,H,H,c-Pr],[R4492;H,OCH$_2$(3-Br-4-F-Ph),Me,H,H,c-Pr],[R4493;H,OCH$_2$(3-Br-4-F-Ph),CHF$_2$,H,H,c-Pr],[R4494;H,OCH$_2$(3-Br-4-F-Ph),CF$_3$,H,H,c-Pr],[R4495;H,OCH$_2$(3-Br-4-F-Ph),H,H,H,c-Pr],[R4496;H,OCH$_2$(3-Br-4-F-Ph),F,H,H,CH$_2$CF$_3$],[R4497;H,OCH$_2$(3-Br-4-F-Ph),Cl,H,H,CH$_2$CF$_3$],[R4498;H,OCH$_2$(3-Br-4-F-Ph),Br,H,H,CH$_2$CF$_3$],[R4499;H,OCH$_2$(3-Br-4-F-Ph),I,H,H,CH$_2$CF$_3$],[R4500;H,OCH$_2$(3-Br-4-F-Ph),Me,H,H,CH$_2$CF$_3$],[R4501;H,OCH$_2$(3-Br-4-F-Ph),CHF$_2$,H,H,CH$_2$CF$_3$],[R4502;H,OCH$_2$(3-Br-4-F-Ph),CF$_3$,H,H,CH$_2$CF$_3$],[R4503;H,OCH$_2$(3-Br-4-F-Ph),H,H,H,CH$_2$CF$_3$],[R4504;H,OCH$_2$(3-Br-4-F-Ph),F,H,H,CH$_2$CHF$_2$],[R4505;H,OCH$_2$(3-Br-4-F-Ph),Cl,H,H,CH$_2$CHF$_2$],[R4506;H,OCH$_2$(3-Br-4-F-Ph),Br,H,H,CH$_2$CHF$_2$],[R4507;H,OCH$_2$(3-Br-4-F-Ph),I,H,H,CH$_2$CHF$_2$],[R4508;H,OCH$_2$(3-Br-4-F-Ph),Me,H,H,CH$_2$CHF$_2$],[R4509;H,OCH$_2$(3-Br-4-F-Ph),CHF$_2$,H,H,CH$_2$CHF$_2$],[R4510;H,OCH$_2$(3-Br-4-F-Ph),CF$_3$,H,H,CH$_2$CHF$_2$],[R4511;H,OCH$_2$(3-Br-4-F-Ph),H,H,H,CH$_2$CHF$_2$],[R4512;H,OCH$_2$(3-Br-4-F-Ph),F,H,H,CF$_2$CH$_3$],[R4513;H,OCH$_2$(3-Br-4-F-Ph),Cl,H,H,CF$_2$CH$_3$],[R4514;H,OCH$_2$(3-Br-4-F-Ph),Br,H,H,CF$_2$CH$_3$],[R4515;H,OCH$_2$(3-Br-4-F-Ph),I,H,H,CF$_2$CH$_3$],[R4516;H,OCH$_2$(3-Br-4-F-Ph),Me,H,H,CF$_2$CH$_3$],[R4517;H,OCH$_2$(3-Br-4-F-Ph),CHF$_2$,H,H,CF$_2$CH$_3$],[R4518;H,OCH$_2$(3-Br-4-F-Ph),CF$_3$,H,H,CF$_2$CH$_3$],[R4519;H,OCH$_2$(3-Br-4-F-Ph),H,H,H,CF$_2$CH$_3$],[R4520;H,OCH$_2$(3-Br-4-F-Ph),F,H,H,NMe$_2$],[R4521;H,OCH$_2$(3-Br-4-F-Ph),Cl,H,H,NMe$_2$],[R4522;H,OCH$_2$(3-Br-4-F-Ph),Br,H,H,NMe$_2$],[R4523;H,OCH$_2$(3-Br-4-F-Ph),I,H,H,NMe$_2$],[R4524;H,OCH$_2$(3-Br-4-F-Ph),Me,H,H,NMe$_2$],[R4525;H,OCH$_2$(3-Br-4-F-Ph),CHF$_2$,H,H,NMe$_2$],[R4526;H,OCH$_2$(3-Br-4-F-Ph),CF$_3$,H,H,NMe$_2$],[R4527;H,OCH$_2$(3-Br-4-F-Ph),H,H,H,NMe$_2$],[R4528;H,OCH$_2$(3-Br-4-F-Ph),F,H,H,Pyrro],[R4529;H,OCH$_2$(3-Br-4-F-Ph),Cl,H,H,Pyrro],[R4530;H,OCH$_2$(3-Br-4-F-Ph),Br,H,H,Pyrro],[R4531;H,OCH$_2$(3-Br-4-F-Ph),I,H,H,Pyrro],[R4532;H,OCH$_2$(3-Br-4-F-Ph),Me,H,H,Pyrro],[R4533;H,OCH$_2$(3-Br-4-F-Ph),CHF$_2$,H,H,Pyrro],[R4534;H,OCH$_2$(3-Br-4-F-Ph),CF$_3$,H,H,Pyrro],[R4535;H,OCH$_2$(3-Br-4-F-Ph),H,H,H,Pyrro].

In a compound represented by formula (IV)

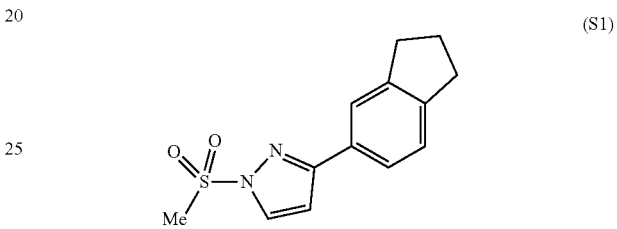

(IV)

the compound wherein a combination of $R^{6D}$, $A^1$, $A^2$, $A^3$ and $Z^D$ represents any combinations of the below-mentioned Substituent Numbers S1 to S231 (hereinafter, the compounds with Substituent Numbers S1 to S231 are referred to as "Present compounds S1 to S231" respectively, and "Present compounds S1 to S231" are collectively referred to as "Present compound S" may be obtained according to the above-mentioned processes.

Here "Substituent Number S1 to 3231" represents a combination of $R^{6D}$, $A^1$, $A^2$, $A^3$, and Z in the compound represented by formula (IV), and hereinafter is indicated as [Substituent Number; $R^{6D}$,$A^1$,$A^2$,$A^3$,$Z^D$].

For example, Substituent Number S1 represents a combination wherein $R^{6D}$ represents a hydrogen atom, $A^1$, $A^2$, and A3 represent CH$_2$, and $Z^D$ represents a methyl group.

For example, the present compound S1 represents a compound represented by formula (IV) wherein the substituent number is S1, and also represents the below-mentioned compound represented by formula (IV) wherein $R^{6D}$ represents a hydrogen atom, $A^1$, $A^2$, and $A^3$ represent CH$_2$, and $Z^D$ represents a methyl group.

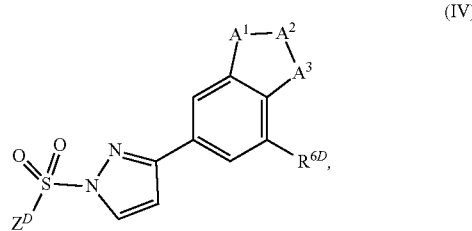

(S1)

[Substituent Number; R$_{6D}$, A$^1$,A$^2$,A$^3$,Z$^D$]:[S1;H,CH$_2$,CH$_2$,CH$_2$,Me],[S2;H,CH$_2$,CH$_2$,CH$_2$,Et],[S3;H,CH$_2$,CH$_2$,CH$_2$,Pr],[S4;H,CH$_2$,CH$_2$,CH$_2$,i-Pr],[S5;H,CH$_2$,CH$_2$,CH$_2$,c-Pr],[S6;H,CH$_2$,CH$_2$,CH$_2$,Bu],[S7;H,CH$_2$,CH$_2$,CH$_2$,CH$_2$CF$_3$],[S8;H,CH$_2$,CH$_2$,CH$_2$,CH$_2$CHF$_2$],[S9;H,CH$_2$,CH$_2$,CH$_2$,CF$_2$CH$_3$],[S10;H,CH$_2$,CH$_2$,CH$_2$,NMe$_2$],[S11;H,CH$_2$,CH$_2$,CH$_2$,Pyrro],[S12;F,CH$_2$,CH$_2$,CH$_2$,Me],[S13;F,CH$_2$,CH$_2$,CH$_2$,Et],[S14;F,CH$_2$,CH$_2$,CH$_2$,Pr],[S15;F,CH$_2$,CH$_2$,CH$_2$,i-Pr],[S16;F,CH$_2$,CH$_2$,CH$_2$,c-Pr],[S17;F,CH$_2$,CH$_2$,CH$_2$,Bu],[S18;F,CH$_2$,CH$_2$,CH$_2$,CH$_2$CF$_3$],[S19;F,CH$_2$,CH$_2$,CH$_2$,CH$_2$CHF$_2$],[S20;F,CH$_2$,CH$_2$,CH$_2$,CF$_2$CH$_3$],[S21;F,CH$_2$,CH$_2$,CH$_2$,NMe$_2$],[S22;F,CH$_2$,CH$_2$,CH$_2$,Pyrro],[S23;Me,CH$_2$,CH$_2$,CH$_2$,Me],[S24;Me,CH$_2$,CH$_2$,CH$_2$,Et],[S25;Me,CH$_2$,CH$_2$,CH$_2$,Pr],[S26;Me,CH$_2$,CH$_2$,CH$_2$,i-Pr],[S27;Me,CH$_2$,CH$_2$,CH$_2$,c-Pr],[S28;Me,CH$_2$,CH$_2$,CH$_2$,nu],[S29;Me,CH$_2$,CH$_2$,CH$_2$,CH$_2$CF$_3$],[S30;Me,CH$_2$,CH$_2$,CH$_2$,CH$_2$CHF$_2$],[S31;Me,CH$_2$,CH$_2$,CH$_2$,CF$_2$CH$_3$],[S32;Me,CH$_2$,CH$_2$,CH$_2$,NMe$_2$],[S33;Me,CH$_2$,CH$_2$,CH$_2$,Pyrro],[S34;H,O,CH$_2$,O,Me], [S35;H,O,CH$_2$,OEt],[S36;H,O,CH$_2$,O,Pr],[S37;H,O,CH$_2$,O,i-Pr],[S38;H,CH$_2$,O,c-Pr],[S39;H,O,CH$_2$,O,Bu],[S40;H,O,CH$_2$,O,CH$_2$CF$_3$],[S41;H,O,CH$_2$,O,CH$_2$CHF$_2$],[S42;H,O,CH$_2$,O,CF$_2$CH$_3$],[S43;H,O,CH$_2$,O,NMe$_2$],[S44;H, O,CH$_2$,O,Pyrro],[S45;F,O,CH$_2$,O,Me],[S46;F,O,CH$_2$,O,Et],[S47;F, O,CH$_2$,O,Pr],[S48;F,O,CH$_2$,O,i-Pr],[S49;F,O,CH$_2$,O,c-Pr],[S50;F,O,CH$_2$,O,Bu],[S51;F,O,CH$_2$,O,CH$_2$CF$_3$],[S52;F,O,CH$_2$,O,CH$_2$CHF$_2$],[S53;F,O,CH$_2$,O,CF$_2$CH$_3$],[S54;F,O,CH$_2$,O,NMe$_2$],[S55;F, O,CH$_2$,O,Pyrro],[S56;Me,O,CH$_2$,O,Me],[S57;Me,O,CH$_2$,O,Et],[S58;Me,O,CH$_2$,O,Pr],[S59;Me,O,CH$_2$,O,i-Pr],[S60;Me,O,CH$_2$,O,c-Pr],[S61;Me,O,CH$_2$,O,Bu],[S62;Me,O,CH$_2$,O,CH$_2$CF$_3$],[S63;Me,O,CH$_2$,O,CH$_2$CHF$_2$],[S64;Me,O,CH$_2$,O,CF$_2$CH$_3$],[S65;Me,O,CH$_2$,O,NMe$_2$],[S66;Me,O,CH$_2$,O,Pyrro],[367;H,O,CF$_2$,O,Me],[S68;H,O,CF$_2$,O,Et],[S69;H,O,CF$_2$,O,Pr],[S70;H,O,CF$_2$,O,i-Pr],[S71;H,O,CF$_2$,O,c-Pr],[S72;H,O,CF$_2$,O,Bu],[S73;H,O,CF$_2$,O,CH$_2$CF$_3$],[S74;H,O,CF$_2$,O, CH$_2$CHF$_2$],[S75;H,O,CF$_2$,O,CF$_2$CH$_3$],[S76;H,O,CF$_2$,O,NMe$_2$],[S77;H,O,CF$_2$,O,Pyrro],[S78;F,O,CF$_2$,O,Me],[S79;F,O,CF$_2$,O,Et],[S80;F,O,CF$_2$,O,Pr],[S81;F,O,CF$_2$, O,i-Pr],[S82;F,O,CF$_2$,O,c-Pr],[S83;F,O,CF$_2$,O,Bu],[S84;F, O,CF$_2$,O,CH$_2$CF$_3$],[S85;F,O,CF$_2$,O,CH$_2$CHF$_2$],[S86;F,O, CF$_2$,O,CF$_2$CH$_3$],[S87;F,O,CF$_2$,O,NMe$_2$],[S88;F, O,CF$_2$,O, Pyrro],[SB9;Me,O,CF$_2$,O,Me],[S90;Me,O,CF$_2$,O,Et],[S91; Me,O,CF$_2$,O,Pr],[S92;Me,O,CF$_2$,O,i-Pr],[393;Me,O,CF$_2$,O, c-Pr],[S94;Me,O,CF$_2$,O,Bu],[S95;Me,O,CF$_2$,O,CH$_2$CF$_3$], [S96;Me,O,CF$_2$,O,CH$_2$CHF$_2$],[S97;Me,O,CF$_2$,O,CF$_2$CH$_3$], [S98;Me,O,CF$_2$,O,NMe$_2$],[S99;Me,O,CF$_2$,O,Pyrro],[S100; H,CH$_2$,O,CH$_2$,Me],[S101;H,CH$_2$,O,CH$_2$,Et],[S102;H,CH$_2$, O,CH$_2$,Pr],[S103;H,CH$_2$,O,CH$_2$,i-Pr],[S104;H,CH$_2$,O,CH$_2$, c-Pr],[S105;H,CH$_2$,O,CH$_2$,O],[S106;H,CH$_2$,O,CH$_2$, CH$_2$CF$_3$],[S107;H,CH$_2$,O,CH$_2$,CH$_2$CHF$_2$],[S108;H,CH$_2$,O, CH$_2$,CF$_2$CH$_3$],[S109;H,CH$_2$,O,CH$_2$, NMe$_2$],[S110;H,CH$_2$, O,CH$_2$,Pyrro],[S111;F,CH$_2$,O,CH$_2$,Me],[S112;F,CH$_2$,O, CH$_2$,Et],[S113;F,CH$_2$,O,CH$_2$,Pr],[S114;F,CH$_2$,O,CH$_2$,i-Pr], [S115;F,CH$_2$,O,CH$_2$,c-Pr],[S116;F,CH$_2$,O,CH$_2$,Bu],[S117; F,CH$_2$,O,CH$_2$,CH$_2$CF$_3$],[S118;F,CH$_2$,O,CH$_2$,CH$_2$CHF$_2$], [S119;F,CH$_2$,O,CH$_2$,CF$_2$CH$_3$],[S120;F,CH$_2$,O,CH$_2$, NMe$_2$],[S121;F,CH$_2$,O,CH$_2$,Pyrro],[S122;Me,CH$_2$,O,CH$_2$, Me],[S123; Me,CH$_2$,O,CH$_2$,Et],[S124;Me,CH$_2$,O,CH$_2$,Pr], [S125;Me,CH$_2$,O,CH$_2$,i-Pr],[S126;Me,CH$_2$,O,CH$_2$,c-Pr], [S127;Me,CH$_2$,O,CH$_2$,Bu],[S128;Me,CH$_2$,O,CH$_2$, CH$_2$CF$_3$],[S129;Me,CH$_2$,O,CH$_2$,CH$_2$CHF$_2$],[S130;Me, CH$_2$,O,CH$_2$,CF$_2$CH$_3$],[5131;Me,CH$_2$,O,CH$_2$,NMe$_2$],[S132; Me,CH$_2$,O,CH$_2$,Pyrro],[S133;H,CF$_2$,O,CH$_2$,Me],[S134;H, CF$_2$,O,CH$_2$,Et],[S135;H,CF$_2$,O,CH$_2$,Pr],[S136;H,CF$_2$,O, CH$_2$,i-Pr],[S137;H,CF$_2$,O,CH$_2$,c-Pr],[S138;H,CF$_2$,O,CH$_2$, Bu],[S139;H,CF$_2$,O,CH$_2$,CH$_2$CF$_3$],[S140;H,CF$_2$,O,CH$_2$, CH$_2$CHF$_2$],[S141;H,CF$_2$,O,CH$_2$,CF$_2$CH$_3$],[S142;H,CF$_2$,O, CH$_2$, NMe$_2$],[S143;H,CF$_2$,O,CH$_2$,Pyrro],[S144;F,CF$_2$,O, CH$_2$,Me],[S145;F,CF$_2$,O,CCH$_2$,Et],[S146;F,CF$_2$,O,CH$_2$, Pr],[S147;F,CF$_2$,O,CH$_2$,i-Pr],[S148;F,CF$_2$,O,CH$_2$,c-Pr], [S149;F,CF$_2$,O,CH$_2$,Bu],[S150;F,CF$_2$,O,CH$_2$,CH$_2$CF$_3$], [S151;F,CF$_2$,O,CH$_2$,CH$_2$CHF$_2$],[S152;F,CF$_2$,O,CH$_2$, CF$_2$CH$_3$],[S153;F, CF$_2$,O,CH$_2$,NMe$_2$],[S154;F,CF$_2$,O,CH$_2$, Pyrro],[S155;Me,CF$_2$,O,CH$_2$,Me],[S156;Me,CF$_2$,O,CH$_2$, Et],[S157;Me,CF$_2$,O,CH$_2$,Pr],[S158;Me,CF$_2$,O,CH$_2$,i-Pr], [S159;Me,CF$_2$,O,CH$_2$,O,CH$_2$,c-Pr],[S160;Me,CF$_2$,O,CH$_2$, Bu],[S161;Me,CF$_2$,O,CH$_2$,CH$_2$CF$_3$],[S162;Me,CF$_2$,O,CH$_2$, CH$_2$CHF$_2$],[S163;Me,CF$_2$,O,CH$_2$,CF$_2$CH$_3$],[S164;Me,CF$_2$, O,CH$_2$,NMe$_2$],[S165;Me,CF$_2$,O,CH$_2$,Pyrro],[S166;H,CH$_2$, O,CF$_2$,Me],[S 167;H,CH$_2$,O,CF$_2$,Et],[S168;H,CH$_2$,O,CF$_2$, Pr],[S169;H,CH$_2$,O,CF$_2$, i-Pr],[S170;H,CH$_2$,O,CF$_2$,c-Pr], [S171;H,CH$_2$,O,CF$_2$,Bu],[S172;H,CCH$_2$,O,CF$_2$,CH$_2$CF$_3$], [S173;H,CH$_2$,O,CF$_2$,CH$_2$CHF$_2$],[S174;H,CH$_2$,O,CF$_2$, CF$_2$CH$_3$],[S175;H,CH$_2$,O,CF$_2$, NMe$_2$],[S176;H,CH$_2$,O, CF$_2$,Pyrro],[S177;F,CH$_2$,O,CF$_2$,Me],[S178;F,CH$_2$,O,CF$_2$, Et],[S179;F,CH$_2$,O,CF$_2$,Pr],[S180;F,CH$_2$,O,CF$_2$,i-Pr], [S181;F,CH$_2$,O,CF$_2$,c-Pr],[S182;F,CH$_2$,O,CF$_2$,Bu],[S183;F, CH$_2$,O,CF$_2$,CH$_2$CF$_3$],[S184;F,CH$_2$,O,CF$_2$,CH$_2$CHF$_2$], [S185;F,CH$_2$,O,CF$_2$,CF$_2$CH$_3$],[S186;F,CH$_2$,O,CF$_2$, NMe$_2$], [S187;F,CH$_2$,O,CF$_2$,Pyrro],[S188;Me,CH$_2$,O,CF$_2$,Me], [S189; Me,CH$_2$,O,CF$_2$,Et],[S190;Me,CH$_2$,O,CF$_2$,Pr], [S191;Me,CH$_2$,O,CF$_2$,i-Pr],[S192;Me,CH$_2$,O,CF$_2$,c-Pr], [S193;Me,CH$_2$,O,CF$_2$,Bu],[S194;Me,CH$_2$,O,CF$_2$,CH$_2$CF$_3$], [S195;Me,CH$_2$,O,CF$_2$,CH$_2$cHF$_2$],[S196;Me,CH$_2$,O,CF$_2$, CF$_2$CH$_3$],[S197;Me,CH$_2$,O,CF$_2$,NMe$_2$],[S198;Me,CH$_2$,O, CF$_2$,Pyrro],[S199;H,CF$_2$,O,CF$_2$,Me],[S 200;H,CF$_2$,O,CF$_2$, Et],[S201;H,CF$_2$,O,CF$_2$,Pr],[S202;H,CF$_2$,O,CF$_2$,i-Pr], [S203;H,CF$_2$,O,CF$_2$,c-Pr],[S204;H,CF$_2$,O,CF$_2$,Bu],[S205; H,CF$_2$,O,CF$_2$,CH$_2$CF$_3$],[S206;H,CF$_2$,O,CF$_2$,CH$_2$CHF$_2$], [S207;H,CF$_2$,O,CF$_2$,CF$_2$CH$_3$],[$_S$208;H,CF$_2$,O,CF$_2$, NMe$_2$], [S209;H,CF$_2$,O,CF$_2$,Pyrro],[S210;F,CF$_2$,O,CF$_2$,Me],[S211; F,CF$_2$,O,CF$_2$,Et],[S212;F,CF$_2$,O,CF$_2$,Pr],[S213;F,CF$_2$,O, CF$_2$,i-Pr],[S214;F,CF$_2$,O,CF$_2$,c-Pr],[S215;F,CF$_2$,O,CF$_2$, Bu],[S216;F,CF$_2$,O,CF$_2$,CH$_2$CF$_3$],[S217;F,CF$_2$,O,CF$_2$, CH$_{2c}$HF$_2$],[S218;F,CF$_2$,O,CF$_2$,CF$_2$CH$_3$],[S219;F,CF$_2$,O, CF$_2$,NMe$_2$],[S220;F,CF$_2$,O,CF$_2$,Pyrro],[S221;Me,CF$_2$,O, CF$_2$,Me],[S222;Me,CF$_2$,O,CF$_2$,Et],[S223;Me,CF$_2$,O,CF$_2$, Pr],[S224;Me,CF$_2$,O,CF$_2$,i-Pr],[S225;Me,CF$_2$,O,CF$_2$,c-Pr], [S226;Me,CF$_2$,O,CF$_2$,Bu],[S227;Me,CF$_2$,O,CF$_2$,CH$_2$CF$_3$], [S228;Me,CF$_2$,O,CF$_2$,CH$_2$CHF$_2$],[S229;Me,CF$_2$,O,CF$_2$, CF$_2$CH$_3$],[S230;Me,CF$_2$,O,CF$_2$,NMe$_2$],[S231;Me,CF$_2$,O, CF$_2$,Pyrro]

"Present compound T" represents Present compound Q, Present compound R and Present compound S.

Next, the Formulation examples are shown below. The "parts" represents "part by weight".

Formulation Example 1

Fifty (50) parts of any one of the present compound T, 3 parts of calcium lignin sulfonate, 2 parts of sodium lauryl sulfate, and 45 parts of wet process silica are well mixed-grinding to obtain a formulation.

Formulation Example 2

Twenty (20) parts of any one of the present compound T, 1.5 parts of sorbitan trioleate are mixed with 28.5 parts of an aqueous solution containing 1 parts of polyvinyl alcohol, and the mixture is the mixture is then finely-ground by a wet grinding method. To the mixture is then added 40 parts of an aqueous solution containing 0.05 parts of xanthan gum and 0.1 parts of magnesium aluminum silicate, and 10 parts of propylene glycol is further added thereto. The mixture is stirred to obtain a formulation.

Formulation Example 3

Two (2) parts of any one of the present compound T, 88 parts of kaolin clay and 10 parts of talc are mixed-grinding to obtain a formulation.

Formulation Example 4

Five (5) parts of any one of the present compound T, 14 parts of polyoxyethylene styryl phenyl ether, 6 parts of calcium dodecylbenzene sulfonate and 75 parts of xylene are mixed-grinding to obtain a formulation.

Formulation Example 5

Five (5) parts of any one of the present compound T, 1 part of wet silica, 2 parts of calcium lignosulfonate, 30 parts of bentonite and 65 parts of kaolin clay are mixed-grinding, and thereto is added water, and the mixture is well kneaded and is then granulated and dried to obtain a formulation.

Formulation Example 6

Thirty five (35) parts of a mixture of ammonium polyoxyethylene alkyl ether sulfate and wet silica (weight ratio: 1:1), 20 parts of any one of the present compound T, and 45 parts of water are well mixed to obtain a formulation.

Next, Test Examples are described.

The untreated groups in the Test example 1 to the Test example 4 means test groups in which the same conditions as those of each of the Test examples were conducted except that dimethyl sulfoxide was dispensed in the place of the dimethyl sulfoxide diluted solution comprising the present compound. Also, the untreated groups in the Test example 5 to the Test example 21 means the groups in which the aqueous diluted solutions of the formulations comprising the present compounds were not applied to stems and leaves. The untreated groups in the Test example 22 means the groups in which a dimethyl sulfoxide comprising the test compounds was not dispensed into a plastic petri dish. The untreated groups in the Test example 23 means the groups in which the spraying solution comprising the test compounds was not sprayed to a leaf disk.

Test Example 1: Control Test Against Tomato Leaf Mold (*Cladosporium fulvum*)

Any of Present compounds 45, 46, 47, 48, 49, 51, 52, 53, 54, 55, 56, 58, 59, 61, 62, 64, 69, 70, 72, 74, 75, and 112 was diluted with dimethyl sulfoxide so as to contain 1500 ppm, and 1 µL of the dilution solutions were dispensed into titer plate (96 well), and thereafter, thereto was then dispensed 150 µL of a potato dextrose broth to which conidia of tomato leaf mold (a QoI resistant strains where among the genes coding cytochrome b, a phenylalanine residue as an amino acid residue at the 129th of the cytochrome b is mutated to an leucine residue) were inoculated in advance. This plate was cultured at 18° C. for 5 days, thereby allowing tomato leaf mold to undergo proliferation, and the absorbance at 550 nm of each well of the titer plate was then measured to determine a degree of growth of the tomato leaf mold. As a result, every of the growth in tomatoes in treated groups treated with each of the present compounds showed 50% or less compared to the growth in an untreated tomato.

Test Example 2: Control Test Against Tomato Leaf Mold (*Cladosporium fulvum*)

Any of Present compounds 32, 33, 34, 37, 38, 39, 40, 42, 43, 44, and 103 was diluted with dimethyl sulfoxide so as to contain 150 ppm, and 1 µL of the dilution solutions were dispensed into titer plate (96 well), and thereafter, thereto was then dispensed 150 µL of a potato dextrose broth to which conidia of tomato leaf mold (a QoI resistant strains where among the genes coding cytochrome b, a phenylalanine residue as an amino acid residue at the 129th of the cytochrome b is mutated to an leucine residue) were inoculated in advance. This plate was cultured at 18° C. for 5 days, thereby allowing tomato leaf mold to undergo proliferation, and the absorbance at 550 nm of each well of the titer plate was then measured to determine a degree of growth of the tomato leaf mold. As a result, every of the growth in tomato in treated groups treated with each of the present compounds showed 50% or less compared to the growth in an untreated tomato.

Test Example 3: Control Test Against *Septoria* Leaf Blotch (*Septoria tritici*)

Any of Present compounds 2, 6, 45, 46, 47, 48, 49, 50, 51, 52, 53, 54, 55, 56, 58, 59, 60, 61, 62, 63, 64, 69, 70, 72, 74, 75, 77, 78, 80, 81, 83, 84, 85, 86, 87, 88, 89, 90, 92, 93, 94, 95, 106, 107, 109, 110, 111, 112, 113, 114, 117, 119, 121 to 128, 130, 131, 133, 135, 136, 138, 141, 142, 145 to 151, 169, and 170 was diluted with dimethyl sulfoxide so as to contain 1500 ppm, and 1 µL of the dilution solutions were dispensed into titer plate (96 well), and thereafter, thereto was then dispensed 150 µL of a potato dextrose broth to which conidia of *Septoria* leaf blotch (a QoI resistant strains where among the genes coding cytochrome b, a phenylalanine residue as an amino acid residue at the 129th of the cytochrome b is mutated to an leucine residue) were inoculated in advance. This plate was cultured at 18° C. for 5 days, thereby allowing *Septoria* leaf blotch to undergo proliferation, and the absorbance at 550 nm of each well of the titer plate was then measured to determine a degree of growth of the *Septoria* leaf blotch. As a result, every of the growth in tomatoes in treated groups treated with each of the present compounds showed 50% or less compared to the growth in an untreated wheat.

Test Example 4: Control Test Against *Septoria* Leaf Blotch (*Septoria tritici*)

Any of Present compounds 11, 17, 19, 20, 21, 23, 24, 25, 26, 29, 30, 31, 32, 33, 34, 36, 37, 38, 40, 42, 43, 44, 57, 101, 103, and 105 was diluted with dimethylsulfoxide so as to contain 150 ppm, and 1 µL of the dilution solutions were dispensed into titer plate (96 well), and thereafter, thereto was then dispensed 150 µL of a potato dextrose broth to which conidia of *Septoria* leaf blotch (a QoI resistant strains where among the genes coding cytochrome b, a phenylalanine residue as an amino acid residue at the 129th of the cytochrome b is mutated to an leucine residue) were inoculated in advance. This plate was cultured at 18° C. for 5 days, thereby allowing *Septoria* leaf blotch to undergo proliferation, and the absorbance at 550 nm of each well of the titer plate was then measured to determine a degree of growth of the *Septoria* leaf blotch. As a result, every of the growth in tomatoes in treated groups treated with each of the present compounds showed 50% or less compared to the growth in an untreated wheat.

Test Example 5: Control Test Against Soybean Rust (*Phakopsora pachyrhizi*)

Each of plastic pots was filled with soil and thereto soybean (cv: Kurosengoku) seeds were sown and the soybeans were grown in a greenhouse for 10 to 14 days. Thereafter, any of the present compounds 2, 3, 4, 5, 6, 7, 9, 10, 11, 13, 16, 17, 20, 21, 22, 29, 33, 34, 36, 40, 41, 42, 43, 44, 45, 46, 47, 48, 49, 51, 53, 54, 55, 56, 58, 59, 60, 62, 63, 67, 68, 69, 70, 71, 72, 73, 74, 75, 77, 78, 79, 80, 81, 82, 84, 85, 93, 94, 95, 102, 103, 104, 105, 106, 108, 111, 115, 117, 130, 143, 144, 145, 149, 161, 162, 167, and 168, each of which was made to a formulation according to the similar method to that of Formulation Example 6, was mixed with water so as to be 200 ppm. The resulting mixtures were sprayed to foliar parts so as to adhere adequately on the leaves of the above-mentioned soybean. After spraying the mixtures, the soybeans were air-dried and after 2 to 5 days, an aqueous suspension of the spores of soybean rust was spraying-inoculated. After the inoculation, the soybeans were placed in a greenhouse of 23° C. during daytime and 20° C. during nighttime under a high humidity for 1 to 2 days, and were then cultivated in the greenhouse for 10 to 14 days, and a lesion area was observed. As a result, every of the lesion areas in soybean treated with each of the present compounds showed 30% or less compared to the lesion area in an untreated soybean.

Test Example 6: Control Test Against Rice Blast (*Magnaporthe grisea*)

Each of plastic pots was filled with soil and thereto rice (cv; HINOHIKARI) seeds were sown and the plants were grown in a greenhouse for 20 days. Thereafter, any of the present compounds 14 and 27, each of which was made to a formulation according to the similar method to that of Formulation Example 6, was mixed with water so as to be 500 ppm. The mixtures were sprayed to foliar parts so as to adhere adequately on the leaves of the above-mentioned rice. After spraying the mixtures, the rices were air-dried and were placed at 24° C. during daytime and 20° C. during nighttime under a high humidity for 6 to 7 days while the above-mentioned spraying-treated rice were contacted rice seedlings (cv; Hinohikari) infected by rice blast, and a lesion area was observed. As a result, every of the lesion areas in rice treated with each of the present compounds showed 30% or less compared to the lesion are in an untreated rice.

Test Example 7: Control Test Against Rice Blast (*Magnaporthe grisea*)

Each of plastic pots was filled with soil and thereto rice (cv; HINOHIKARI) seeds were sown and the plants were grown in a greenhouse for 20 days. Thereafter, any of the present compounds 3, 7, 20, 28 and 33, each of which was made to a formulation according to the similar method to that of Formulation Example 6, was mixed with water so as to be 200 ppm. The mixtures were sprayed to foliar parts so as to adhere adequately on the leaves of the above-mentioned rice. After spraying the mixtures, the rice were air-dried and were placed at 24° C. during daytime and 20° C. during nighttime under a high humidity for 6 to 7 days while the above-mentioned spraying-treated rice were contacted rice seedlings (cv; Hinohikari) infected by rice blast, and a lesion area was observed. As a result, every of the lesion areas in rice treated with each of the present compounds showed 30% or less compared to the lesion are in an untreated rice.

Test Example 8: Control Test Against *Septoria* Leaf Blotch (*Septoria tritici*)

Each of plastic pots was filled with soil and thereto wheat (cv; Apogee) seeds were sown and the wheats were grown in a greenhouse for 10 days. Thereafter, any of the present compounds 2, 4, 6, 10, 11, 15, 16, 23, 26, 31, 34, 37, 40, 41, 45, 47, 48, 49, 51, 55, 56, 57, 58, 59, 61, 63, 64, 65, 68, 72, 77, 79, 80, 81, 104, 105, 108, 110, 112, 113, and 116, each of which was made to a formulation according to the similar method to that of Formulation Example 6, was mixed with water so as to be 500 ppm. The mixtures were sprayed to foliar parts so as to adhere adequately on the leaves of the above-mentioned wheat. After spraying the mixtures, the wheats were air-dried and after 4 days, an aqueous suspension of the spores of *Septoria* leaf blotch was spraying-inoculated. After the inoculation, the wheats were placed at 18° C. under a high humidity for 3 days and then under lighting for 14 to 18 days, and a lesion area was observed. As a result, every of the lesion areas in wheats treated with each of the present compounds showed 30% or less compared to the lesion area in an untreated wheat.

Test Example 9: Control Test Against *Septoria* Leaf Blotch (*Septoria tritici*)

Each of plastic pots was filled with soil and thereto wheat (cv; Apogee) seeds were sown and the wheats were grown in a greenhouse for 10 days. Thereafter, any of the present compounds 1, 2, 3, 4, 6, 7, 8, 10, 11, 13, 14, 15, 16, 20, 21, 22, 26, 28, 29, 30, 33, 34, 37, 40, 44, 45, 47, 49, 51, 52, 57, 58, 59, 61, 64, 67, 68, 77, 79, 85, 104, 110, 111, 115, 116, 120, 124, 125, 127, 128, 131, 137 to 139, 141 to 143, 145, 147 to 150, 151, 159, 168, 170, 173 to 177, 179, 180, and 181, each of which was made to a formulation according to the similar method to that of Formulation Example 6, was mixed with water so as to be 200 ppm. The mixtures were sprayed to foliar parts so as to adhere adequately on the leaves of the above-mentioned wheat. After spraying the mixtures, the wheats were air-dried and after 4 days, an aqueous suspension of the spores of *Septoria* leaf blotch was spraying-inoculated. After the inoculation, the wheats were placed at 18° C. under a high humidity for 3 days and then under lighting for 14 to 18 days, and a lesion area was observed. As a result, every of the lesion areas in wheats treated with each of the present compounds showed 30% or less compared to the lesion area in an untreated wheat.

Test Example 10: Control Test Against *Septoria* Leaf Blotch (*Septoria tritici*)

Each of plastic pots was filled with soil and thereto wheat (cv; Apogee) seeds were sown and the wheats were grown in a greenhouse for 10 days. Thereafter, any of the present compounds 6, 10, 11, 12, 23, 24, 168, and 173, each of which was made to a formulation according to the similar method to that of Formulation Example 6, was mixed with water so as to be 200 ppm. The mixtures were sprayed to foliar parts so as to adhere adequately on the leaves of the above-mentioned wheat. After spraying the mixtures, the wheats were air-dried and were placed under lighting for 14 to 18 days, and a lesion area was observed. As a result, every of the lesion areas in wheats treated with each of the present compounds showed 30% or less compared to the lesion area in an untreated wheat.

Test Example 11: Control Test Against Wheat Brown Rust (*Puccinia recondita*)

Each of plastic pots was filled with soil and thereto wheat (cv; SHIROGANE) seeds were sown and the wheats were grown in a greenhouse for 9 days. Any of the present compounds 13 and 27, each of which was made to a formulation according to the similar method to that of Formulation Example 6, was mixed with water so as to be 500 ppm, and the mixtures were sprayed to foliar parts so as to adhere adequately on the leaves of the above-mentioned wheat. After spraying the mixtures, the wheats were air-dried and were then cultivated at 20° C. under lighting for 5 to 7 days. The spores of wheat brown rust were sprinkling-inoculated. After the inoculation, the wheats were placed under a dark and humid condition at 23° C. for 1 day and were then cultivated at 20° C. under lighting for 8 days, and a lesion area was observed. As a result, every of the lesion areas in wheats treated with each of the present compounds showed 30% or less compared to the lesion area in an untreated wheat.

Test Example 12: Control Test Against Wheat Brown Rust (*Puccinia recondita*)

Each of plastic pots was filled with soil and thereto wheat (cv; SHIROGANE) seeds were sown and the wheats were grown in a greenhouse for 9 days. Any of the present compounds 31, 112, 119, 120, 127, 136, 144, 148, 153, 154, 159, and 173, each of which was made to a formulation according to the similar method to that of Formulation Example 6, was mixed with water so as to be 200 ppm, and the mixtures were sprayed to foliar parts so as to adhere adequately on the leaves of the above-mentioned wheat. After spraying the mixtures, the wheats were air-dried and were then cultivated at 20° C. under lighting for 5 to 7 days.

The spores of wheat brown rust were sprinkling-inoculated. After the inoculation, the wheats were placed under a dark and humid condition at 23° C. for 1 day and were then cultivated at 20° C. under lighting for 8 days, and a lesion area was observed. As a result, every of the lesion areas in wheats treated with each of the present compounds showed 30% or less compared to the lesion area in an untreated wheat.

Test Example 13: Control Test Against Soybean Powdery Mildew (*Microsphaera diffusa*)

Each of plastic pots was filled with soil and thereto soybean (cv: Kurosengoku) seeds were sown, the soybeans were grown in a greenhouse for 7 to 13 days, and spores of soybean seedlings suffered from soybean powdery mildew (cv: Kurosengoku) was spraying-inoculated. The soybeans were placed in a greenhouse of 24° C. during daytime and 20° C. during nighttime for 2 days. Thereafter, any of the present compound 36, each of which was made to a formulation according to the similar method to that of Formulation Example 6, was mixed with water so as to be 200 ppm. The mixtures were sprayed to foliar parts so as to adhere adequately on the leaves of the above-mentioned soybean. After the spraying, the soybeans were air-dried, and were then cultivated in the greenhouse for 7 to 11 days, and a lesion area was observed. As a result, every of the lesion areas in soybean treated with each of the present compounds showed 30% or less compared to the lesion area in an untreated soybean.

Test Example 14: Control Test Against Barley Net Blotch (*Pyrenophora teres*)

Each of plastic pots was filled with soil and thereto barley (cv; NISHINOHOSHI) seeds were sown and the barleys were grown in a greenhouse for 7 days. Thereafter, any of the present compounds 4, 56, 75, 79, 80, and 173, each of which was made to a formulation according to the similar method to that of Formulation Example 6, was mixed with water so as to be a prescribed concentration (500 ppm). The resulting mixtures were sprayed to foliar parts so as to adhere adequately on the leaves of the above-mentioned barley. After spraying the mixtures, the barleys were air-dried and after 2 days, an aqueous suspension of the spores of barley net blotch was spraying-inoculated. After the inoculation, the barleys were placed at 23° C. during daytime and 20° C. during nighttime under a high humidity for 3 day and then cultivated in a greenhouse for 7 days, and a lesion area was observed. As a result, every of the lesion areas in barleys treated with each of the present compounds showed 30% or less compared to the lesion area in an untreated barley.

Test Example 15: Control Test Against Barley Net Blotch (*Pyrenophora teres*)

Each of plastic pots was filled with soil and thereto barley (cv; NISHINOHOSHI) seeds were sown and the barleys were grown in a greenhouse for 7 days. Thereafter, any of the present compounds 1, 15, 29, 32, 57, 72, and 141, each of which was made to a formulation according to the similar method to that of Formulation Example 6, was mixed with water so as to be a prescribed concentration (200 ppm). The resulting mixtures were sprayed to foliar parts so as to adhere adequately on the leaves of the above-mentioned barley. After spraying the mixtures, the barleys were air-dried and after 1 day, an aqueous suspension of the spores of barley net blotch was spraying-inoculated. After the inoculation, the barleys were placed at 23° C. during daytime and 20° C. during nighttime under a high humidity for 3 day and then cultivated in a greenhouse for 7 days, and a lesion area was observed. As a result, every of the lesion areas in barleys treated with each of the present compounds showed 30% or less compared to the lesion area in an untreated barley.

Test Example 16: Control Test Against Barley Scald (*Rhynchosporium secalis*)

Each of plastic pots was filled with soil and thereto barley (cv; NISHINOHOSHI) seeds were sown and the barleys were grown in a greenhouse for 7 days. Thereafter, any of the present compounds 1, 5, 7, 9, 15, 23, 26, 29, 32, and 57, each of which was made to a formulation according to the similar method to that of Formulation Example 6, was mixed with water so as to be a prescribed concentration (200 ppm). The resulting mixtures were sprayed to foliar parts so as to adhere adequately on the leaves of the above-mentioned barley. After spraying the mixtures, the barleys were air-dried and after 1 day, an aqueous suspension of the spores of barley scald was spraying-inoculated. After the inoculation, the barleys were placed at 23° C. during daytime and 20° C. during nighttime under a high humidity for 3 day and then cultivated in a greenhouse for 7 days, and a lesion area was observed. As a result, every of the lesion areas in barleys treated with each of the present compounds showed 30% or less compared to the lesion area in an untreated barley.

Test Example 17: Control Test Against Kidney Bean Stem Rot (*Sclerotinia sclerotiorum*)

Each of plastic pots was filled with soil and thereto Kidney bean (cv; NAGAUZURA SAITO) seeds were sown and the kidney beans were grown in a greenhouse for 8 days. Thereafter, any of the present compounds 22 and 28, each of which was made to a formulation according to the similar method to that of Formulation Example 6, was mixed with water so as to be a prescribed concentration (500 ppm). The resulting mixtures were sprayed to the foliar parts so as to adhere adequately on the leaves of the above-mentioned kidney bean. After spraying the mixtures, the kidney beans were air-dried and a PDA medium containing hyphae of kidney bean *Sclerotinia* rot was placed on the leaves of the kidney bean. After the inoculation, all kidney beans were placed under a high humidity during only night and after 4 days, a lesion area was observed. As a result, every of the lesion areas in kidney beans treated with each of the present compounds showed 30% or less compared to the lesion area in an untreated kidney beans.

Test Example 18: Control Test Against Cucumber Powdery Mildew (*Sphaerotheca fuliginea*)

Each of plastic pots was filled with soil and thereto cucumber (cv; SAGAMIHANJIRO) seeds were sown and the cucumber were grown in a greenhouse for 12 days. Thereafter, any of the present compounds 17 and 28, each of which was made to a formulation according to the similar method to that of Formulation Example 6, was mixed with water so as to be a prescribed concentration (500 ppm). The mixtures were sprayed to foliar parts so as to adhere adequately on the leaves of the above-mentioned cucumber. After spraying the mixtures, the cucumbers were air-dried and the spores of cucumber powdery mildew (a QoI resistant strains where among the genes coding cytochrome b, a glycine residue as an amino acid residue at the 143th of the cytochrome b is mutated to an alanine residue) were sprinkling-inoculated. The cucumbers were cultivated in a greenhouse of 24° C. during daytime and 20° C. during nighttime for 8 days, and a lesion area was observed. As a result, every of the lesion areas in cucumbers treated with each of the present compounds showed 30% or less compared to the lesion area in an untreated cucumber.

Test Example 19: Control Test Against Cucumber Powdery Mildew (*Sphaerotheca fuliginea*)

Each of plastic pots was filled with soil and thereto cucumber (cv; SAGAMIHANJIRO) seeds were sown and the cucumber were grown in a greenhouse for 12 days. Thereafter, any of the present compounds 147, 166 and 167, each of which was made to a formulation according to the similar method to that of Formulation Example 6, was mixed with water so as to be a prescribed concentration (200 ppm). The mixtures were sprayed to foliar parts so as to adhere adequately on the leaves of the above-mentioned cucumber. After spraying the mixtures, the cucumbers were air-dried and the spores of cucumber powdery mildew (a QoI resistant strains where among the genes coding cytochrome b, a glycine residue as an amino acid residue at the 143th of the cytochrome b is mutated to an alanine residue) were sprinkling-inoculated. The cucumbers were cultivated in a greenhouse of 24° C. during daytime and 20° C. during nighttime for 8 days, and a lesion area was observed. As a result, every of the lesion areas in cucumbers treated with each of the present compounds showed 30% or less compared to the lesion area in an untreated cucumber.

Test Example 20: Control Test Against Cucumber Brown Spot (*Corynespora cassiicola*)

Each of plastic pots was filled with soil and thereto cucumber (cv; SAGAMIHANJIRO) seeds were sown and the cucumbers were grown in a greenhouse for 19 days. Thereafter, any of the present compounds 6, 11, 16, 21, 25, and 27, each of which was made to a formulation according to the similar method to that of Formulation Example 6, was mixed with water so as to be 200 ppm. The mixtures were sprayed to foliar parts so as to adhere adequately on the leaves of the above-mentioned cucumber. After spraying the mixtures, the cucumbers were air-dried and after 1 day, an aqueous suspension of cucumber brown spot was spraying-inoculated. The cucumbers were cultivated in a greenhouse of 24° C. during daytime and 20° C. during nighttime for 7 days, and a lesion area was observed. As a result, every of the lesion areas in cucumbers treated with each of the present compounds showed 30% or less compared to the lesion area in an untreated cucumber.

Test Example 21: Control Test Against Cucumber Anthracnose (*Colletotrichum lagenarium*)

Each of plastic pots was filled with soil and thereto cucumber (cv; SAGAMIHANJIRO) seeds were sown and the cucumbers were grown in a greenhouse for 19 days. Thereafter, any of the present compounds 18 and 20, each of which was made to a formulation according to the similar method to that of Formulation Example 6, was mixed with water so as to be 200 ppm. The mixtures were sprayed to foliar parts so as to adhere adequately on the leaves of the above-mentioned cucumber. After spraying the mixtures, the cucumbers were air-dried and after 1 day, an aqueous suspension of cucumber anthracnose was spraying-inoculated. After the inoculation, the cucumbers were placed firstly at 23° C. under a high humidity for 1 day and were then cultivated in a greenhouse of 24° C. during daytime and 20° C. during nighttime for 6 days, and a lesion area was observed. As a result, every of the lesion areas in cucumbers treated with each of the present compounds showed 30% or less compared to the lesion area in an untreated cucumber.

Test Example 22: Control Test Against Soybean Rust (*Phakopsora pachyrhizi*)

In a plastic petri dish with a diameter of 3.5 cm, agar medium (agar concentration 1.2%) 3 mL was put and solidified. The present compound was diluted with dimethyl sulfoxide so as to contain 10000 ppm. One (1) μL thereof was dispensed to a plastic petri dish, and thereafter, ion exchange water 500 μL was dispensed to the plastic petri dish, and an aqueous suspension of soybean rust spores that was prepared by suspending soybean rust spores ($1.0 \times 10^4$/mL) 499 μL was further dispensed to the plastic petri dish. This plastic petri dish was cultivated at 23° C. for 1 day, and thereafter, the number of soybean rust was counted. As a result, in the case of 10 ppm as the treated concentration, when any one of the present compounds 2, 4, 6, 7, 10, 11, 16, 22, 24, 29, 30, 34, 36 to 59, 62, 63, 69 to 71, 73 to 82, 84 to 95, 104 to 109, 111, 112, 117 to 120, 123 to 126, 128 to 130, 135 to 138, 140 to 150, 154, 155, 156, 158, 168, and 172 was used as a test compound, the number of germinated spores showed 40% or less compared to the number of germinated spores in an untreated group.

Test Example 23

Soybean leaf (cv; Kurosengoku) was punched out to 1 cm diameter to prepare a leaf disk. Each 1 mL of an agar medium (agar concentration 1.2%) was dispensed in 24 well microplate. A piece of the leaf disk was placed on each well. To a mixture of 0.5 μL of Sorpol (registered trademark) 1200KX, 4.5 μL of DMS, and 5 μL of xylene was added 20 μL of a solution containing 10000 ppm of the test compound in DMSO. The resulting mixture was diluted with ion exchange water to prepare a spray solution containing a predetermined concentration of the test compound. The spray solution was sprayed in 10 μL per one leaf disk. After 1 day, an aqueous suspension of spores of soybean rust (*Phakopsora pachyrhizi*) having an amino acid substitution of F129L on mitochondrial cytochrome b protein ($1.0 \times 10^5$/mL) was inoculated onto the leaf disks. After the inoculation, the microplate was placed in a growth chamber (light on for 6 hours, light off for 18 hours, 23° C. temperature, 60% humidity). After 1 day, the leaf disks were air-dried to disappear water droplets on the surface of the leaf disk, and the microplate was placed again in the growth chamber for 12 days. Thereafter, a lesion area of soybean rust disease was assessed.

Next, the comparative test examples are described.

161

Comparative Test Example

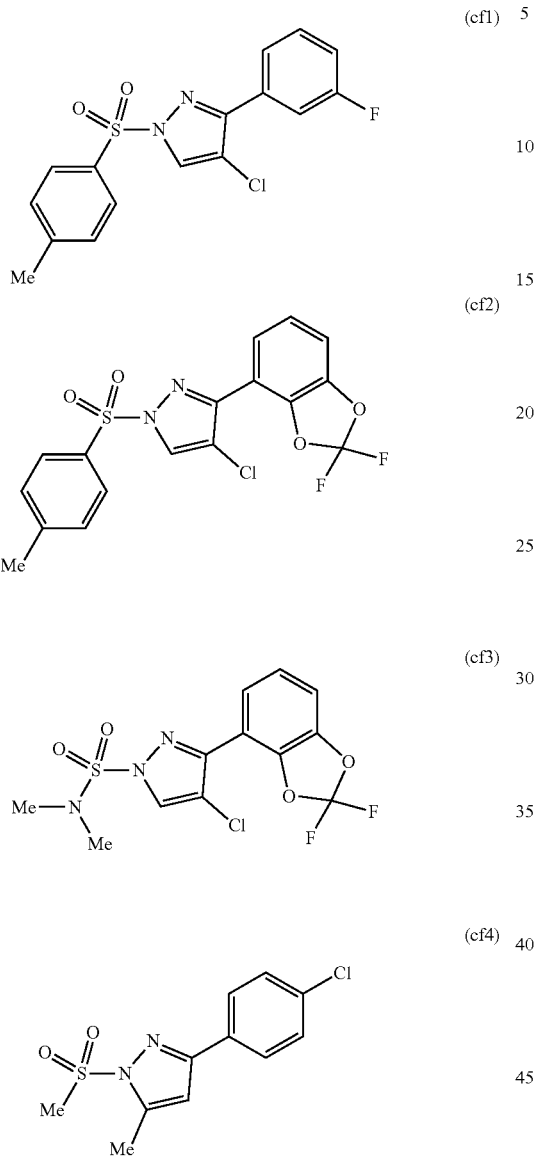

(cf1)

(cf2)

(cf3)

(cf4)

The test was conducted by using the compound represented by formula (cf1) that are described in WO 96/02138, the compound represented by formula (cf2) that are described in EP patent publication No. 538156, the compound represented by formula (cf3) that are described in EP patent publication No. 538156, or the compound represented by formula (cf4) that are described in WO 98/12182, according to the Test example 5, and as a result of the test, every of the lesion areas in soybean treated with each of the compounds showed 70% or more compared to the lesion areas in an untreated soybean.

INDUSTRIAL APPLICABILITY

The present compound X has a control efficacy against plant diseases, and can be thus used to control plant diseases.

162

The invention claimed is:
1. A compound represented by formula (II):

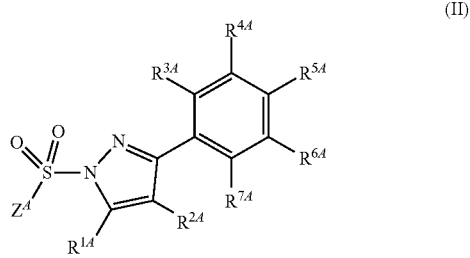

(II)

wherein
$Z^A$ represents —NR$^{8A}$R$^{9A}$, a C1-C6 chain hydrocarbon group optionally having one or more substituents selected from Group I$^A$, a C3-C6 cycloalkyl group optionally having one or more halogen atoms, or a three to seven membered non-aromatic heterocyclic group, wherein the three to seven membered non-aromatic heterocyclic group may optionally have one or more substituents selected from the group consisting of a C1-C3 alkyl group optionally having one or more halogen atoms and a halogen atom, $R^{8A}$ and $R^{9A}$ are identical to or different from each other and represent a C1-C6 chain hydrocarbon group optionally having one or more substituents selected from Group I$^A$, a C3-C6 cycloalkyl group optionally having one or more halogen atoms or a hydrogen atom, $R^{1A}$, $R^{2A}$, $R^{3A}$ and $R^{7A}$ represent a hydrogen atom,
a combination of $R^{4A}$, $R^{5A}$ and $R^{6A}$ represents any combination of a or b, a: a combination wherein $R^{5A}$ represents a hydrogen atom, $R^{4A}$ represents a C1-C6 chain hydrocarbon group optionally having one or more substituents selected from Group I$^B$, a halogen atom, a cyano group, —OR$^{15B}$, —CR$^{39B}$R$^{40B}$OR$^{41B}$, —CR$^{43B}$R$^{44B}$SR$^{45B}$, —S(O)$_q$R$^{16B}$, —C(O)R$^{17B}$, —CR$^{18B}$=N—O—R$^{19B}$, —O—N=CR$^{20B}$R$^{46B}$, —N=N—CR$^{21B}$R$^{47B}$, —C(O)NR$^{22B}$R$^{23B}$, —NR$^{24B}$C(O)R$^{25B}$, —C(O)N(OR$^{26B}$)R$^{27B}$, —N(OR$^{28B}$)C(O)R$^{29B}$, —NR$^{30B}$C(O)NR$^{31B}$R$^{32B}$, —OC(O)NR$^{33B}$R$^{34B}$, —NR$^{35B}$C(O)OR$^{36B}$, —NR$^{48B}$C(O)C(O)NR$^{49B}$R$^{50B}$, —CR$^{51B}$R$^{52B}$NR$^{53B}$C(O)C(O)NR$^{54B}$R$^{55B}$, —NR$^{56B}$C(O)C(O)N(OR$^{57B}$)R$^{58B}$, a C3-C6 cycloalkyl group, a C6-C10 aryl group, or a five to ten membered aromatic heterocyclic group, wherein each of the C3-C6 cycloalkyl group, the C6-C10 aryl group and the five to ten membered aromatic heterocyclic group may optionally have one or more substituents selected from Group K$^B$, and $R^{6A}$ represents a C1-C6 chain hydrocarbon group optionally having one or more substituents selected from Group I$^B$, a hydrogen atom, a halogen atom, a cyano group, —OR$^{15B}$, —CR$^{39B}$R$^{40B}$OR$^{41B}$, —CR$^{43B}$R$^{44B}$SR$^{45B}$, —S(O)$_q$R$^{16B}$, —C(O)R$^{17B}$, —CR$^{18B}$=N—O—R$^{19B}$, —O—N=CR$^{20B}$R$^{46B}$, —N=N—CR$^{21B}$R$^{47B}$, —C(O)NR$^{22B}$R$^{23B}$, —NR$^{24B}$C(O)R$^{25B}$, —C(O)N(OR$^{26B}$)R$^{27B}$, —N(OR$^{28B}$)C(O)R$^{29B}$, —NR$^{30B}$C(O)NR$^{31B}$R$^{32B}$, —OC(O)NR$^{33B}$R$^{34B}$, —NR$^{35B}$C(O)OR$^{36B}$, —NR$^{48B}$C(O)C(O)NR$^{49B}$R$^{50B}$, —CR$^{51B}$R$^{52B}$NR$^{53B}$C(O)C(O)NR$^{54B}$R$^{55B}$, —NR$^{56B}$C(O)C(O)N(OR$^{57B}$)R$^{58B}$, a C3-C6 cycloalkyl group, a C6-C10 aryl group, or a five to ten membered aromatic heterocyclic group, wherein each of the C3-C6 cycloalkyl group, the C6-C10 aryl group and the five to ten membered aromatic heterocyclic group may optionally have one or more substituents selected from Group $K^B$;

b: a combination wherein $R^{5A}$ represents a halogen atom, a nitro group, a C1-C6 chain hydrocarbon group, a C3-C6 cycloalkyl group, or —S(O)$_2$R$^{11A}$, wherein each of the C1-C6 chain hydrocarbon group and the C3-C6 cycloalkyl group may optionally have one or more halogen atoms, wherein $R^{11A}$ represents a C1-C4 chain hydrocarbon group optionally having one or more halogen atoms, and $R^{4A}$ and $R^{6A}$ are identical to or different from each other and represent a C1-C6 chain hydrocarbon group optionally having one or more halogen atoms, a hydrogen atom, a halogen atom, or a nitro group, $R^{4A}$ and $R^{5A}$ may be taken together with a carbon to which they are attached to form a C4-C7 carbocycle group, or a five to seven membered heterocyclic group, wherein each of the C4-C7 carbocycle group and the five to seven membered heterocyclic group may optionally have one or more substituents selected from the group consisting of a halogen atom and a C1-C3 chain hydrocarbon group, $R^{15B}$ represents a hydrogen atom, a C1-C6 chain hydrocarbon group optionally having one or more substituents selected from Group $L^B$, a C3-C6 cycloalkyl group, a C6-C10 aryl group, or a five to ten membered aromatic heterocyclic group, with the proviso that a pyridyl group is excluded, wherein each of the C3-C6 cycloalkyl group, the C6-C10 aryl group and the five to ten membered aromatic heterocyclic group, with the proviso that a pyridyl group is excluded, may optionally have one or more substituents selected from Group $K^B$, $R^{17B}$, $R^{18B}$, $R^{19B}$, $R^{20B}$, $R^{21B}$, $R^{22B}$, $R^{23B}$, $R^{24B}$, $R^{25B}$, $R^{26B}$, $R^{27B}$, $R^{28B}$, $R^{29B}$, $R^{30B}$, $R^{31B}$, $R^{32B}$, $R^{33B}$, $R^{34B}$, $R^{35B}$, $R^{39B}$, $R^{40B}$, $R^{41B}$, $R^{43B}$, $R^{44B}$, $R^{45B}$, $R^{46B}$, $R^{47B}$, $R^{48B}$, $R^{49B}$, $R^{50B}$, $R^{51B}$, $R^{52B}$, $R^{53B}$, $R^{54B}$, $R^{55B}$, $R^{56B}$, $R^{57B}$, and $R^{58B}$ are identical to or different from each other and represent a hydrogen atom, a C1-C6 chain hydrocarbon group optionally having one or more substituents selected from Group $L^A$, a C3-C6 cycloalkyl group, a C6-C10 aryl group, or a five to ten membered aromatic heterocyclic group, wherein each of the C3-C6 cycloalkyl group, the C6-C10 aryl group and the five to ten membered aromatic heterocyclic group may optionally have one or more substituents selected from Group $K^A$, $R^{36B}$ represents a C1-C6 chain hydrocarbon group optionally having one or more substituents selected from Group $L^A$, a C3-C6 cycloalkyl group, a C6-C10 aryl group, or a five to ten membered aromatic heterocyclic group, wherein each of the C3-C6 cycloalkyl group, the C6-C10 aryl group and the five to ten membered aromatic heterocyclic group may optionally have one or more substituents selected from Group $K^A$, $R^{16B}$ represents a C1-C6 chain hydrocarbon group optionally having one or more substituents selected from Group $L^A$, or a C3-C6 cycloalkyl group, wherein the C3-C6 cycloalkyl group may optionally have one or more substituents selected from the group consisting of a halogen atom and a cyano group, q is 0, 1 or 2, Group $I^A$: a group consisting of a halogen atom, a cyano group, a C3-C6 cycloalkyl group, a C1-C3 alkoxy group and a C1-C3 alkylthio group, wherein each of the C3-C6 cycloalkyl group, the C1-C3 alkoxy group and the C1-C3 alkylthio group may optionally have one or more halogen atoms, Group $K^A$: a group consisting of a halogen atom, a cyano group, a C1-C3 chain hydrocarbon group, a C3-C6 cycloalkyl group, a C1-C3 alkoxy group, and a C1-C3 alkylthio group, wherein each of the C1-C3 chain hydrocarbon group, the C3-C6 cycloalkyl group, the C1-C3 alkoxy group and the C1-C3 alkylthio group may optionally have one or more substituents selected from the group consisting of a halogen atom and a cyano group, Group $L^A$: a group consisting of a halogen atom, a cyano group, a C1-C3 alkoxy group, a C1-C3 alkylthio group, a C3-C6 cycloalkyl group, a C6-C10 aryl group, and a five to ten membered aromatic heterocyclic group, wherein each of the C1-C3 alkoxy group and the C1-C3 alkylthio group may optionally have one or more halogen atoms, and each of the C3-C6 cycloalkyl group, the C6-C10 aryl group and the five to ten membered aromatic heterocyclic group may optionally have one or more substituents selected from Group $K^A$, Group $I^B$: a group consisting of a halogen atom, a cyano group, a C3-C6 cycloalkyl group, a C1-C3 alkoxy group and a C1-C3 alkylthio group, wherein each of the C3-C6 cycloalkyl group, the C1-C3 alkoxy group and the C1-C3 alkylthio group may optionally have one or more halogen atoms, Group $K^B$: a group consisting of a halogen atom, a cyano group, a C1-C3 chain hydrocarbon group, a C3-C6 cycloalkyl group, a C1-C3 alkoxy group, and a C1-C3 alkylthio group, wherein each of the C1-C3 chain hydrocarbon group, the C3-C6 cycloalkyl group, the C1-C3 alkoxy group and the C1-C3 alkylthio group may optionally have one or more substituents selected from the group consisting of a halogen atom and a cyano group, Group $L^B$: a group consisting of a halogen atom, a cyano group, a C1-C3 alkoxy group, a C1-C3 alkylthio group, a C3-C6 cycloalkyl group, a C6-C10 aryl group, and a five to ten membered aromatic heterocyclic group, wherein each of the C1-C3 alkoxy group and the C1-C3 alkylthio group may optionally have one or more halogen atoms, and each of the C3-C6 cycloalkyl group, the C6-C10 aryl group and the five to ten membered aromatic heterocyclic group may optionally have one or more substituents selected from Group $K^A$.

2. The compound according to claim 1 wherein $R^{5A}$ represents a hydrogen atom, $R^{4A}$ represents a C1-C6 chain hydrocarbon group optionally having one or more substituents selected from Group $I^A$, a halogen atom, a cyano group, —OR$^{15B}$, —CR$^{39B}$R$^{40B}$OR$^{41B}$, —CR$^{43B}$R$^{44B}$SR$^{45B}$, —S(O)$_q$R$^{16B}$, —C(O)R$^{17B}$, —CR$^{18B}$=N—O—R$^{19B}$, —O—N=CR$^{20B}$R$^{46B}$, —N=N—CR$^{21B}$R$^{47B}$, —C(O)NR$^{22B}$R$^{23B}$, —NR$^{24B}$C(O)R$^{25B}$, —C(O)N(OR$^{26B}$)R$^{27B}$, —N(OR$^{28B}$)C(O)R$^{29B}$, —NR$^{30B}$C(O)NR$^{31B}$R$^{32B}$, —OC(O)NR$^{33B}$R$^{34B}$, —NR$^{35B}$C(O)OR$^{36B}$, —NR$^{48B}$C(O)C(O)NR$^{49B}$R$^{50B}$, —CR$^{51B}$R$^{52B}$NR$^{53B}$C(O)C(O)NR$^{54B}$R$^{55B}$, —NR$^{56B}$C(O)C(O)N(OR$^{57B}$)R$^{58B}$, a C3-C6 cycloalkyl group, a C6-C10 aryl group, or a five to ten membered aromatic heterocyclic group, wherein each of the C3-C6 cycloalkyl group, the C6-C10 aryl group and the five to ten membered aromatic heterocyclic group may optionally have one or more substituents selected from Group $K^A$, $R^{6A}$ represents a C1-C6 chain hydrocarbon group optionally having one or more substituents selected from Group $I^A$, a hydrogen atom, a halogen atom, a cyano group, $-OR^{15B}$, $-CR^{39B}R^{40B}OR^{41B}$, $-CR^{43B}R^{44B}SR^{45B}$, $-S(O)_qR^{16B}$, $-C(O)R^{17B}$, $-CR^{18B}=N-O-R^{19B}$, $-O-N=CR^{20B}R^{46B}$, $-N=N-CR^{21B}R^{47B}$, $-C(O)NR^{22B}R^{23B}$, $-NR^{24B}C(O)R^{25B}$, $-C(O)N(OR^{26B})R^{27B}$, $-N(OR^{28B})C(O)R^{29B}$, $-NR^{30B}C(O)NR^{31B}R^{32B}$, $-OC(O)NR^{33B}R^{34B}$, $-NR^{35B}C(O)OR^{36B}$, $-NR^{48B}C(O)C(O)NR^{49B}R^{50B}$, $-CR^{51B}R^{52B}NR^{53B}C(O)C(O)NR^{54B}R^{55B}$, $-NR^{56B}C(O)C(O)N(OR^{57B})R^{58B}$, a C3-C6 cycloalkyl group, a C6-C10 aryl group, or a five to ten membered aromatic heterocyclic group, wherein each of the C3-C6 cycloalkyl group, the C6-C10 aryl group and the five to ten membered aromatic heterocyclic group may optionally have one or more substituents selected from Group $K^A$.

3. The compound according to claim 1 wherein $Z^A$ represents a C1-C6 chain hydrocarbon group, a C3-C6 cycloalkyl group, a three to five membered nitrogen atom-containing non-aromatic heterocyclic group in which the ring-constituting nitrogen atom is attached to $S(O)_2$, or $-NR^{8A}R^{9A}$, $R^{8A}$ and $R^{9A}$ are identical to or different from each other and represent a C1-C6 chain hydrocarbon group, $R^{5A}$ represents a halogen atom, a nitro group, $-S(O)_2R^{11A}$, a C1-C6 chain hydrocarbon group, or a C3-C6 cycloalkyl group, wherein each of the C1-C6 chain hydrocarbon group and the C3-C6 cycloalkyl group may optionally have one or more halogen atoms, $R^{11A}$ represents a C1-C4 chain hydrocarbon group optionally having one or more halogen atoms, $R^{4A}$ and $R^{6A}$ are identical to or different from each other and represent a C1-C6 chain hydrocarbon group optionally having one or more halogen atoms, a halogen atom, a nitro group, or a hydrogen atom, $R^{4A}$ and $R^{5A}$ may be taken together with a carbon atom to which they are attached to form a C4-C7 carbocycle group, or a five to seven membered heterocyclic group, wherein each of the C4-C7 carbocycle group and the five to seven membered heterocyclic group may optionally have one or more substituents selected from a halogen atom and a C1-C3 chain hydrocarbon group.

4. A composition for controlling a plant disease comprising the compound described in claim 1.

5. A method for controlling a plant disease which comprises applying an effective amount of the compound according to claim 1 to a plant or a soil.

6. A composition, comprising:
at least one ingredient selected from the group consisting of Group (a), Group (b), Group (c), and Group (d); and the compound of claim 1,
Group (a): a group consisting of insecticidal ingredients, miticidal ingredients, and nematicidal ingredients;
Group (b): fungicidal ingredients;
Group (c): plant growth modulating ingredients;
Group (d): repellent ingredients.

7. A seed or vegetative reproductive organ carrying an effective amount of the compound according to claim 1.

8. A seed or vegetative reproductive organ carrying an effective amount of the composition according to claim 6.

* * * * *

UNITED STATES PATENT AND TRADEMARK OFFICE
CERTIFICATE OF CORRECTION

PATENT NO. : 12,225,904 B2
APPLICATION NO. : 17/285687
DATED : February 18, 2025
INVENTOR(S) : Nao Maehata et al.

It is certified that error appears in the above-identified patent and that said Letters Patent is hereby corrected as shown below:

On the Title Page

Item (30), the Foreign Application Priority Data:
"Oct. 18, 2019" should read -- Oct. 18, 2018 --

Signed and Sealed this
Thirteenth Day of May, 2025

Coke Morgan Stewart
*Acting Director of the United States Patent and Trademark Office*